(12) United States Patent
Hayday et al.

(10) Patent No.: US 10,875,916 B2
(45) Date of Patent: Dec. 29, 2020

(54) NUCLEIC ACID MOLECULES ENCODING MONOCLONAL ANTIBODIES SPECIFIC FOR IL-17F

(71) Applicant: IMMUNOQURE AG, Dusseldorf (DE)

(72) Inventors: Adrian Hayday, Kent (GB); Kai Krohn, Samentaka (FI); Annamari Ranki, Helsinki (FI); Part Peterson, Tallinn (EE); Kai Kisand, Tartu (EE); Edward Stuart, Meerbusch (DE); Annalisa Macagno, Schlieren (CH); Shimobi Onuoha, Bishop's Stortford (GB)

(73) Assignee: ImmunoQure AG

( * ) Notice: Subject to any disclaimer, the term of this patent is extended or adjusted under 35 U.S.C. 154(b) by 58 days.

(21) Appl. No.: 16/153,091

(22) Filed: Oct. 5, 2018

(65) Prior Publication Data

US 2019/0023779 A1  Jan. 24, 2019

Related U.S. Application Data

(62) Division of application No. 15/258,263, filed on Sep. 7, 2016, now Pat. No. 10,131,709, which is a division of application No. 14/369,467, filed as application No. PCT/EP2013/050024 on Jan. 2, 2013, now Pat. No. 9,475,872.

(60) Provisional application No. 61/580,837, filed on Dec. 28, 2011.

(30) Foreign Application Priority Data

Dec. 28, 2011 (EP) .................................. 11195952

(51) Int. Cl.
A61K 39/395 (2006.01)
C07K 16/24 (2006.01)
A61K 39/00 (2006.01)

(52) U.S. Cl.
CPC ...... *C07K 16/244* (2013.01); *A61K 2039/505* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 6,309,636 | B1 | 10/2001 | do Couto et al. |
| 9,475,872 | B2 | 10/2016 | Hayday et al. |
| 1,013,170 | A1 | 11/2018 | Hayday et al. |
| 2003/0099649 | A1 | 5/2003 | Jacobs et al. |
| 2009/0130120 | A1 | 5/2009 | Kauvar et al. |
| 2014/0335098 | A1 | 11/2014 | Hayday et al. |

FOREIGN PATENT DOCUMENTS

| JP | H05-271281 | 10/1993 |
| JP | H09-218203 | 8/1997 |
| JP | 2006-008694 | 1/2006 |
| JP | 2007-075115 | 3/2007 |
| JP | 2010-150260 | 7/2010 |
| WO | WO 2004/076677 | 9/2004 |
| WO | WO 2007/068758 | 6/2007 |
| WO | WO 2007/149032 | 12/2007 |
| WO | WO 2008/081008 | 7/2008 |
| WO | WO 2008/110372 | 9/2008 |
| WO | WO 2009/130459 | 10/2009 |
| WO | WO 2009/136286 | 11/2009 |
| WO | WO 2010/003529 | 1/2010 |
| WO | WO 2010/128407 | 11/2010 |

OTHER PUBLICATIONS

International Search Report for International (PCT) Patent Application No. PCT/EP2013/050026 dated May 7, 2013, 5 pages.
International Search Report for International (PCT) Patent Application No. PCT/EP2013/050024 dated Jun. 11, 2013, 8 pages.
International Preliminary Report on Patentability and Written Opinion for International (PCT) Patent Application No. PCT/EP2013/050024 dated Jul. 10, 2014, 18 pages.
Ahlgren et al. "Increased IL-17A secretion in response to Candida albicans in autoimmune polyendocrine syndrome type 1 and its animal model," Clinical Immunology, Jan. 2011, vol. 41, No. 1, pp. 235-245.
Cludts et al. "Detection of neutralizing interleukin-17 antibodies in autoimmune polyendocrinopathy syndrome-1 (APS-1) patients using a novel non-cell based electrochemiluminescence assay," Cytokine, May 2010, vol. 50, No. 2, pp. 129-137.
Decker et al., "Immunostimulatory CpG-oligonucleotides induce functional high affinity IL-2 receptors on B-CLL cells; costimulation with IL-2 results in a highly immunogenic Pheynotype," Experimental Hematology, 2000, vol. 28, pp. 558-568.
Fraussen et al., "A novel methof for making human monoclonal antibodies," J. Autoimmunity, 2010, vol. 35, pp. 130-134.
Gerhardt et al. "Structure of IL-17A in Complex with a Potent, Fully Human Neutralizing Antibody," Journal of Molecular Biology, Dec. 2009, vol. 394, No. 5, pp. 905-921.

(Continued)

*Primary Examiner* — Dong Jiang
(74) *Attorney, Agent, or Firm* — Sheridan Ross P.C.

(57) ABSTRACT

Provided are novel binding molecules of human origin, particularly human antibodies as well as fragments, derivatives and variants thereof that recognize antigens such as native endogenous proteins associated with, e.g., immune response, autoimmune disorders, inflammatory diseases, metabolic disorders, vascular function, neurodegenerative diseases or tumors. More particularly, a human Auto-Immunosome and corresponding monoclonal antibody reservoir are provided. In addition, pharmaceutical compositions, kits and methods for use in diagnosis and therapy of are described.

24 Claims, 59 Drawing Sheets

Specification includes a Sequence Listing.

(56) References Cited

OTHER PUBLICATIONS

Hu et al., "The IL-17 pathway as a major therapeutic target in autoimmune diseases," Annals of the New York Academy of Sciences, 2011, vol. 1217, pp. 60-76.

Jury et al., "Isolation and Functional Characterization of Recombinant GAD65 Autoantibodies Derived by IgG Repertoire Cloning From Patients With Type 1 Diabetes," Diabetes, 2001, vol. 50, Iss. 9, pp. 1976-1982.

Kisand et al., "Chronic mucocutaneous candidiasis in APECED or thymoma patients correlates with autoimmunity to Th17-associated cytokines," Journal of Experimental Medicine, 2010, vol. 207, No. 2, pp. 299-308.

Kisand et al., "Interferon autoantibodies associated with AIRE deficiency decrease the expression of IFN-stimulated genes," Blood, 2008, vol. 112, No. 7, pp. 2657-2666.

MacCallum et al., "Antibody-antigen Interactions: Contact Analysis and Binding Site Topography," J. Mol. Biol., 1996, vol. 262, pp. 732-745.

Madec et al., "Four IgG Anti-Islet Human Monoclonal Antibodies Isolated from a Type 1 Diabetes Patient Recognize Distinct Epitopes of Glutamic Acid Decarboxylase 65 and Are Somatically Mutated," Journal of Immunology, 1996, vol. 156, No. 9, pp. 3541-3549.

Meager et al., "Anti-Interferon Autoantibodies in Autoimmune Polyendocrinopathy Syndrome Type 1," PLOS Medicine, 2006, vol. 3, Iss. 7, pp. 1152-1164.

Meyer et al. "AIRE-Deficient Patients Harbor Unique High-Affinity Disease-Ameliorating Autoantibodies," Cell, Jul. 2016, vol. 166, pp. 582-595.

Oftedal et al. "Measuring Autoantibodies against IL-17F and IL-22 in Autoimmune Polyendocrine Syndrome Type I by Radioligand Binding Assay Using Fusion Proteins," Scandinavian Journal of Immunology, Sep. 2011, vol. 74, No. 3, pp. 327-333.

Padlan et al., "Structure of an antibody-antigen complex: Crystal structure of the HyHEL-10 Fab-lysozyme complex," Proc. Natl. Acad. Sci. USA, 1989, vol. 86, pp. 5938-5942.

Puel et al., "Autoantibodies against IL-17A, IL-17F, and IL-22 in patients with chronic mucocutaneous candidiasis and autoimmune polyendocrine syndrome type I," Journal of Experimental Medicine, 2010, vol. 207, No. 2, pp. 291-297.

Simpson et al., "Autoantibodies to Alzheimer and Normal Brain Structures from Virus-Transformed Lymphocytes," Journal of Neuroimmunology, 1986, vol. 13, No. 1, pp. 1-8.

Traggiai et al, "An efficient method to make human monoclonal antibodies from memory B cells: potent neutralization of SARS coronavirus," Nature Medicine, 2004, vol. 10, No. 8, pp. 871-875.

Tsuchiyama et al, "Synergy between anti-CD40 MAb and Epstein-Barr virus in activation and transformation of human B lymphocytes," Human Antibodies, 1997, vol. 8, No. 1, pp. 43-47.

Restriction Requirement for U.S. Appl. No. 14/369,467, dated Jun. 24, 2015, 7 pages.

Official Action for U.S. Appl. No. 14/369,467, dated Sep. 8, 2015, 14 pages.

Final Action for U.S. Appl. No. 14/369,467, dated Mar. 1, 2016, 8 pages.

Notice of Allowance for U.S. Appl. No. 14/369,467, dated Jun. 30, 2016, 8 pages.

Official Action for U.S. Appl. No. 14/368,749, dated Jun. 30, 2106, 11 pages.

Final Action for U.S. Appl. No. 14/368,749, dated Dec. 5, 2016, 11 pages.

Official Action for U.S. Appl. No. 15/258,263, dated Aug. 22, 2017 6 pages Restriction Requirement.

Official Action for U.S. Appl. No. 15/258,263, dated Nov. 2, 2017 14 pages.

Official Action for U.S. Appl. No. 15/258,263, dated May 17, 2018 8 pages.

Notice of Allowance for U.S. Appl. No. 15/258,263, dated Aug. 15, 2018 9 pages.

A
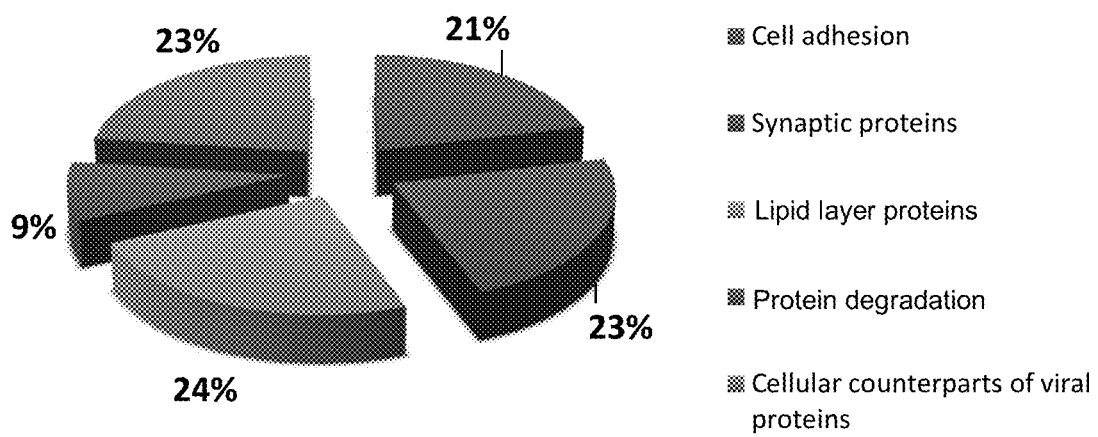
B
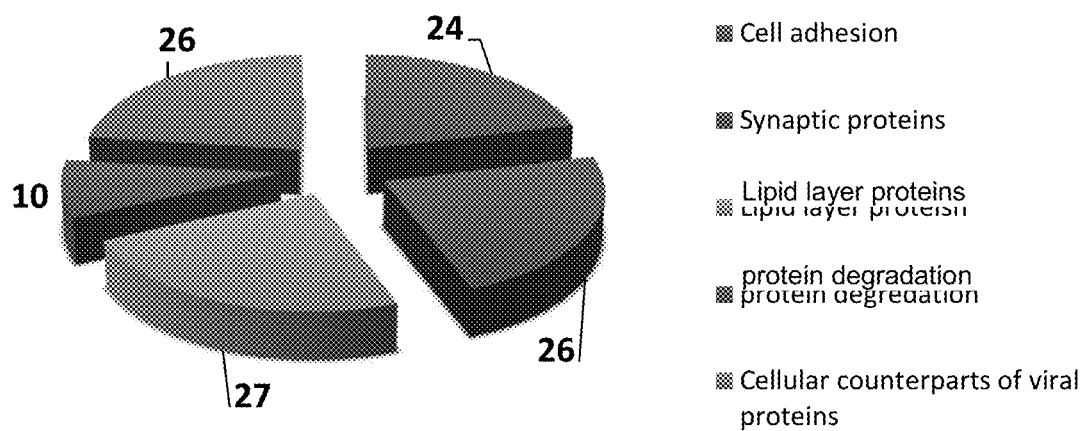
Fig.2

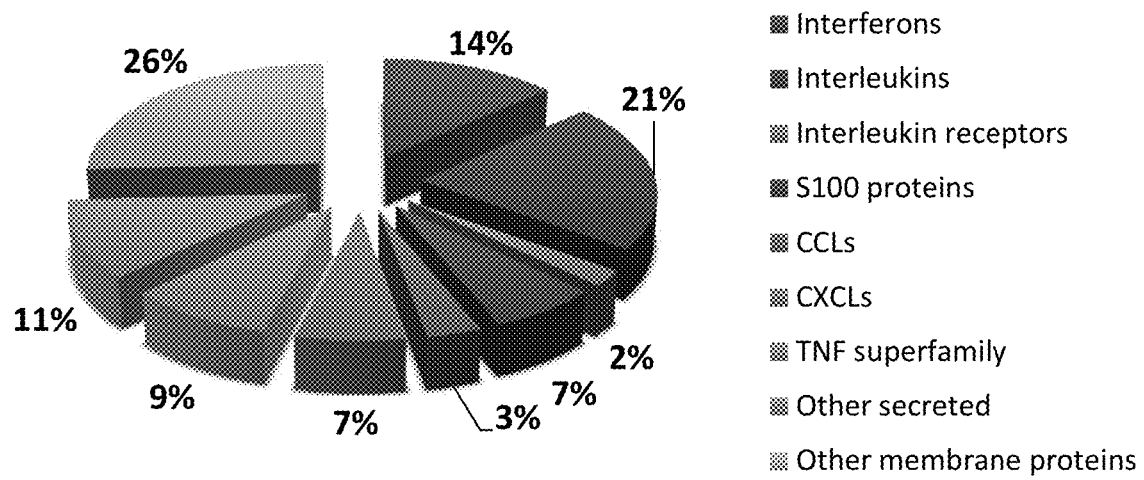
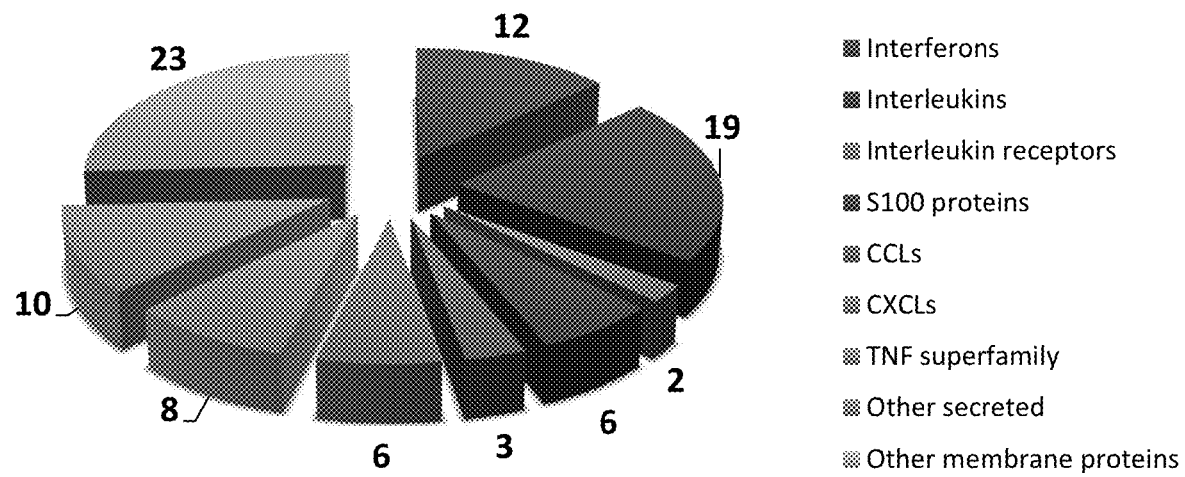
Fig.3

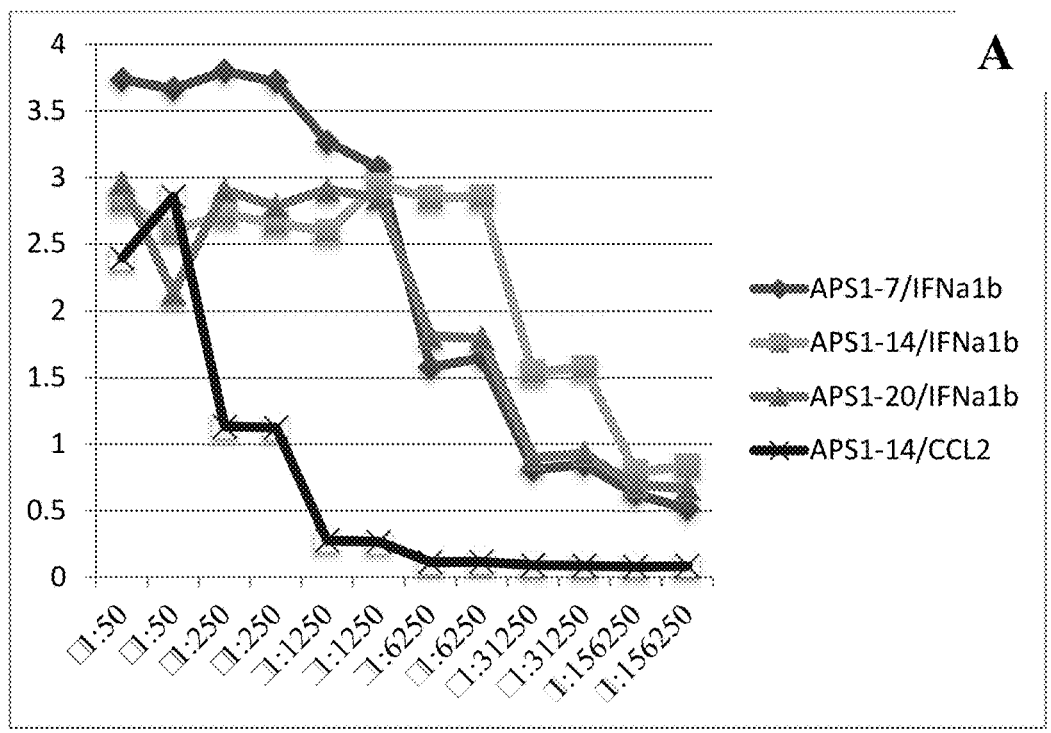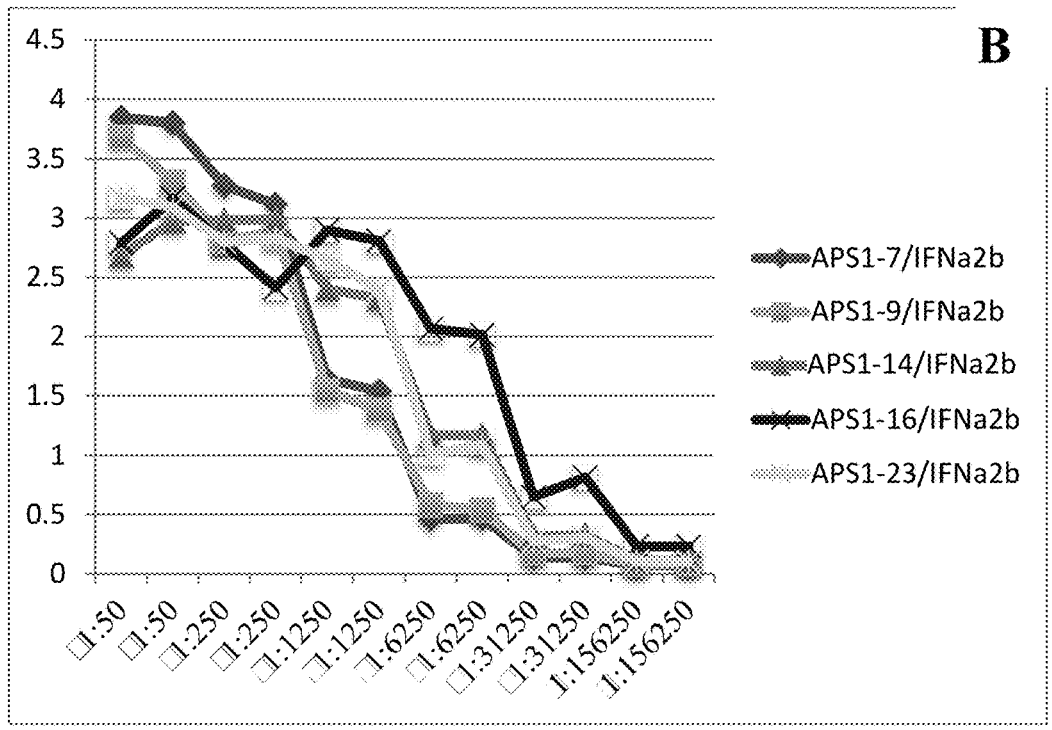
Fig.7

A  9A2 (variable heavy chain sequence VH) – SEQ ID NO: 7
```
FR1-------------------------------CDR1--FR2----------CDR2-------------
EVQLEESGGGLVQPGGSLRLSCAASGFPFSNYEMNWVRQAPGKGLEWISYISVSGGPAHYADSVKG FR3-----------------------------------CDR3------------FR4--------
RFTISRDDATKSLFLQMNRLRADDTAVYYCVRREYVTGRNYNYYPYMDVWGTGTTVTVSP
```

9A2  (variable kappa chain sequence VL) – SEQ ID NO: 9
```
FR1----------------------CDR1-------FR2------------CDR2---
DIQMTQSPSSLSASVGDRVTITCRASQTISDYLNWYQHKPGEAPKLLIYSASTLQR FR3---------------------------------CDR3------FR4--------
GVPSRFSGSGSGTDFVFTISSLQSDDFATYYCQQTSSTALTFGGGTKVEVK
```

B  17E3 (variable heavy chain sequence VH) – SEQ ID NO: 15
```
FR1-------------------------------CDR1-FR2-----------CDR2-------------
QVQLVQSGAEVAKPGASVRLSCKASGFSFIKYYMHWVRQAPGQGLEWMGVIEPTGGGTSSAQKFRD FR2-----------------------------------CDR3--------------FR4--------
RVTLSRDTSTATVHLEVSRLTLEDTGIYFCVRDSIYCKHGTCHRTVIDAFDIWGQGTAVTVSS
```

17E3 (variable kappa chain sequence VL) – SEQ ID NO: 17
```
FR1---------------------CDR1-------FR2-------------CDR2---
DIQMTQSPSSLSASVGDRVTITCRSSQDIKNDLAWYQQKPGKAPERLIYAASNLQS FR3-----------------------------CDR3-------FR4--------
GVPSRFSGSGSGTEFSLTISGLQPEDFATYYCLQHNSYPLLTFGGGTKVEIK
```

C  24D3 (variable heavy chain sequence VH) – SEQ ID NO: 23
```
FR1-------------------------------CDR1-FR2----------CDR2---------------
EVKLEESGGDLVKPGGSLRLSCVASGFTFGTAWMSWVRQAPGKGLEWVGRISNKDTGGRIDYAAPVRG FR3--------------------------------CDR3---------FR4--------
RFAISRDDSKATLFLQMNSLKTEDTAVYFCTTNFYDVLTGDHVDYWGQGTVVVVSS
```

24D3 (variable lambda chain sequence VL) – SEQ ID NO: 25
```
FR1---------------------CDR1-------FR2-------------CDR2---
SYELTQPPSVSVSPGETARIPCSGETLPKKLVYWYQQKPGQAPVLMIYKDSERPS FR3--------------------------------CDR3------FR4--------
RISERFSGSNSGTMASLTISGVQAEDEADYYCQTSDSSGVVFGGGTKLTVL
```

Fig. 15

D    30G1 (variable heavy chain sequence VH) – SEQ ID NO: 31

```
FR1--------------------------------CDR1-FR2----------CDR2-------------
EVQLLESGGGLVQPGGSLRLSCAASGFTFSTYAMSWVRQAPGKGLEWVSTITSSGGATYHADSVKG

FR3-------------------------------CDR3-----------FR4--------
RLTISRDNSKNTLYLEMNSLRVEDTAVYYCAKDWGRTVYAVIKDLDIWGQGTLVTVSS
```

30G1 (variable kappa chain sequence VL) – SEQ ID NO: 33

```
FR1--------------------CDR1--------FR2--------------CDR2---
EIVMTQSPAILSVSPGERATLSCRASQSVSNYLAWFQQKPGQAPRLLIYDTSKRAT

FR3------------------------------CDR3------FR4-------
GTPARFSGSGSGTDFTLTISSLEPEDFAVYFCQQRSDWPQYTFGQGTKLEIK
```

E    35G11 (variable heavy chain sequence VH) – SEQ ID NO: 39

```
FR1---------------------------CDR1-FR2-----------CDR2--------------
QVQLVQSGSELRRPGASVNISCKASGYGFNTYAMNWVRQAPGQGPEWMGWINTDTGDPTYAQGFTG

FR3------------------------------CDR3-------------FR4--------
RFAFFLDTSASTAFLQITRLTGEDTAVYFCARTRNNWNGVYYHYSGLDVWGQGTTVTVSS
```

35G11 (variable lambda chain sequence VL) ) – SEQ ID NO: 41

```
FR1-------------------CDR1---------FR2-------------CDR2---
QSVLTQPPSASGTPGQTVTISCSGSSPNLGDNYVYWYHQVPGTAPKLLIFRNTQRPS

FR3---------------------------CDR3------FR4-------
GVTDRFSGSKYGTSASLAISDLRSDDEGDFYCASWDDRLSRLVFGGGTKLTVL
```

F    41D11 (variable heavy chain sequence VH) – SEQ ID NO: 47

```
FR1-----------------------------CDR1---FR2-----------CDR2-------------
QVQLHESGPGLVKPSETLSVTCSLSGGSISSSSHLWAWIRQPPEKGLEYIGRIHYRGSVSYNPSLKS

FR3------------------------------CDR3----FR4--------
RAAISVDTAKNQFSLTLSAVTAADTSFYYCARLDMGAIDKWGQGTLVIVSS
```

41D11 (variable lambda chain sequence VL) – SEQ ID NO: 49

```
FR1-------------------CDR1--------FR2-------------CDR2-------
QPVLTQSPSASASLGASIKLTCTLSSGHSNYDIAWHQQSGKGPRFLMRVNNGGSHNKGD

FR3-----------------------------CDR3-----FR4-------
GIPDRFSGSSSGAERYLTISSLQSEDEADYYCQTWGTGTHVFGTGTKVTVL
```

Fig. 15 (continued)

G        51G4 (variable heavy chain sequence VH) – SEQ ID NO: 55

```
FR1------------------------------CDR1-FR2-----------CDR2-------------
EVQLVQSGAEVKKPGASVKVSCKTSGYKFALYDIHWVRQAPGQGLEWMGWINAANGDTEYSQKFEG

FR3-------------------------------CDR3------FR4--------
RVTITRDTSATTVYMELNSLTYGDTAVYYCAREEGLYNWFDPWGQGTLVTVSS
```

51G4 (variable lambda chain sequence VL) – SEQ ID NO: 57

```
FR1---------------------CDR1-------FR2-------------CDR2---
SYELTQDPAVSVALGQTVRITCQGDSLRIYYANWYQQKPGQAPVLVIYGKSNRPS

FR3----------------------------------CDR3----------FR4--------
GIPDRFSASSSGNTASLTITGAQAEDEADYYCNSRDSSDKHPVPFGGGTKLTVL
```

Fig. 15 (continued)

Expt 7   LIF Protocol: YH006            PPL: 80/2480

A

| My # | Treatment | Group |
|---|---|---|
| 1 | IgG+Vas | A |
| 2 | IgG+Vas | A |
| 3 | IgG+Vas | A |
| 7 | IgG+IMQ | B |
| 8 | IgG+IMQ | B |
| 9 | IgG+IMQ | B |
| 10 | IgG+IMQ | B |
| 4 | aIL22+Vas | C |
| 5 | aIL22+Vas | C |
| 6 | aIL22+Vas | C |
| 11 | aIL22+IMQ | D |
| 12 | aIL22+IMQ | D |
| 13 | aIL22+IMQ | D |
| 14 | aIL22+IMQ | D |

B

| | Conc | Volume/IP | Amount/IP | Total | Total |
|---|---|---|---|---|---|
| human IgG | 1mg/mL | 200ul | 200ug | 7x3x200ug | 4.2mg |
| aIL-22 | 1mg/mL | 200ul | 200ug | 7x3x200ug | 4.2mg |

C

Experimental day

| -3 | -1 | 0 | 1 | 2 | 3 | 4 | 5 | 6 | 7 |
|---|---|---|---|---|---|---|---|---|---|
| | IP-1 | IMQ-1 | IP-2 IMQ-2 | | IP-3 IMQ-3 | IMQ-4 | IMQ-5 Sacrifice | Bref 4hrs | FACS |

Shave (*not -2)
(*2 Sacrifice of Ex6)

Weigh, clinical score and back thickness

LN stim o/n     Fix/I.Stain
*Unstim/B*      CD3
*PMA/Iono/B*    TCRgd
*IL23/IL1b/B*   IL22
Spleen          IL17
weight          IFNg
Skin OCT        Dead
Skin for RNA

Fig. 16

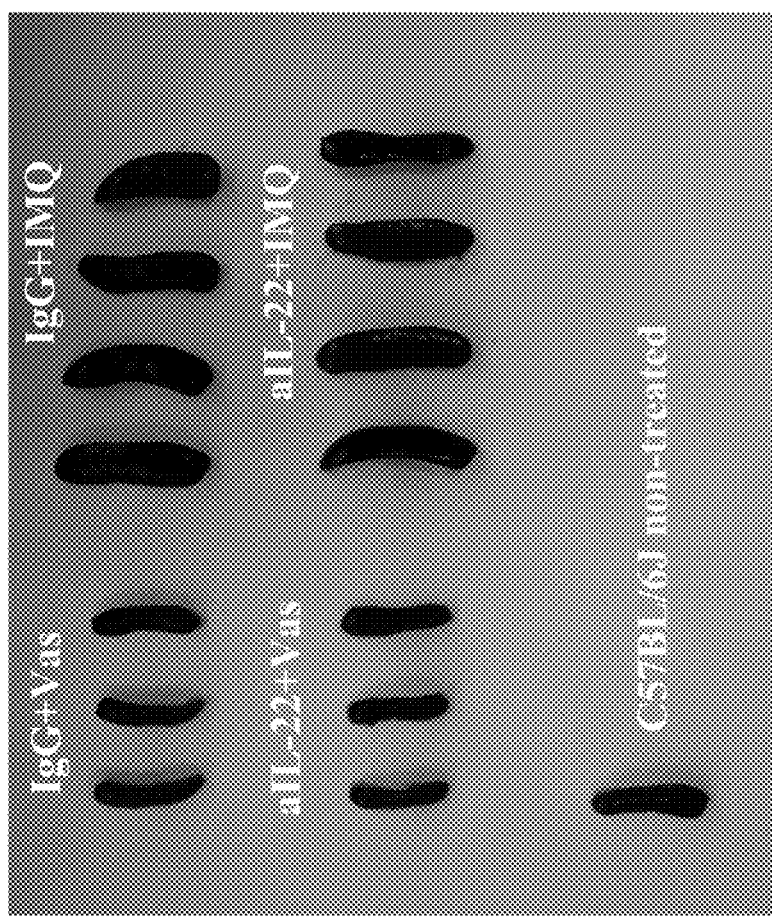
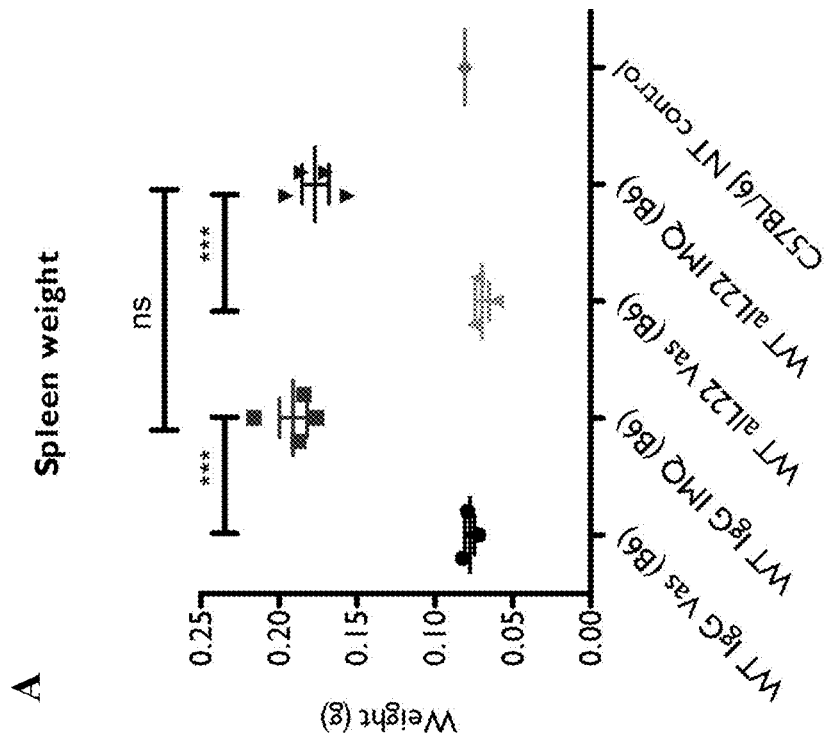
Fig. 27

Fig. 33

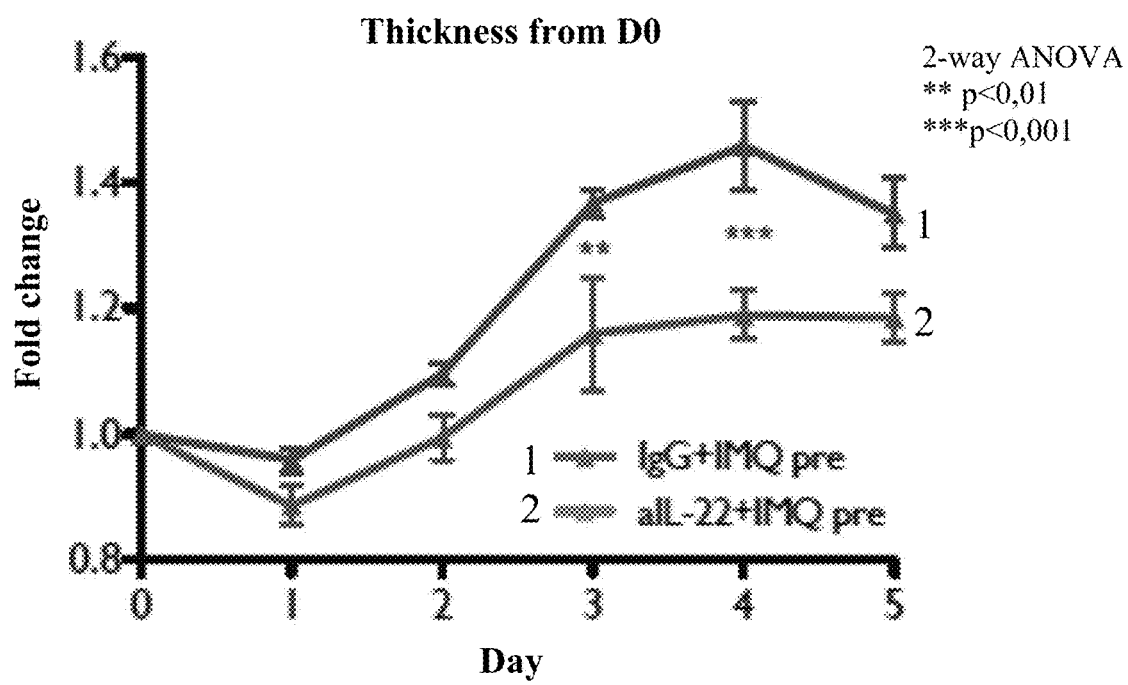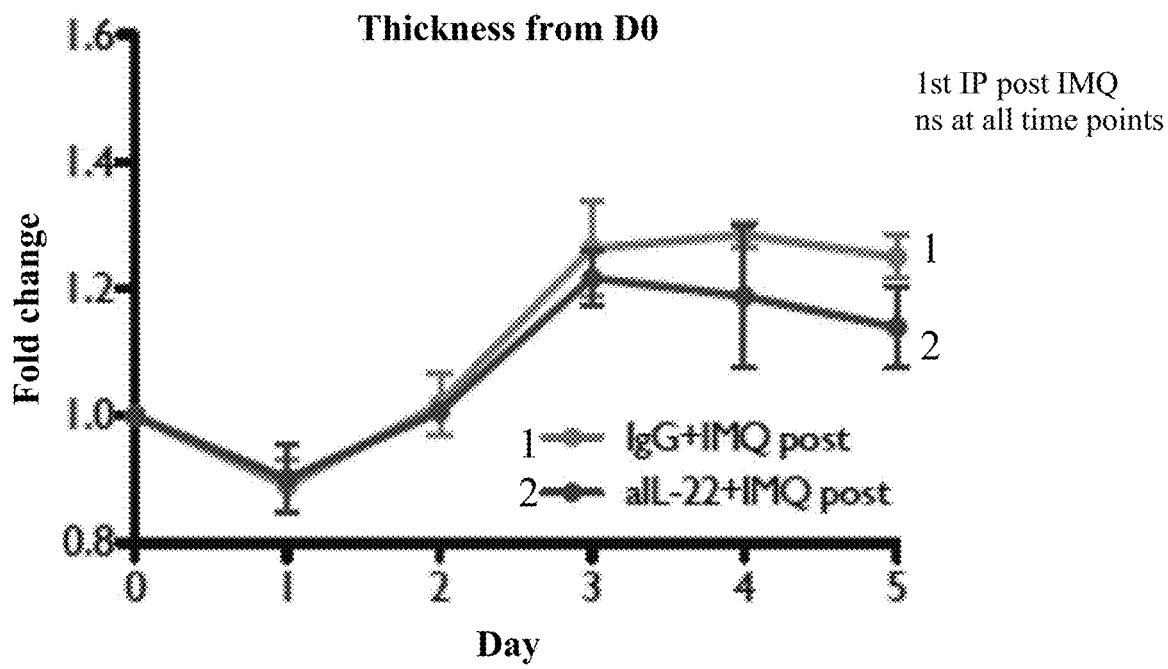
Fig. 34

Fig. 35

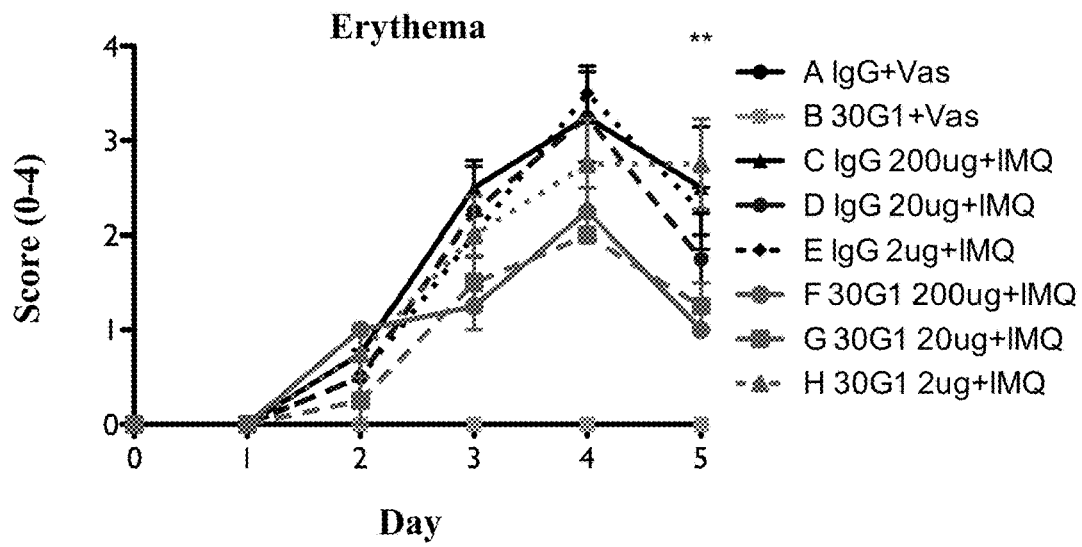
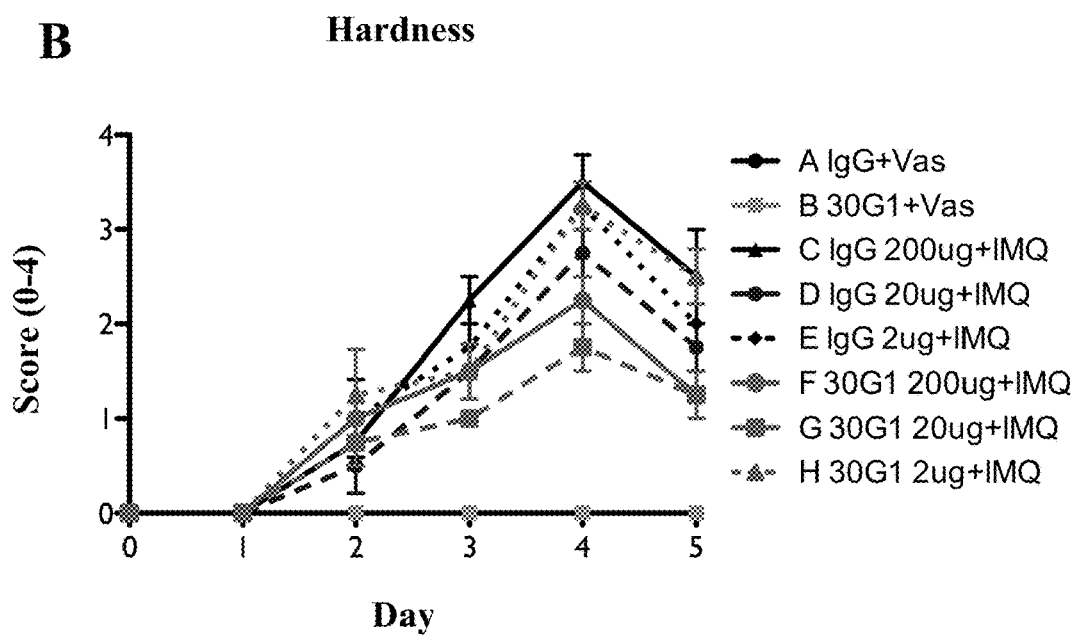
Fig. 38

C V F D4, D5 ** P<0,01
E V H ns at all points

E
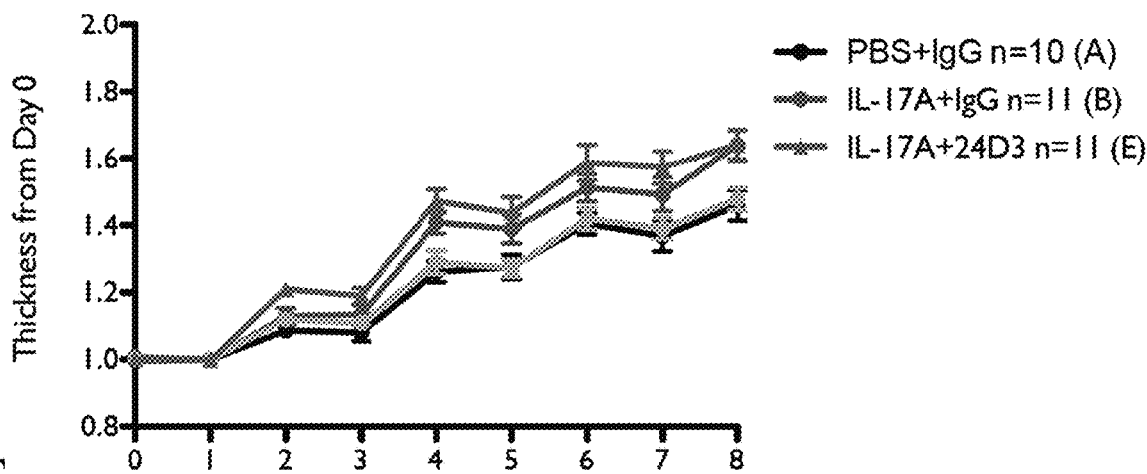
F
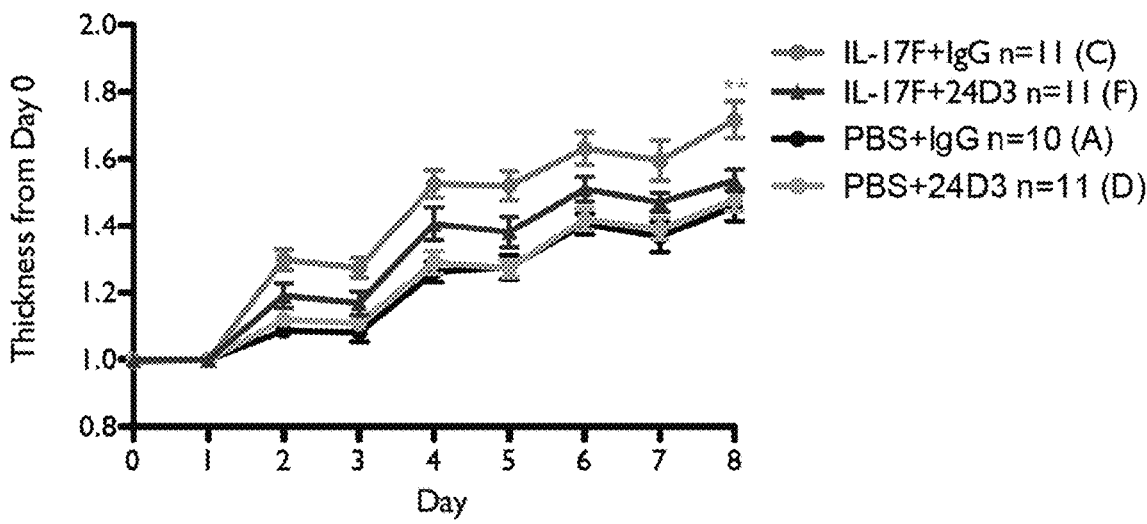
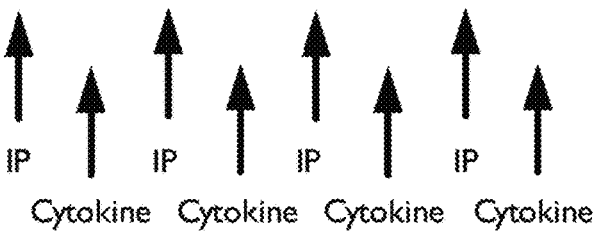
Fig. 39 (continued)

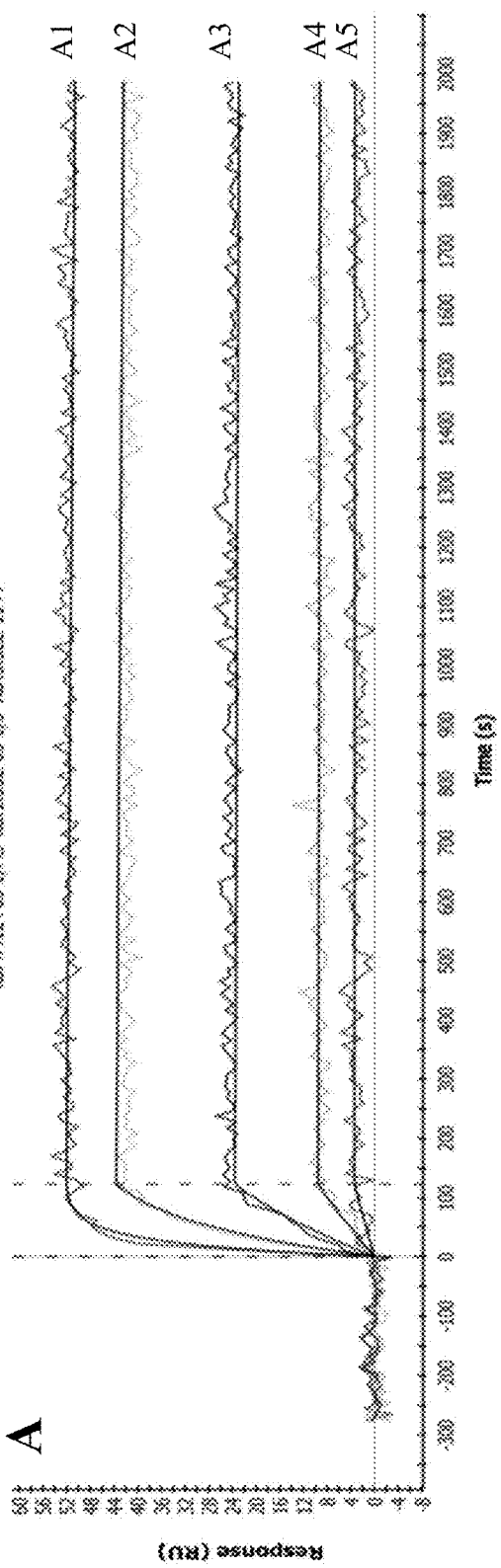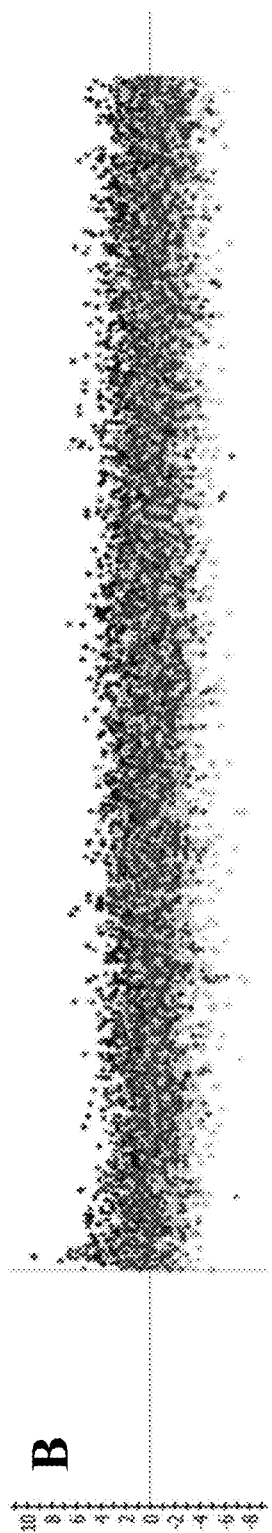
Fig. 45

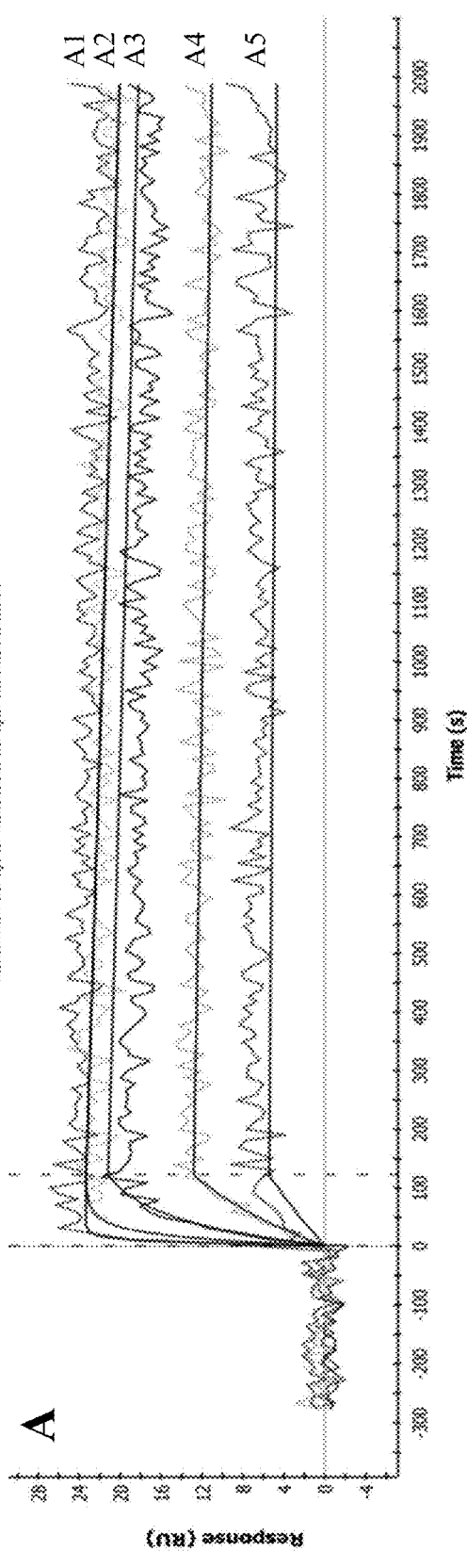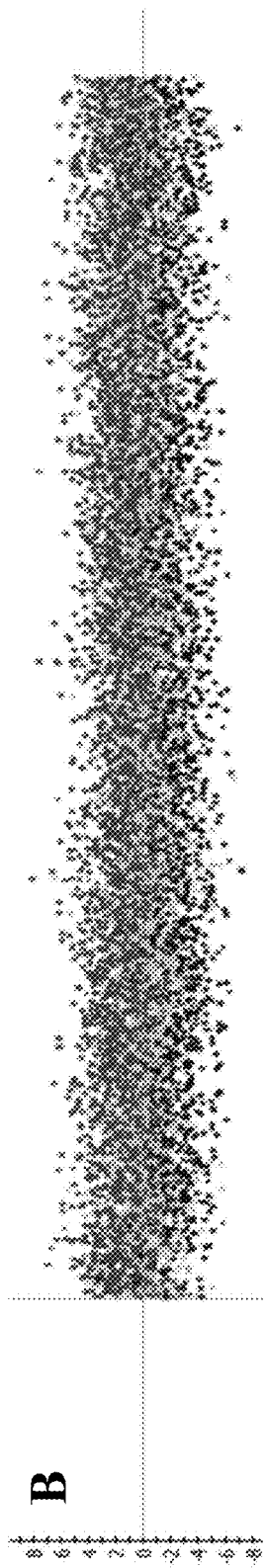
Fig. 46

Providing fresh or frozen PBMCs (10-20 Mio) obtained from peripheral blood of patient donors (seropositive to human antigen of interest in ELISA, ELISPOT, and/or neutralizing assay) using density centrifugation with lympholyte H

↓

Selecting CD22 positive, CD3-, CD56-, CD8-negative, and IgM and IgD double negative B cells from fresh or frozen PBMC using FACS

↓

Stimulating B cells by exposing the bulk, polyclonal culture of B cells (for example 30.000 to 80.000 memory B cells) to maximum 50% v/v EBV supernatant in the culture medium (one volume B cells / one volume supernatant of EBV producing cells) for an appropriate period of time to preserve viability and induce subsequent cell proliferation (e.g. for 3-5 hours)

↓

Washing stimulated B cells with the cell culture medium (> 1:200 dilution of EBV; or EBV washed out by cell centrifugation)

↓

Activation of memory B cells by placing them in culture in oligoclonal conditions (10 cells/well of a, e.g., 96-well plate) in CpG, e.g. CpG 2006 containing medium (2.5 ug/ml) with 30-50,000 irradiated feeder PBMCs prepared from healthy donors cells / well for appropriate time (1-2 weeks, preferably about 10 days)

↓

Screening of supernatants (e.g. ELISA) from each well for selection of cultures producing the antibody of interest. Several screening assays can be run simultaneously to detect reactivities against multiple antigens.

↓

Single cell sort of positive cultures by using FACS

↓

Single cell PCR and sequencing of variable region of heavy and light chain genes.

↓

Cloning of variable regions of heavy and light chains genes in expression vectors and production of recombinant antibodies to identify single cells producing the antibody of interest using appropriate vectors and host cells

↓

Immunoglobulin genes (variable and constant regions of heavy and light chains) are sequenced from cells producing the antibody of interest and cloned in expression vectors.

↓

Recombinant antibodies with complete variable regions derived from patients are produced for further characterization.

Fig. 50

```
                        SEQUENCE LISTING

<160> NUMBER OF SEQ ID NOS: 81

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide (primer) 6F

<400> SEQUENCE: 1
tgcaggctgt gggaactcca                                              20

<210> SEQ ID NO 2
<211> LENGTH: 22
<212> TYPE: DNA
<213> ORGANISM: Artificial Sequence
<220> FEATURE:
<223> OTHER INFORMATION: Oligonucleotide (primer) 6R

<400> SEQUENCE: 2
agaaaaagag ctgtaccctg tg                                           22

<210> SEQ ID NO 3
<211> LENGTH: 22
<212> TYPE: DNA
<213> ORGANISM: Artificial Sequence
<220> FEATURE:
<223> OTHER INFORMATION: Oligonucleotide (primer) 3R

<400> SEQUENCE: 3
tgcaaggaag agggcgtca gc                                            22

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide (primer) 49300F

<400> SEQUENCE: 4
tccaccacaa gccgaggaga t                                            21

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide (primer) 49622R

<400> SEQUENCE: 5
acgggctcct caaacaccac t                                            21

<210> SEQ ID NO 6
<211> LENGTH: 378
<212> TYPE: DNA
<213> ORGANISM: Homo sapiens
<220> FEATURE:
<221> NAME/KEY: CDS
<222> LOCATION: (1)..(378)
<223> OTHER INFORMATION: 9A2-VH variable heavy chain (VH) sequence; 9A2:
      IgG1, kappa
<220> FEATURE:
```

```
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(345)
<223> OTHER INFORMATION: complementarity determining region (CDR)
      VH-CDR3

<400> SEQUENCE: 6 gag gtg caa ttg gag gag tct ggc gga ggc ttg gtt cag cct gga ggg      48
Glu Val Gln Leu Glu Glu Ser Gly Gly Gly Leu Val Gln Pro Gly Gly
1               5                   10                  15 tcc ctg aga ctc tcc tgt gca gcc tct gga ttc ccc ttc agc aac tat      96
Ser Leu Arg Leu Ser Cys Ala Ala Ser Gly Phe Pro Phe Ser Asn Tyr
            20                  25                  30 gaa atg aat tgg gtc cgc cag gct ccc ggg aag gga ctg gag tgg att     144
Glu Met Asn Trp Val Arg Gln Ala Pro Gly Lys Gly Leu Glu Trp Ile
        35                  40                  45 tca tac att agt gtg agc ggt ggt ccc gct cac tac gca gac tct gtg     192
Ser Tyr Ile Ser Val Ser Gly Gly Pro Ala His Tyr Ala Asp Ser Val
50                  55                  60 aag ggc cga ttc acc att tcc aga gac gac gcc aca aag tca ctg ttt     240
Lys Gly Arg Phe Thr Ile Ser Arg Asp Asp Ala Thr Lys Ser Leu Phe
65                  70                  75                  80 ctg caa atg aac cgc ctg aga gcc gac gac acg gca gtt tat tac tgt     288
Leu Gln Met Asn Arg Leu Arg Ala Asp Asp Thr Ala Val Tyr Tyr Cys
            85                  90                  95 gtg cgc cgc gaa tat gtc act ggc cgc aat tac aac tac tac ccc tac     336
Val Arg Arg Glu Tyr Val Thr Gly Arg Asn Tyr Asn Tyr Tyr Pro Tyr
        100                 105                 110 atg gac gtc tgg ggc act ggg acc acg gtc acc gtc tcc cca             378
Met Asp Val Trp Gly Thr Gly Thr Thr Val Thr Val Ser Pro
115                 120                 125

<210> SEQ ID NO 7
<211> LENGTH: 126
<212> TYPE: PRT
<213> ORGANISM: Homo sapiens

<400> SEQUENCE: 7

Glu Val Gln Leu Glu Glu Ser Gly Gly Gly Leu Val Gln Pro Gly Gly
1               5                   10                  15

Ser Leu Arg Leu Ser Cys Ala Ala Ser Gly Phe Pro Phe Ser Asn Tyr
            20                  25                  30

Glu Met Asn Trp Val Arg Gln Ala Pro Gly Lys Gly Leu Glu Trp Ile
        35                  40                  45

Ser Tyr Ile Ser Val Ser Gly Gly Pro Ala His Tyr Ala Asp Ser Val
    50                  55                  60

Lys Gly Arg Phe Thr Ile Ser Arg Asp Asp Ala Thr Lys Ser Leu Phe
65                  70                  75                  80

Leu Gln Met Asn Arg Leu Arg Ala Asp Asp Thr Ala Val Tyr Tyr Cys
            85                  90                  95

Val Arg Arg Glu Tyr Val Thr Gly Arg Asn Tyr Asn Tyr Tyr Pro Tyr
        100                 105                 110

Met Asp Val Trp Gly Thr Gly Thr Thr Val Thr Val Ser Pro
```

<210> SEQ ID NO 8
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: 9A2-VL variable light chain (VL) sequence, kappa type
<220> FEATURE:
<221> NAME/KEY: V_region
<222> LOCATION: (70)..(102)
<223> OTHER INFORMATION: complementarity determining region (CDR) VL-CDR1
<220> FEATURE:
<221> NAME/KEY: V_region
<222> LOCATION: (148)..(168)
<223> OTHER INFORMATION: complementarity determining region (CDR) VL-CDR2
<220> FEATURE:
<221> NAME/KEY: V_region
<222> LOCATION: (265)..(291)
<223> OTHER INFORMATION: complementarity determining region (CDR) VL-CDR3

<400> SEQUENCE: 8

```
gac atc cag atg acc cag tct ccg tcc tcc ctg tct gct tct gtt ggg      48
Asp Ile Gln Met Thr Gln Ser Pro Ser Ser Leu Ser Ala Ser Val Gly
1               5                   10                  15 gac aga gtc acc atc act tgc cgg gca agt cag acc ata agt gat tat      96
Asp Arg Val Thr Ile Thr Cys Arg Ala Ser Gln Thr Ile Ser Asp Tyr
            20                  25                  30 tta aat tgg tac cag cac aaa cca ggg gaa gcc cct aaa ctc cta atc     144
Leu Asn Trp Tyr Gln His Lys Pro Gly Glu Ala Pro Lys Leu Leu Ile
        35                  40                  45 tat tct gca tcc acc ttg caa cgt ggg gtg cct tca cgg ttc agt ggc     192
Tyr Ser Ala Ser Thr Leu Gln Arg Gly Val Pro Ser Arg Phe Ser Gly
    50                  55                  60 agt gga tct ggg aca gat ttc gtt ttc acc att agt agt ctg cag tct     240
Ser Gly Ser Gly Thr Asp Phe Val Phe Thr Ile Ser Ser Leu Gln Ser
65                  70                  75                  80 gat gat ttt gcg act tac tac tgt caa cag act tcc agt acc gcc ctc     288
Asp Asp Phe Ala Thr Tyr Tyr Cys Gln Gln Thr Ser Ser Thr Ala Leu
                85                  90                  95 act ttc ggc gga ggg acc aag gtg gag gtc aaa                         321
Thr Phe Gly Gly Gly Thr Lys Val Glu Val Lys
                100                 105
```

<210> SEQ ID NO 9
<211> LENGTH: 107
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asp Tyr
            20                  25                  30

Leu Asn Trp Tyr Gln His Lys Pro Gly Glu Ala Pro Lys Leu Leu Ile
        35                  40                  45

Tyr Ser Ala Ser Thr Leu Gln Arg Gly Val Pro Ser Arg Phe Ser Gly
    50                  55                  60

Ser Gly Ser Gly Thr Asp Phe Val Phe Thr Ile Ser Ser Leu Gln Ser

```
                65                  70                  75                  80
Asp Asp Phe Ala Thr Tyr Tyr Cys Gln Gln Thr Ser Ser Thr Ala Leu
                        85                  90                  95

Thr Phe Gly Gly Gly Thr Lys Val Glu Val Lys
                100                 105

<210> SEQ ID NO 10
<211> LENGTH: 993
<212> TYPE: DNA
<213> ORGANISM: Homo sapiens
<220> FEATURE:
<221> NAME/KEY: CDS
<222> LOCATION: (1)..(990)
<223> OTHER INFORMATION: 9A2-CH constant heavy chain (CH) sequence

<400> SEQUENCE: 10 gcc tcc acc aag ggc cca tcg gtc ttc ccc ctg gca ccc tcc tcc aag       48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac       96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc      144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc      192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc      240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag      288
Tyr Ile Cys Asn Val Asn His Lys Pro Ser Asn Thr Lys Val Asp Lys
                85                  90                  95 aaa gtt gag ccc aaa tct tgt gac aaa act cac aca tgc cca ccg tgc      336
Lys Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca      384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc      432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg      480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag      528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg      576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac      624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg      672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gat gag      720
Gln Pro Arg Glu Pro Gln Val Tyr Thr Leu Pro Pro Ser Arg Asp Glu
225                 230                 235                 240
```

```
ctg acc aag aac cag gtc agc ctg acc tgc ctg gtc aaa ggc ttc tat      768
Leu Thr Lys Asn Gln Val Ser Leu Thr Cys Leu Val Lys Gly Phe Tyr
            245                 250                 255 ccc agc gac atc gcc gtg gag tgg gag agc aat ggg cag ccg gag aac      816
Pro Ser Asp Ile Ala Val Glu Trp Glu Ser Asn Gly Gln Pro Glu Asn
        260                 265                 270 aac tac aag acc acg cct ccc gtg ctg gac tcc gac ggc tcc ttc ttc      864
Asn Tyr Lys Thr Thr Pro Pro Val Leu Asp Ser Asp Gly Ser Phe Phe
    275                 280                 285 ctc tac agc aag ctc acc gtg gac aag agc agg tgg cag cag ggg aac      912
Leu Tyr Ser Lys Leu Thr Val Asp Lys Ser Arg Trp Gln Gln Gly Asn
290                 295                 300 gtc ttc tca tgc tcc gtg atg cat gag gct ctg cac aac cac tac acg      960
Val Phe Ser Cys Ser Val Met His Glu Ala Leu His Asn His Tyr Thr
305                 310                 315                 320 cag aag agc ctc tcc ctg tct ccg ggt aaa tga                           993
Gln Lys Ser Leu Ser Leu Ser Pro Gly Lys
                325                 330

<210> SEQ ID NO 11
<211> LENGTH: 330
<212> TYPE: PRT
<213> ORGANISM: Homo sapiens

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
```

```
                        245                 250                 255
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 12
<211> LENGTH: 324
<212> TYPE: DNA
<213> ORGANISM: Homo sapiens
<220> FEATURE:
<221> NAME/KEY: CDS
<222> LOCATION: (1)..(321)
<223> OTHER INFORMATION: 9A2-CL constant kappa chain (CL) sequence
<220> FEATURE:
<221> NAME/KEY: misc_feature
<222> LOCATION: (260)..(260)
<223> OTHER INFORMATION: not sequenced but obtained from database
<220> FEATURE:
<221> NAME/KEY: misc_feature
<222> LOCATION: (298)..(324)
<223> OTHER INFORMATION: not sequenced but obtained from database

<400> SEQUENCE: 12 cga act gtg gct gca cca tct gtc ttc atc ttc ccg cca tct gat gag      48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc      96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa     144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc     192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag     240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg     288
Lys His Lys Val Tyr Ala Cys Glu Val Thr His Gln Gly Leu Ser Ser
                85                  90                  95 ccc gtc aca aag agc ttc aac agg gga gag tgt tag                     324
Pro Val Thr Lys Ser Phe Asn Arg Gly Glu Cys
            100                 105

<210> SEQ ID NO 13
<211> LENGTH: 107
<212> TYPE: PRT
<213> ORGANISM: Homo sapiens

<400> SEQUENCE: 13

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30
```

```
                                         -continued

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 14
<211> LENGTH: 387
<212> TYPE: DNA
<213> ORGANISM: Homo sapiens
<220> FEATURE:
<221> NAME/KEY: CDS
<222> LOCATION: (1)..(387)
<223> OTHER INFORMATION: 17E3-VH variable heavy chain (VH) sequence;
      17E3: IgG1, kappa
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(354)
<223> OTHER INFORMATION: complementarity determining region (CDR)
      VH-CDR3

<400> SEQUENCE: 14 cag gtg caa ctg gtc cag tct ggg gct gaa gtg gcg aag cct ggg gcc      48
Gln Val Gln Leu Val Gln Ser Gly Ala Glu Val Ala Lys Pro Gly Ala
 1               5                  10                  15 tca gtg aga ctt tcc tgc aag gcg tct gga ttc agt ttt atc aag tat      96
Ser Val Arg Leu Ser Cys Lys Ala Ser Gly Phe Ser Phe Ile Lys Tyr
            20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
         35                  40                  45 ggg gtc atc gag ccc acc ggt ggt ggc aca agc tcc gca cag aag ttc     192
Gly Val Ile Glu Pro Thr Gly Gly Gly Thr Ser Ser Ala Gln Lys Phe
 50                  55                  60 cga gac aga gtc acc ctg agc agg gac acg tcc acg gcc act gtc cat     240
Arg Asp Arg Val Thr Leu Ser Arg Asp Thr Ser Thr Ala Thr Val His
 65                  70                  75                  80 ttg gaa gtg agt agg ctg act ctt gag gac acg ggc att tat ttc tgt     288
Leu Glu Val Ser Arg Leu Thr Leu Glu Asp Thr Gly Ile Tyr Phe Cys
                 85                  90                  95 gtg aga gac tcc ata tat tgt aaa cat ggg acc tgt cat cgg act gtg     336
Val Arg Asp Ser Ile Tyr Cys Lys His Gly Thr Cys His Arg Thr Val
            100                 105                 110 atc gat gct ttt gac att tgg ggc caa ggg acg gcg gtc acc gtc tct     384
Ile Asp Ala Phe Asp Ile Trp Gly Gln Gly Thr Ala Val Thr Val Ser
         115                 120                 125 tca                                                                  387
Ser
```

<210> SEQ ID NO 15
<211> LENGTH: 129
<212> TYPE: PRT
<213> ORGANISM: Homo sapiens

<400> SEQUENCE: 15

Gln Val Gln Leu Val Gln Ser Gly Ala Glu Val Ala Lys Pro Gly Ala
1               5                   10                  15

Ser Val Arg Leu Ser Cys Lys Ala Ser Gly Phe Ser Phe Ile Lys Tyr
            20                  25                  30

Tyr Met His Trp Val Arg Gln Ala Pro Gly Gln Gly Leu Glu Trp Met
        35                  40                  45

Gly Val Ile Glu Pro Thr Gly Gly Thr Ser Ser Ala Gln Lys Phe
    50                  55                  60

Arg Asp Arg Val Thr Leu Ser Arg Asp Thr Ser Thr Ala Thr Val His
65                  70                  75                  80

Leu Glu Val Ser Arg Leu Thr Leu Glu Asp Thr Gly Ile Tyr Phe Cys
                85                  90                  95

Val Arg Asp Ser Ile Tyr Cys Lys His Gly Thr Cys His Arg Thr Val
                100                 105                 110

Ile Asp Ala Phe Asp Ile Trp Gly Gln Gly Thr Ala Val Thr Val Ser
            115                 120                 125

Ser

<210> SEQ ID NO 16
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: 17E3-VL variable light chain (VL) sequence,
      kappa type
<220> FEATURE:
<221> NAME/KEY: V_region
<222> LOCATION: (70)..(102)
<223> OTHER INFORMATION: complementarity determining region (CDR)
      VL-CDR1
<220> FEATURE:
<221> NAME/KEY: V_region
<222> LOCATION: (148)..(168)
<223> OTHER INFORMATION: complementarity determining region (CDR)
      VL-CDR2
<220> FEATURE:
<221> NAME/KEY: V_region
<222> LOCATION: (265)..(294)
<223> OTHER INFORMATION: complementarity determining region (CDR)
      VL-CDR3

<400> SEQUENCE: 16 gac atc cag atg acc cag tct cca tcc tcc ctg tct gca tca gta gga      48
Asp Ile Gln Met Thr Gln Ser Pro Ser Ser Leu Ser Ala Ser Val Gly
1               5                   10                  15 gac cga gtc acc atc act tgc cgg tca agt cag gac ata aaa aat gat     96
Asp Arg Val Thr Ile Thr Cys Arg Ser Ser Gln Asp Ile Lys Asn Asp
            20                  25                  30 tta gcc tgg tat cag cag aag cca gga aaa gcc cct gag cgc ctg atc    144
Leu Ala Trp Tyr Gln Gln Lys Pro Gly Lys Ala Pro Glu Arg Leu Ile
        35                  40                  45 tat gct gca tcc aat ttg cag agt ggg gtc cca tca agg ttc agc ggc    192
Tyr Ala Ala Ser Asn Leu Gln Ser Gly Val Pro Ser Arg Phe Ser Gly
    50                  55                  60 agt ggc tct ggg aca gaa ttc agt ctt aca atc agt ggc ctg cag cct    240
Ser Gly Ser Gly Thr Glu Phe Ser Leu Thr Ile Ser Gly Leu Gln Pro

```
                65                  70                  75                  80
gaa gat ttt gca act tat tac tgt cta cag cat aat agt tac cct ctg           288
Glu Asp Phe Ala Thr Tyr Tyr Cys Leu Gln His Asn Ser Tyr Pro Leu
                85                  90                  95 ctc act ttc ggc gga ggg acc aag gtg gag atc aaa                           324
Leu Thr Phe Gly Gly Gly Thr Lys Val Glu Ile Lys
        100                 105

<210> SEQ ID NO 17
<211> LENGTH: 108
<212> TYPE: PRT
<213> ORGANISM: Homo sapiens

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asp Ile Lys Asn Asp
            20                  25                  30

Leu Ala Trp Tyr Gln Gln Lys Pro Gly Lys Ala Pro Glu Arg Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Glu Phe Ser Leu Thr Ile Ser Gly Leu Gln Pro
65                  70                  75                  80

Glu Asp Phe Ala Thr Tyr Tyr Cys Leu Gln His Asn Ser Tyr Pro Leu
                85                  90                  95

Leu Thr Phe Gly Gly Gly Thr Lys Val Glu Ile Lys
            100                 105

<210> SEQ ID NO 18
<211> LENGTH: 993
<212> TYPE: DNA
<213> ORGANISM: Homo sapiens
<220> FEATURE:
<221> NAME/KEY: CDS
<222> LOCATION: (1)..(990)
<223> OTHER INFORMATION: 17E3-CH constant heavy chain (CH) sequence

<400> SEQUENCE: 18 gcc tcc acc aag ggc cca tcg gtc ttc ccc ctg gca ccc tcc tcc aag           48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac           96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc          144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc          192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc          240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag          288
Tyr Ile Cys Asn Val Asn His Lys Pro Ser Asn Thr Lys Val Asp Lys
                85                  90                  95 aaa gtt gag ccc aaa tct tgt gac aaa act cac aca tgc cca ccg tgc          336
Lys Val Glu Pro Lys Ser Cys Asp Lys Thr His Thr Cys Pro Pro Cys
            100                 105                 110
```

```
cca gca cct gaa ctc ctg ggg gga ccg tca gtc ttc ctc ttc ccc cca      384
Pro Ala Pro Glu Leu Leu Gly Gly Pro Ser Val Phe Leu Phe Pro Pro
            115                 120                 125 aaa ccc aag gac acc ctc atg atc tcc cgg acc cct gag gtc aca tgc      432
Lys Pro Lys Asp Thr Leu Met Ile Ser Arg Thr Pro Glu Val Thr Cys
        130                 135                 140 gtg gtg gtg gac gtg agc cac gaa gac cct gag gtc aag ttc aac tgg      480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag      528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg      576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac      624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg      672
Lys Ala Leu Pro Ala Pro Ile Glu Lys Thr Ile Ser Lys Ala Lys Gly
210                 215                 220 cag ccc cga gaa cca cag gtg tac acc ctg ccc cca tcc cgg gat gag      720
Gln Pro Arg Glu Pro Gln Val Tyr Thr Leu Pro Pro Ser Arg Asp Glu
225                 230                 235                 240 ctg acc aag aac cag gtc agc ctg acc tgc ctg gtc aaa ggc ttc tat      768
Leu Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac      816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc      864
Asn Tyr Lys Thr Thr Pro Pro Val Leu Asp Ser Asp Gly Ser Phe Phe
        275                 280                 285 ctc tac agc aag ctc acc gtg gac aag agc agg tgg cag cag ggg aac      912
Leu Tyr Ser Lys Leu Thr Val Asp Lys Ser Arg Trp Gln Gln Gly Asn
    290                 295                 300 gtc ttc tca tgc tcc gtg atg cat gag gct ctg cac aac cac tac acg      960
Val Phe Ser Cys Ser Val Met His Glu Ala Leu His Asn His Tyr Thr
305                 310                 315                 320 cag aag agc ctc tcc ctg tct ccg ggt aaa tga                          993
Gln Lys Ser Leu Ser Leu Ser Pro Gly Lys
                325                 330

<210> SEQ ID NO 19
<211> LENGTH: 330
<212> TYPE: PRT
<213> ORGANISM: Homo sapiens

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 20
<211> LENGTH: 324
<212> TYPE: DNA
<213> ORGANISM: Homo sapiens
<220> FEATURE:
<221> NAME/KEY: CDS
<222> LOCATION: (1)..(321)
<223> OTHER INFORMATION: 17E3-CL constant kappa chain (CL) sequence
<220> FEATURE:
<221> NAME/KEY: misc_feature
<222> LOCATION: (298)..(324)
<223> OTHER INFORMATION: not sequenced but obtained from database

<400> SEQUENCE: 20 cga act gtg gct gca cca tct gtc ttc atc ttc ccg cca tct gat gag      48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc      96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa     144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc     192
Ser Gly Asn Ser Gln Glu Ser Val Thr Glu Gln Asp Ser Lys Asp Ser
    50                  55                  60
```

```
acc tac agc ctc agc agc acc ctg acg ctg agc aaa gca gac tac gag    240
Thr Tyr Ser Leu Ser Ser Thr Leu Thr Leu Ser Lys Ala Asp Tyr Glu
 65                  70                  75                  80 aaa cac aaa gtc tac gcc tgc gaa gtc acc cat cag ggc ctg agc tcg    288
Lys His Lys Val Tyr Ala Cys Glu Val Thr His Gln Gly Leu Ser Ser
                 85                  90                  95 ccc gtc aca aag agc ttc aac agg gga gag tgt tag                    324
Pro Val Thr Lys Ser Phe Asn Arg Gly Glu Cys
            100                 105
```

<210> SEQ ID NO 21
<211> LENGTH: 107
<212> TYPE: PRT
<213> ORGANISM: Homo sapiens

<400> SEQUENCE: 21

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 22
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: 24D3-VH variable heavy chain (VH) sequence;
      24D3: IgG1, lambda
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(204)
<223> OTHER INFORMATION: complementarity determining region (CDR)
      VH-CDR2
<220> FEATURE:
<221> NAME/KEY: V_region
<222> LOCATION: (301)..(339)
<223> OTHER INFORMATION: complementarity determining region (CDR)
      VH-CDR3

<400> SEQUENCE: 22

```
gag gtg aag ttg gag gag tct ggg gga gac ctg gta aag cct ggg ggg    48
Glu Val Lys Leu Glu Glu Ser Gly Gly Asp Leu Val Lys Pro Gly Gly
 1               5                  10                  15 tct ctt aga ctc tcc tgt gta gcc tct gga ttc act ttc ggc acc gcc    96
Ser Leu Arg Leu Ser Cys Val Ala Ser Gly Phe Thr Phe Gly Thr Ala
             20                  25                  30 tgg atg agc tgg gtc cgc cag gct cca ggg aag ggg ctg gag tgg gtt   144
Trp Met Ser Trp Val Arg Gln Ala Pro Gly Lys Gly Leu Glu Trp Val
```

```
                Trp Met Ser Trp Val Arg Gln Ala Pro Gly Lys Gly Leu Glu Trp Val
                        35                  40                  45 ggc cgt att agc aac aaa gac act ggt ggg aga ata gac tac gcc gca        192
Gly Arg Ile Ser Asn Lys Asp Thr Gly Gly Arg Ile Asp Tyr Ala Ala
 50                  55                  60 ccc gtg aga ggc aga ttc gcc atc tca aga gat gat tcg aaa gcc acc        240
Pro Val Arg Gly Arg Phe Ala Ile Ser Arg Asp Asp Ser Lys Ala Thr
 65                  70                  75                  80 ctg ttt ctg caa atg aac agc ctg aaa acc gag gac aca gcc gtg tat        288
Leu Phe Leu Gln Met Asn Ser Leu Lys Thr Glu Asp Thr Ala Val Tyr
                    85                  90                  95 ttt tgt act aca aat ttt tac gat gtt ttg act ggt gat cat gtt gac        336
Phe Cys Thr Thr Asn Phe Tyr Asp Val Leu Thr Gly Asp His Val Asp
                100                 105                 110 tat tgg ggc cag gga acc gtg gtc gtc gtc tcc tca                        372
Tyr Trp Gly Gln Gly Thr Val Val Val Val Ser Ser
        115                 120
```

<210> SEQ ID NO 23
<211> LENGTH: 124
<212> TYPE: PRT
<213> ORGANISM: Homo sapiens

<400> SEQUENCE: 23

```
Glu Val Lys Leu Glu Glu Ser Gly Gly Asp Leu Val Lys Pro Gly Gly
 1               5                  10                  15

Ser Leu Arg Leu Ser Cys Val Ala Ser Gly Phe Thr Phe Gly Thr Ala
                20                  25                  30

Trp Met Ser Trp Val Arg Gln Ala Pro Gly Lys Gly Leu Glu Trp Val
            35                  40                  45

Gly Arg Ile Ser Asn Lys Asp Thr Gly Gly Arg Ile Asp Tyr Ala Ala
 50                  55                  60

Pro Val Arg Gly Arg Phe Ala Ile Ser Arg Asp Asp Ser Lys Ala Thr
 65                  70                  75                  80

Leu Phe Leu Gln Met Asn Ser Leu Lys Thr Glu Asp Thr Ala Val Tyr
                    85                  90                  95

Phe Cys Thr Thr Asn Phe Tyr Asp Val Leu Thr Gly Asp His Val Asp
                100                 105                 110

Tyr Trp Gly Gln Gly Thr Val Val Val Val Ser Ser
        115                 120
```

<210> SEQ ID NO 24
<211> LENGTH: 318
<212> TYPE: DNA
<213> ORGANISM: Homo sapiens
<220> FEATURE:
<221> NAME/KEY: CDS
<222> LOCATION: (1)..(318)
<223> OTHER INFORMATION: 24D3-VL variable light chain (VL) sequence,
      lambda type
<220> FEATURE:
<221> NAME/KEY: V_region
<222> LOCATION: (67)..(99)
<223> OTHER INFORMATION: complementarity determining region (CDR)
      VL-CDR1
<220> FEATURE:
<221> NAME/KEY: V_region
<222> LOCATION: (145)..(165)
<223> OTHER INFORMATION: complementarity determining region (CDR)
      VL-CDR2
<220> FEATURE:
<221> NAME/KEY: V_region
<222> LOCATION: (262)..(288)
<223> OTHER INFORMATION: complementarity determining region (CDR)

VL-CDR2

<400> SEQUENCE: 24

| | | | | | | | | | | | | | | | | |
|---|---|---|---|---|---|---|---|---|---|---|---|---|---|---|---|---|
| tcc | tat | gag | ctg | aca | cag | cca | ccc | tcg | gtg | tca | gtg | tcc | cca | gga | gag | 48 |
| Ser | Tyr | Glu | Leu | Thr | Gln | Pro | Pro | Ser | Val | Ser | Val | Ser | Pro | Gly | Glu | |
| 1 | | | | 5 | | | | | 10 | | | | | 15 | | |
| acg | gcc | agg | atc | ccc | tgc | tct | gga | gaa | aca | ttg | cca | aag | aaa | ctt | gtt | 96 |
| Thr | Ala | Arg | Ile | Pro | Cys | Ser | Gly | Glu | Thr | Leu | Pro | Lys | Lys | Leu | Val | |
| | | | 20 | | | | | 25 | | | | | 30 | | | |
| tat | tgg | tat | cag | cag | aag | cca | ggc | cag | gcc | cct | gta | ttg | atg | att | tat | 144 |
| Tyr | Trp | Tyr | Gln | Gln | Lys | Pro | Gly | Gln | Ala | Pro | Val | Leu | Met | Ile | Tyr | |
| | | | 35 | | | | | 40 | | | | | 45 | | | |
| aaa | gac | agt | gag | agg | ccc | tca | cga | ata | tct | gag | cga | ttc | tct | ggc | tcc | 192 |
| Lys | Asp | Ser | Glu | Arg | Pro | Ser | Arg | Ile | Ser | Glu | Arg | Phe | Ser | Gly | Ser | |
| | 50 | | | | | 55 | | | | | 60 | | | | | |
| aac | tca | ggg | aca | atg | gcc | tcc | ttg | acc | atc | agt | gga | gtc | cag | gca | gaa | 240 |
| Asn | Ser | Gly | Thr | Met | Ala | Ser | Leu | Thr | Ile | Ser | Gly | Val | Gln | Ala | Glu | |
| 65 | | | | | 70 | | | | | 75 | | | | | 80 | |
| gac | gag | gct | gac | tat | tac | tgt | caa | aca | tca | gac | agc | agt | ggt | gtg | gtt | 288 |
| Asp | Glu | Ala | Asp | Tyr | Tyr | Cys | Gln | Thr | Ser | Asp | Ser | Ser | Gly | Val | Val | |
| | | | | 85 | | | | | 90 | | | | | 95 | | |
| ttc | ggc | gga | ggg | acc | aag | ttg | acc | gtc | tta | | | | | | | 318 |
| Phe | Gly | Gly | Gly | Thr | Lys | Leu | Thr | Val | Leu | | | | | | | |
| | | | 100 | | | | | 105 | | | | | | | | |

<210> SEQ ID NO 25
<211> LENGTH: 106
<212> TYPE: PRT
<213> ORGANISM: Homo sapiens

<400> SEQUENCE: 25

Ser Tyr Glu Leu Thr Gln Pro Pro Ser Val Ser Val Ser Pro Gly Glu
1               5                   10                  15

Thr Ala Arg Ile Pro Cys Ser Gly Glu Thr Leu Pro Lys Lys Leu Val
            20                  25                  30

Tyr Trp Tyr Gln Gln Lys Pro Gly Gln Ala Pro Val Leu Met Ile Tyr
        35                  40                  45

Lys Asp Ser Glu Arg Pro Ser Arg Ile Ser Glu Arg Phe Ser Gly Ser
    50                  55                  60

Asn Ser Gly Thr Met Ala Ser Leu Thr Ile Ser Gly Val Gln Ala Glu
65                  70                  75                  80

Asp Glu Ala Asp Tyr Tyr Cys Gln Thr Ser Asp Ser Ser Gly Val Val
                85                  90                  95

Phe Gly Gly Gly Thr Lys Leu Thr Val Leu
            100                 105

<210> SEQ ID NO 26
<211> LENGTH: 993
<212> TYPE: DNA
<213> ORGANISM: Homo sapiens
<220> FEATURE:
<221> NAME/KEY: CDS
<222> LOCATION: (1)..(990)
<223> OTHER INFORMATION: 24D3-CH constant heavy chain (CH) sequence

<400> SEQUENCE: 26

| | | | | | | | | | | | | | | | | |
|---|---|---|---|---|---|---|---|---|---|---|---|---|---|---|---|---|
| gcc | tcc | acc | aag | ggc | cca | tcg | gtc | ttc | ccc | ctg | gca | ccc | tcc | tcc | aag | 48 |
| Ala | Ser | Thr | Lys | Gly | Pro | Ser | Val | Phe | Pro | Leu | Ala | Pro | Ser | Ser | Lys | |
| 1 | | | | 5 | | | | | 10 | | | | | 15 | | |
| agc | acc | tct | ggg | ggc | aca | gcg | gcc | ctg | ggc | tgc | ctg | gtc | aag | gac | tac | 96 |
| Ser | Thr | Ser | Gly | Gly | Thr | Ala | Ala | Leu | Gly | Cys | Leu | Val | Lys | Asp | Tyr | |

-continued

```
                20                  25                  30
ttc ccc gaa ccg gtg acg gtg tcg tgg aac tca ggc gcc ctg acc agc      144
Phe Pro Glu Pro Val Thr Val Ser Trp Asn Ser Gly Ala Leu Thr Ser
         35                  40                  45 ggc gtg cac acc ttc ccg gct gtc cta cag tcc tca gga ctc tac tcc      192
Gly Val His Thr Phe Pro Ala Val Leu Gln Ser Ser Gly Leu Tyr Ser
 50                  55                  60 ctc agc agc gtg gtg acc gtg ccc tcc agc agc ttg ggc acc cag acc      240
Leu Ser Ser Val Val Thr Val Pro Ser Ser Ser Leu Gly Thr Gln Thr
 65                  70                  75                  80 tac atc tgc aac gtg aat cac aag ccc agc aac acc aag gtg gac aag      288
Tyr Ile Cys Asn Val Asn His Lys Pro Ser Asn Thr Lys Val Asp Lys
                 85                  90                  95 aaa gtt gag ccc aaa tct tgt gac aaa act cac aca tgc cca ccg tgc      336
Lys Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca      384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc      432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg      480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag      528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg      576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac      624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg      672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gat gag      720
Gln Pro Arg Glu Pro Gln Val Tyr Thr Leu Pro Pro Ser Arg Asp Glu
225                 230                 235                 240 ctg acc aag aac cag gtc agc ctg acc tgc ctg gtc aaa ggc ttc tat      768
Leu Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac      816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc      864
Asn Tyr Lys Thr Thr Pro Pro Val Leu Asp Ser Asp Gly Ser Phe Phe
        275                 280                 285 ctc tac agc aag ctc acc gtg gac aag agc agg tgg cag cag ggg aac      912
Leu Tyr Ser Lys Leu Thr Val Asp Lys Ser Arg Trp Gln Gln Gly Asn
    290                 295                 300 gtc ttc tca tgc tcc gtg atg cat gag gct ctg cac aac cac tac acg      960
Val Phe Ser Cys Ser Val Met His Glu Ala Leu His Asn His Tyr Thr
305                 310                 315                 320 cag aag agc ctc tcc ctg tct ccg ggt aaa tga                          993
Gln Lys Ser Leu Ser Leu Ser Pro Gly Lys
                325                 330
```

<210> SEQ ID NO 27
<211> LENGTH: 330
<212> TYPE: PRT
<213> ORGANISM: Homo sapiens

<400> SEQUENCE: 27

```
Ala Ser Thr Lys Gly Pro Ser Val Phe Pro Leu Ala Pro Ser Ser Lys
 1               5                  10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 28
<211> LENGTH: 321
<212> TYPE: DNA
<213> ORGANISM: Homo sapiens
<220> FEATURE:
<221> NAME/KEY: CDS
<222> LOCATION: (1)..(318)
<223> OTHER INFORMATION: 24D3-CL constant lambda chain (CL) sequence

```
<220> FEATURE:
<221> NAME/KEY: misc_feature
<222> LOCATION: (250)..(321)
<223> OTHER INFORMATION: not sequenced but obtained from database

<400> SEQUENCE: 28 ggt cag ccc aag gct gcc ccc tcg gtc act ctg ttc ccg ccc tcc tct      48
Gly Gln Pro Lys Ala Ala Pro Ser Val Thr Leu Phe Pro Pro Ser Ser
1               5                   10                  15 gag gag ctt caa gcc aac aag gcc aca ctg gtg tgt ctc ata agt gac      96
Glu Glu Leu Gln Ala Asn Lys Ala Thr Leu Val Cys Leu Ile Ser Asp
            20                  25                  30 ttc tac ccg gga gcc gtg aca gtg gcc tgg aag gca gat agc agc ccc     144
Phe Tyr Pro Gly Ala Val Thr Val Ala Trp Lys Ala Asp Ser Ser Pro
        35                  40                  45 gtc aag gcg gga gtg gag acc acc aca ccc tcc aaa caa agc aac aac     192
Val Lys Ala Gly Val Glu Thr Thr Thr Pro Ser Lys Gln Ser Asn Asn
50                  55                  60 aag tac gcg gcc agc agc tat ctg agc ctg acg cct gag cag tgg aag     240
Lys Tyr Ala Ala Ser Ser Tyr Leu Ser Leu Thr Pro Glu Gln Trp Lys
65                  70                  75                  80 tcc cac aga agc tac agc tgc cag gtc acg cat gaa ggg agc acc gtg     288
Ser His Arg Ser Tyr Ser Cys Gln Val Thr His Glu Gly Ser Thr Val
                85                  90                  95 gag aag aca gtg gcc cct aca gaa tgt tca tag                         321
Glu Lys Thr Val Ala Pro Thr Glu Cys Ser
            100                 105

<210> SEQ ID NO 29
<211> LENGTH: 106
<212> TYPE: PRT
<213> ORGANISM: Homo sapiens

<400> SEQUENCE: 29

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 30
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: 30G1-VH variable heavy chain (VH) sequence;
      30G1: IgG1, kappa
<220> FEATURE:
<221> NAME/KEY: V_region
<222> LOCATION: (91)..(105)
<223> OTHER INFORMATION: complementarity determining region (CDR)
      VH-CDR1
```

```
<220> FEATURE:
<221> NAME/KEY: V_region
<222> LOCATION: (148)..(198)
<223> OTHER INFORMATION: complementarity determining region (CDR)
       VH-CDR2
<220> FEATURE:
<221> NAME/KEY: V_region
<222> LOCATION: (295)..(339)
<223> OTHER INFORMATION: complementarity determining region (CDR)
       VH-CDR3

<400> SEQUENCE: 30 gag gtg cag ctg ttg gaa tcg ggg gga ggc ttg gtt cag ccg ggg ggg      48
Glu Val Gln Leu Leu Glu Ser Gly Gly Gly Leu Val Gln Pro Gly Gly
1               5                   10                  15 tcc ctg aga ctc tcc tgt gca gcc tct gga ttc acc ttt agt acc tat      96
Ser Leu Arg Leu Ser Cys Ala Ala Ser Gly Phe Thr Phe Ser Thr Tyr
            20                  25                  30 gcc atg agt tgg gtc cgc cag gct cca ggg aag ggg ctg gag tgg gtc     144
Ala Met Ser Trp Val Arg Gln Ala Pro Gly Lys Gly Leu Glu Trp Val
        35                  40                  45 tca act ata act agc agt ggt ggt gcc act tac cac gca gac tcc gtg     192
Ser Thr Ile Thr Ser Ser Gly Gly Ala Thr Tyr His Ala Asp Ser Val
50                  55                  60 aag ggc cgg ctc acc atc tcc aga gac aat tcc aag aac acg ctg tat     240
Lys Gly Arg Leu Thr Ile Ser Arg Asp Asn Ser Lys Asn Thr Leu Tyr
65                  70                  75                  80 ttg gag atg aac agc ctg aga gtc gag gac acg gcc gtc tat tac tgt     288
Leu Glu Met Asn Ser Leu Arg Val Glu Asp Thr Ala Val Tyr Tyr Cys
                85                  90                  95 gcg aaa gat tgg gga aga acg gtt tat gcg gtg atc aag gac ctt gac     336
Ala Lys Asp Trp Gly Arg Thr Val Tyr Ala Val Ile Lys Asp Leu Asp
            100                 105                 110 atc tgg ggc cag gga acc ctg gtc acc gtc tcc tca                     372
Ile Trp Gly Gln Gly Thr Leu Val Thr Val Ser Ser
        115                 120

<210> SEQ ID NO 31
<211> LENGTH: 124
<212> TYPE: PRT
<213> ORGANISM: Homo sapiens

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Thr Ile Thr Ser Ser Gly Gly Ala Thr Tyr His Ala Asp Ser Val
50                  55                  60

Lys Gly Arg Leu Thr Ile Ser Arg Asp Asn Ser Lys Asn Thr Leu Tyr
65                  70                  75                  80

Leu Glu Met Asn Ser Leu Arg Val Glu Asp Thr Ala Val Tyr Tyr Cys
                85                  90                  95

Ala Lys Asp Trp Gly Arg Thr Val Tyr Ala Val Ile Lys Asp Leu Asp
            100                 105                 110

Ile Trp Gly Gln Gly Thr Leu Val Thr Val Ser Ser
        115                 120

<210> SEQ ID NO 32
```

<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: 30G1-VL variable light chain (VL) sequence, kappa type
<220> FEATURE:
<221> NAME/KEY: V_region
<222> LOCATION: (70)..(102)
<223> OTHER INFORMATION: complementarity determining region (CDR) VL-CDR1
<220> FEATURE:
<221> NAME/KEY: V_region
<222> LOCATION: (148)..(168)
<223> OTHER INFORMATION: complementarity determining region (CDR) VL-CDR2
<220> FEATURE:
<221> NAME/KEY: V_region
<222> LOCATION: (265)..(294)
<223> OTHER INFORMATION: complementarity determining region (CDR) VL-CDR3

<400> SEQUENCE: 32

```
gaa att gtg atg aca cag tct cca gcc atc ctg tct gtg tct cca ggg      48
Glu Ile Val Met Thr Gln Ser Pro Ala Ile Leu Ser Val Ser Pro Gly
1               5                   10                  15 gaa aga gcc acc ctc tcc tgc agg gcc agt cag agt gtt agc aac tac      96
Glu Arg Ala Thr Leu Ser Cys Arg Ala Ser Gln Ser Val Ser Asn Tyr
            20                  25                  30 tta gcc tgg ttc caa caa aag cct ggc cag gct ccc agg ctc ctc atc     144
Leu Ala Trp Phe Gln Gln Lys Pro Gly Gln Ala Pro Arg Leu Leu Ile
        35                  40                  45 tat gac aca tct aag agg gcc act ggc acc ccc gcc agg ttc agt ggc     192
Tyr Asp Thr Ser Lys Arg Ala Thr Gly Thr Pro Ala Arg Phe Ser Gly
    50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
65                  70                  75                  80 gaa gat ttt gca gtt tat ttc tgt cag cag cgt agc gac tgg cct cag     288
Glu Asp Phe Ala Val Tyr Phe Cys Gln Gln Arg Ser Asp Trp Pro Gln
                85                  90                  95 tac act ttt ggc cag ggg acc aaa ctg gag atc aaa                     324
Tyr Thr Phe Gly Gln Gly Thr Lys Leu Glu Ile Lys
                100                 105
```

<210> SEQ ID NO 33
<211> LENGTH: 108
<212> TYPE: PRT
<213> ORGANISM: Homo sapiens

<400> SEQUENCE: 33

```
Glu Ile Val Met Thr Gln Ser Pro Ala Ile Leu Ser Val Ser Pro Gly
1               5                   10                  15

Glu Arg Ala Thr Leu Ser Cys Arg Ala Ser Gln Ser Val Ser Asn Tyr
            20                  25                  30

Leu Ala Trp Phe Gln Gln Lys Pro Gly Gln Ala Pro Arg Leu Leu Ile
        35                  40                  45

Tyr Asp Thr Ser Lys Arg Ala Thr Gly Thr Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Arg Ser Asp Trp Pro Gln
                85                  90                  95
```

<210> SEQ ID NO 34
<211> LENGTH: 993
<212> TYPE: DNA
<213> ORGANISM: Homo sapiens
<220> FEATURE:
<221> NAME/KEY: CDS
<222> LOCATION: (1)..(990)
<223> OTHER INFORMATION: 30G1-CH constant heavy chain (CH) sequence

<400> SEQUENCE: 34

```
gcc tcc acc aag ggc cca tcg gtc ttc ccc ctg gca ccc tcc tcc aag      48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc     240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag     288
Tyr Ile Cys Asn Val Asn His Lys Pro Ser Asn Thr Lys Val Asp Lys
                85                  90                  95 aaa gtt gag ccc aaa tct tgt gac aaa act cac aca tgc cca ccg tgc     336
Lys Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca     384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc     432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg     480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag     528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg     576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac     624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg     672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gat gag     720
Gln Pro Arg Glu Pro Gln Val Tyr Thr Leu Pro Pro Ser Arg Asp Glu
225                 230                 235                 240 ctg acc aag aac cag gtc agc ctg acc tgc ctg gtc aaa ggc ttc tat     768
Leu Thr Lys Asn Gln Val Ser Leu Thr Cys Leu Val Lys Gly Phe Tyr
                245                 250                 255
```

```
ccc agc gac atc gcc gtg gag tgg gag agc aat ggg cag ccg gag aac      816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc      864
Asn Tyr Lys Thr Thr Pro Pro Val Leu Asp Ser Asp Gly Ser Phe Phe
        275                 280                 285 ctc tac agc aag ctc acc gtg gac aag agc agg tgg cag cag ggg aac      912
Leu Tyr Ser Lys Leu Thr Val Asp Lys Ser Arg Trp Gln Gln Gly Asn
    290                 295                 300 gtc ttc tca tgc tcc gtg atg cat gag gct ctg cac aac cac tac acg      960
Val Phe Ser Cys Ser Val Met His Glu Ala Leu His Asn His Tyr Thr
305                 310                 315                 320 cag aag agc ctc tcc ctg tct ccg ggt aaa tga                          993
Gln Lys Ser Leu Ser Leu Ser Pro Gly Lys
                325                 330
```

<210> SEQ ID NO 35
<211> LENGTH: 330
<212> TYPE: PRT
<213> ORGANISM: Homo sapiens

<400> SEQUENCE: 35

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 36
<211> LENGTH: 324
<212> TYPE: DNA
<213> ORGANISM: Homo sapiens
<220> FEATURE:
<221> NAME/KEY: CDS
<222> LOCATION: (1)..(321)
<223> OTHER INFORMATION: 30G1-CL constant kappa chain (CL) sequence
<220> FEATURE:
<221> NAME/KEY: misc_feature
<222> LOCATION: (248)..(324)
<223> OTHER INFORMATION: not sequenced but obtained from database

<400> SEQUENCE: 36 cga act gtg gct gca cca tct gtc ttc atc ttc ccg cca tct gat gag      48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc      96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa     144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc     192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag     240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg     288
Lys His Lys Val Tyr Ala Cys Glu Val Thr His Gln Gly Leu Ser Ser
                85                  90                  95 ccc gtc aca aag agc ttc aac agg gga gag tgt tag                     324
Pro Val Thr Lys Ser Phe Asn Arg Gly Glu Cys
            100                 105

<210> SEQ ID NO 37
<211> LENGTH: 107
<212> TYPE: PRT
<213> ORGANISM: Homo sapiens

<400> SEQUENCE: 37

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80
```

```
Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105

<210> SEQ ID NO 38
<211> LENGTH: 378
<212> TYPE: DNA
<213> ORGANISM: Homo sapiens
<220> FEATURE:
<221> NAME/KEY: CDS
<222> LOCATION: (1)..(378)
<223> OTHER INFORMATION: 35G11-VH variable heavy chain (VH) sequence;
      35G11: IgG4, lambda
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(345)
<223> OTHER INFORMATION: complementarity determining region (CDR)
      VH-CDR3

<400> SEQUENCE: 38 cag gtg cag ctg gtt caa tct ggg tct gag ttg agg agg cct ggg gcc       48
Gln Val Gln Leu Val Gln Ser Gly Ser Glu Leu Arg Arg Pro Gly Ala
1               5                   10                  15 tca gtg aac att tcc tgc aag gct tct ggt tac ggc ttc aat act tat       96
Ser Val Asn Ile Ser Cys Lys Ala Ser Gly Tyr Gly Phe Asn Thr Tyr
            20                  25                  30 gct atg aat tgg gtg cga cag gcc cct gga caa ggg cct gag tgg atg      144
Ala Met Asn Trp Val Arg Gln Ala Pro Gly Gln Gly Pro Glu Trp Met
        35                  40                  45 gga tgg atc aac acc gac act ggg gac cca acg tac gcc cag ggg ttc      192
Gly Trp Ile Asn Thr Asp Thr Gly Asp Pro Thr Tyr Ala Gln Gly Phe
    50                  55                  60 acg gga cgg ttt gcc ttc ttc ttg gac acg tct gcc agc acg gca ttt      240
Thr Gly Arg Phe Ala Phe Phe Leu Asp Thr Ser Ala Ser Thr Ala Phe
65                  70                  75                  80 ctg cag atc act cgc cta acg ggt gag gac act gcc gtg tat ttc tgt      288
Leu Gln Ile Thr Arg Leu Thr Gly Glu Asp Thr Ala Val Tyr Phe Cys
                85                  90                  95 gcg aga act cgg aac aac tgg aac ggc gtt tac tat cac tac tcc ggt      336
Ala Arg Thr Arg Asn Asn Trp Asn Gly Val Tyr Tyr His Tyr Ser Gly
            100                 105                 110 ttg gac gtc tgg ggc caa ggg acc acg gtc acc gtc tcc tca              378
Leu Asp Val Trp Gly Gln Gly Thr Thr Val Thr Val Ser Ser
        115                 120                 125

<210> SEQ ID NO 39
<211> LENGTH: 126
<212> TYPE: PRT
<213> ORGANISM: Homo sapiens

<400> SEQUENCE: 39

Gln Val Gln Leu Val Gln Ser Gly Ser Glu Leu Arg Arg Pro Gly Ala
1               5                   10                  15

Ser Val Asn Ile Ser Cys Lys Ala Ser Gly Tyr Gly Phe Asn Thr Tyr
```

```
                        20                  25                  30
Ala Met Asn Trp Val Arg Gln Ala Pro Gly Gln Gly Pro Glu Trp Met
                35                  40                  45

Gly Trp Ile Asn Thr Asp Thr Gly Asp Pro Thr Tyr Ala Gln Gly Phe
        50                  55                  60

Thr Gly Arg Phe Ala Phe Leu Asp Thr Ser Ala Ser Thr Ala Phe
65                  70                  75                  80

Leu Gln Ile Thr Arg Leu Thr Gly Glu Asp Thr Ala Val Tyr Phe Cys
                85                  90                  95

Ala Arg Thr Arg Asn Asn Trp Asn Gly Val Tyr Tyr His Tyr Ser Gly
            100                 105                 110

Leu Asp Val Trp Gly Gln Gly Thr Thr Val Thr Val Ser Ser
            115                 120                 125

<210> SEQ ID NO 40
<211> LENGTH: 330
<212> TYPE: DNA
<213> ORGANISM: Homo sapiens
<220> FEATURE:
<221> NAME/KEY: CDS
<222> LOCATION: (1)..(330)
<223> OTHER INFORMATION: 35G11-VL variable light chain (VL), lambda type
<220> FEATURE:
<221> NAME/KEY: V_region
<222> LOCATION: (67)..(105)
<223> OTHER INFORMATION: complementarity determining region (CDR)
       VL-CDR1
<220> FEATURE:
<221> NAME/KEY: V_region
<222> LOCATION: (151)..(171)
<223> OTHER INFORMATION: complementarity determining region (CDR)
       VL-CDR2
<220> FEATURE:
<221> NAME/KEY: V_region
<222> LOCATION: (268)..(300)
<223> OTHER INFORMATION: complementarity determining region (CDR)
       VL-CDR3

<400> SEQUENCE: 40 cag tct gtg ctg act cag cct ccc tct gcg tct ggg acc ccc ggg cag      48
Gln Ser Val Leu Thr Gln Pro Pro Ser Ala Ser Gly Thr Pro Gly Gln
1               5                   10                  15 acg gtc acc atc tcc tgt tct gga agc agc ccc aac ctc gga gac aat      96
Thr Val Thr Ile Ser Cys Ser Gly Ser Ser Pro Asn Leu Gly Asp Asn
            20                  25                  30 tat gta tac tgg tac cac caa gtc cca gga acg gcc ccc aaa ctc ctc     144
Tyr Val Tyr Trp Tyr His Gln Val Pro Gly Thr Ala Pro Lys Leu Leu
        35                  40                  45 att ttt agg aat act cag cgg ccc tca ggg gtc act gac cga ttc tct     192
Ile Phe Arg Asn Thr Gln Arg Pro Ser Gly Val Thr Asp Arg Phe Ser
    50                  55                  60 ggc tcc aag tat ggc acc tca gcc tcc ctg gcc ata agt gat ctc cgg     240
Gly Ser Lys Tyr Gly Thr Ser Ala Ser Leu Ala Ile Ser Asp Leu Arg
65                  70                  75                  80 tcc gac gat gaa ggt gat ttt tac tgt gct tcg tgg gat gac cgc ctg     288
Ser Asp Asp Glu Gly Asp Phe Tyr Cys Ala Ser Trp Asp Asp Arg Leu
                85                  90                  95 agt cgt ctg gtg ttc ggc gga ggg acc aag ctg acc gtc cta             330
Ser Arg Leu Val Phe Gly Gly Gly Thr Lys Leu Thr Val Leu
            100                 105                 110

<210> SEQ ID NO 41
<211> LENGTH: 110
<212> TYPE: PRT
```

<213> ORGANISM: Homo sapiens

<400> SEQUENCE: 41

| | | | | | | | | | | | | | | | |
|---|---|---|---|---|---|---|---|---|---|---|---|---|---|---|---|
|Gln|Ser|Val|Leu|Thr|Gln|Pro|Pro|Ser|Ala|Ser|Gly|Thr|Pro|Gly|Gln|
|1| | | |5| | | | |10| | | | |15| |

| | | | | | | | | | | | | | | |
|---|---|---|---|---|---|---|---|---|---|---|---|---|---|---|
|Thr|Val|Thr|Ile|Ser|Cys|Ser|Gly|Ser|Ser|Pro|Asn|Leu|Gly|Asp|Asn|
| | | |20| | | | |25| | | | |30| |

Tyr Val Tyr Trp Tyr His Gln Val Pro Gly Thr Ala Pro Lys Leu Leu
             35                40            45

Ile Phe Arg Asn Thr Gln Arg Pro Ser Gly Val Thr Asp Arg Phe Ser
    50               55              60

Gly Ser Lys Tyr Gly Thr Ser Ala Ser Leu Ala Ile Ser Asp Leu Arg
65                70              75             80

Ser Asp Asp Glu Gly Asp Phe Tyr Cys Ala Ser Trp Asp Asp Arg Leu
           85              90             95

Ser Arg Leu Val Phe Gly Gly Gly Thr Lys Leu Thr Val Leu
        100            105          110

<210> SEQ ID NO 42
<211> LENGTH: 984
<212> TYPE: DNA
<213> ORGANISM: Homo sapiens
<220> FEATURE:
<221> NAME/KEY: CDS
<222> LOCATION: (1)..(981)
<223> OTHER INFORMATION: 35G11-CH constant heavy chain (CH) sequence

<400> SEQUENCE: 42

```
gct tcc acc aag ggc cca tcc gtc ttc ccc ctg gcg ccc tgc tcc agg        48
Ala Ser Thr Lys Gly Pro Ser Val Phe Pro Leu Ala Pro Cys Ser Arg
1               5                   10                  15 agc acc tcc gag agc aca gcc gcc ctg ggc tgc ctg gtc aag gac tac        96
Ser Thr Ser Glu Ser Thr Ala Ala Leu Gly Cys Leu Val Lys Asp Tyr
                20                  25                  30 ttc ccc gaa ccg gtg acg gtg tcg tgg aac tca ggc gcc ctg acc agc       144
Phe Pro Glu Pro Val Thr Val Ser Trp Asn Ser Gly Ala Leu Thr Ser
            35                  40                  45 ggc gtg cac acc ttc ccg gct gtc cta cag tcc tca gga ctc tac tcc       192
Gly Val His Thr Phe Pro Ala Val Leu Gln Ser Ser Gly Leu Tyr Ser
        50                  55                  60 ctc agc agc gtg gtg acc gtg ccc tcc agc agc ttg ggc acg aag acc       240
Leu Ser Ser Val Val Thr Val Pro Ser Ser Ser Leu Gly Thr Lys Thr
65                  70                  75                  80 tac acc tgc aac gta gat cac aag ccc agc aac acc aag gtg gac aag       288
Tyr Thr Cys Asn Val Asp His Lys Pro Ser Asn Thr Lys Val Asp Lys
                85                  90                  95 aga gtt gag tcc aaa tat ggt ccc cca tgc cca tca tgc cca gca cct       336
Arg Val Glu Ser Lys Tyr Gly Pro Pro Cys Pro Ser Cys Pro Ala Pro
                100                 105                 110 gag ttc ctg ggg gga cca tca gtc ttc ctg ttc ccc cca aaa ccc aag       384
Glu Phe Leu Gly Gly Pro Ser Val Phe Leu Phe Pro Pro Lys Pro Lys
            115                 120                 125 gac act ctc atg atc tcc cgg acc cct gag gtc acg tgc gtg gtg gtg       432
Asp Thr Leu Met Ile Ser Arg Thr Pro Glu Val Thr Cys Val Val Val
        130                 135                 140 gac gtg agc cag gaa gac ccc gag gtc cag ttc aac tgg tac gtg gat       480
Asp Val Ser Gln Glu Asp Pro Glu Val Gln Phe Asn Trp Tyr Val Asp
145                 150                 155                 160 ggc gtg gag gtg cat aat gcc aag aca aag ccg cgg gag gag cag ttc       528
Gly Val Glu Val His Asn Ala Lys Thr Lys Pro Arg Glu Glu Gln Phe
```

|  |  |  |  |  |  |  |  |  |  |  |  |  |  |  |  |
|---|---|---|---|---|---|---|---|---|---|---|---|---|---|---|---|
|  | 165 |  |  |  | 170 |  |  |  | 175 |  |  |  |  |  |  |

```
aac agc acg tac cgt gtg gtc agc gtc ctc acc gtc ctg cac cag gac       576
Asn Ser Thr Tyr Arg Val Val Ser Val Leu Thr Val Leu His Gln Asp
        180                 185                 190 tgg ctg aac ggc aag gag tac aag tgc aag gtc tcc aac aaa ggc ctc       624
Trp Leu Asn Gly Lys Glu Tyr Lys Cys Lys Val Ser Asn Lys Gly Leu
    195                 200                 205 ccg tcc tcc atc gag aaa acc atc tcc aaa gcc aaa ggg cag ccc cga       672
Pro Ser Ser Ile Glu Lys Thr Ile Ser Lys Ala Lys Gly Gln Pro Arg
210                 215                 220 gag cca cag gtg tac acc ctg ccc cca tcc cag gag gag atg acc aag       720
Glu Pro Gln Val Tyr Thr Leu Pro Pro Ser Gln Glu Glu Met Thr Lys
225                 230                 235                 240 aac cag gtc agc ctg acc tgc ctg gtc aaa ggc ttc tac ccc agc gac       768
Asn Gln Val Ser Leu Thr Cys Leu Val Lys Gly Phe Tyr Pro Ser Asp
                245                 250                 255 atc gcc gtg gag tgg gag agc aat ggg cag ccg gag aac aac tac aag       816
Ile Ala Val Glu Trp Glu Ser Asn Gly Gln Pro Glu Asn Asn Tyr Lys
                260                 265                 270 acc acg cct ccc gtg ctg gac tcc gac ggc tcc ttc ttc ctc tac agc       864
Thr Thr Pro Pro Val Leu Asp Ser Asp Gly Ser Phe Phe Leu Tyr Ser
            275                 280                 285 agg cta acc gtg gac aag agc agg tgg cag gag ggg aat gtc ttc tca       912
Arg Leu Thr Val Asp Lys Ser Arg Trp Gln Glu Gly Asn Val Phe Ser
        290                 295                 300 tgc tcc gtg atg cat gag gct ctg cac aac cac tac aca cag aag agc       960
Cys Ser Val Met His Glu Ala Leu His Asn His Tyr Thr Gln Lys Ser
305                 310                 315                 320 ctc tcc ctg tct ctg ggt aaa tga                                       984
Leu Ser Leu Ser Leu Gly Lys
                325
```

<210> SEQ ID NO 43
<211> LENGTH: 327
<212> TYPE: PRT
<213> ORGANISM: Homo sapiens

<400> SEQUENCE: 43

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 44
<211> LENGTH: 321
<212> TYPE: DNA
<213> ORGANISM: Homo sapiens
<220> FEATURE:
<221> NAME/KEY: CDS
<222> LOCATION: (1)..(318)
<223> OTHER INFORMATION: 35G11-CL constant lambda chain (CL) sequence
<220> FEATURE:
<221> NAME/KEY: variation
<222> LOCATION: (211)..(213)
<223> OTHER INFORMATION: tac may be also tat
<220> FEATURE:
<221> NAME/KEY: misc_feature
<222> LOCATION: (250)..(321)
<223> OTHER INFORMATION: not sequenced but obtained from database

<400> SEQUENCE: 44 ggt cag ccc aag gct gcc ccc tcg gtc act ctg ttc ccg ccc tcc tct        48
Gly Gln Pro Lys Ala Ala Pro Ser Val Thr Leu Phe Pro Pro Ser Ser
1               5                   10                  15 gag gag ctt caa gcc aac aag gcc aca ctg gtg tgt ctc ata agt gac        96
Glu Glu Leu Gln Ala Asn Lys Ala Thr Leu Val Cys Leu Ile Ser Asp
            20                  25                  30 ttc tac ccg gga gcc gtg aca gtg gcc tgg aag gca gat agc agc ccc        144
Phe Tyr Pro Gly Ala Val Thr Val Ala Trp Lys Ala Asp Ser Ser Pro
        35                  40                  45 gtc aag gcg gga gtg gag acc acc aca ccc tcc aaa caa agc aac aac        192
Val Lys Ala Gly Val Glu Thr Thr Thr Pro Ser Lys Gln Ser Asn Asn
    50                  55                  60 aag tac gcg gcc agc agc tac ctg agc ctg acg cct gag cag tgg aag        240
Lys Tyr Ala Ala Ser Ser Tyr Leu Ser Leu Thr Pro Glu Gln Trp Lys
65                  70                  75                  80 tcc cac aga agc tac agc tgc cag gtc acg cat gaa ggg agc acc gtg        288
Ser His Arg Ser Tyr Ser Cys Gln Val Thr His Glu Gly Ser Thr Val
                85                  90                  95 gag aag aca gtg gcc cct aca gaa tgt tca tag                            321
```

```
Glu Lys Thr Val Ala Pro Thr Glu Cys Ser
        100                 105
```

<210> SEQ ID NO 45
<211> LENGTH: 106
<212> TYPE: PRT
<213> ORGANISM: Homo sapiens

<400> SEQUENCE: 45

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 46
<211> LENGTH: 354
<212> TYPE: DNA
<213> ORGANISM: Homo sapiens
<220> FEATURE:
<221> NAME/KEY: CDS
<222> LOCATION: (1)..(354)
<223> OTHER INFORMATION: 41D11-VH variable heavy chain (VH) sequence;
      41D11: IgG1, lambda
<220> FEATURE:
<221> NAME/KEY: V_region
<222> LOCATION: (91)..(111)
<223> OTHER INFORMATION: complementarity determining region (CDR)
      VH-CDR1
<220> FEATURE:
<221> NAME/KEY: V_region
<222> LOCATION: (154)..(201)
<223> OTHER INFORMATION: complementarity determining region (CDR)
      VH-CDR2
<220> FEATURE:
<221> NAME/KEY: V_region
<222> LOCATION: (298)..(321)
<223> OTHER INFORMATION: complementarity determining region (CDR)
      VH-CDR3

<400> SEQUENCE: 46

```
cag gtg caa cta cat gag tcg ggc cca gga ctg gtg aag cct tcg gag      48
Gln Val Gln Leu His Glu Ser Gly Pro Gly Leu Val Lys Pro Ser Glu
1               5                   10                  15 acc ctg tcc gta acc tgc agt ctc tct ggt ggc tcc atc agt agt agt      96
Thr Leu Ser Val Thr Cys Ser Leu Ser Gly Gly Ser Ile Ser Ser Ser
            20                  25                  30 agt cac ctg tgg gcc tgg atc cgc cag ccc cca gag aag gga ctg gaa     144
Ser His Leu Trp Ala Trp Ile Arg Gln Pro Pro Glu Lys Gly Leu Glu
        35                  40                  45 tat atc ggg cgt att cat tat agg ggc agt gtg tcc tac aat ccg tcc     192
Tyr Ile Gly Arg Ile His Tyr Arg Gly Ser Val Ser Tyr Asn Pro Ser
    50                  55                  60 ctc aag agt cgc gcc gcc att tcc gtc gac acg gcc aag aac cag ttc     240
Leu Lys Ser Arg Ala Ala Ile Ser Val Asp Thr Ala Lys Asn Gln Phe
65                  70                  75                  80
```

-continued

```
tcc ctg acg ttg agt gct gtg acc gcc gca gac acg tct ttt tat tac    288
Ser Leu Thr Leu Ser Ala Val Thr Ala Ala Asp Thr Ser Phe Tyr Tyr
                85                  90                  95 tgt gcg aga ctg gac atg ggg gca ata gac aag tgg ggc cag gga acc    336
Cys Ala Arg Leu Asp Met Gly Ala Ile Asp Lys Trp Gly Gln Gly Thr
            100                 105                 110 ctg gtc atc gtc tcc tca                                            354
Leu Val Ile Val Ser Ser
        115

<210> SEQ ID NO 47
<211> LENGTH: 118
<212> TYPE: PRT
<213> ORGANISM: Homo sapiens

<400> SEQUENCE: 47

Gln Val Gln Leu His Glu Ser Gly Pro Gly Leu Val Lys Pro Ser Glu
1               5                   10                  15

Thr Leu Ser Val Thr Cys Ser Leu Ser Gly Gly Ser Ile Ser Ser Ser
            20                  25                  30

Ser His Leu Trp Ala Trp Ile Arg Gln Pro Pro Glu Lys Gly Leu Glu
        35                  40                  45

Tyr Ile Gly Arg Ile His Tyr Arg Gly Ser Val Ser Tyr Asn Pro Ser
    50                  55                  60

Leu Lys Ser Arg Ala Ala Ile Ser Val Asp Thr Ala Lys Asn Gln Phe
65                  70                  75                  80

Ser Leu Thr Leu Ser Ala Val Thr Ala Ala Asp Thr Ser Phe Tyr Tyr
                85                  90                  95

Cys Ala Arg Leu Asp Met Gly Ala Ile Asp Lys Trp Gly Gln Gly Thr
            100                 105                 110

Leu Val Ile Val Ser Ser
        115

<210> SEQ ID NO 48
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION: 41D11-VL variable light chain (VL) sequence,
      lambda type
<220> FEATURE:
<221> NAME/KEY: V_region
<222> LOCATION: (67)..(102)
<223> OTHER INFORMATION: complementarity determining region (CDR)
      VL-CDR1
<220> FEATURE:
<221> NAME/KEY: V_region
<222> LOCATION: (148)..(180)
<223> OTHER INFORMATION: complementarity determining region (CDR)
       VL-CDR2
<220> FEATURE:
<221> NAME/KEY: V_region
<222> LOCATION: (277)..(303)
<223> OTHER INFORMATION: complementarity determining region (CDR)
      VL-CDR3

<400> SEQUENCE: 48 cag cct gtg ctg act caa tcg ccc tct gcc tct gcc tcc ctg gga gcc    48
Gln Pro Val Leu Thr Gln Ser Pro Ser Ala Ser Ala Ser Leu Gly Ala
1               5                   10                  15 tcg atc aaa ctc acc tgc act ctg agc agt gga cac agc aac tac gac    96
Ser Ile Lys Leu Thr Cys Thr Leu Ser Ser Gly His Ser Asn Tyr Asp
```

```
                       20                  25                  30
atc gct tgg cat caa cag cag tcg ggg aag ggc cct cga ttc ttg atg        144
Ile Ala Trp His Gln Gln Gln Ser Gly Lys Gly Pro Arg Phe Leu Met
         35                  40                  45 aga gtt aac aat ggt gga agc cac aac aag ggg gac ggg atc cct gat        192
Arg Val Asn Asn Gly Gly Ser His Asn Lys Gly Asp Gly Ile Pro Asp
 50                  55                  60 cgt ttc tca ggc tcc agc tct ggg gca gag cgc tac ctc aca atc tcc        240
Arg Phe Ser Gly Ser Ser Ser Gly Ala Glu Arg Tyr Leu Thr Ile Ser
 65                  70                  75                  80 agt ctc cag tct gag gat gag gct gac tat tat tgt cag aca tgg ggc        288
Ser Leu Gln Ser Glu Asp Glu Ala Asp Tyr Tyr Cys Gln Thr Trp Gly
             85                  90                  95 act ggc act cat gtc ttc ggc act ggg act aag gtc acc gtc ctg            333
Thr Gly Thr His Val Phe Gly Thr Gly Thr Lys Val Thr Val Leu
             100                 105                 110

<210> SEQ ID NO 49
<211> LENGTH: 111
<212> TYPE: PRT
<213> ORGANISM: Homo sapiens

<400> SEQUENCE: 49

Gln Pro Val Leu Thr Gln Ser Pro Ser Ala Ser Ala Ser Leu Gly Ala
1               5                   10                  15

Ser Ile Lys Leu Thr Cys Thr Leu Ser Ser Gly His Ser Asn Tyr Asp
            20                  25                  30

Ile Ala Trp His Gln Gln Gln Ser Gly Lys Gly Pro Arg Phe Leu Met
        35                  40                  45

Arg Val Asn Asn Gly Gly Ser His Asn Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gln Thr Trp Gly
                85                  90                  95

Thr Gly Thr His Val Phe Gly Thr Gly Thr Lys Val Thr Val Leu
            100                 105                 110

<210> SEQ ID NO 50
<211> LENGTH: 993
<212> TYPE: DNA
<213> ORGANISM: Homo sapiens
<220> FEATURE:
<221> NAME/KEY: CDS
<222> LOCATION: (1)..(990)
<223> OTHER INFORMATION: 41D11-CH constant heavy chain (CH) sequence
<220> FEATURE:
<221> NAME/KEY: variation
<222> LOCATION: (877)..(879)
<223> OTHER INFORMATION: ttc may be also ctc, thus Phe may be also Leu
      at position 293 of the amino acid sequence

<400> SEQUENCE: 50 gcc tcc acc aag ggc cca tcg gtc ttc ccc ctg gca ccc tcc tcc aag        48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac        96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc        144
Phe Pro Glu Pro Val Thr Val Ser Trp Asn Ser Gly Ala Leu Thr Ser
        35                  40                  45
```

```
ggc gtg cac acc ttc ccg gct gtc cta cag tcc tca gga ctc tac tcc      192
Gly Val His Thr Phe Pro Ala Val Leu Gln Ser Ser Gly Leu Tyr Ser
 50              55                  60 ctc agc agc gtg gtg acc gtg ccc tcc agc agc ttg ggc acc cag acc      240
Leu Ser Ser Val Val Thr Val Pro Ser Ser Ser Leu Gly Thr Gln Thr
 65              70                  75                  80 tac atc tgc aac gtg aat cac aag ccc agc aac acc aag gtg gac aag      288
Tyr Ile Cys Asn Val Asn His Lys Pro Ser Asn Thr Lys Val Asp Lys
                 85                  90                  95 aga gtt gag ccc aaa tct tgt gac aaa act cac aca tgc cca ccg tgc      336
Arg Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca      384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc      432
Lys Pro Lys Asp Thr Leu Met Ile Ser Arg Thr Pro Glu Val Thr Cys
130                 135                 140 gtg gtg gtg gac gtg agc cac gaa gac cct gag gtc aag ttc aac tgg      480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag      528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg      576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac      624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg      672
Lys Ala Leu Pro Ala Pro Ile Glu Lys Thr Ile Ser Lys Ala Lys Gly
210                 215                 220 cag ccc cga gaa cca cag gtg tac acc ctg ccc cca tcc cgg gag gag      720
Gln Pro Arg Glu Pro Gln Val Tyr Thr Leu Pro Pro Ser Arg Glu Glu
225                 230                 235                 240 atg acc aag aac cag gtc agc ctg acc tgc ctg gtc aaa ggc ttc tat      768
Met Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac      816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc      864
Asn Tyr Lys Thr Thr Pro Pro Val Leu Asp Ser Asp Gly Ser Phe Phe
        275                 280                 285 ctc tat agc aag ttc acc gtg gac aag agc agg tgg cag cag ggg aac      912
Leu Tyr Ser Lys Phe Thr Val Asp Lys Ser Arg Trp Gln Gln Gly Asn
    290                 295                 300 gtc ttc tca tgc tcc gtg atg cat gag gct ctg cac aac cac tac acg      960
Val Phe Ser Cys Ser Val Met His Glu Ala Leu His Asn His Tyr Thr
305                 310                 315                 320 cag aag agc ctc tcc ctg tcc ccg ggt aaa tga                          993
Gln Lys Ser Leu Ser Leu Ser Pro Gly Lys
                325                 330

<210> SEQ ID NO 51
<211> LENGTH: 330
<212> TYPE: PRT
<213> ORGANISM: Homo sapiens
```

<400> SEQUENCE: 51

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Phe Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 52
<211> LENGTH: 321
<212> TYPE: DNA
<213> ORGANISM: Homo sapiens
<220> FEATURE:
<221> NAME/KEY: CDS
<222> LOCATION: (1)..(318)
<223> OTHER INFORMATION: 41D11-CL constant lambda chain (CL) sequence
<220> FEATURE:
<221> NAME/KEY: misc_feature
<222> LOCATION: (250)..(321)
<223> OTHER INFORMATION: not sequenced but obtained from database

<400> SEQUENCE: 52

```
ggt cag ccc aag gcc aac ccc act gtc act ctg ttc ccg ccc tcc tct        48
Gly Gln Pro Lys Ala Asn Pro Thr Val Thr Leu Phe Pro Pro Ser Ser
1               5                   10                  15 gag gag ctc caa gcc aac aag gcc aca cta gtg tgt ctg atc agt gac        96
Glu Glu Leu Gln Ala Asn Lys Ala Thr Leu Val Cys Leu Ile Ser Asp
            20                  25                  30 ttc tac ccg gga gct gtg aca gtg gcc tgg aag gca gat ggc agc ccc       144
Phe Tyr Pro Gly Ala Val Thr Val Ala Trp Lys Ala Asp Gly Ser Pro
        35                  40                  45 gtc aag gcg gga gtg gag acc acc aaa ccc tcc aaa cag agc aac aac       192
Val Lys Ala Gly Val Glu Thr Thr Lys Pro Ser Lys Gln Ser Asn Asn
50                  55                  60 aag tac gcg gcc agc agc tac ctg agc ctg acg ccc gag cag tgg aag       240
Lys Tyr Ala Ala Ser Ser Tyr Leu Ser Leu Thr Pro Glu Gln Trp Lys
65                  70                  75                  80 tcc cac aga agc tac agc tgc cag gtc acg cat gaa ggg agc acc gtg       288
Ser His Arg Ser Tyr Ser Cys Gln Val Thr His Glu Gly Ser Thr Val
                85                  90                  95 gag aag aca gtg gcc cct aca gaa tgt tca tag                           321
Glu Lys Thr Val Ala Pro Thr Glu Cys Ser
            100                 105
```

<210> SEQ ID NO 53
<211> LENGTH: 106
<212> TYPE: PRT
<213> ORGANISM: Homo sapiens

<400> SEQUENCE: 53

```
Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 54
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION: 51G4-VH-variable heavy chain (VH) sequence;
      51G4: IgG2, lambda
<220> FEATURE:
<221> NAME/KEY: misc_feature
<222> LOCATION: (1)..(18)
<223> OTHER INFORMATION: not sequenced but derived from primer used for
      molecular cloning
<220> FEATURE:
<221> NAME/KEY: V_region
<222> LOCATION: (91)..(105)
<223> OTHER INFORMATION: complementarity determining region (CDR)
      VH-CDR1

```
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(324)
<223> OTHER INFORMATION: complementarity determining region (CDR)
      VH-CDR3
<220> FEATURE:
<221> NAME/KEY: misc_feature
<222> LOCATION: (340)..(357)
<223> OTHER INFORMATION: not sequenced but derived from primer used for
      molecular cloning

<400> SEQUENCE: 54 gag gtg cag ctg gtg cag tct ggg gct gag gtg aag aag cct ggg gcc      48
Glu Val Gln Leu Val Gln Ser Gly Ala Glu Val Lys Lys Pro Gly Ala
1               5                   10                  15 tca gtg aag gtt tca tgt aaa act tct gga tac aaa ttc gct ctc tat      96
Ser Val Lys Val Ser Cys Lys Thr Ser Gly Tyr Lys Phe Ala Leu Tyr
            20                  25                  30 gat att cat tgg gtg cgc cag gcc ccc gga caa ggg ctt gag tgg atg     144
Asp Ile His Trp Val Arg Gln Ala Pro Gly Gln Gly Leu Glu Trp Met
        35                  40                  45 ggc tgg atc aac gct gcc aat ggt gac aca gaa tat tca cag aag ttt     192
Gly Trp Ile Asn Ala Ala Asn Gly Asp Thr Glu Tyr Ser Gln Lys Phe
    50                  55                  60 gag ggc aga gtc acc att acc agg gac aca tcg gcg act aca gtc tac     240
Glu Gly Arg Val Thr Ile Thr Arg Asp Thr Ser Ala Thr Thr Val Tyr
65                  70                  75                  80 atg gag ttg aac agt ctg aca tat ggc gac acg gcc gtg tac tac tgt     288
Met Glu Leu Asn Ser Leu Thr Tyr Gly Asp Thr Ala Val Tyr Tyr Cys
                85                  90                  95 gcg aga gag gaa ggt ctc tac aac tgg ttc gac ccc tgg ggc cag gga     336
Ala Arg Glu Glu Gly Leu Tyr Asn Trp Phe Asp Pro Trp Gly Gln Gly
            100                 105                 110 acc ctg gtc acc gtc tcc tca                                          357
Thr Leu Val Thr Val Ser Ser
        115

<210> SEQ ID NO 55
<211> LENGTH: 119
<212> TYPE: PRT
<213> ORGANISM: Homo sapiens

<400> SEQUENCE: 55

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Lys Phe Ala Leu Tyr
            20                  25                  30

Asp Ile His Trp Val Arg Gln Ala Pro Gly Gln Gly Leu Glu Trp Met
        35                  40                  45

Gly Trp Ile Asn Ala Ala Asn Gly Asp Thr Glu Tyr Ser Gln Lys Phe
    50                  55                  60

Glu Gly Arg Val Thr Ile Thr Arg Asp Thr Ser Ala Thr Thr Val Tyr
65                  70                  75                  80

Met Glu Leu Asn Ser Leu Thr Tyr Gly Asp Thr Ala Val Tyr Tyr Cys
                85                  90                  95

Ala Arg Glu Glu Gly Leu Tyr Asn Trp Phe Asp Pro Trp Gly Gln Gly
            100                 105                 110
```

-continued

```
Thr Leu Val Thr Val Ser Ser
        115

<210> SEQ ID NO 56
<211> LENGTH: 327
<212> TYPE: DNA
<213> ORGANISM: Homo sapiens
<220> FEATURE:
<221> NAME/KEY: CDS
<222> LOCATION: (1)..(327)
<223> OTHER INFORMATION: 51G4-variable light chain (VL) sequence, lambda
      type
<220> FEATURE:
<221> NAME/KEY: misc_feature
<222> LOCATION: (1)..(18)
<223> OTHER INFORMATION: not sequenced but derived from primer used for
      molecular cloning
<220> FEATURE:
<221> NAME/KEY: V_region
<222> LOCATION: (67)..(99)
<223> OTHER INFORMATION: complementarity determining region (CDR)
      VL-CDR1
<220> FEATURE:
<221> NAME/KEY: V_region
<222> LOCATION: (145)..(165)
<223> OTHER INFORMATION: complementarity determining region (CDR)
      VL-CDR2
<220> FEATURE:
<221> NAME/KEY: V_region
<222> LOCATION: (262)..(297)
<223> OTHER INFORMATION: complementarity determining region (CDR)
      VL-CDR3

<400> SEQUENCE: 56 tcc tat gag ctg aca cag gac cct gct gtg tct gtg gcc ttg gga cag        48
Ser Tyr Glu Leu Thr Gln Asp Pro Ala Val Ser Val Ala Leu Gly Gln
1               5                   10                  15 aca gtc agg atc aca tgc caa gga gac agc ctc aga atc tat tat gca        96
Thr Val Arg Ile Thr Cys Gln Gly Asp Ser Leu Arg Ile Tyr Tyr Ala
            20                  25                  30 aac tgg tac cag cag aag cca gga cag gcc cct gtt ctt gtc atc tat       144
Asn Trp Tyr Gln Gln Lys Pro Gly Gln Ala Pro Val Leu Val Ile Tyr
        35                  40                  45 ggt aaa agc aac cgg ccc tca ggg atc cca gac cga ttc tct gcc tcc       192
Gly Lys Ser Asn Arg Pro Ser Gly Ile Pro Asp Arg Phe Ser Ala Ser
50                  55                  60 agc tca gga aac aca gct tcc ttg acc atc act ggg gct cag gcg gaa       240
Ser Ser Gly Asn Thr Ala Ser Leu Thr Ile Thr Gly Ala Gln Ala Glu
65                  70                  75                  80 gat gag gct gac tat tac tgt aac tcc cgg gac agc agt gat aag cat       288
Asp Glu Ala Asp Tyr Tyr Cys Asn Ser Arg Asp Ser Ser Asp Lys His
                85                  90                  95 ccc gtg cct ttc ggc ggg ggg acc aag ctg acc gtc cta                   327
Pro Val Pro Phe Gly Gly Gly Thr Lys Leu Thr Val Leu
                100                 105

<210> SEQ ID NO 57
<211> LENGTH: 109
<212> TYPE: PRT
<213> ORGANISM: Homo sapiens

<400> SEQUENCE: 57

Ser Tyr Glu Leu Thr Gln Asp Pro Ala Val Ser Val Ala Leu Gly Gln
1               5                   10                  15

Thr Val Arg Ile Thr Cys Gln Gly Asp Ser Leu Arg Ile Tyr Tyr Ala
            20                  25                  30

Asn Trp Tyr Gln Gln Lys Pro Gly Gln Ala Pro Val Leu Val Ile Tyr
```

35                  40                  45
Gly Lys Ser Asn Arg Pro Ser Gly Ile Pro Asp Arg Phe Ser Ala Ser
         50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Asp Lys His
                 85                  90                  95

Pro Val Pro Phe Gly Gly Gly Thr Lys Leu Thr Val Leu
            100                 105

<210> SEQ ID NO 58
<211> LENGTH: 981
<212> TYPE: DNA
<213> ORGANISM: Homo sapiens
<220> FEATURE:
<221> NAME/KEY: CDS
<222> LOCATION: (1)..(978)
<223> OTHER INFORMATION: 51G4-CH constant heavy chain (CH) sequence
<220> FEATURE:
<221> NAME/KEY: misc_feature
<222> LOCATION: (1)..(47)
<223> OTHER INFORMATION: not sequenced but obtained from database

<400> SEQUENCE: 58 gcc tcc acc aag ggc cca tcg gtc ttc ccc ctg gcg ccc tgc tcc agg    48
Ala Ser Thr Lys Gly Pro Ser Val Phe Pro Leu Ala Pro Cys Ser Arg
 1               5                  10                  15 agc acc tcc gag agc aca gcg gcc ctg ggc tgc ctg gtc aag gac tac    96
Ser Thr Ser Glu Ser Thr Ala Ala Leu Gly Cys Leu Val Lys Asp Tyr
                 20                  25                  30 ttc ccc gaa ccg gtg acg gtg tcg tgg aac tca ggt gct ctg acc agc   144
Phe Pro Glu Pro Val Thr Val Ser Trp Asn Ser Gly Ala Leu Thr Ser
             35                  40                  45 ggc gtg cac acc ttc cca gct gtc cta cag tcc tca gga ctc tac tcc   192
Gly Val His Thr Phe Pro Ala Val Leu Gln Ser Ser Gly Leu Tyr Ser
         50                  55                  60 ctc agc agc gtg gtg acc gtg ccc tcc agc aac ttc ggc acc cag acc   240
Leu Ser Ser Val Val Thr Val Pro Ser Ser Asn Phe Gly Thr Gln Thr
 65                  70                  75                  80 tac acc tgc aac gta gat cac aag ccc agc aac acc aag gtg gac aag   288
Tyr Thr Cys Asn Val Asp His Lys Pro Ser Asn Thr Lys Val Asp Lys
                 85                  90                  95 aca gtt gag cgc aaa tgt tgt gtc gag tgc cca ccg tgc cca gca cca   336
Thr Val Glu Arg Lys Cys Cys Val Glu Cys Pro Pro Cys Pro Ala Pro
                100                 105                 110 cct gtg gca gga ccg tca gtc ttc ctc ttc ccc cca aaa ccc aag gac   384
Pro Val Ala Gly Pro Ser Val Phe Leu Phe Pro Pro Lys Pro Lys Asp
            115                 120                 125 acc ctc atg atc tcc cgg acc cct gag gtc acg tgc gtg gtg gtg gac   432
Thr Leu Met Ile Ser Arg Thr Pro Glu Val Thr Cys Val Val Val Asp
        130                 135                 140 gtg agc cac gaa gac ccc gag gtc cag ttc aac tgg tac gtg gac ggc   480
Val Ser His Glu Asp Pro Glu Val Gln Phe Asn Trp Tyr Val Asp Gly
145                 150                 155                 160 gtg gag gtg cat aat gcc aag aca aag cca cgg gag gag cag ttc aac   528
Val Glu Val His Asn Ala Lys Thr Lys Pro Arg Glu Glu Gln Phe Asn
                165                 170                 175 agc acg ttc cgt gtg gtc agc gtc ctc acc gtt gtg cac cag gac tgg   576
Ser Thr Phe Arg Val Val Ser Val Leu Thr Val Val His Gln Asp Trp
            180                 185                 190 ctg aac ggc aag gag tac aag tgc aag gtc tcc aac aaa ggc ctc cca   624

```
Leu Asn Gly Lys Glu Tyr Lys Cys Lys Val Ser Asn Lys Gly Leu Pro
            195                 200                 205 gcc ccc atc gag aaa acc atc tcc aaa acc aaa ggg cag ccc cga gaa       672
Ala Pro Ile Glu Lys Thr Ile Ser Lys Thr Lys Gly Gln Pro Arg Glu
210                 215                 220 cca cag gtg tac acc ctg ccc cca tcc cgg gag gag atg acc aag aac       720
Pro Gln Val Tyr Thr Leu Pro Pro Ser Arg Glu Glu Met Thr Lys Asn
225                 230                 235                 240 cag gtc agc ctg acc tgc ctg gtc aaa ggc ttc tac ccc agc gac atc       768
Gln Val Ser Leu Thr Cys Leu Val Lys Gly Phe Tyr Pro Ser Asp Ile
            245                 250                 255 gcc gtg gag tgg gag agc aat ggg cag ccg gag aac aac tac aag acc       816
Ala Val Glu Trp Glu Ser Asn Gly Gln Pro Glu Asn Asn Tyr Lys Thr
        260                 265                 270 aca cct ccc atg ctg gac tcc gac ggc tcc ttc ttc ctc tac agc aag       864
Thr Pro Pro Met Leu Asp Ser Asp Gly Ser Phe Phe Leu Tyr Ser Lys
    275                 280                 285 ctc acc gtg gac aag agc agg tgg cag cag ggg aac gtc ttc tca tgc       912
Leu Thr Val Asp Lys Ser Arg Trp Gln Gln Gly Asn Val Phe Ser Cys
290                 295                 300 tcc gtg atg cat gag gct ctg cac aac cac tac acg cag aag agc ctc       960
Ser Val Met His Glu Ala Leu His Asn His Tyr Thr Gln Lys Ser Leu
305                 310                 315                 320 tcc ctg tct ccg ggt aaa tga                                           981
Ser Leu Ser Pro Gly Lys
            325
```

<210> SEQ ID NO 59
<211> LENGTH: 326
<212> TYPE: PRT
<213> ORGANISM: Homo sapiens

<400> SEQUENCE: 59

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190
```

```
Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 60
<211> LENGTH: 321
<212> TYPE: DNA
<213> ORGANISM: Homo sapiens
<220> FEATURE:
<221> NAME/KEY: CDS
<222> LOCATION: (1)..(318)
<223> OTHER INFORMATION: 51G4-CL constant lambda chain (CL) sequence
<220> FEATURE:
<221> NAME/KEY: misc_feature
<222> LOCATION: (27)..(321)
<223> OTHER INFORMATION: not sequenced but obtained from lambda constant
      chain of 24D3 from the same patient

<400> SEQUENCE: 60 agt cag ccc aag gct gcc ccc tcg gtc act ctg ttc ccg ccc tcc tct      48
Ser Gln Pro Lys Ala Ala Pro Ser Val Thr Leu Phe Pro Pro Ser Ser
1               5                   10                  15 gag gag ctt caa gcc aac aag gcc aca ctg gtg tgt ctc ata agt gac      96
Glu Glu Leu Gln Ala Asn Lys Ala Thr Leu Val Cys Leu Ile Ser Asp
            20                  25                  30 ttc tac ccg gga gcc gtg aca gtg gcc tgg aag gca gat agc agc ccc     144
Phe Tyr Pro Gly Ala Val Thr Val Ala Trp Lys Ala Asp Ser Ser Pro
        35                  40                  45 gtc aag gcg gga gtg gag acc acc aca ccc tcc aaa caa agc aac aac     192
Val Lys Ala Gly Val Glu Thr Thr Thr Pro Ser Lys Gln Ser Asn Asn
    50                  55                  60 aag tac gcg gcc agc agc tat ctg agc ctg acg cct gag cag tgg aag     240
Lys Tyr Ala Ala Ser Ser Tyr Leu Ser Leu Thr Pro Glu Gln Trp Lys
65                  70                  75                  80 tcc cac aga agc tac agc tgc cag gtc acg cat gaa ggg agc acc gtg     288
Ser His Arg Ser Tyr Ser Cys Gln Val Thr His Glu Gly Ser Thr Val
                85                  90                  95 gag aag aca gtg gcc cct aca gaa tgt tca tag                         321
Glu Lys Thr Val Ala Pro Thr Glu Cys Ser
            100                 105

<210> SEQ ID NO 61
<211> LENGTH: 106
<212> TYPE: PRT
<213> ORGANISM: Homo sapiens

<400> SEQUENCE: 61
```

```
Ser Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 62
<211> LENGTH: 34
<212> TYPE: DNA
<213> ORGANISM: Artificial Sequence
<220> FEATURE:
<223> OTHER INFORMATION: Forward Oligonucleotide/Primer F1 for
    amplification of a fragment encoding aa 34-76 of IL-22

<400> SEQUENCE: 62
tttgggatcc tcgcgcccat cagctcccac tgca                            34

<210> SEQ ID NO 63
<211> LENGTH: 35
<212> TYPE: DNA
<213> ORGANISM: Artificial Sequence
<220> FEATURE:
<223> OTHER INFORMATION: Reverse Oligonucleotide/Primer R1 for
    amplification of a fragment encoding aa 34-76 of IL-22

<400> SEQUENCE: 63
tttgcggccg ctcacccaat gagacgaacg tctgt                           35

<210> SEQ ID NO 64
<211> LENGTH: 34
<212> TYPE: DNA
<213> ORGANISM: Artificial Sequence
<220> FEATURE:
<223> OTHER INFORMATION: Forward oligonucleotide/primer F2 for
    amplification of a fragment encoding aa 74-114 of IL-22

<400> SEQUENCE: 64
tttgggatcc tcctcattgg ggagaaactg ttcc                            34

<210> SEQ ID NO 65
<211> LENGTH: 35
<212> TYPE: DNA
<213> ORGANISM: Artificial Sequence
<220> FEATURE:
<223> OTHER INFORMATION: Reverse oligonucleotide/primer R2 for
    amplification of a fragment encoding aa 74-114 of IL-22

<400> SEQUENCE: 65
tttgcggccg ctcaataagg ctggaaccta tcaga                           35

<210> SEQ ID NO 66
<211> LENGTH: 32
<212> TYPE: DNA
<213> ORGANISM: Artificial Sequence

```
<220> FEATURE:
<223> OTHER INFORMATION: Forward oligonucleotide/primer F3 for
      amplification of a fragment encoding aa 113-179 of IL-22

<400> SEQUENCE: 66
tttgggatcc tcccttatat gcaggaggtg gt                                    32

<210> SEQ ID NO 67
<211> LENGTH: 33
<212> TYPE: DNA
<213> ORGANISM: Artificial Sequence
<220> FEATURE:
<223> OTHER INFORMATION: Reverse oligonucleotide/primer R3 for
      amplification of a fragment encoding aa 113-179 of IL-22

<400> SEQUENCE: 67
tttgcggccg ctcaaatgca ggcatttctc aga                                   33

<210> SEQ ID NO 68
<211> LENGTH: 34
<212> TYPE: DNA
<213> ORGANISM: Artificial Sequence
<220> FEATURE:
<223> OTHER INFORMATION: Forward oligonucleotide/primer 34-114-F1 for
      amplification of a fragment encoding aa 34-114 of IL-22

<400> SEQUENCE: 68
tttgggatcc tcgcgcccat cagctcccac tgca                                  34

<210> SEQ ID NO 69
<211> LENGTH: 35
<212> TYPE: DNA
<213> ORGANISM: Artificial Sequence
<220> FEATURE:
<223> OTHER INFORMATION: Reverse oligonucleotide/primer 34-114-R2 for
      amplification of a fragment encoding aa 34-114 of IL-22

<400> SEQUENCE: 69
tttgcggccg ctcaataagg ctggaaccta tcaga                                 35

<210> SEQ ID NO 70
<211> LENGTH: 34
<212> TYPE: DNA
<213> ORGANISM: Artificial Sequence
<220> FEATURE:
<223> OTHER INFORMATION: Forward oligonucleotide/primer 74-179-F2 for
      amplification of a fragment encoding aa 74-179 of IL-22

<400> SEQUENCE: 70
tttgggatcc tcctcattgg ggagaaactg ttcc                                  34

<210> SEQ ID NO 71
<211> LENGTH: 33
<212> TYPE: DNA
<213> ORGANISM: Artificial Sequence
<220> FEATURE:
<223> OTHER INFORMATION: Reverse oligonucleotide/primer 74-179-R3 for
      amplification of a fragment encoding aa 74-179 of IL-22

<400> SEQUENCE: 71
tttgcggccg ctcaaatgca ggcatttctc aga                                   33

<210> SEQ ID NO 72
<211> LENGTH: 34
<212> TYPE: DNA
<213> ORGANISM: Artificial Sequence
<220> FEATURE:
```

```
<223> OTHER INFORMATION: Forward oligonucleotide/primer F1 for
      amplification of a fragment encoding aa 24-69 of IFN-alpha2a

<400> SEQUENCE: 72
tttgggatcc tctgtgatct gcctcaaacc caca                                   34

<210> SEQ ID NO 73
<211> LENGTH: 35
<212> TYPE: DNA
<213> ORGANISM: Artificial Sequence
<220> FEATURE:
<223> OTHER INFORMATION: Reverse oligonucleotide/primer R1 for
      amplification of a fragment encoding aa 24-69 of IFN-alpha2a

<400> SEQUENCE: 73
tttgcggccg ctcactggtt gccaaactcc tcctg                                  35

<210> SEQ ID NO 74
<211> LENGTH: 33
<212> TYPE: DNA
<213> ORGANISM: Artificial Sequence
<220> FEATURE:
<223> OTHER INFORMATION: Forward oligonucleotide/primer F2 for
      amplification of a fragment encoding aa 67-124 of IFN-alpha2a

<400> SEQUENCE: 74
tttgggatcc tcggcaacca gttccaaaag gct                                    33

<210> SEQ ID NO 75
<211> LENGTH: 35
<212> TYPE: DNA
<213> ORGANISM: Artificial Sequence
<220> FEATURE:
<223> OTHER INFORMATION: Reverse oligonucleotide/primer R2 for
      amplification of a fragment encoding aa 67-124 of IFN-alpha2a

<400> SEQUENCE: 75
tttgcggccg ctcactgtat cacacaggct tccag                                  35

<210> SEQ ID NO 76
<211> LENGTH: 33
<212> TYPE: DNA
<213> ORGANISM: Artificial Sequence
<220> FEATURE:
<223> OTHER INFORMATION: Forward oligonucleotide/primer F3 for
      amplification of a fragment encoding aa 123-188 of IFN-alpha2a

<400> SEQUENCE: 76
tttgggatcc tcatacaggg ggtgggggtg aca                                    33

<210> SEQ ID NO 77
<211> LENGTH: 33
<212> TYPE: DNA
<213> ORGANISM: Artificial Sequence
<220> FEATURE:
<223> OTHER INFORMATION: Reverse oligonucleotide/primer R3 for
      amplification of a fragment encoding aa 123-188 of IFN-alpha2a

<400> SEQUENCE: 77
tttgcggccg cttacttctt aaactttctt gca                                    33

<210> SEQ ID NO 78
<211> LENGTH: 34
<212> TYPE: DNA
<213> ORGANISM: Artificial Sequence
<220> FEATURE:
<223> OTHER INFORMATION: Forward oligonucleotide/primer 24-124-F1 for
```

-continued

```
        amplification of a fragment encoding aa 24-124 of IFN-alpha2a

<400> SEQUENCE: 78
tttgggatcc tctgtgatct gcctcaaacc caca                                34

<210> SEQ ID NO 79
<211> LENGTH: 35
<212> TYPE: DNA
<213> ORGANISM: Artificial Sequence
<220> FEATURE:
<223> OTHER INFORMATION: Reverse oligonucleotide/primer 24-124-R2 for
        amplification of a fragment encoding aa 24-124 of IFN-alpha2a

<400> SEQUENCE: 79
tttgcggccg ctcactgtat cacacaggct tccag                               35

<210> SEQ ID NO 80
<211> LENGTH: 33
<212> TYPE: DNA
<213> ORGANISM: Artificial Sequence
<220> FEATURE:
<223> OTHER INFORMATION: Forward oligonucleotide/primer 67-188-F2 for
        amplification of a fragment encoding aa 67-188 of IFN-alpha2a

<400> SEQUENCE: 80
tttgggatcc tcggcaacca gttccaaaag gct                                 33

<210> SEQ ID NO 81
<211> LENGTH: 33
<212> TYPE: DNA
<213> ORGANISM: Artificial Sequence
<220> FEATURE:
<223> OTHER INFORMATION: Forward oligonucleotide/primer 67-188-F3 for
        amplification of a fragment encoding aa 67-188 of IFN-alpha2a

<400> SEQUENCE: 81
tttgcggccg cttacttctt aaactttctt gca                                 33
```

NUCLEIC ACID MOLECULES ENCODING MONOCLONAL ANTIBODIES SPECIFIC FOR IL-17F

CROSS-REFERENCE TO RELATED APPLICATIONS

This application is a divisional application of U.S. patent application Ser. No. 15/258,263, filed Sep. 7, 2016, and patented as U.S. Pat. No. 10,131,709 issued Nov. 20, 2018, which is a divisional application of U.S. patent application Ser. No. 14/369,467, filed Jun. 27, 2014, and patented as U.S. Pat. No. 9,475,872 issued on Oct. 25, 2016, which is a national stage application under 35 U.S.C. 371 and claims the benefit of PCT Application No. PCT/EP2013/050024 having an international filing date of Jan. 2, 2013, which designated the United States, which PCT application claimed the benefit of U.S. Provisional Application No. 61/580,837 filed Dec. 28, 2011, and European Application No. 11195952.4 filed Dec. 28, 2011, the disclosures of each of which are incorporated herein by reference.

REFERENCE TO SEQUENCE LISTING

This application contains a Sequence Listing submitted as an electronic text file named "WO2013098419_SequenceListing.txt", having a size in bytes of 126 KB, and created on Jun. 12, 2014. The information contained in this electronic file is hereby incorporated by reference in its entirety pursuant to 37 CFR § 1.52(e)(5).

FIELD OF THE INVENTION

The present invention generally relates to novel binding molecules of mammal, preferably human origin, particularly human monoclonal antibodies as well as fragments, derivatives and variants thereof that recognize antigens such as native endogenous proteins associated with, e.g., immune response, autoimmune disorders, inflammatory diseases, metabolic disorders, vascular function, neurodegenerative diseases or tumors. In addition, compositions comprising such binding molecules and mimics thereof, methods of screening for novel binding molecules, which may or may not be antibodies, targets and drugs useful in the treatment and diagnosis of disorders are described. Furthermore, the present invention relates to autoantibodies as agents for use in immunotherapy as well as targets in the therapeutic intervention of autoimmune and autoinflammatory disorders as well as malignancies. More specifically, the present invention relates to monoclonal autoantibodies isolated from B cells derived from subjects affected with an impaired central and/or peripheral tolerance or loss of self-tolerance typically due to a mutation in a gene involved in immune regulation.

BACKGROUND OF THE INVENTION

Inappropriate responses of the immune system may cause stressful symptoms to the involved organism. Exaggerated immune answers to foreign substances or physical states which usually do not have a significant effect on the health of an animal or human may lead to allergies with symptoms ranging from mild reactions, such as skin irritations to life-threatening situations such as an anaphylactic shock or various types of vasculitis. Immune answers to endogenous antigens may cause autoimmune disorders such as systemic lupus erythematosus, idiopathic autoimmune hemolytic anemia, pernicious anemia, type 1 diabetes mellitus, blistering skin diseases and different kinds of arthritis.

Immune responses occur in a coordinated manner, involving several cells and requiring communication by signaling molecules such as cytokines between the cells involved. This communication may be influenced or inhibited by, e.g., interception of the signals or block of the respective receptors.

Cytokines are secreted soluble proteins, peptides and glycoproteins acting as humoral regulators at nano- to picomolar concentrations behaving like classical hormones in that they act at a systemic level and which, either under normal or pathological conditions, modulate the functional activities of individual cells and tissues. Cytokines differ from hormones in that they are not produced by specialized cells organized in specialized glands, i.e. there is not a single organ or cellular source for these mediators as they are expressed by virtually all cells involved in innate and adaptive immunity such as epithelial cells, macrophages, dendritic cells (DC), natural killer (NK) cells and especially by T cells, prominent among which are T helper (Th) lymphocytes. At this time, Th1, Th2, Th17 and iTreg T-cell subclasses have been defined depending on the specific spectrum of cytokines expressed, and respective immunological responses modulated by them.

In this respect, principal cytokine products of Th1-cells are IFN-gamma, lymphotoxin-alpha and Interleukin 2 (IL-2). Th1-cells mediate immune responses against intracellular pathogens and are responsible for some autoimmune diseases (Mosmann et al., *Annu. Rev. Immunol.* 7 (1989), 145-173, Paul and Seder, *Cell* 76 (1994), 241-251). Th2-cells produce primarily IL-4, IL-5, IL-9, IL-10, IL-13. IL-25 and amphiregulin. Th2-cells mediate immune responses against extracellular parasites, and are involved in autoimmunity and allergies such as asthma, Type 1 diabetes mellitus, Multiple sclerosis (MS) and Rheumatoid arthritis (RA); see, e.g., Mosmann et al. (1989) and Paul and Seder, (1994), supra.

Some lymphocytes, such as subsets of gamma delta T cells and Natural Killer T (NKT) cells produce both Th1 and Th2 cytokines. Principal products of induced regulatory (iTreg) cells are IL-10, IL-35 and TGF-beta. The iTreg cells are involved in immune tolerance, lymphocyte homeostasis and regulation of immune responses.

Principal cytokine products of Th17-cells are IL-17 and IL-22; Th17-cells mediate immune responses against extracellular bacteria and funghi and are also involved in the mediation of inflammation and in autoimmune diseases such as psoriasis (Zhu and Paul, *Blood* 112 (2008), 1557-1569; Shevach, *Immunity* 25 (2006), 195-201). This spectrum of cytokine production pathophysiological activities is closely paralleled by subsets of gamma delta T cells.

Depending on their respective functions, cytokines may be classified into three functional categories: regulating innate immune responses, regulating adaptive immune responses and stimulating hematopoiesis. Due to their pleiotropic activities within said three categories, e.g., concerning cell activation, proliferation, differentiation, recruitment, or other physiological responses, e.g., secretion of proteins characteristic for inflammation by target cells, disturbances of the cell signaling mediated by aberrantly regulated cytokine production have been found as a cause of many disorders associated with defective immune response, for example, inflammation and cancer. Central in inflammation and autoimmune diseases are cytokines IL-17A and IL-17F, IL-22, IL-12, IL-23 and subtypes of the IFN-alpha and IFN-omega. Except IL-12, IL-23 and IFNs, said cytokines are expressed by the effector T-cell subset Th17 which have well-described roles in several autoimmune and allergic disorders and in tumour immunology.

Unregulated Th17 responses are associated with chronic inflammation and severe immunopathologic conditions. Studies on animal models and tissues of affected patients have confirmed the involvement of the Th17 pathway in chronic inflammatory diseases such as Acne vulgaris; Arthritis such as Gouty arthritis, Systemic lupus erythematosus (SLE), Osteoarthritis, Psoriatic arthritis, Rheumatoid arthritis (RA); Asthma; Celiac disease; Crohn's disease (CD); Chronic prostatitis; Dermatitis (e.g., atopic dermatitis); Diabetes mellitus Type 1: Glomerulonephritis; Hypersensitivities: Myocarditis; Multiple sclerosis: Inflammatory bowel diseases; Pelvic inflammatory disease; Polymyositis: Psoriasis (PS); Sarcoidosis: Vasculitis: Interstitial cystitis or in inflammation occuring due to reperfusion injury or transplant rejection. IL-17A induces the production of proinflammatory cytokines, chemokines, and matrix metalloproteins. This provokes inflammatory cell infiltration and destruction of extracellular matrix. In addition to IL-17A, the related cytokine IL-17F, that can heterodimerize with IL-17A, has recently been implicated in the pathogenesis of RA and CD.

IL-22, a third Th-17 related cytokine (Zenewicz and Flavell, *Eur. J. Immunol.* 38 (2008), 3265-3268) is a cytokine that acts mainly on epithelial cells. In the skin, it mediates keratinocyte proliferation and epidermal hyperplasia and plays a central role in inflammatory diseases, such as psoriasis. IL-22 is a signature product of Th17 cells, also secreted at functionally significant levels by other immune cells, especially NKp44/NKp46-expressing natural killer (NK) cells and lymphoid tissue inducer cells after IL-23 stimulation. Interleukin-22 (IL-22) is a member of the IL-10 family of anti-inflammatory cytokines that mediates epithelial immunity. IL-22 expression is enhanced in inflamed colon mucosa in individuals with inflammatory bowel disease. Importantly, IL-22 does not serve the communication between immune cells. It mainly acts on epithelial cells and e.g. hepatocytes, where it favors the antimicrobial defense, regeneration, and protection against damage and induces acute phase reactants and some chemokines (Wolk et al., *Semin. Immunopathol.* 32 (2010), 17-31).

IL-23 is a key cytokine in promotion of chronic inflammation, secreted by activated inflammatory cells like macrophages and dendritic cells (see for review Langrish et al., *Immunological Reviews* 202 (2004), 96-105: Ferraccioli and Zizzo, *Discov. Med.* 60 (2011), 413-24; further Langrish et al., *J. Exp. Med.* 201 (2005), 233-40: Vaknin-Dembinsky et al., *J. Neuroimmunol.* 195 (2008), 140-145: Melis et al., *Ann. Rheum. Dis.* 69 (2010), 618-23). Initially, IL-23 was found to have a role in supporting the expansion and maintenance of Th17 cells (Aggarwal et al., *J. Biol. Chem.* 278 (2003), 1910-1914; Weaver et al., *Annu. Rev. Immunol.* 25 (2007), 821-852). However, it was shown as having multiple effects on the immune response, including restraining the activity (intestinal accumulation) of Foxp3-positive regulatory T-cells (Barnes and Powrie, *Immunity* 31 (2009), 401-411; Izcue et al., *Immunity* 28 (2008), 559-570: Ahern. *Immunity* 33 (2010), 279-88) and inducing the expression of Th17-type cytokines from non-T-cell sources (Buonocore et al., *Nature* 464 (2010), 1371-1375; Morrison et al., *Immunology* 133 (2011), 397-408). It contributes to inflammation, e.g., in psoriasis and inflammatory bowel diseases (see publications supra and Duvallet et al., *Ann. Med* 43 (2011), 503-511). IL-23 is composed of two subunits, p19 and p40; the latter subunit is shared with IL-12.

IL-17A, IL-22, oncostatin M, TNF-alpha, and IL-1alpha are potent cytokines produced by skin infiltrating immune cells and/or keratinocytes and they induce cutaneous inflammation (Boniface et al., *J. Immunol.* 178 (2007), 4615-4622; Nograles et al., *Br. J. Dermatol.* 159 (2008), 1092-1102; Guilloteau et al., *J. Immunol.* 184 (2010), 5263-5270).

Recent therapeutic approaches for chronic inflammatory diseases such as severe RA and PS involve blockage of tumor necrosis factor-α (TNF-α). While this method is highly effective in some cases, many patients are 'non-responders.' Furthermore, a sustained neutralization of TNF-α can enhance susceptibility to microbial infections, highlighting the need for alternative and more specific therapeutic approaches. So far, modulation of Th-17 cell function and/or differentiation has been most successful with monoclonal antibodies to IL-12 p40, which target both IL-12 (a heterodimer of p35 and p40) and IL-23 (a heterodimer of p19 and p40, a growth factor for Th17 cells). Such antibodies, ustekinumab and ABT-874 that target IL-12 p40, have been successful in moderate to severe chronic plaque psoriasis and CD (Miossec et al., *N. Engl. J. Med.* 361 (2009), 888-898, Steinman, *Nat. Immunol.* 11 (2010), 41-44).

The most feasible way to control the biologic effects of Th17 cells and cells with related properties, e.g., IL-17-producing gamma delta T cells, would be to target them and a selection of the effector cytokines they produce. This novel approach would enable a blockage of IL-22 in PS, and of IL-17A (and IL-17F) in RA and CD, leaving the other non-pathogenic arms intact for fighting pathogens and, in the case of IL-22, for exerting its tissue reparative and antimicrobial functions. Also, in some initial responders, the efficacy of the anti-TNF therapy drug wanes over time. Thus, severe cases not responding to monotherapy might require combination therapy with two or more biological drugs. Monoclonal antibodies against IL-17A have been developed for clinical application. Phase 2 trials of a monoclonal antibody against IL-17A (AIN457) for PS, CD and psoriatic arthritis are under way. So far, inhibitors of IL-22 have been tested only in pre-clinical models of autoimmune diseases (Miossec et al., *N. Engl. J. Med.* 361 (2009), 888-898, Steinman, *Nat. Immunol.* 11 (2010), 41-44).

Due to immunological responses to foreign antibodies, as mouse antibodies in humans (HAMA-response: Schroff et al., *Cancer Res.* 45 (1985), 879-885: Shawler et al., *J. Immunol.* 135 (1985), 1530-1535), mostly humanized versions of antibodies are used in present therapeutic approaches (Chan et Carter, *Nature Reviews Immunology* 10 (2010), 301-316; Nelson et al., *Nature Reviews Drug Discovery* 9 (2010), 767-774). One approach to gain such antibodies was to transplant the complementarity determining regions (CDR) into a completely human framework, a process known as antibody humanization (Jones et al., *Nature* 321 (1986), 522-525). This approach is often complicated by the fact that mouse CDR do not easily transfer to a human variable domain framework, resulting in lower affinity of the humanized antibody over their parental murine antibody. Therefore, additional and elaborate mutagenesis experiments are often required, to increase the affinity of the so engineered antibodies. Another approach for achieving humanized antibodies is to immunize mice which have had their innate antibody genes replaced with human antibody genes and to isolate the antibodies produced by these animals. However, this method still requires immunization with an antigen, which is not possible with all antigens because of the toxicity of some of them. Furthermore, this method is limited to the production of transgenic mice of a specific strain.

Another method is to use libraries of human antibodies, such as phage display, as described, for example, for the generation of IL-13 specific antibodies in international application WO 2005/007699. Here, bacteriophages are engineered to display human scFviFab fragments on their surface by inserting a human antibody gene into the phage population. Unfortunately, there is a number of disadvantages of this method as well, including size limitation of the protein sequence for polyvalent display, the requirement of secretion of the proteins, i.e. antibody scFv/Fab fragments, from bacteria, the size limits of the library, limited number of possible antibodies produced and tested, a reduced proportion of antibodies with somatic hypermutations produced by natural immunisation and that all phage-encoded proteins are fusion proteins, which may limit the activity or accessibility for the binding of some proteins. Similarly, European patent application EP 0 616 640 A1 describes the production of auto-antibodies from antibody segment repertoires displayed on phage. Phage libraries are generated from unimmunized humans in this respect (see, e.g., Example 1: page 16, lines 43-51; Example 2, at page 17, paragraph [0158], lines 57-58). However, also the methods described in this patent application suffer from above mentioned general disadvantages of antibodies generated from phage libraries, in comparison to antibodies produced and matured in a mammalian, i.e. human body.

In view of the above, there is still a need for additional and new compounds like binding molecules of high specificity which are tolerable in humans either for monotherapy or combinatorial approaches.

The solution to this problem is provided by the embodiments of the present invention as characterized in the claims and disclosed in the description and illustrated in the Examples further below.

SUMMARY OF THE INVENTION

The present invention generally relates to means and methods for isolating autoantigen binding molecules, i.e. antibodies from mammals, in particular humans, which are affected with an impaired central and/or peripheral tolerance or loss of self-tolerance which may be due to or associated with a disrupted or deregulated genesis of self-tolerance, preferably caused by a monogenic autoimmune disorder. Examples of mammals which provide a particularly suitable source for autoantibodies in accordance with the present invention are mammals, e.g., humans having a disorder associated with a mutation in the AIRE (Autoimmune Regulator) gene such as Autoimmune polyendocrinopathy syndrome type 1 (APS1) (Peterson et al., Nat. Rev. Immunol. 8 (2008), 948-957).

The present invention is generally based on the surprising findings that patients with Autoimmune polyendocrinopathy syndrome type 1 (APS1) provide a source for monoclonal autoantibodies to proteins which alone or in combination are responsible for and/or associated with autoimmune or autoinflammatory diseases in which respective cytokines or other molecules as indicated above are heavily implicated in initiation and maintenance of pathogenic immune responses, such as systemic lupus erythematosus (SLE), arthritis, Type 1 Diabetes mellitus (TIDM) or others as indicated in detail hereinabove and below. Moreover, the present invention for the first time provides a means to display and isolate the complete reservoir of monoclonal antibodies elicited in mammals, in particular humans to in principle every autoantigen, for which the present invention coined the term "AutoImmunosome" and "Mab-Auto-Immunosome", respectively, hereinafter also referred to as "MabAuto-Immunosome", "MabAutoImmunosome". "Mab-AutoImmunosome" or "MAI". Hence, by providing the "Mab-Auto-Immunosome" in accordance with the present invention, new means for the treatment of disorders associated with autoimmunity and inflammation including metabolic disorders, vascular function, neurodegenerative diseases or tumors are envisaged, as indicated in detail in respect of the seroactivity of the antibodies provided by the present invention in Tables 1 to 14, and FIGS. 1 to 4. The general concept of the present invention based on the above-described observations, i.e. the isolation of therapeutically useful human antibodies from humans who are affected with an impaired central and/or peripheral tolerance or loss of self-tolerance which may be due to or associated with a disrupted or deregulated genesis of self-tolerance could be confirmed with samples from patients with Autoimmune polyendocrinopathy syndrome type 2 (APS2) and immunodysregulation polyendocrinopathy enteropathy X-linked syndrome (IPEX); see Example 17 and Tables 29 to 31.

In one aspect, the present invention relates to high affinity neutralizing monoclonal antibodies to several cytokines. Thus, monoclonal human antibodies (mAbs, or MABs) against several cytokines, which will be described in detail below, derived from the naturally matured humoral immune response of a predetermined subject are provided by the method of the present invention, which are considered to be safe and effective therapeutics for disorders in which those cytokine are involved.

In particular, anti-IL-17F and IL-22 antibodies as well as antigen-binding fragments thereof are provided, which demonstrate the immunological binding characteristics and/or biological properties as outlined for the antibodies illustrated in the Examples. Where present, the term "immunological binding characteristics," or other binding characteristics of an antibody with an antigen, in all of its grammatical forms, refers to the specificity, affinity, cross-reactivity, and other binding characteristics of an antibody.

Naturally, the present invention extends to antibody producing cell lines and recombinant cells. The present invention further relates to pharmaceutical compositions, diagnostic assays and kits that comprise the binding molecules or peptides recognized by the antibodies isolated in accordance with the present invention and to therapeutic methods based thereon.

B: APS1 patient seroreactivity (total number of distinct proteins recognized by sera of at least one patient) against extracellular proteins that have been implicated in physiological functioning of tissues or pathophysiology of human disease.

FIG. 2: A: APS1 patient seroreactivity (as a percentage of total shown number of reactivities that have been measured in at least one patient) against extracellular proteins that have been implicated in physiological functioning of tissues. Seroreactivities are independent of those shown in FIGS. 1A and B.

B: APS1 patient seroreactivity (total number of distinct proteins recognized by sera of at least one patient) against extracellular proteins that have been implicated in physiological functioning of tissues. Seroreactivities are independent of those shown in FIGS. 1A and B.

FIG. 3: A: APS1 patient seroreactivities (as a percentage of total shown number of reactivities that have been measured in at least one patient) against extracellular proteins implicated in inflammation and autoimmunity-related pathways.

B: APS1 patient seroreactivities (total number of distinct proteins recognized by sera of at least one patient) against extracellular proteins implicated in inflammation and autoimmunity-related pathways.

Figure 4:
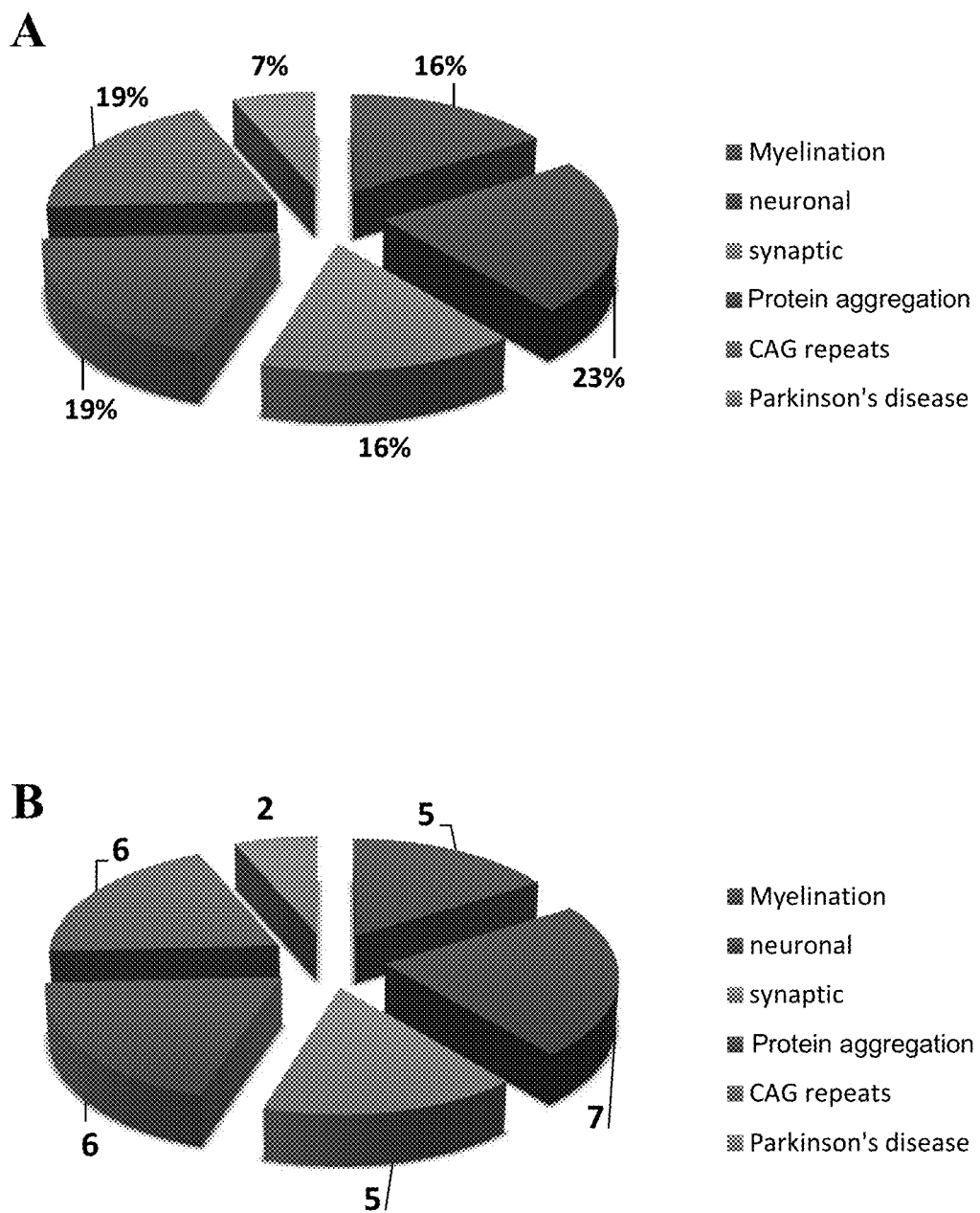

FIG. 4: A: APS1 patient seroreactivities (as a percentage of total shown number of reactivities that have been measured in at least one patient) against extracellular proteins implicated in neurodegenerative diseases.

B: APS1 patient seroreactivities (total number of distinct proteins recognized by sera of at least one patient) against extracellular proteins implicated in neurodegenerative diseases.

Figure 5:
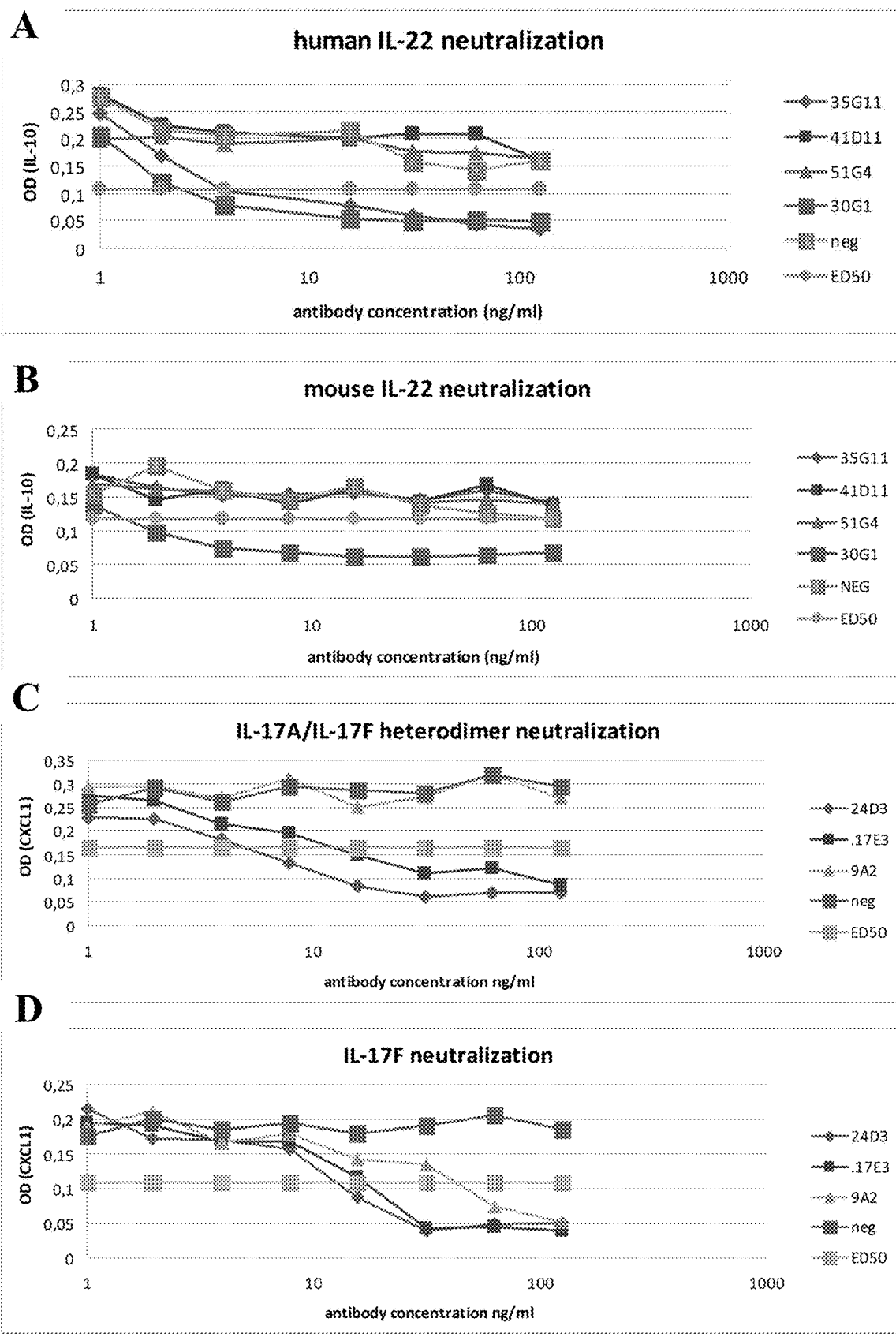

FIG. 5: In-vitro neutralizing capacities of recombinant antibodies of the present invention. A: Neutralizing capacities against human IL-22. IC50 for recombinant antibody 30G1 is 2.5 ng/ml and for 35G11 4 ng/ml using 0.5 ng/ml of IL-22. Recombinant antibodies 41D11 and 51G4 are not neutralizing at tested concentrations. B: Neutralizing capacities against mouse IL-22. IC50 for recombinant antibody 30G1 is 1.5 ng/ml using 0.3 ng/ml mouse IL-22. Recombinant antibodies 35G11, 41D11 and 51G4 are not neutralizing at tested concentrations. C: Neutralizing capacities against IL17A/IL-17F heterodimer. IC50 for recombinant antibody 24D3 is 6 ng/ml, for 17E3 12 ng/ml using 10 ng/ml IL17A/IL-17F heterodimer. Recombinant antibody 9A2 is not neutralizing at tested concentrations. D: Neutralizing capacities against IL17F. IC50 for recombinant antibody 24D3 is 12 ng/ml, for 17E3 15 ng/ml and for 9A2 45 ng/ml using 10 ng/ml IL17F.

Figure 6:
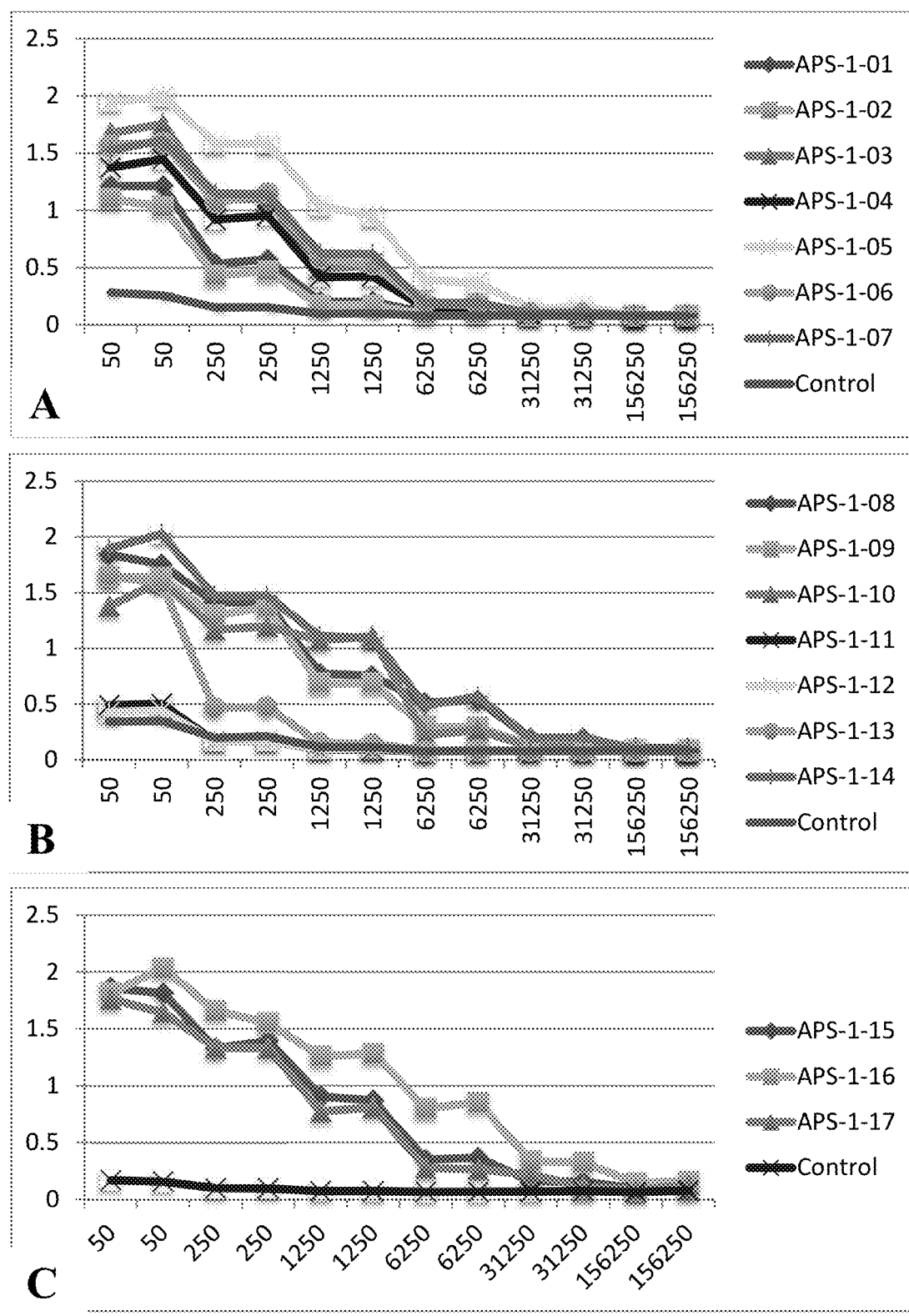

FIG. 6: Antibody response against IFN-alpha1 in APS1 patients (A: APS-patients 1-01 to 1-07, B: patients 1-08 to 1-14, C: patients 1-15 to 1-17). Test sera obtained from patients suffering from the genetic condition APS1/APECED were tested for presence of IFN-alpha 1 antibodies in an ELISA-assay at different dilutions ranging from 1:50 to 1:156250, as indicated at the X-axis. Control serum was obtained from healthy laboratory personnel, age matched with the patients. Y-axis indicates OD values.

Figure 7:
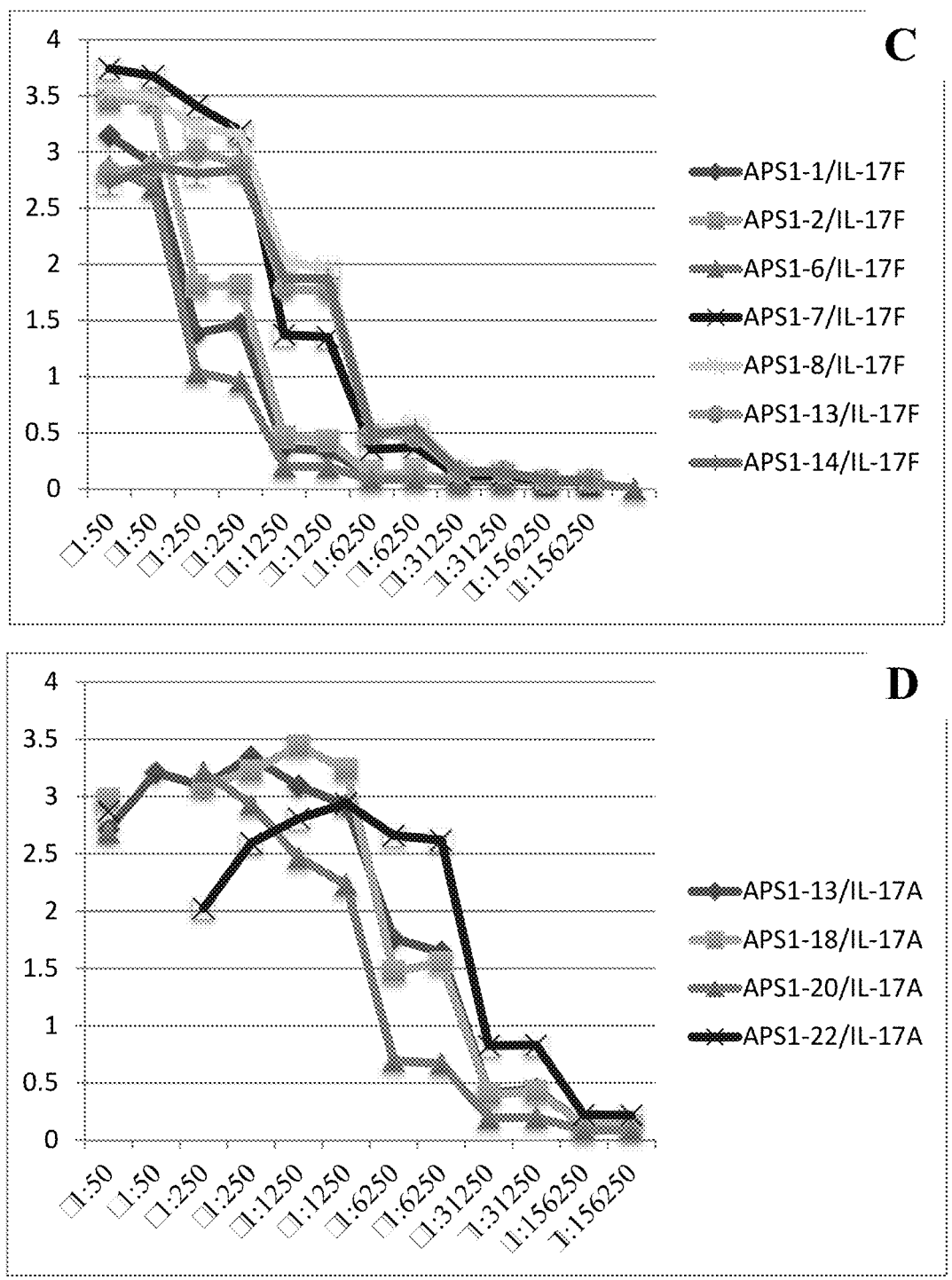
Figure 7:
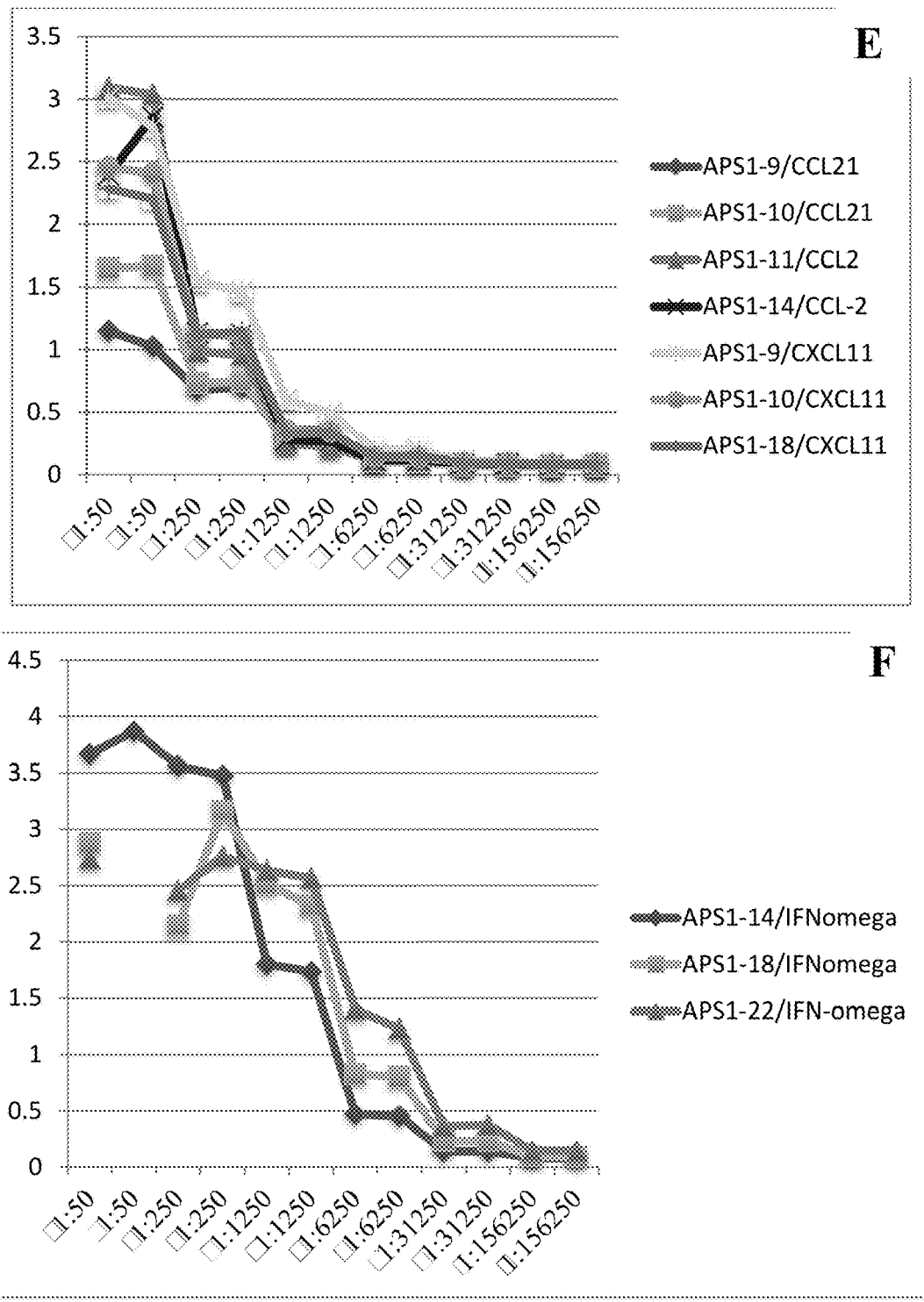
Figure 7:
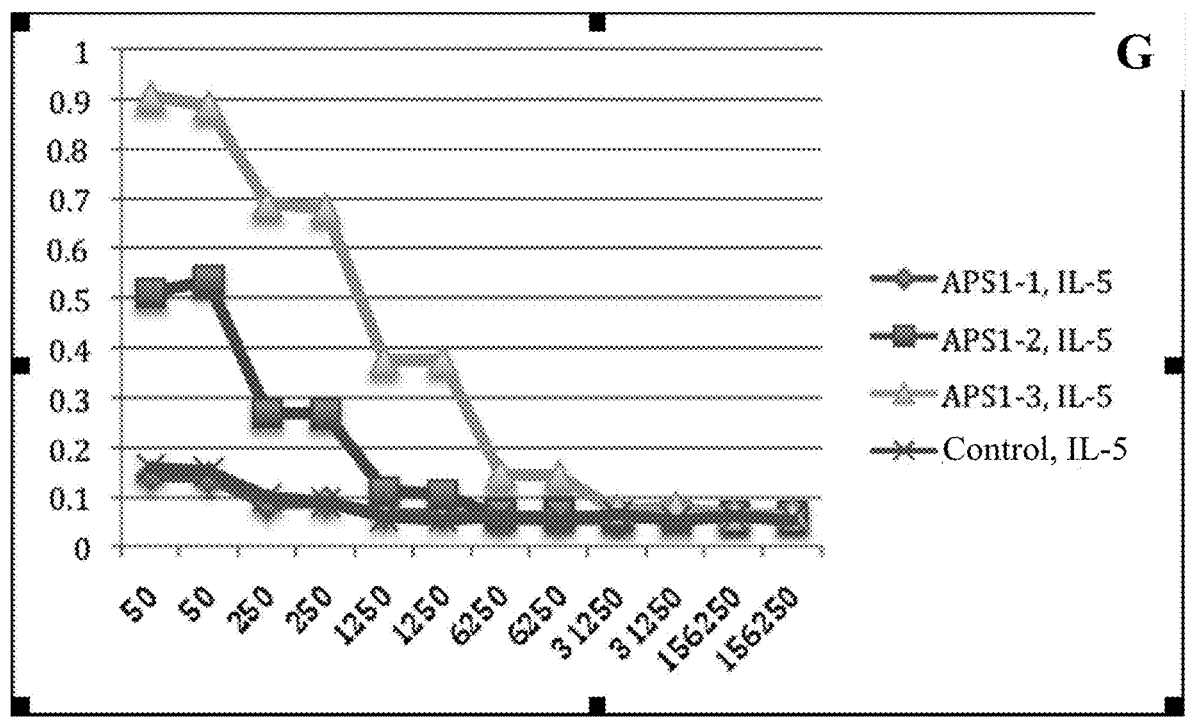

FIG. 7: ELISA titration of sera isolated from selected APS1 patients to Interferon alpha 1b (IFNa1b) and CCL2 (A); IFNa2b (B); IL-17F (C); IL-17A (D); chemokine (C-C motif) ligand 21 (CCL21), CCL2 and chemokine (C-X-C motif) ligand 11 (CXCL11) (E); IFN-omega (F) and IL-5 (G). X-axis indicates dilutions of the test sera and Y-axis OD values.

Figure 8:
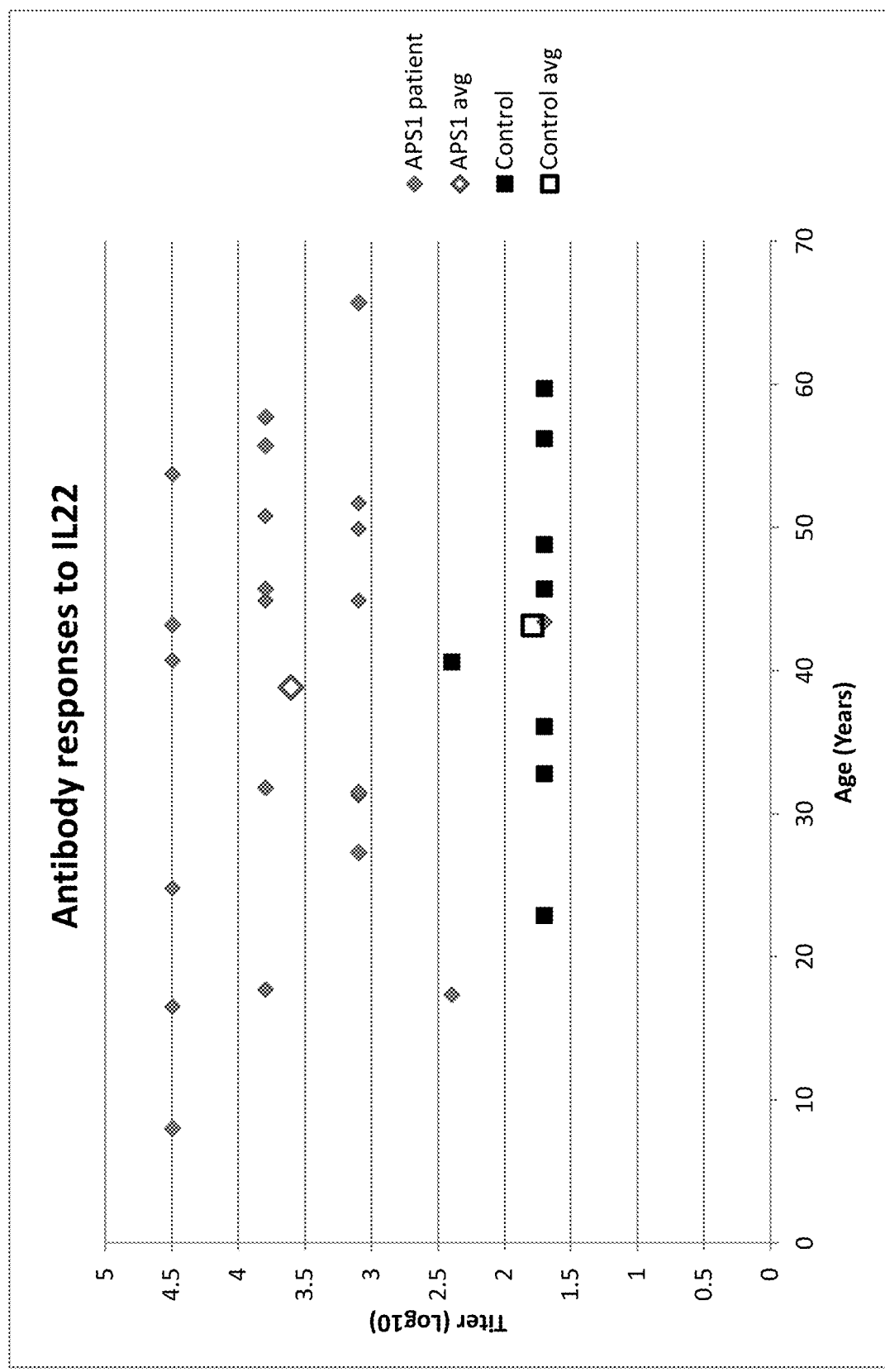

FIG. 8: ELISA titers of sera isolated from APS1 patients (APS1-1 to APS1-22: filled diamonds) and controls (healthy subjects: C1 to C8: filled squares) against IL-22. X-axis shows the age of the subject and Y-axis the titer seen on a LOG 10 scale. The large open diamond and open square shows the mean titer in the two subject groups. Note that the median age of the controls and patients are similar, but titers in patients are approximately 100 times higher that in controls. The age of each individual is indicated on the X-axis and the titer (LOG 10 scale) on the Y-axis.

Figure 9:
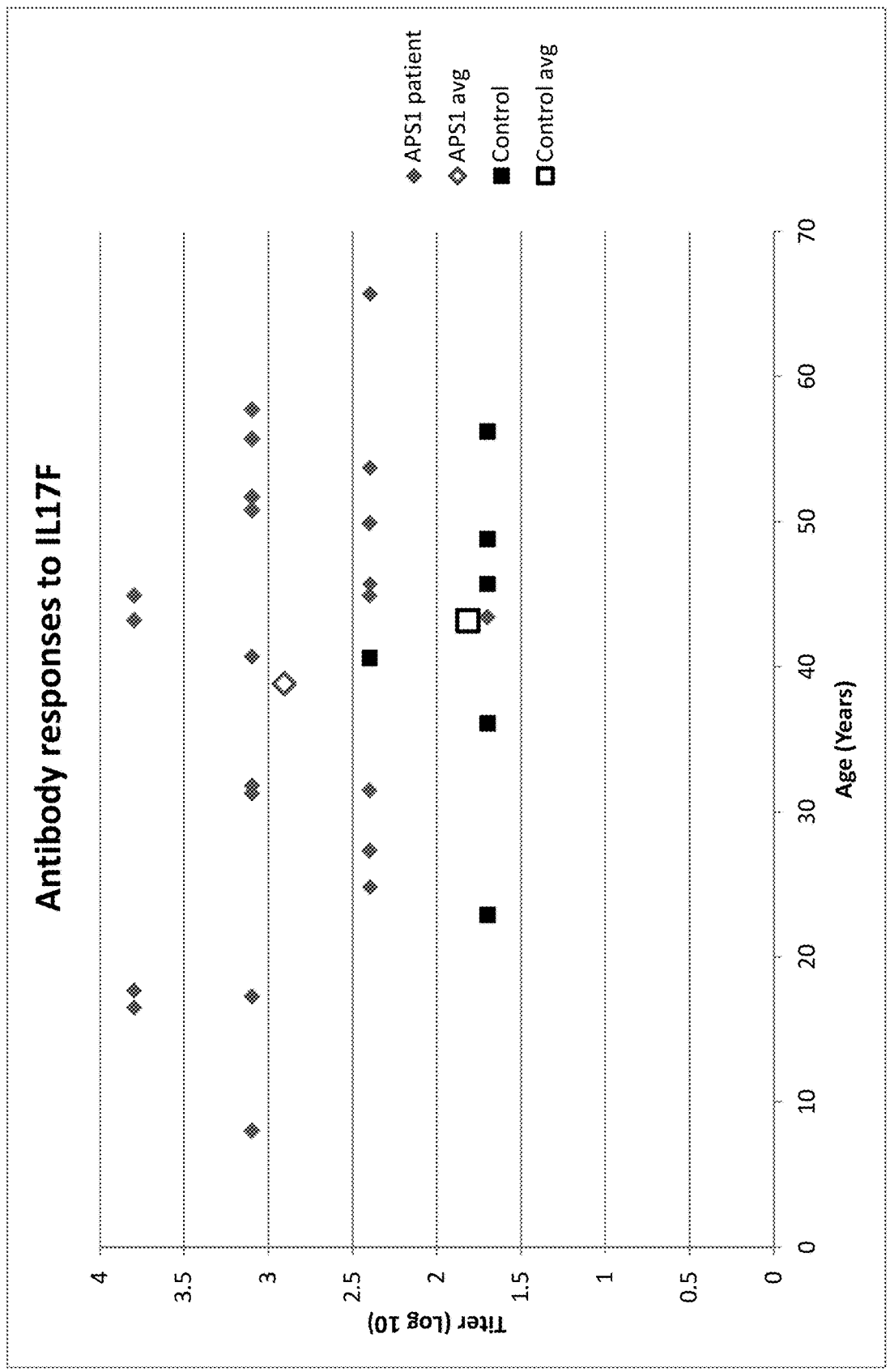

FIG. 9: ELISA titers of sera isolated from APS1 patients (APS1-1 to APS1-22: filled diamonds) and controls (healthy subjects; C1 to C6; filled squares) against IL-17F. X-axis shows the age of the subject and Y-axis the titer (LOG 10 scale) seen. The large open square and open diamond shows the mean titer in the two subject groups. Note that the median age of the controls and patients are similar, but titers in patients are approximately 20 times higher than in controls.

Figure 10:
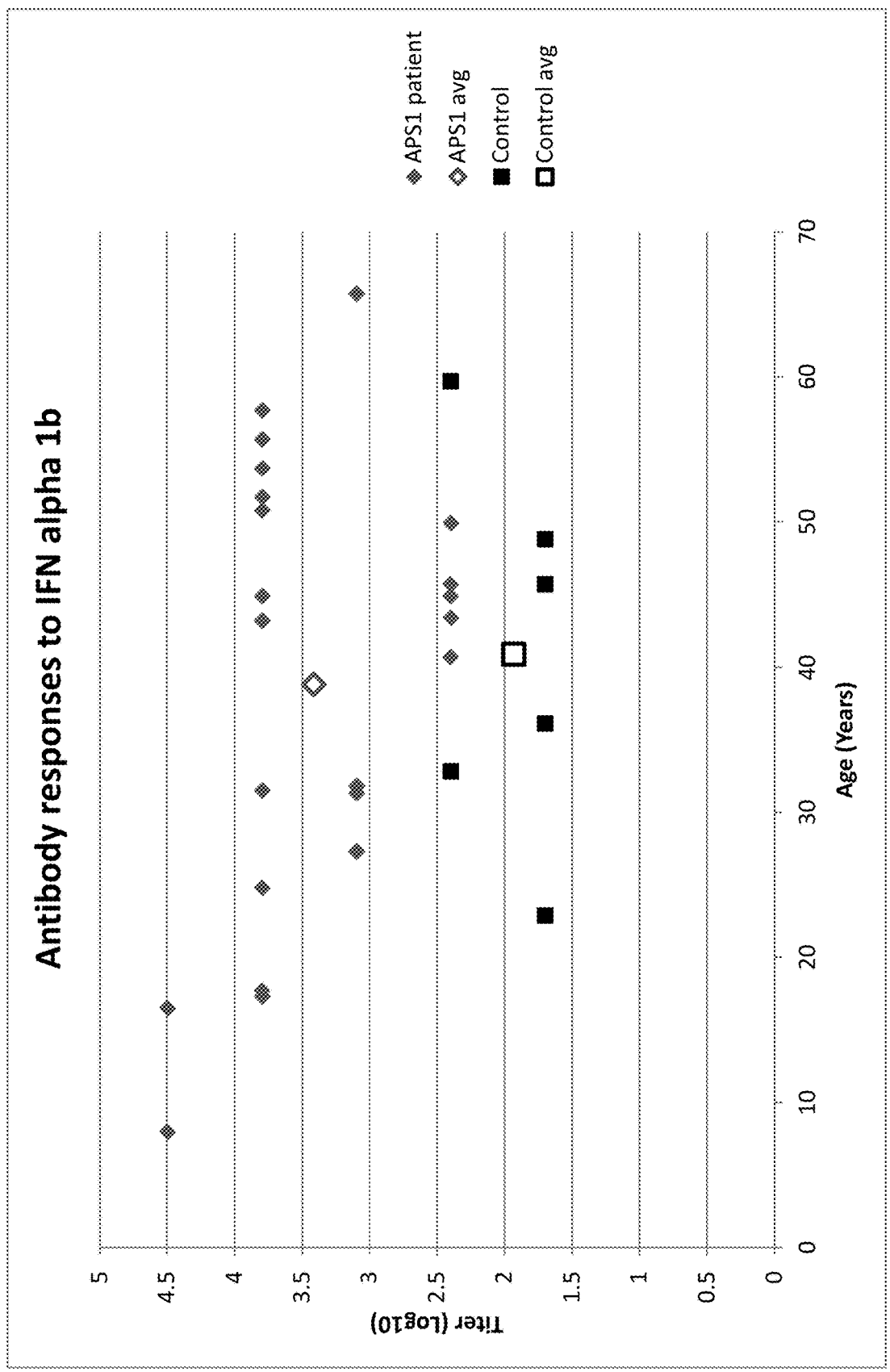

FIG. 10: ELISA titers of sera isolated from APS1 patients (APS1-1 to APS1-22; filled diamonds) and controls (healthy subjects; C1 to C6; filled squares) against IFN-alpha1b. X-axis shows the age of the subject and Y-axis (LOG 10 scale) the titer seen. The large open diamond and open square shows the mean titer in the two subject groups. Note that the median age of the controls and patients are similar, but titers in patients are approximately 100 times higher that in controls.

Figure 11:
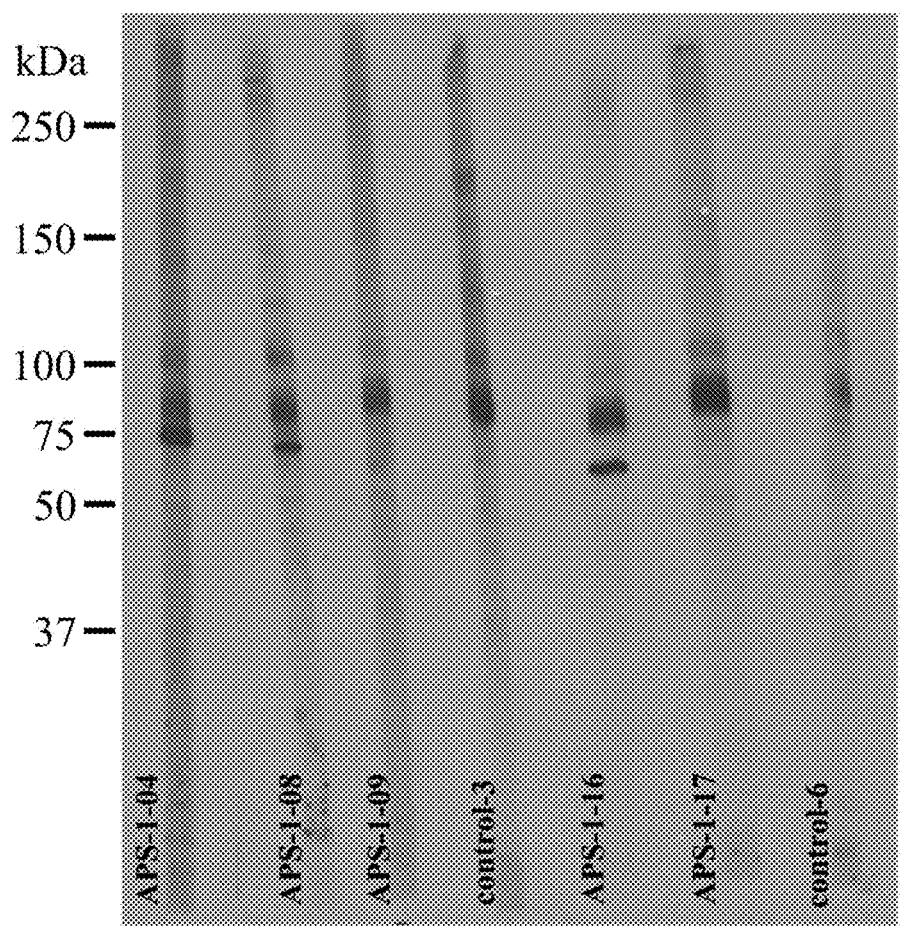

FIG. 11: Western blot reaction against normal adenoid tissue with a serum from an APS1/APECED patient indicating the presence of several antigens recognized by the APS1 serum.

Figure 12:
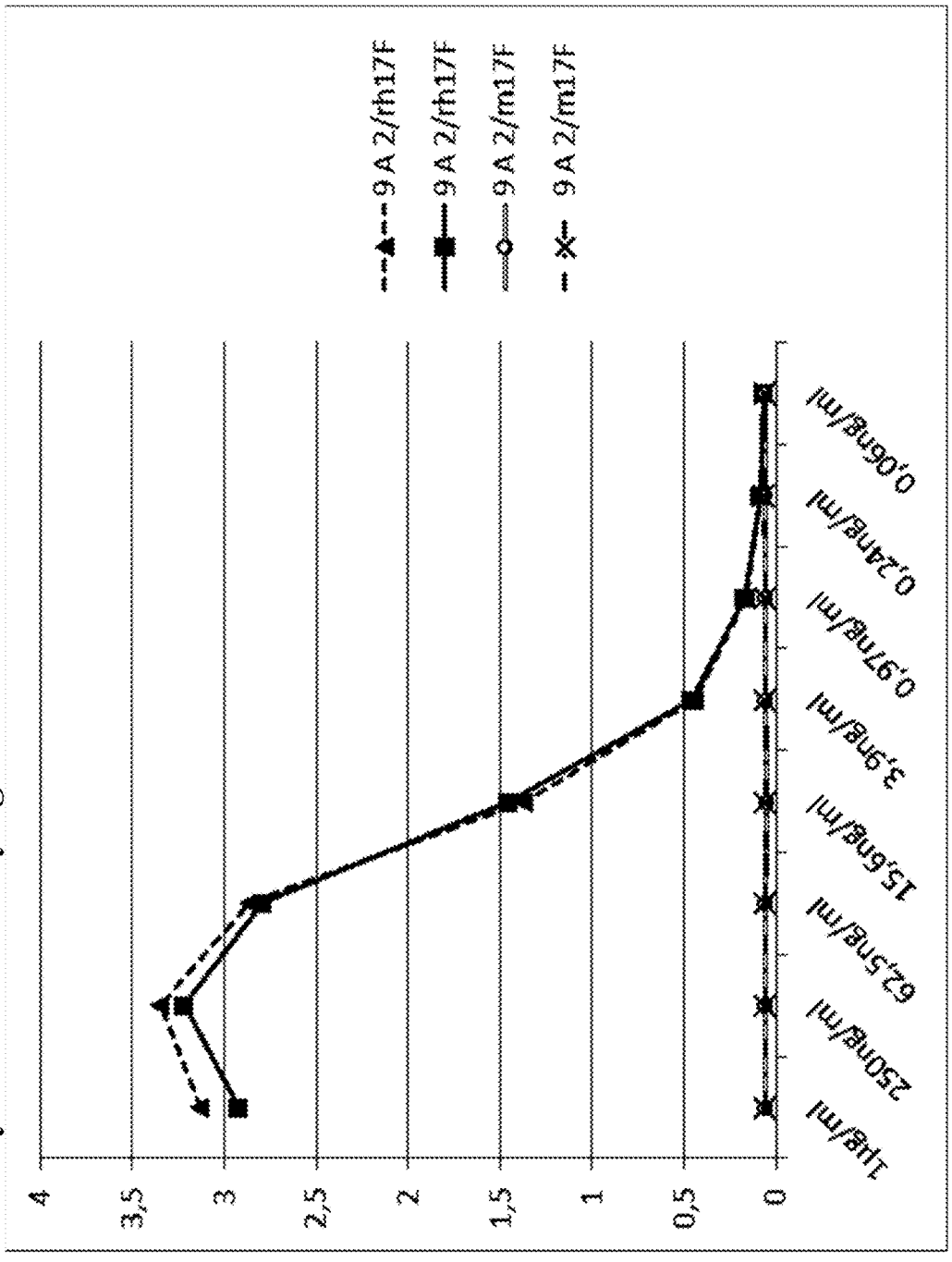

FIG. 12: Reactivity of 9A2 antibody against recombinant human and murine IL17F. Very strong preference in reactivity of 9A2 antibody towards human IL17F can be observed.

Figure 13:
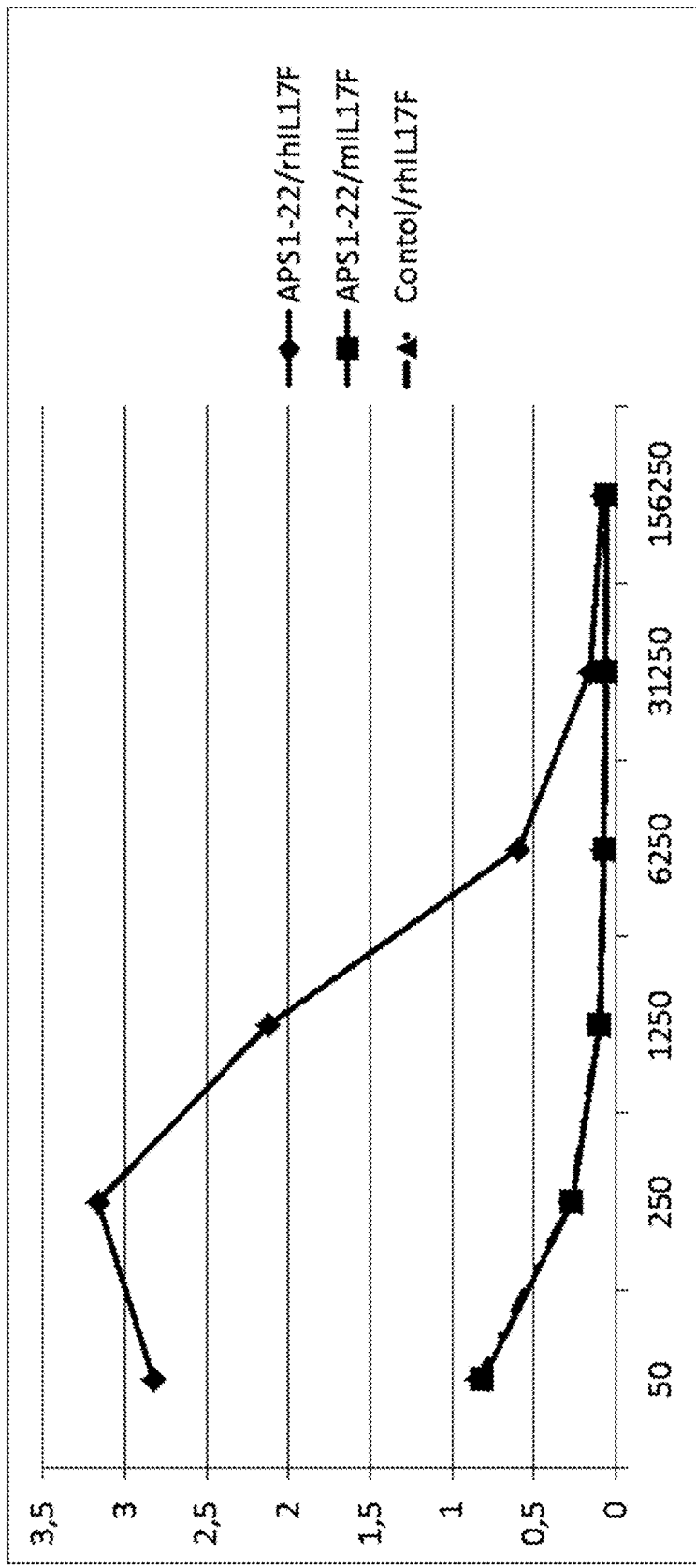

FIG. 13: Cross reactivity of APS1-22 serum against recombinant human and murine IL17F. There is no cross-reactivity to the murine antigen.

Figure 14:
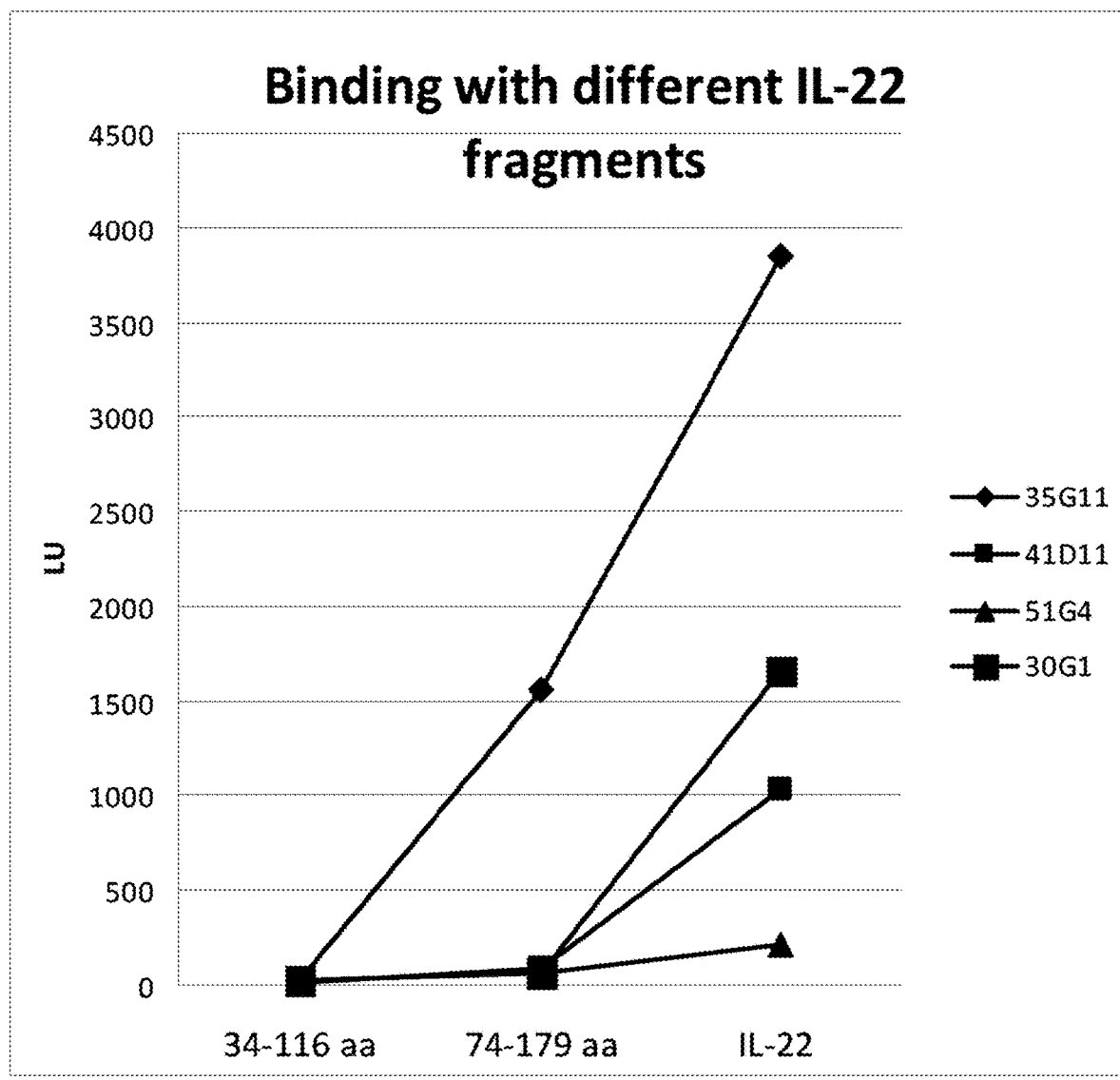

FIG. 14: Full-length IL-22 (34-179 aa), N-terminally truncated (74-179 aa) or C-terminally truncated (34-116 aa) IL-22 sequences were cloned into fusion with firefly luciferase at its C-terminus using pPK-CMV-F4 (PromoCell GmbH, Heidelberg; Germany) mammalian expression vector. After transfection into HEK 293 cells, crude protein extracts were used as antigen in immunoprecipitation assay. The figure shows that the recombinant antibodies specific for IL-22 are binding the full-length IL-22 most efficiently indicating to the predominance of conformational epitopes. LU-light units.

FIG. 15: Amino acid sequences of the variable region, i.e. heavy chain and kappa/lambda light chain (VH, VL) of IL-17A, IL17F or IL-22 specific human antibodies of the present invention. A: IL-17F specific antibody 9A2: IgG1, kappa (VH3; Glm17; VK1, Km3). B: IL-17F and IL-17A specific antibody 17E3: IgG1, kappa (VH1, Glm17; VK1, Km3). C: IL-17F specific antibody 24D3: IgG1, lambda (VH3, Glm17; VL3). D: IL-22 specific antibody 30G1: IgG1, kappa (VH3, Glm17; VK3, Km3 or Km1, 2). E: IL-22 specific antibody 35G11: IgG4, lambda (VH7, IGHG4*01: VL1), F: IL-22 specific antibody 41D11: IgG1, lambda (VH4. Glm3 L410F; VL4) and G: IL-22 specific antibody 51G4: IgG2, lambda (VH1, IGHG2*01; VL3). Framework (FR) and complementarity determining regions (CDRs) are indicated with the CDRs being underlined. Due to the cloning strategy the amino acid sequence at the N-terminus of the heavy chain and light chain may potentially contain primer-induced alterations in FRI, which however do not substantially affect the biological activity of the antibody. In order to provide a consensus human antibody, the nucleotide and amino acid sequences of the original clone are aligned with and tuned in accordance with the pertinent human germ line variable region sequences in the database; see, e.g., Vbase (http://vbase.mrc-cpe.cam.ac.uk) hosted by the MRC Centre for Protein Engineering (Cambridge, UK).

Figure 17:
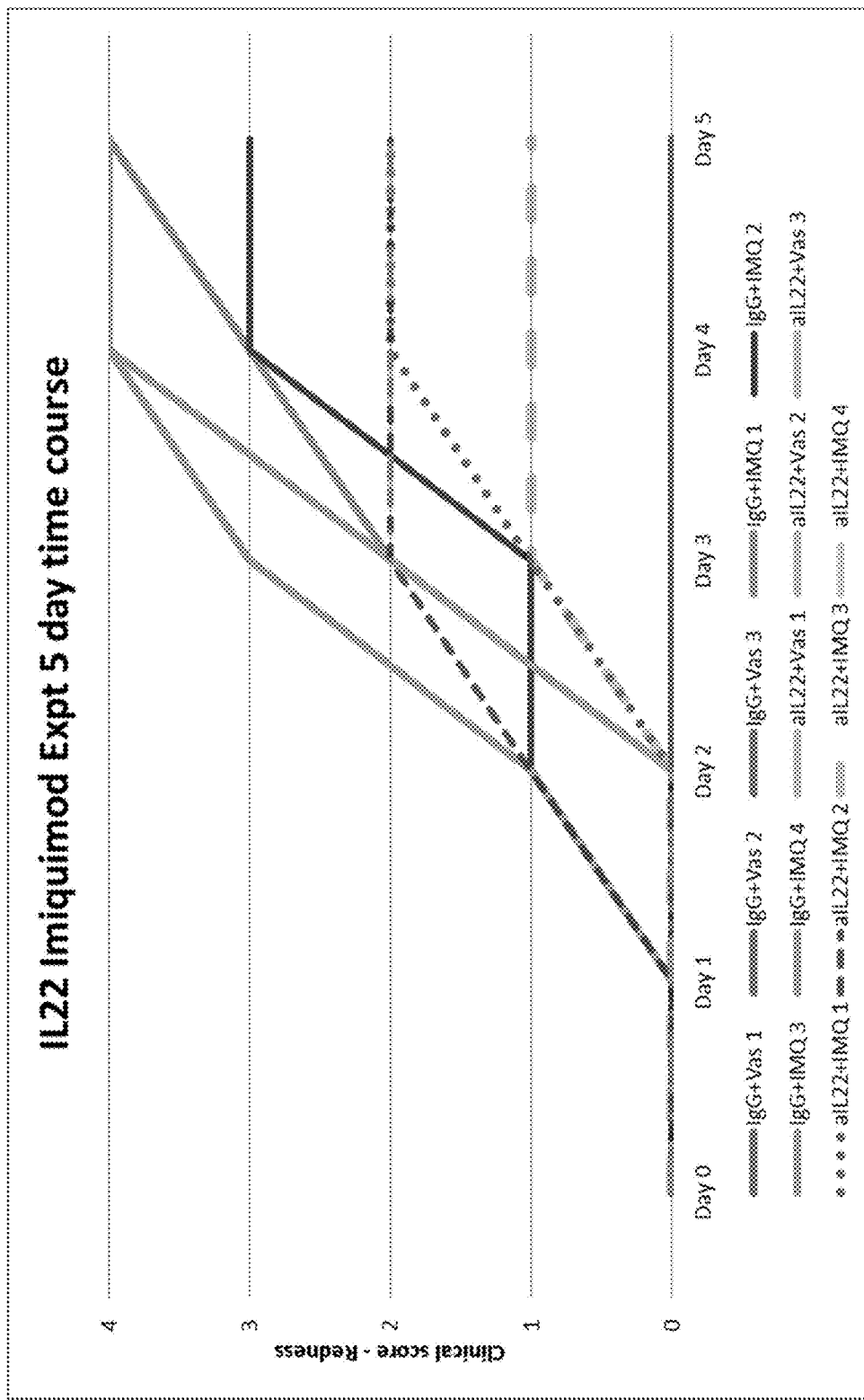

FIG. 16: Anti-IL22+Imiquimod psoriasiform lesion in vivo study. Experimental protocol and timeline of anti-IL22 antibody and imiquimod (IMQ) treatment of C57BL/6J mice. Age at shaving 9 weeks, Non-treated control DOB: at 10 weeks. A: Tables indicating the treatment composition of the four animal groups. B: Amounts of the control and anti-IL22 antibody applied to the animals. C: Experimental timeline. Vas=Vaseline FIG. 17: Redness clinical scores in C57BL/6J mice over 5 day time course (blind scored on scale 0-4). Graph form of scores—solid lines (red/pink) are IgG+IMQ mice, dotted (blue) lines are anti-IL-22+IMQ, all non-IMQ treated mice score consistently 0.

Figure 18:
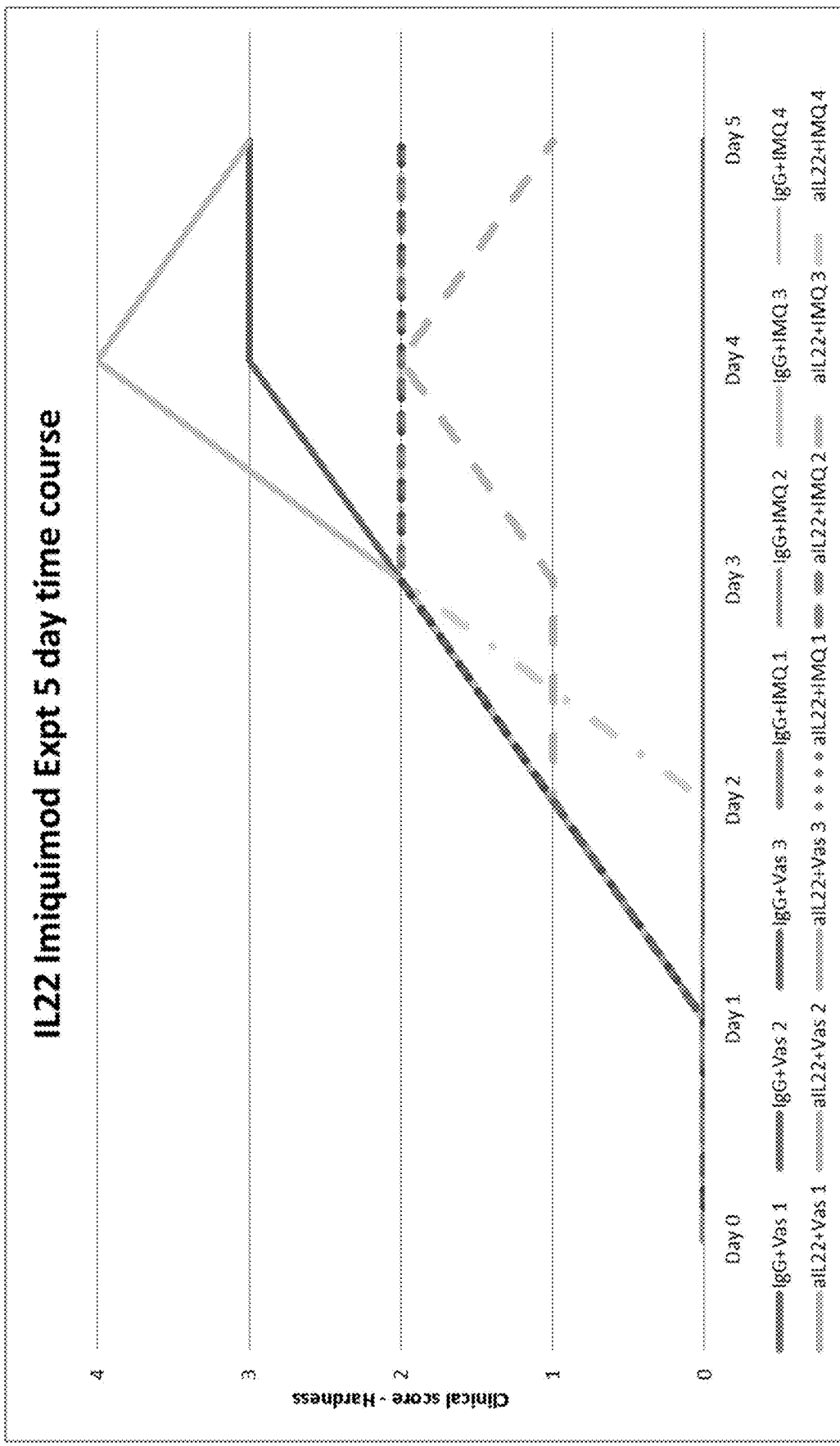

FIG. 18: Hardness clinical scores in C57BL/6J mice over 5 day time course (scored on scale 0-4). Graph form of scores—solid (red/pink) lines are IgG+IMQ mice, dotted (blue) lines are anti-IL-22+IMQ, all non-IMQ treated mice score consistently 0

Figure 19:
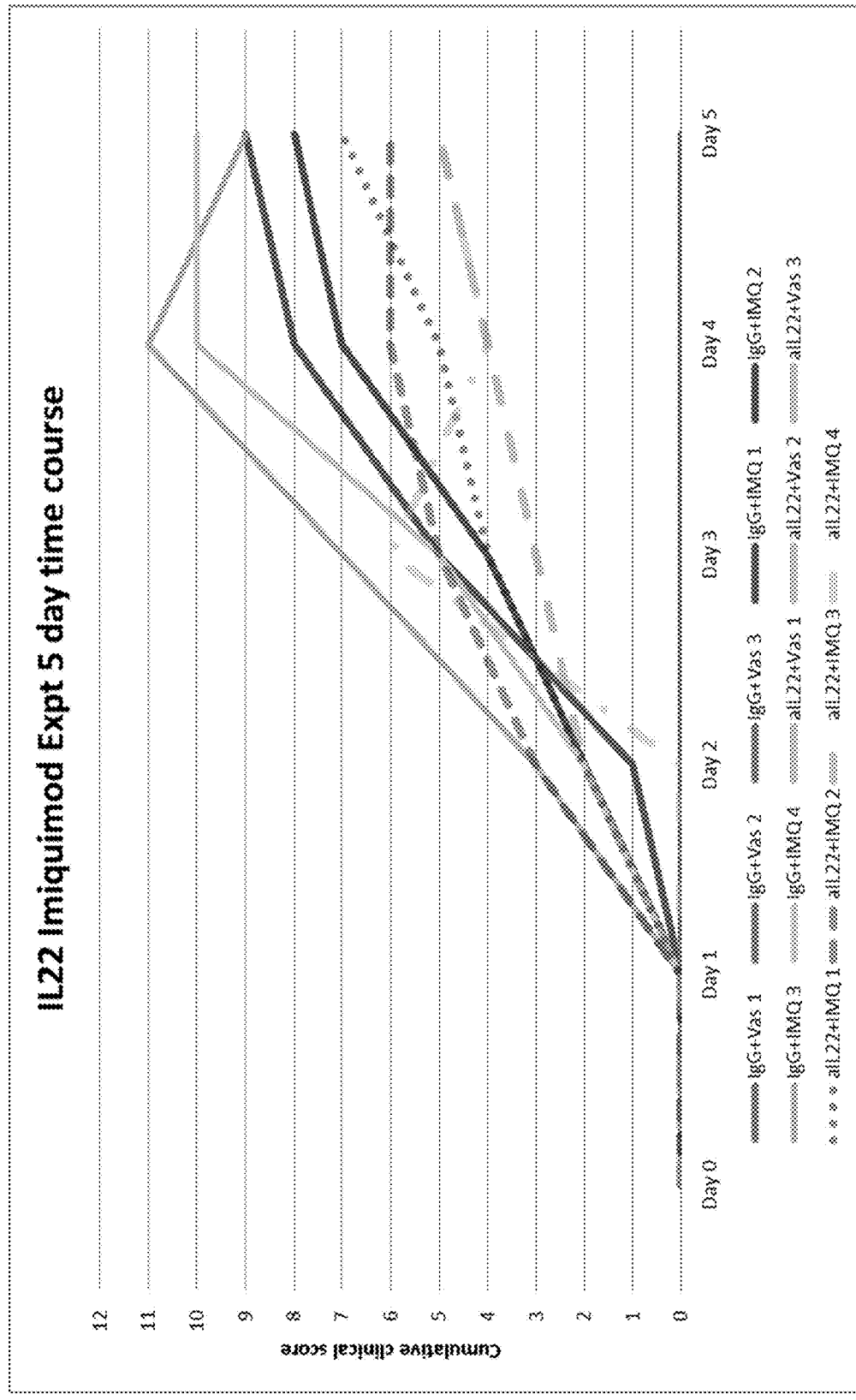

FIG. 19: Cumulative clinical scores (redness+hardness+scales) in C57BL/6J mice over 5 day time course (scored on scale 0-4, totalled). Graph form of scores—solid (red/pink) lines are IgG+IMQ mice, dotted (blue) lines are anti-IL-22+IMQ, all non-IMQ treated mice score consistently 0

Figure 20:
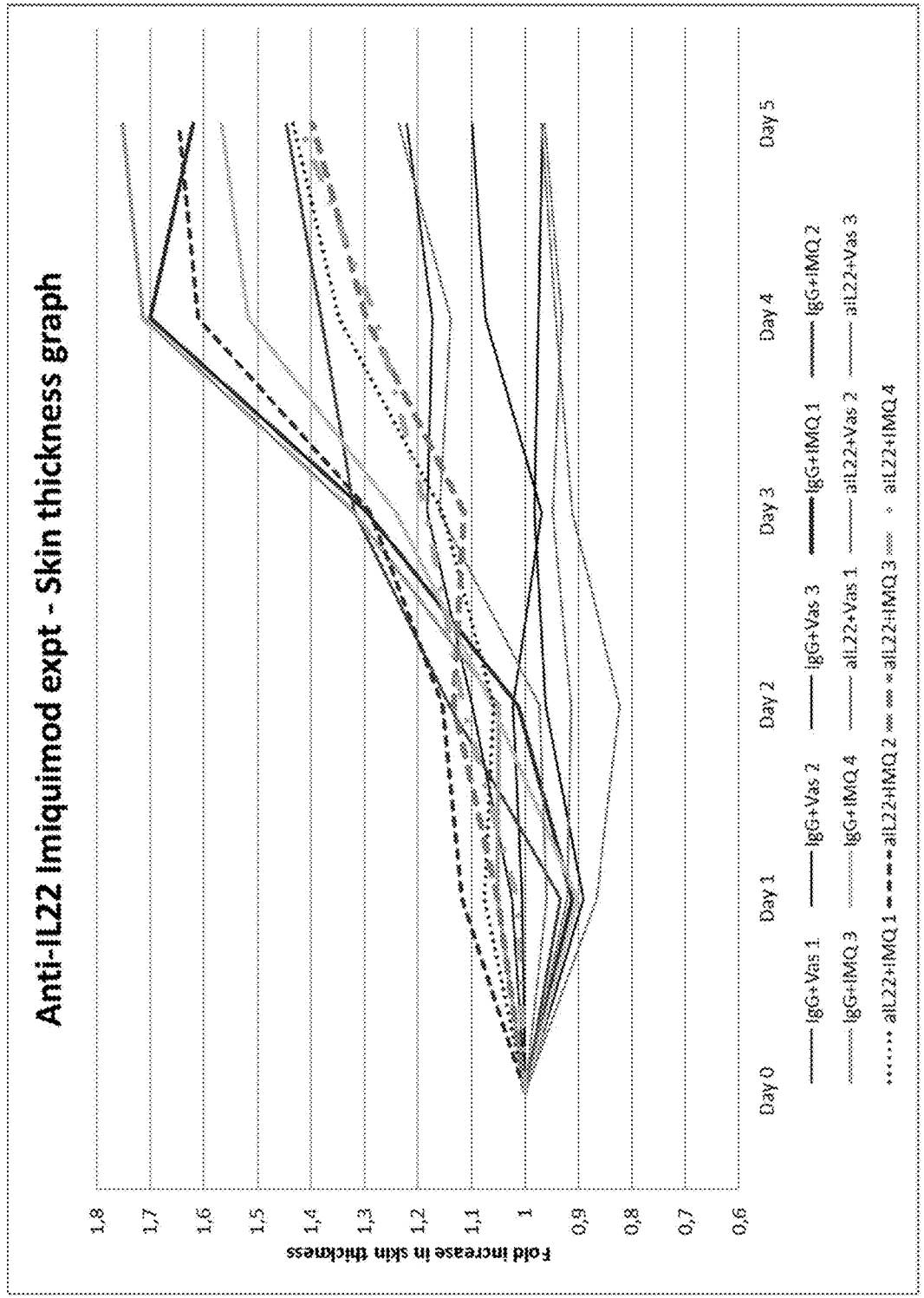

FIG. 20: Skin thickness clinical measurements in C57BL/6J mice over 5 day time course (average of 2 measurements, represented as fold increase compared to Day 0 time point). Graph form of scores—solid (red/pink) lines are IgG+IMQ mice, dotted (blue) lines are anti-IL-22+IMQ.

Figure 21:
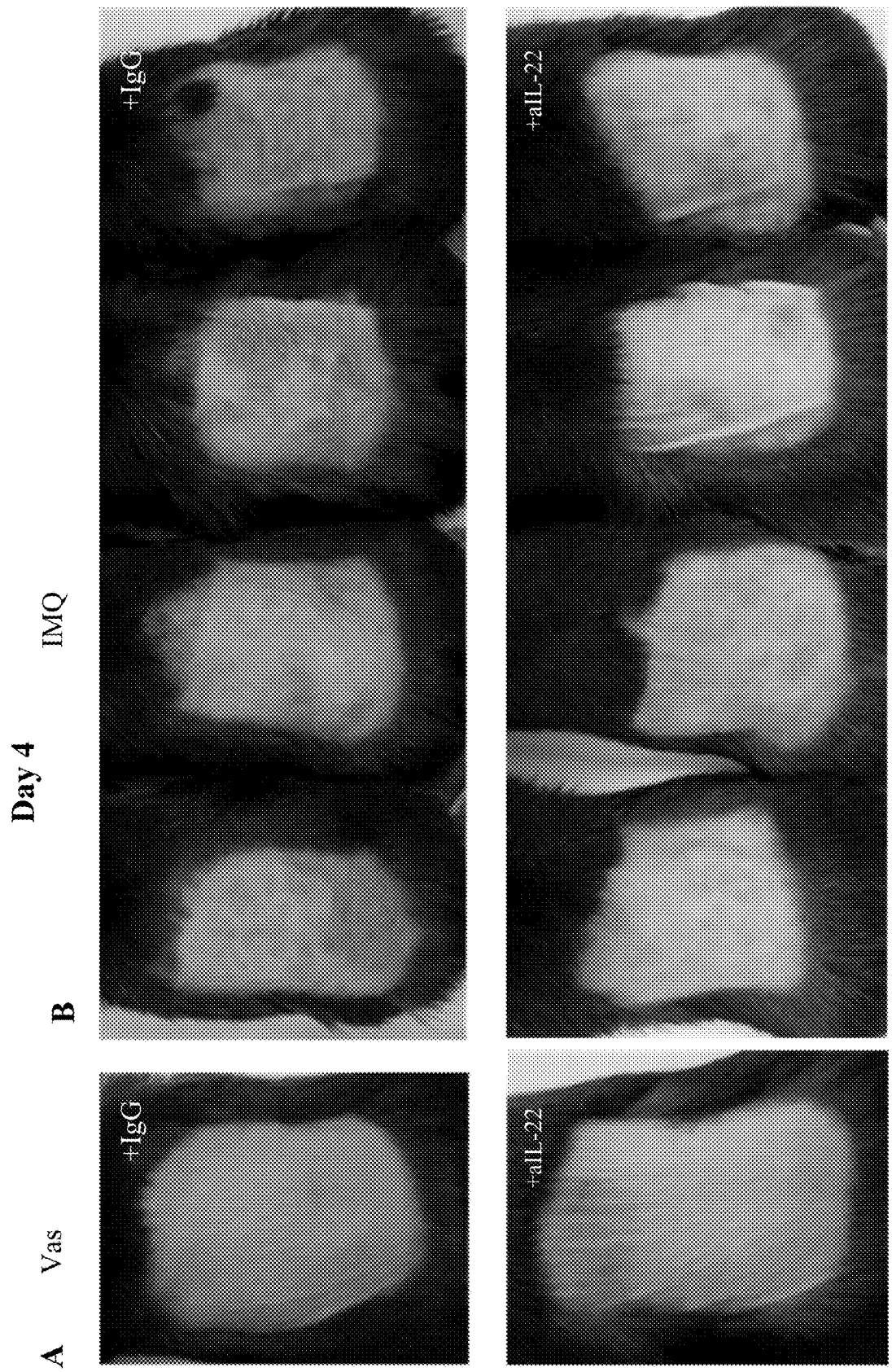

FIG. 21: Day 4 of treatment. A: Vaseline+IgG control. B: IMQ+IgG control. C: Vaseline+anti-IL-22. D: IMQ+anti-IL-22

Figure 22:
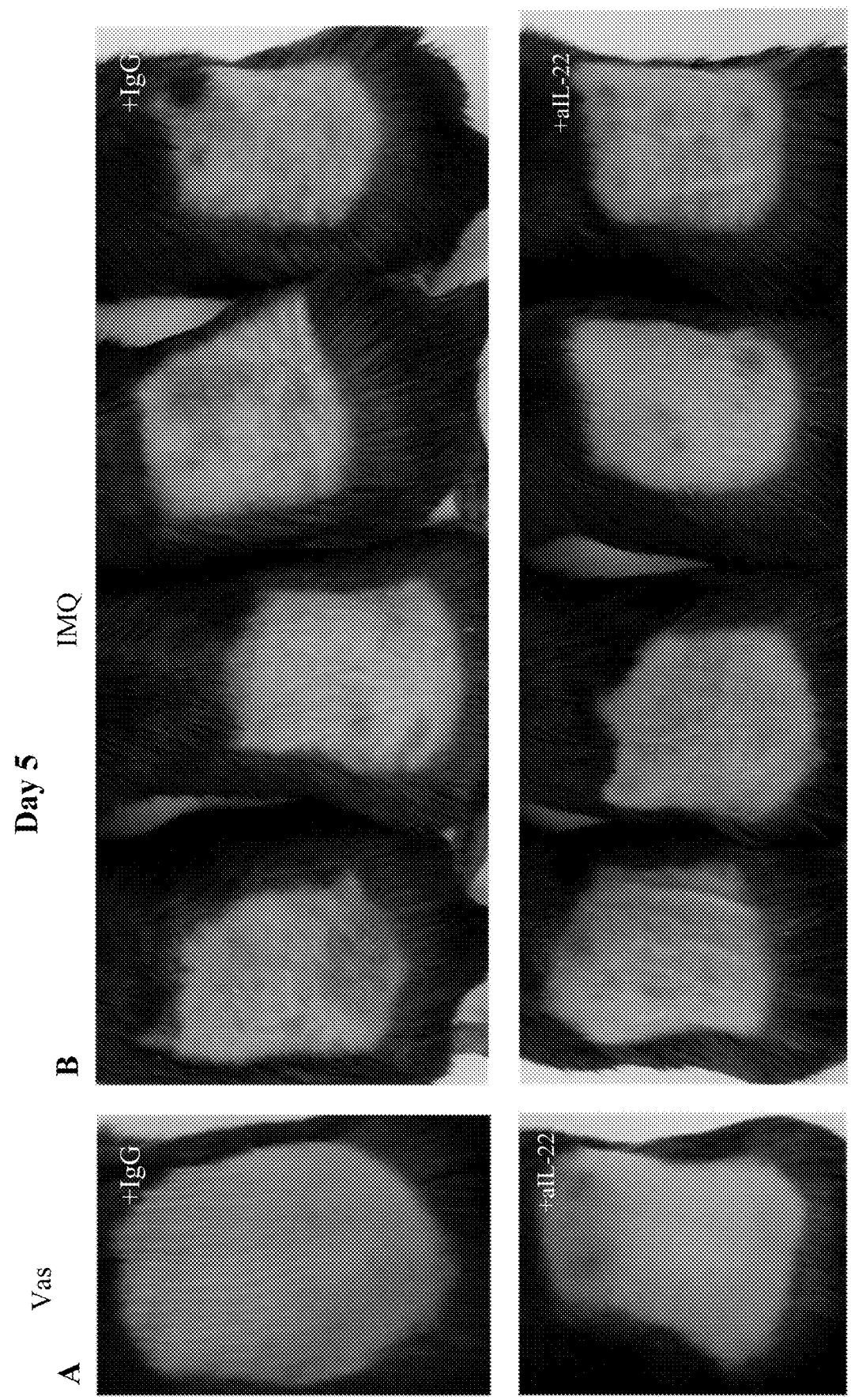

FIG. 22: Day 5 of treatment. A: Vaseline+IgG control. B: IMQ+IgG control. C: Vaseline+anti-IL-22. D: IMQ+anti-IL-22

Figure 23:
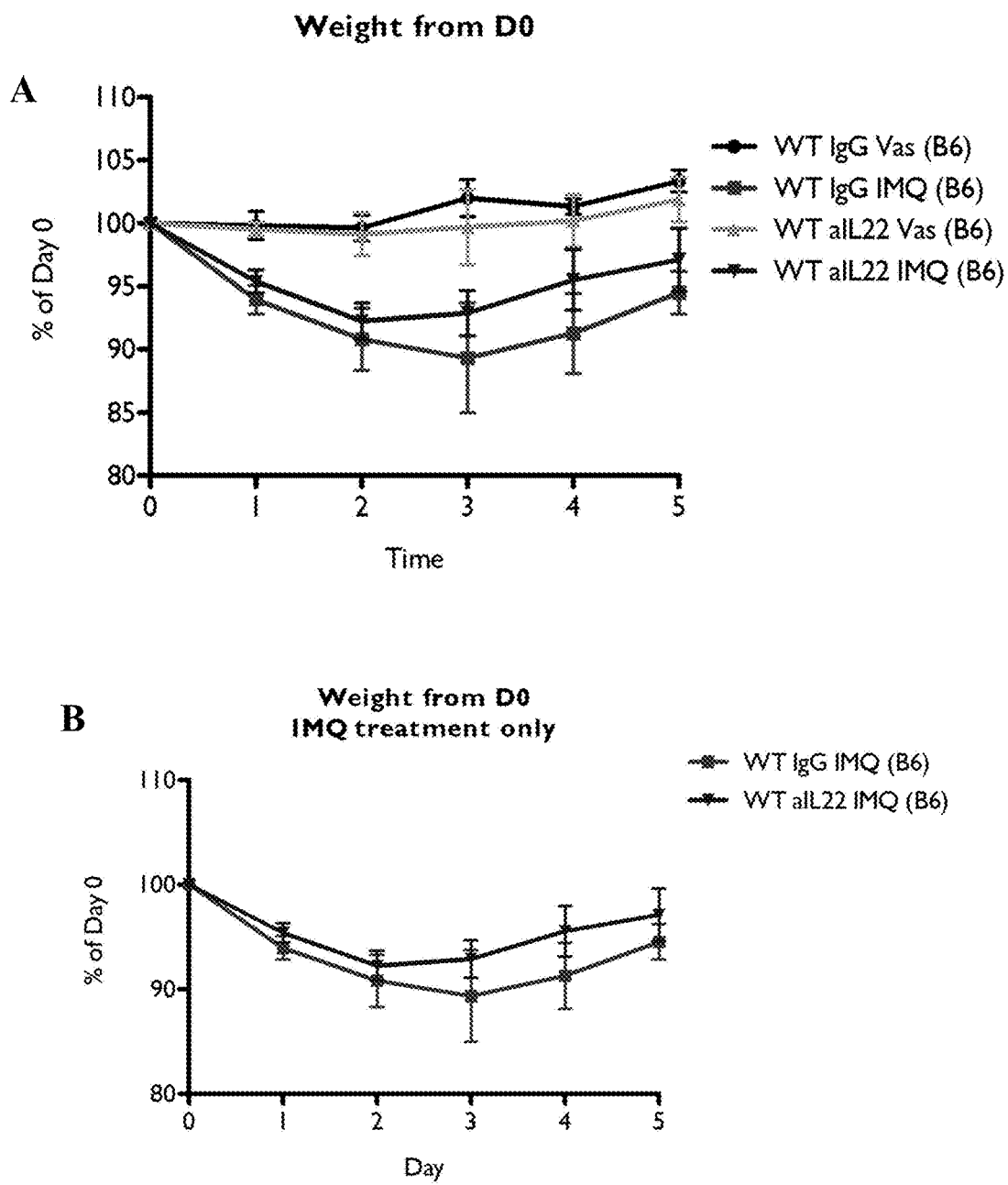

FIG. 23: Weight development of the animals during experiment starting from Day 0. A: weight development in all experimental groups. B: weight development in the IMQ group only without Vaseline controls. Not significant (ns) at all time points.

Figure 24:
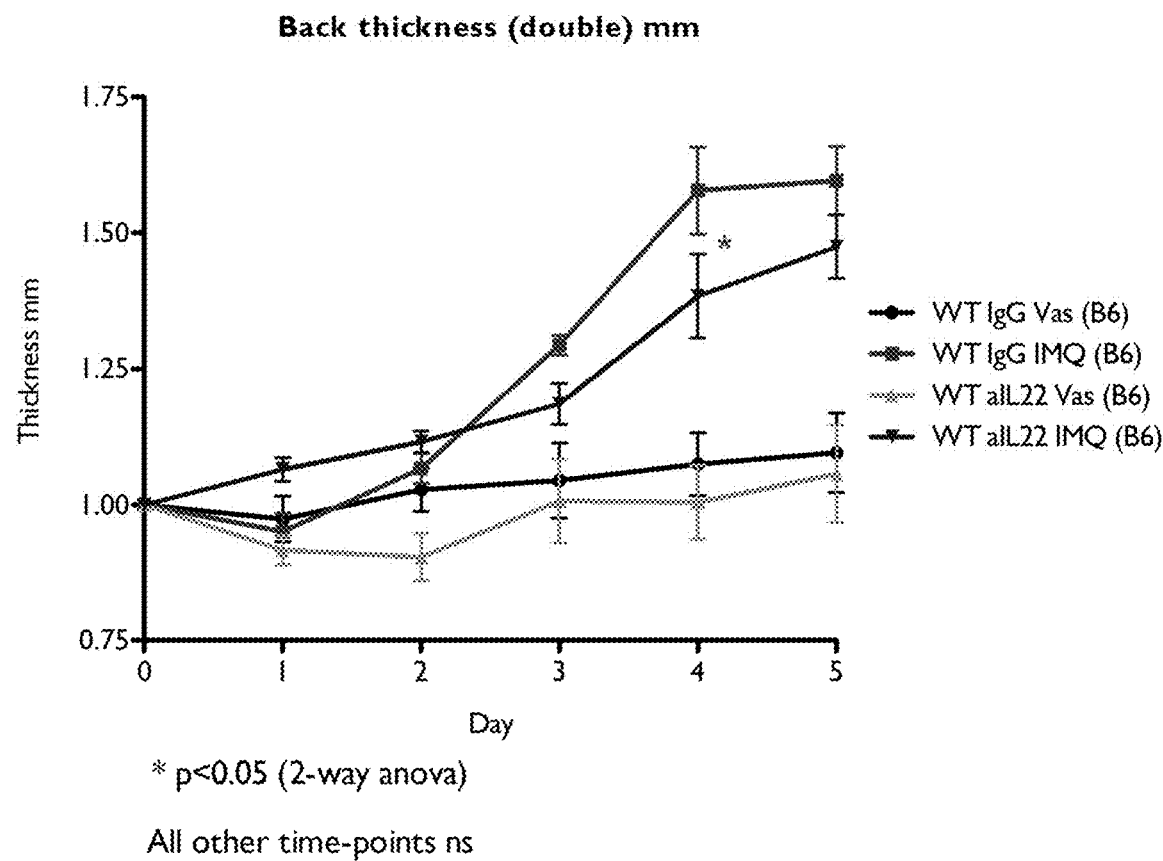

FIG. 24: Mice given IgG+IMQ have significantly thicker skin at Day 4 compared to anti-IL-22+IMQ. Back thickness of animals is shown in mm over time. * p<0.05 (2-way anova; all other time-points ns)

Figure 25:
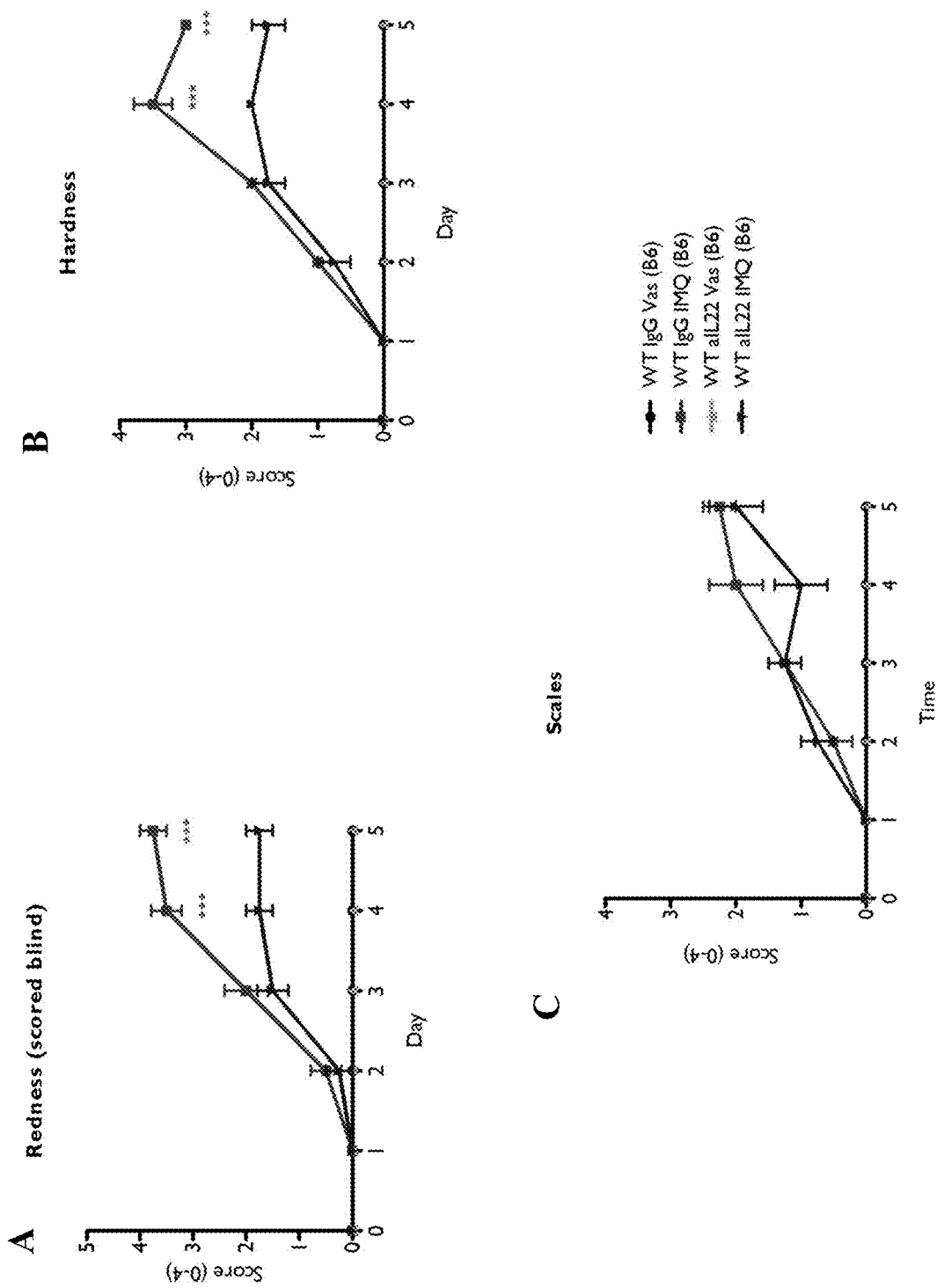

FIG. 25: Treatment with aIL-22 (30G1) significantly reduces clinical psoriasis scoring in IMQ-treated mice. Redness, Hardness and Scales of the plaques were evaluated according to the Psoriasis Area and Severity Index (PASI) score. The three features of a psoriatic were each assigned a number from 0 to 4 with 4 being worst. *** p<0.001 (2-way anova) in (A) and (B). (C) ns at all time points (2-way anova).

Figure 26:
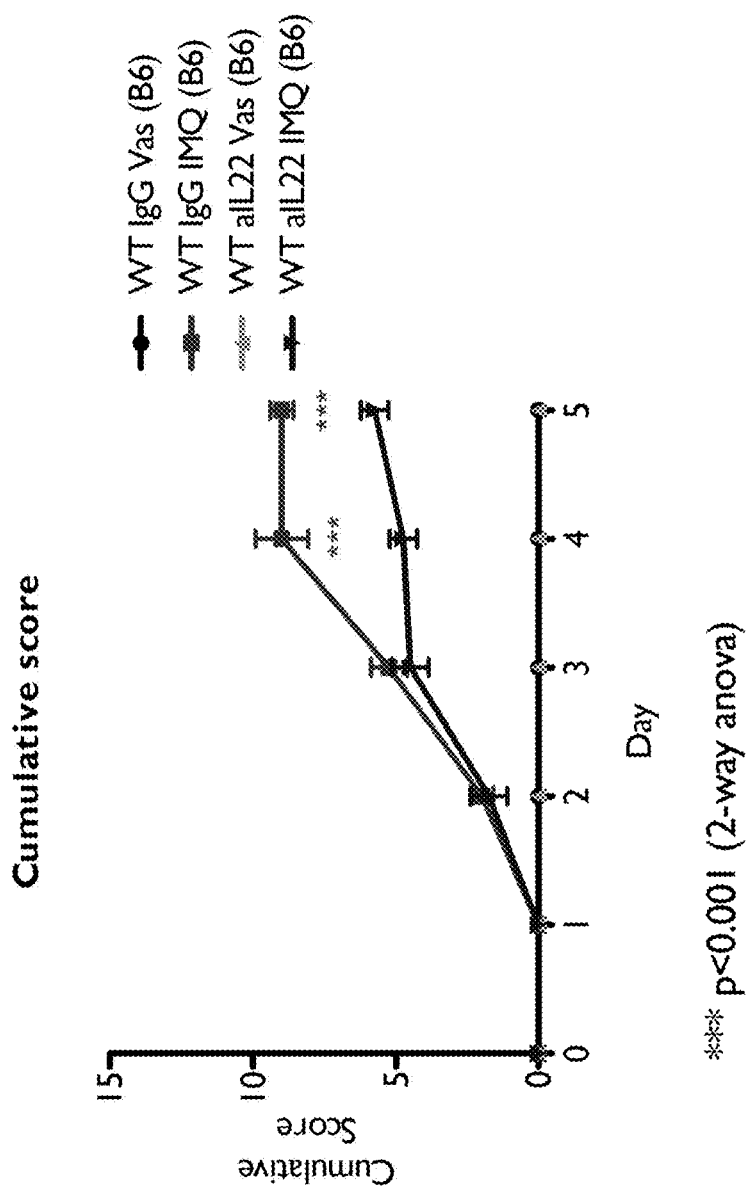

FIG. 26: Mice given a-IL-22+IMQ have significantly different (reduced) clinical severity at Day 4 and Day 5, especially in skin erythema (scored blind) and hardness. ***p<0.001 (2-way anova)

FIG. 27: Mice given IMQ have significantly larger spleens compared to vaseline treated mice. There is no significant difference between IgG+IMQ and anti-IL-22+IMQ treated mice. A: spleen weight in the different treatment and control groups; unpaired, two-tailed t-test. B: spleens size overview of the different treatment and control groups.

Figure 28:
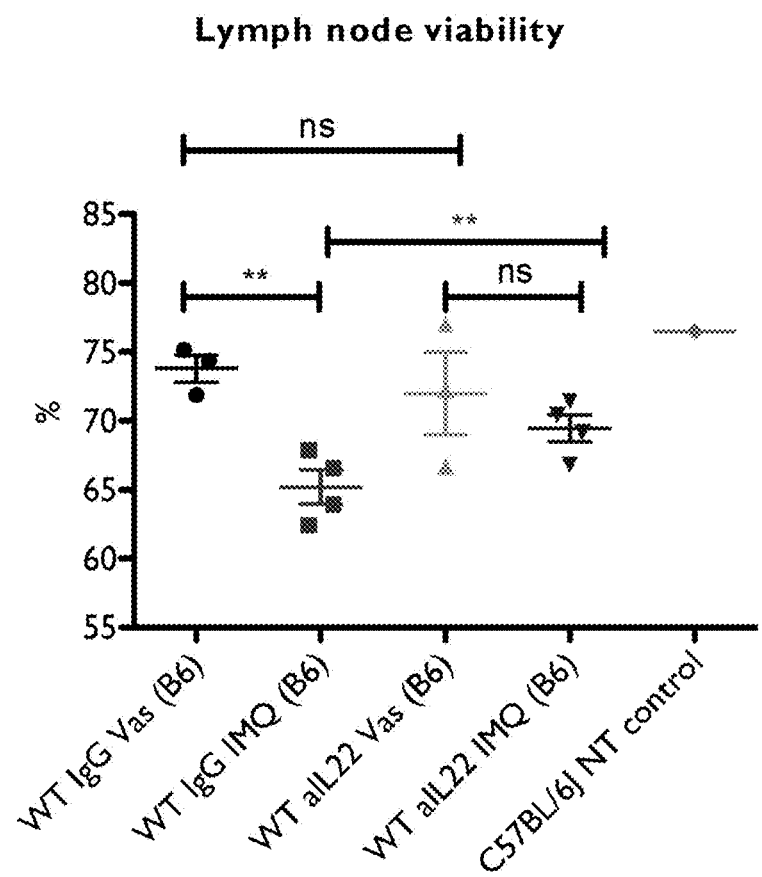

FIG. 28: Lymph node (LN) cells from IMQ treated mice are less viable than mice treated with Vaseline. Viability of LN cells is significantly different between IgG+IMQ and anti-IL-22+IMQ treated mice; unpaired, two-tailed t-test, ** p<0.005.

Figure 29:
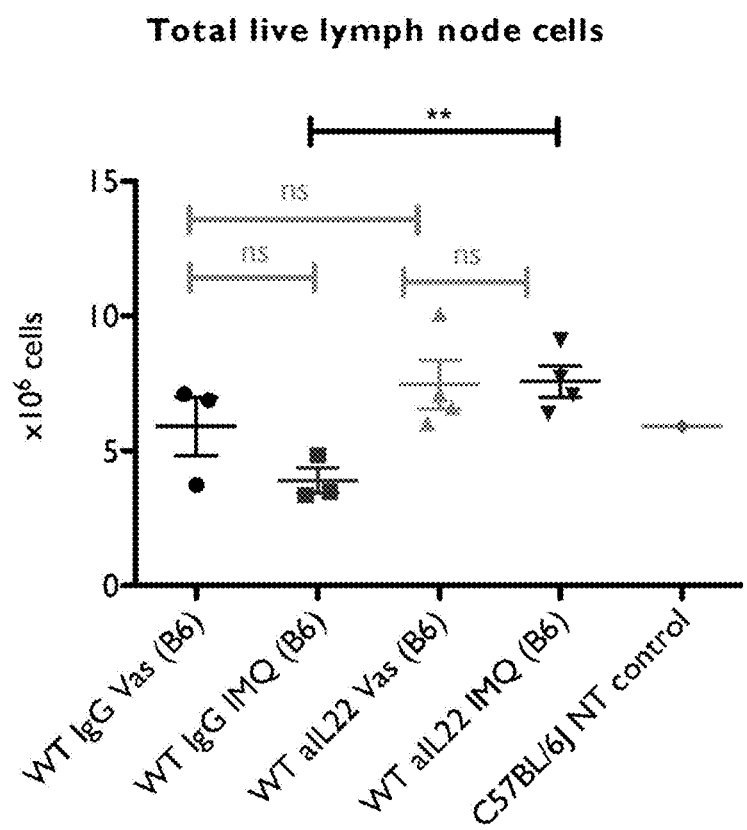

FIG. 29: The total number of viable live LN cells is significantly different between IgG+IMQ and anti-IL-22+IMQ treated mice. Unpaired, two-tailed t-test: ** p<0.005.

Figure 30:
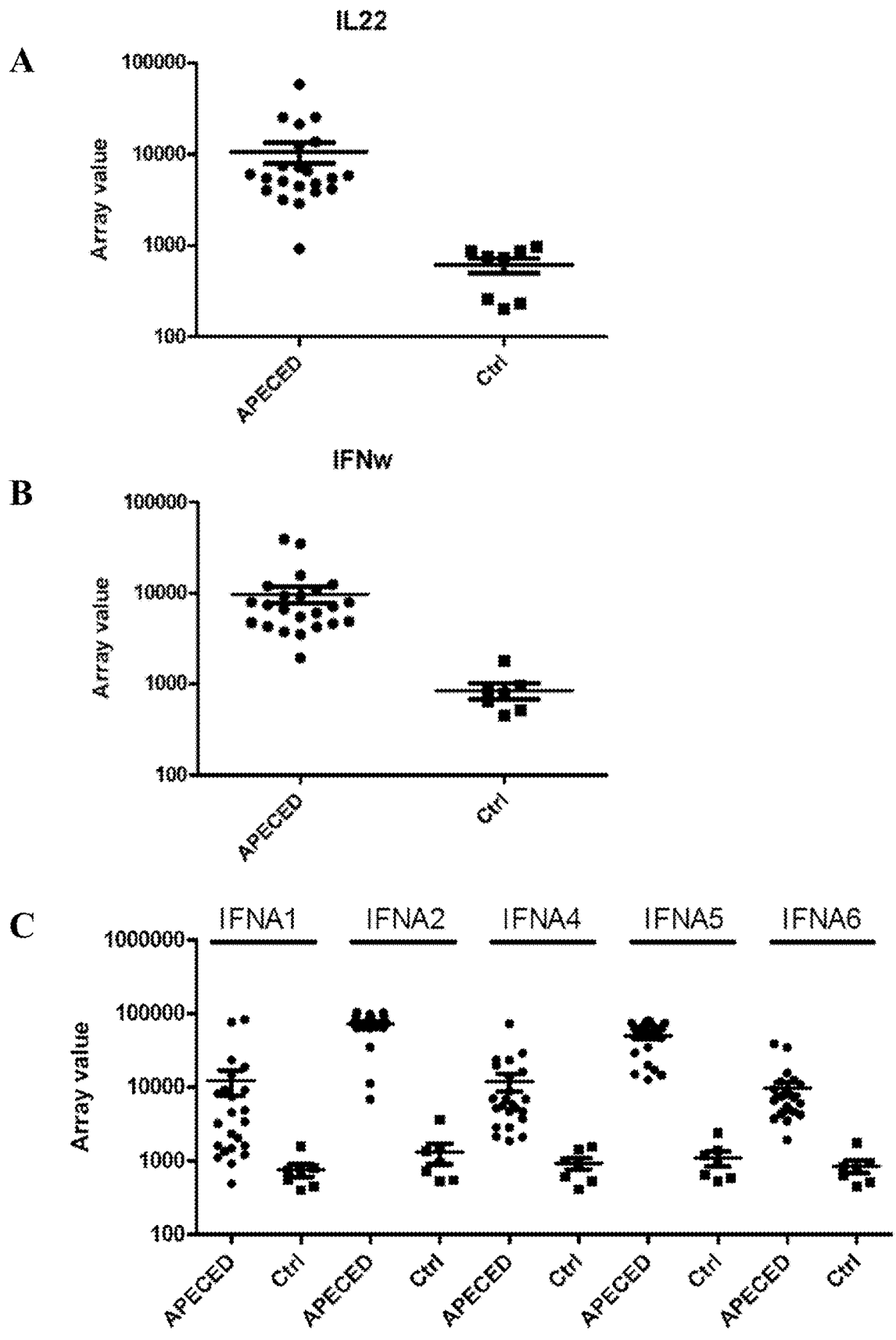

FIG. 30: Sera of APECED patients react strongly with IL-22 (A), IFN-omega (B) and IFN-alpha (C). The Protoarray results are shown for IFN-alpha subunits (IFNA1, IFNA2, IFNA4, IFNA5 and IFNA6), IFN-omega and for IL-22 cytokines. The data shows the fluorescence values of Invitrogen Protoarray provided herein probed with sera of 23 Finnish APECED patients (APECED) and 7 healthy control (Ctrl) sera (log scale). The mean values with SEM for each patient-control group are shown.

Figure 31:
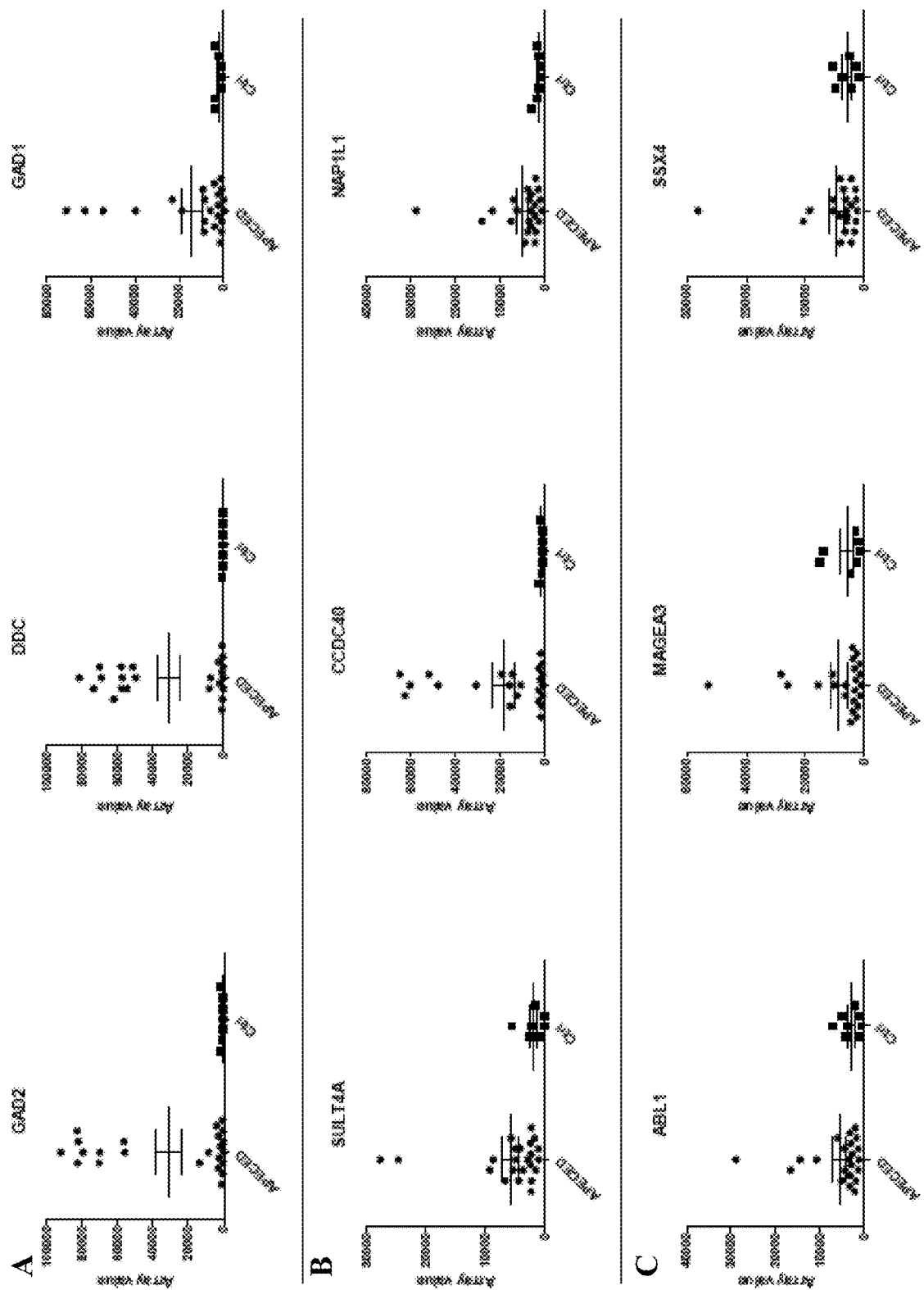

FIG. 31: Autoimmune reactivity of sera from APECED patients with: Column (A)—previously reported APECED autoantigens GAD2 (glutamate decarboxylase 2), DDC (dopa decarboxylase (aromatic L-amino acid decarboxylase)) and GAD1 (glutamate decarboxylase 1); Column (B)—novel (unreported) autoantigens SULT4A (sulfotransferase family 4A, member 1), CCDC40 (coiled-coil domain containing 40), NAPIL (nucleosome assembly protein 1-like 1); and Column (C)—with cancer antigens ABL1 (c-abl oncogene 1, non-receptor tyrosine kinase). MAGEA3 (melanoma antigen family A3) and SSX4 (synovial sarcoma, X breakpoint 4). The Protoarray results are shown as fluorescence values of Invitrogen Protoarray provided herein probed with sera of 23 Finnish APECED patients (APECED) and 7 healthy control (Ctrl) sera. The mean values with SEM for each patient/control group are shown.

Figure 32:
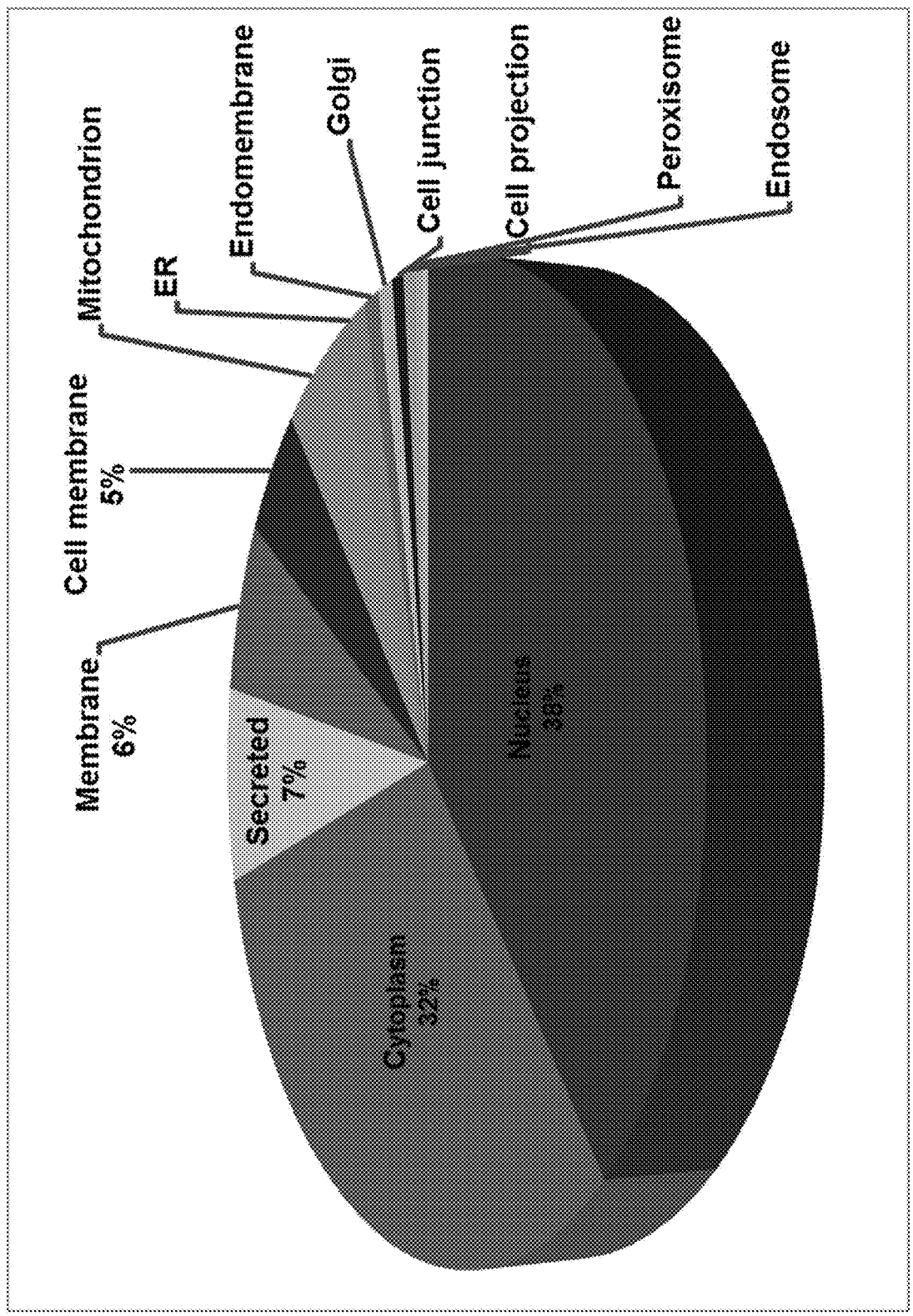

FIG. 32: Subcellular location of APECED antigens. Recognized proteins are predominantly nuclear (38%) or cytoplasmatic (32), followed by secreted (7%) and cell membrane proteins (5%).

Figure 33:
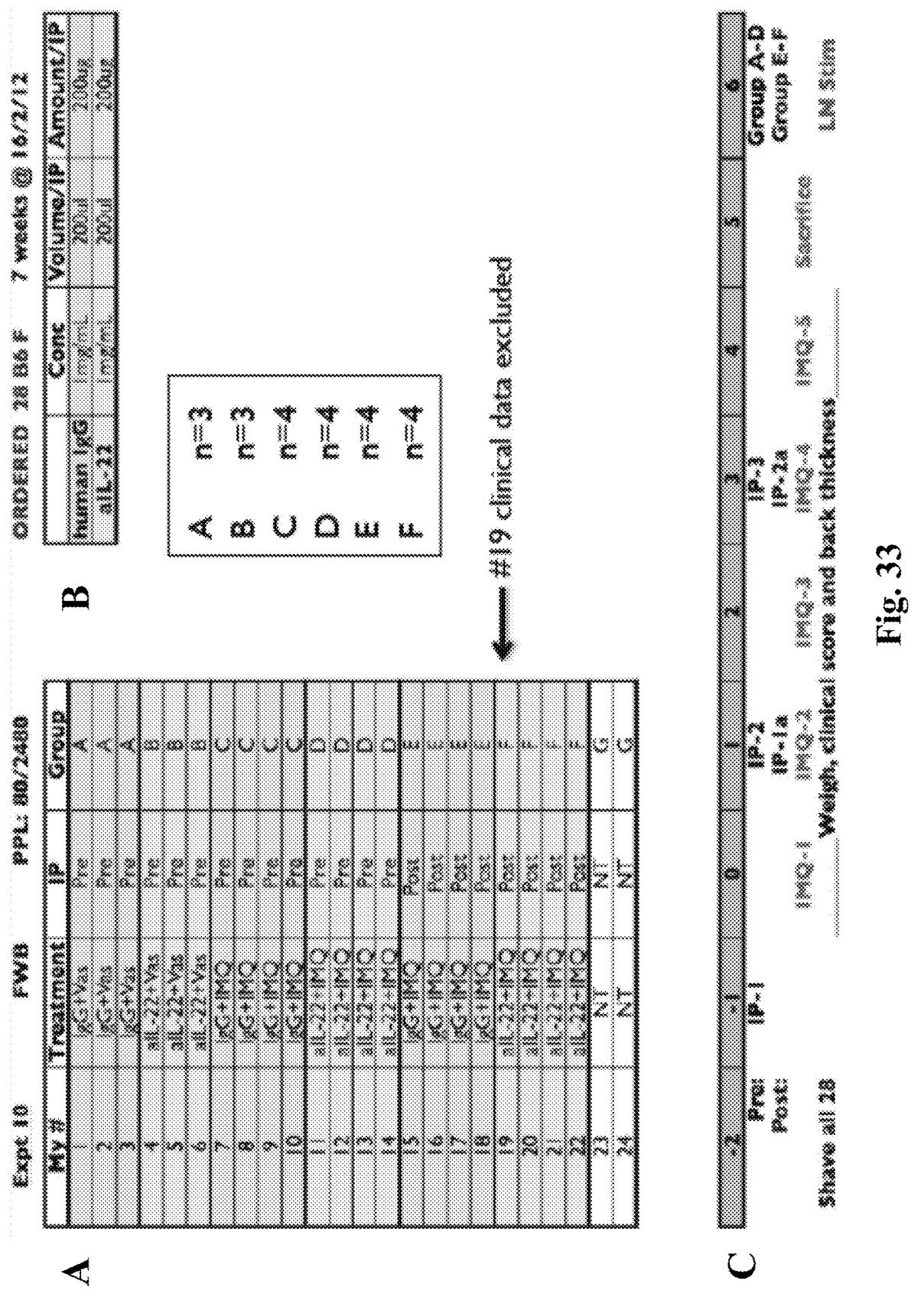

FIG. 33: Anti-IL22 (30G1)+IMQ psoriasiform lesion in vivo study. Experimental protocol and timeline detailing anti-IL22 antibody administration both pre and post (24 hours after) IMQ induction in C57BL/6J mice. Age at shaving 9 weeks, Non-treated control DOB (Date of birth): at 10 weeks A: Tables indicating the treatment composition of the animal groups A to G. B: Amounts of the control and anti-IL22 antibody applied to the animals. C: Experimental timeline. Vas=Vaseline. LN stim=Lymph node stimulation. Clinical data of animal #19 was excluded from analysis due to severe weight loss. Indications shown here are the same as for experiments shown in FIG. 16.

FIG. 34: Administration of exemplary aIL-22 antibody 30G1 significantly reduces skin thickening in imiquimod-treated mice, a therapeutic effect can be observed as implicated by the reduced clinical psoriasis scoring in mice receiving the 30G1 IL-22-antibody post IMQ induction. The lines in the graphs are numbered in the figure for a better readability.

Figure 35:
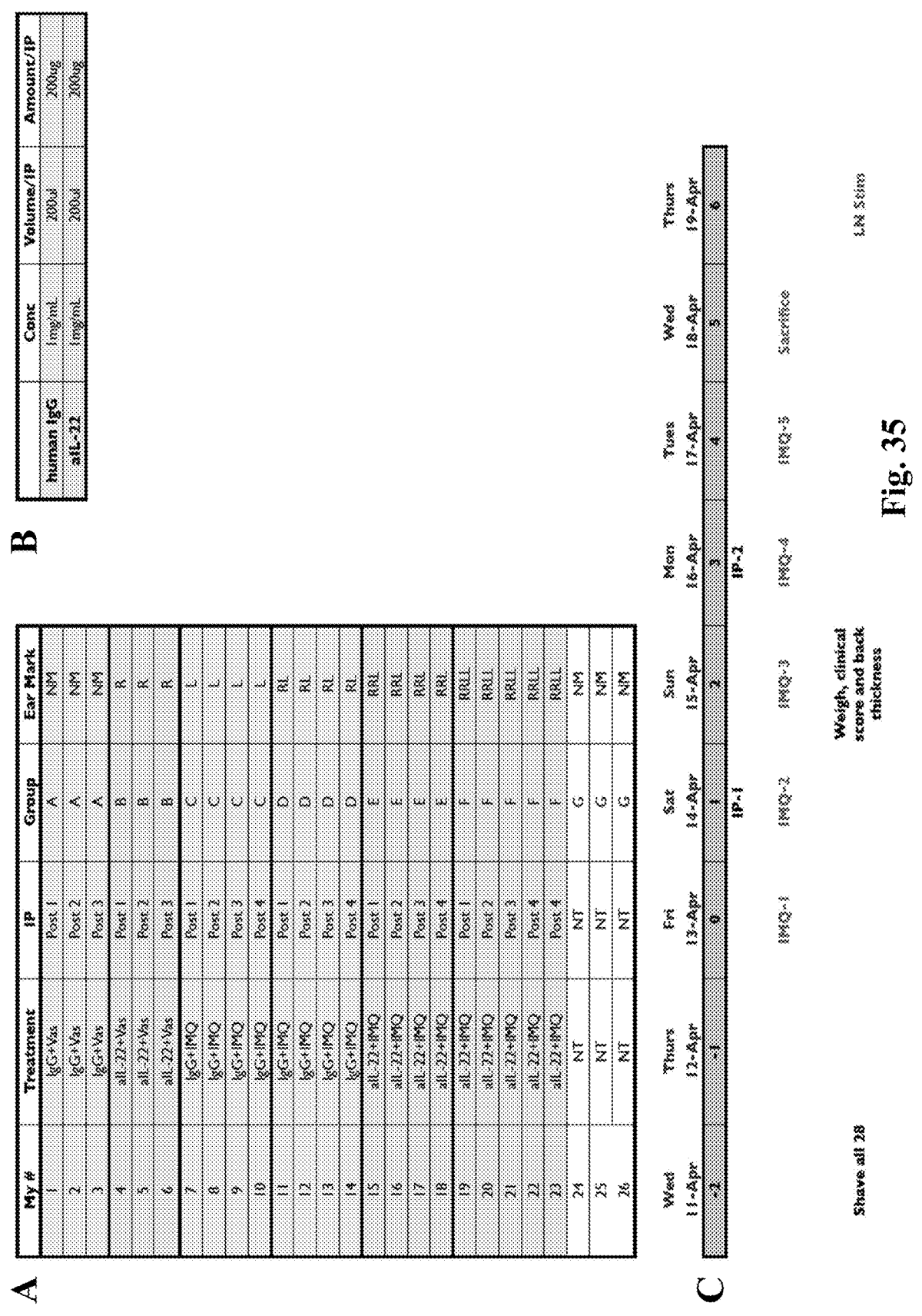

FIG. 35: Anti-IL22 (30G1)+IMQ psoriasiform lesion in vivo study. Experimental protocol and timeline detailing anti-IL22 antibody administration post (24 hours after) IMQ induction in C57BL-6J mice—with increased numbers of animals tested. Subfigures A, B and C as described above for FIG. 34.

Figure 36:
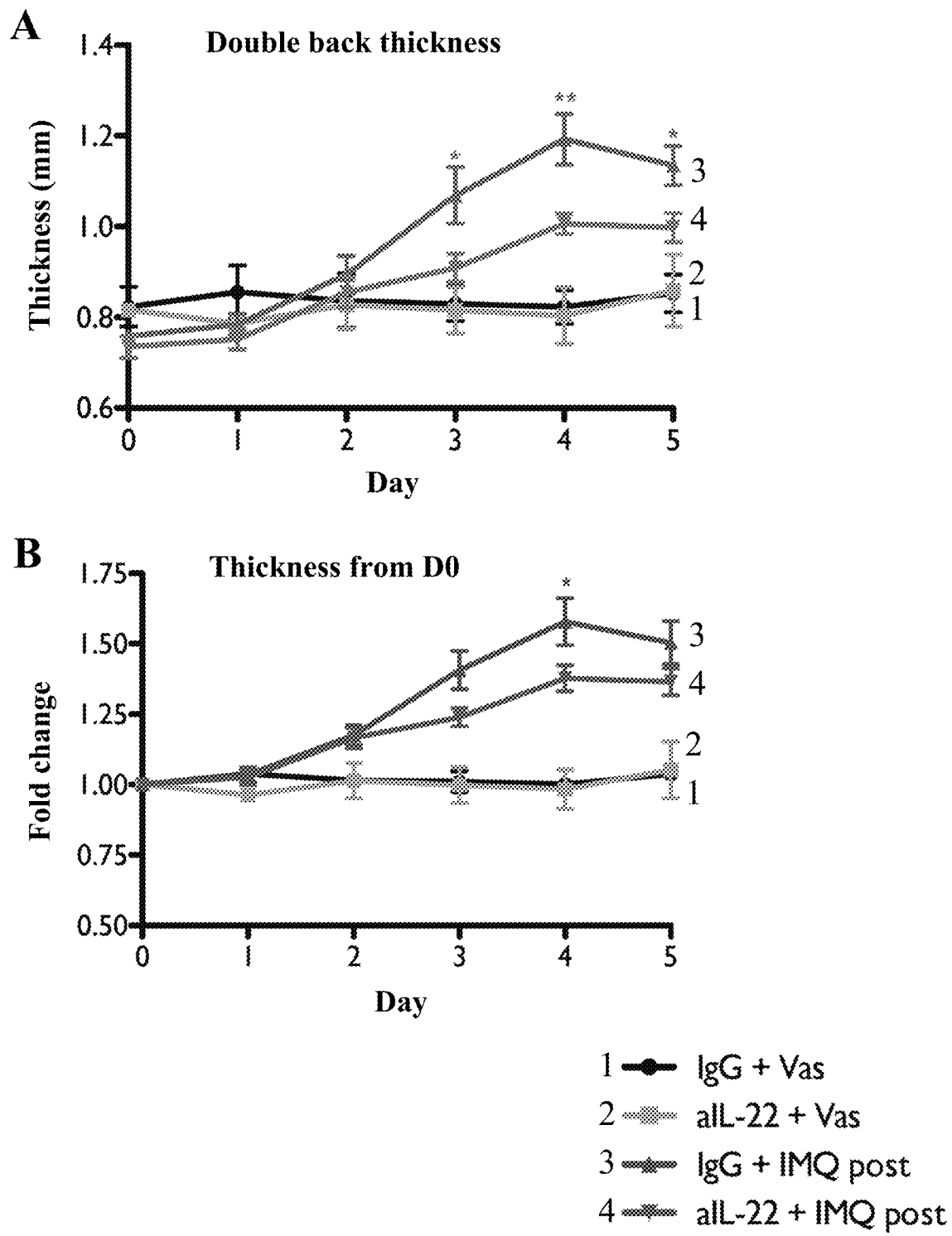

FIG. 36: Administration of exemplary aIL-22 antibody 30G1 significantly reduces skin thickening in IMQ-induced mice, even if administered "therapeutically"—24 hours post IMQ induction rather than prior to IMQ induction. Significant difference could be observed in skin thickness between IgG+IMQ and aIL-22+IMQ treated groups at Day 4. A: duplicate skin thickness measurements on the back of the treated animals in mm. B: fold change in the skin thickness of said animals. The lines in the graphs are numbered in the figure for a better readability.

Figure 37:
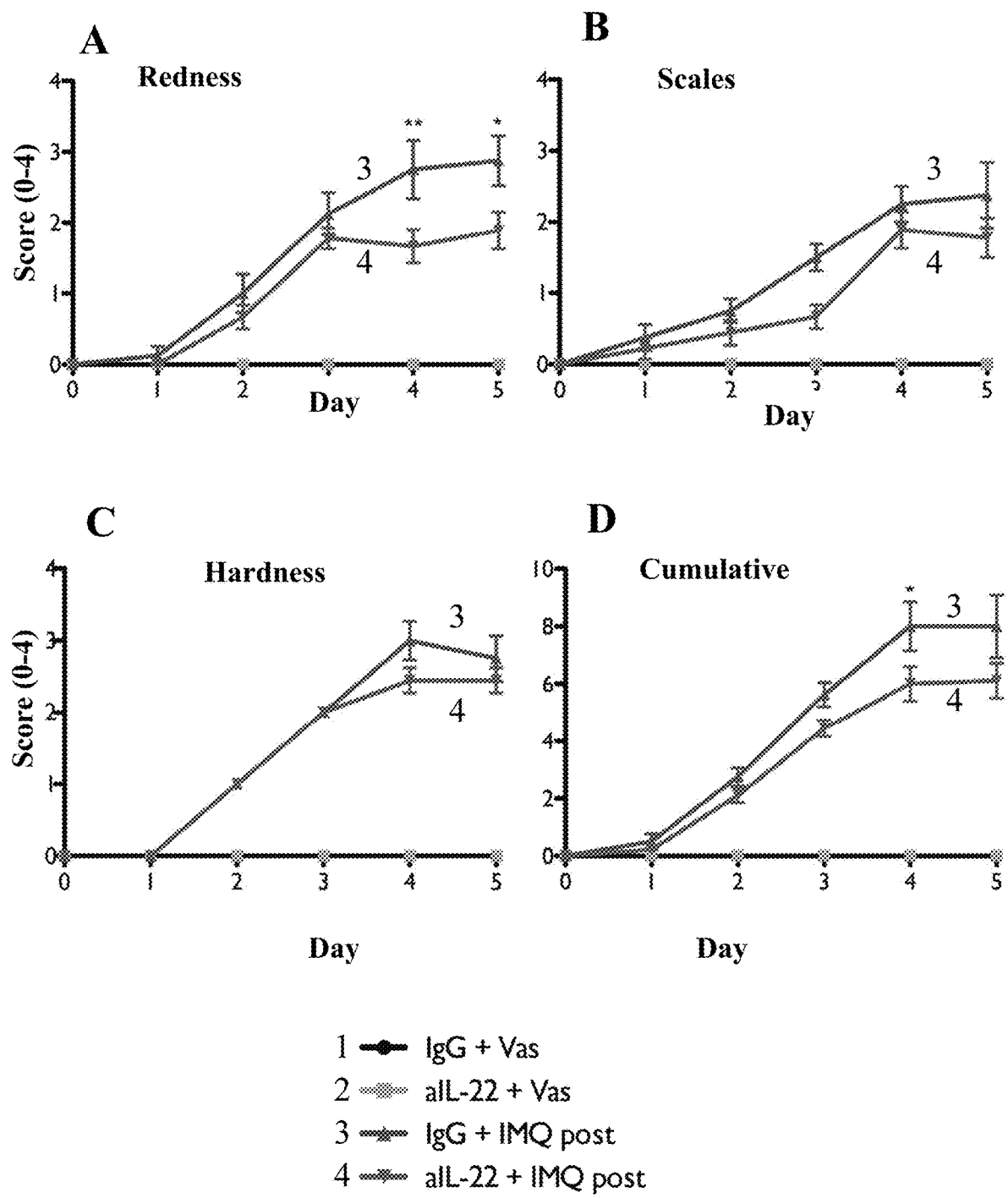

FIG. 37: Administration of exemplary aIL-22 antibody 30G1 significantly reduces skin erythema clinical psoriasis scoring in IMQ-induced mice, even when administered "therapeutically". (A-C) Significant difference in skin erythema could be observerd between IgG+IMQ and aIL+IMQ treated groups at days 4 and 5. Redness (A). Scales (B) and Hardness (C) of the plaques were evaluated according to the Psoriasis Area and Severity Index (PASI) score. The three features of a psoriatic were each assigned a number from 0 to 4 with 4 being worst. ** $p<0.01$, * $p<0.05$ (2-way anova) in (A). (B) and (C) ns at all time points (2-way anova). (D) Significant difference in the cumulative clinical scoring could be observed at Day 4. The lines in the graphs are numbered in the figure for a better readability; lines 1 and 2 are concurrent with the X-axis.

Figure 38:
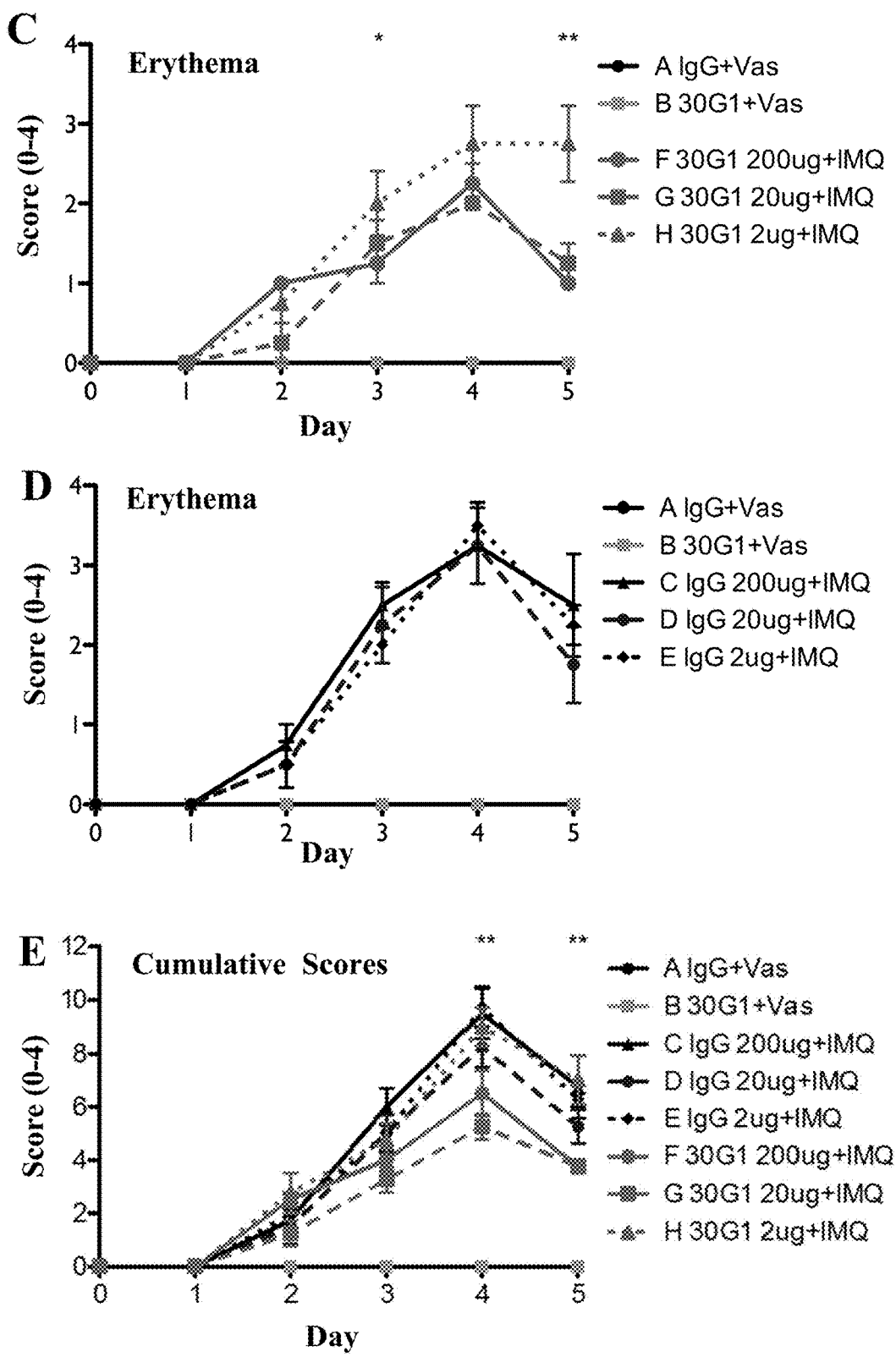

FIG. 38: Dose-dependent effect of exemplary anti-IL22 antibody 30G1 of the present invention in IMQ-induced psoriasis. Three different doses—200 µg, 20 µg and 2 µg were administered post IMQ-induction. (A) skin erythema and (B) hardness of the plaques were evaluated as described in previous Figs. (C) and (D) show the values for respective aIL-22 or control treatment. (E) shows the cumulative scores for the different treatments. The mouse cross-reactive, exemplary anti-IL22 antibody of the present invention 30G1 shows indications of dose dependence, proving less effective when titrated down to 1/100 of the initial dose.

Figure 39:
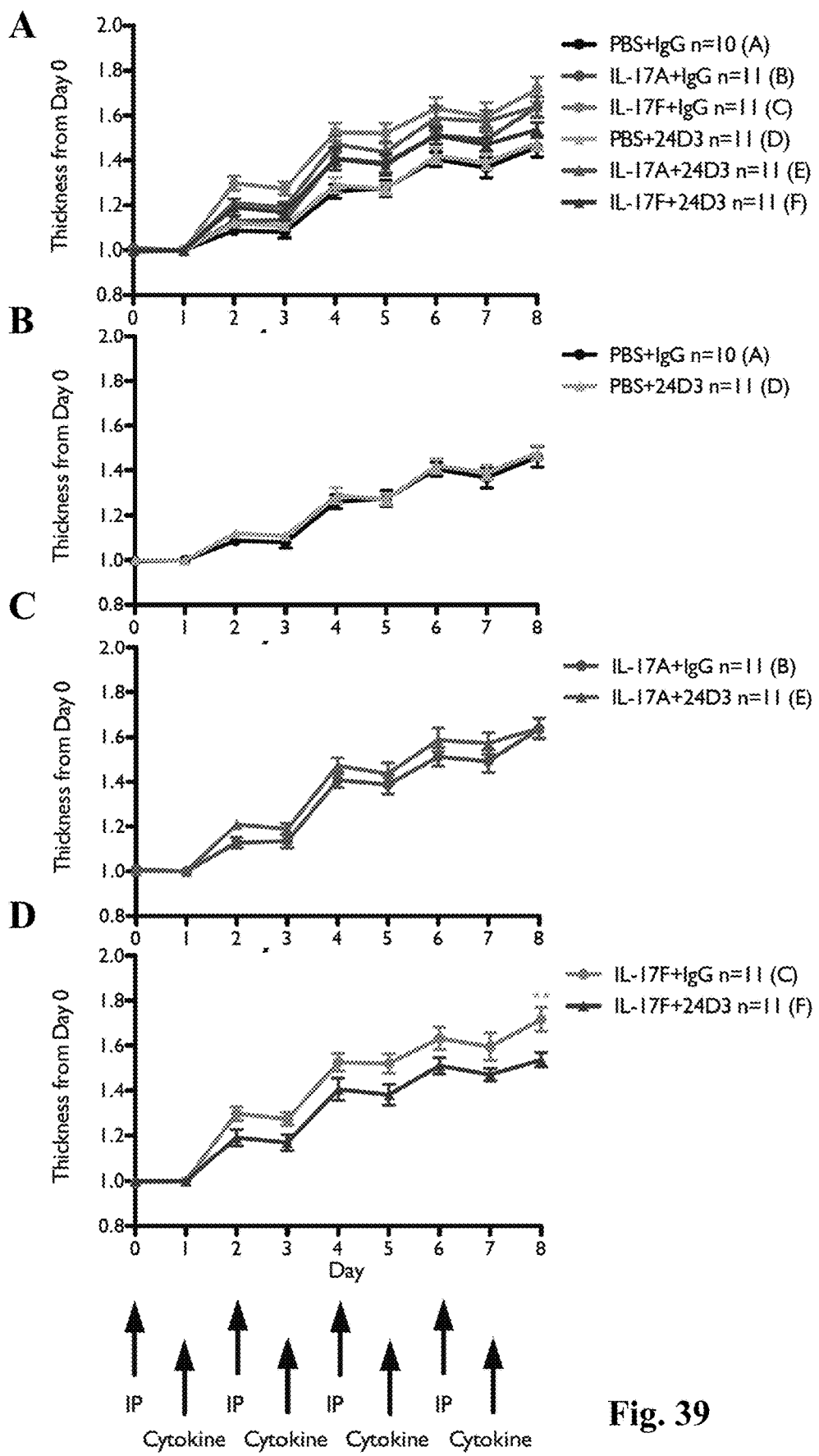
Figure 39:
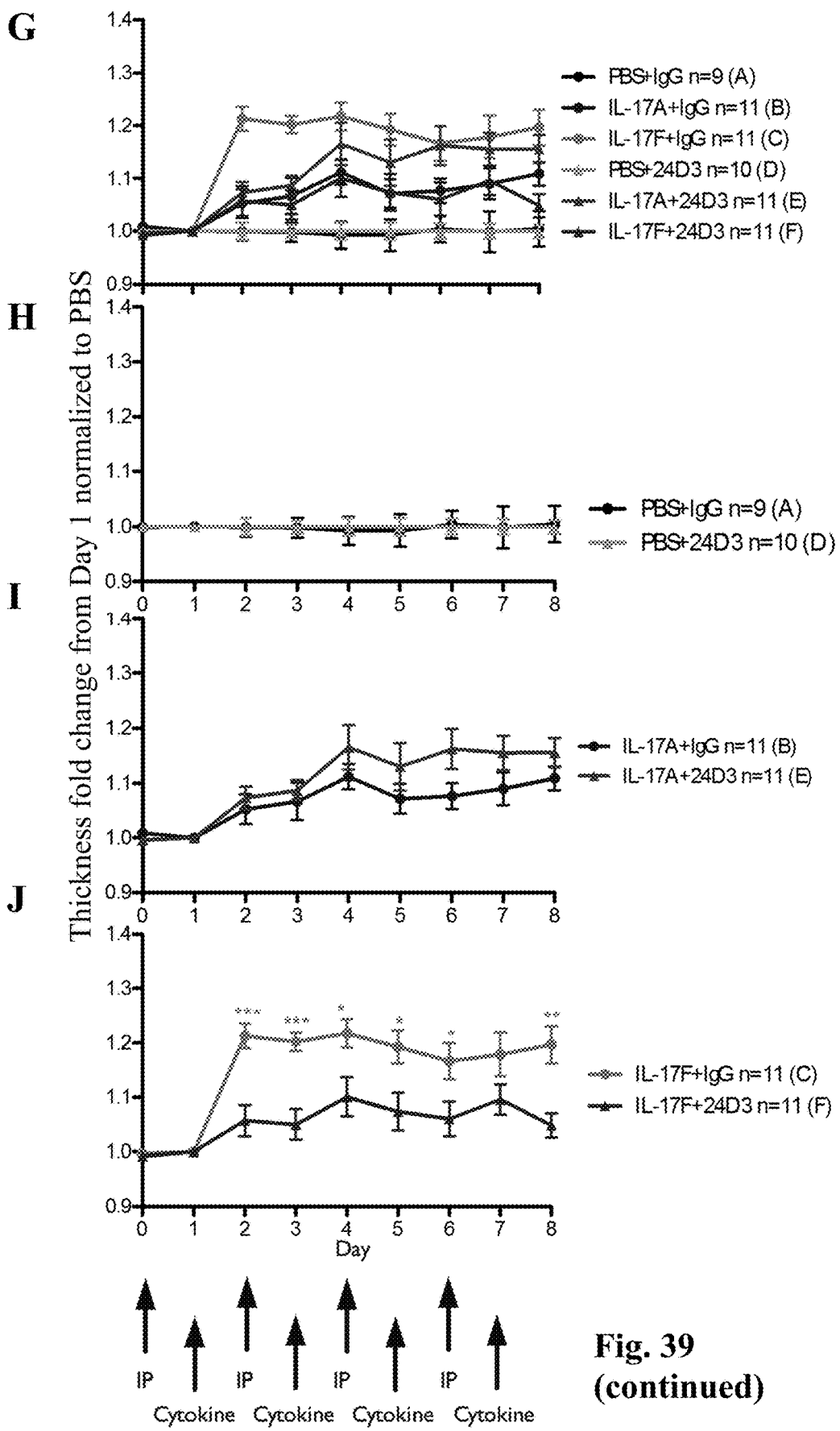
Figure 39:
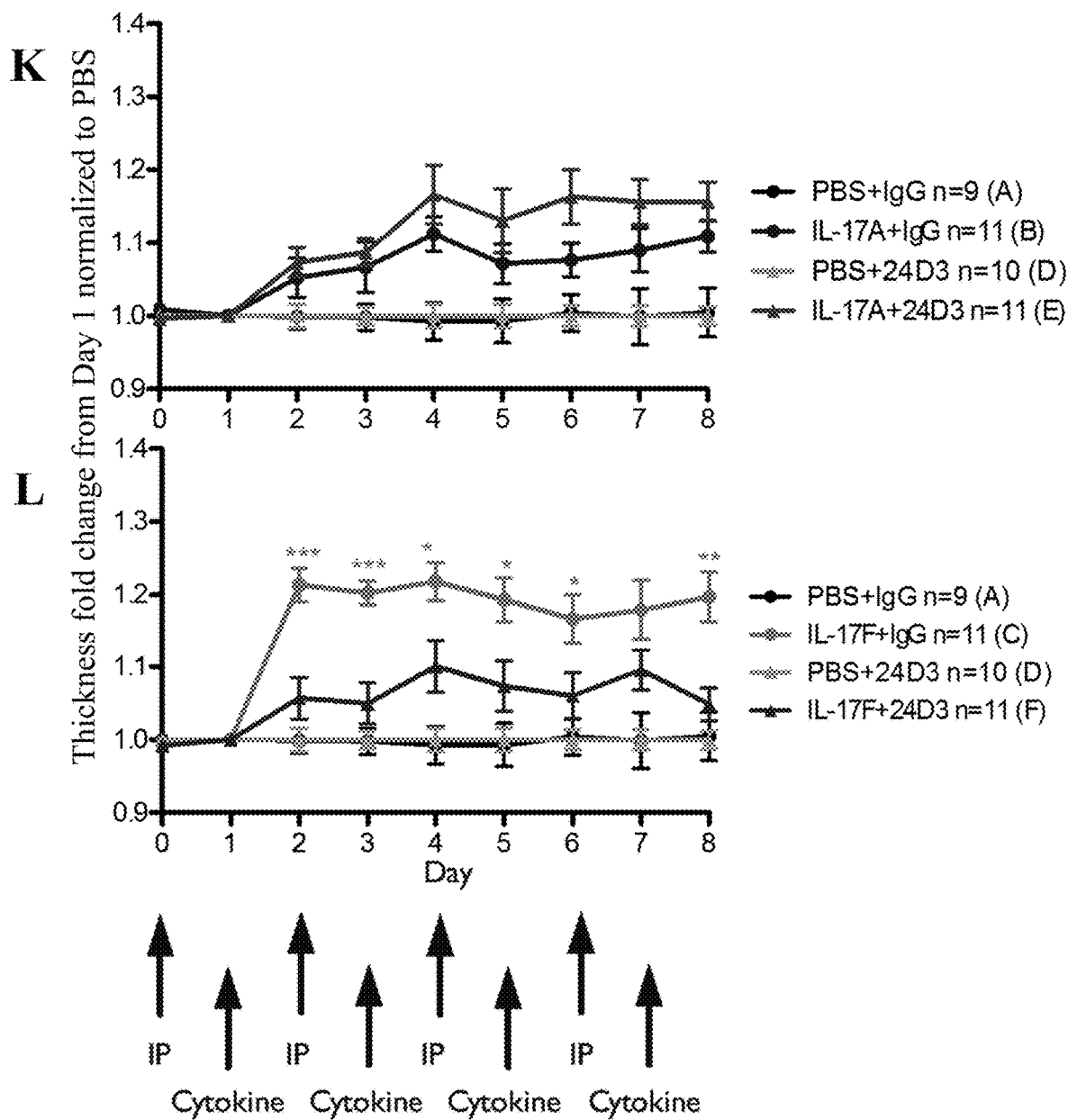

FIG. 39: Combined results of two independent CytoEar experiments—measurements of ear thickness over time show a reduction of the IL17F induced ear inflammation phenotype by injections of exemplary aIL-17 24D3 antibody of the present invention. (A) Overview of the results. (B) Control experiments—injection of PBS. (C) Induction of inflammation by IL17A-injections. (D) Induction of inflammation by IL17F-injections—reduced induction because of 24D3 injections. (E) shows combined graphs of Figs. B and C. (F) shows combined graphs of Figs. B and D. Significant difference (Day 8) could be observed in ear thickness between the Groups C and F in mice given IL-17F and treated with IgG or 24D3 (D, F). (D and F) 2-Way ANOVA ns at Day 0 to Day 7 **$p<0.01$ at Day 8. Figures G-L show the data of corresponding Figures A-F after normalization to PBS. (J and L) 2-Way ANOVA: ns at Day 7; *$p<0.1$ at Days 3-5: $p<0.01$ at Day 8; *$p<0.001$ at Days 1 and 2.

Figure 40:
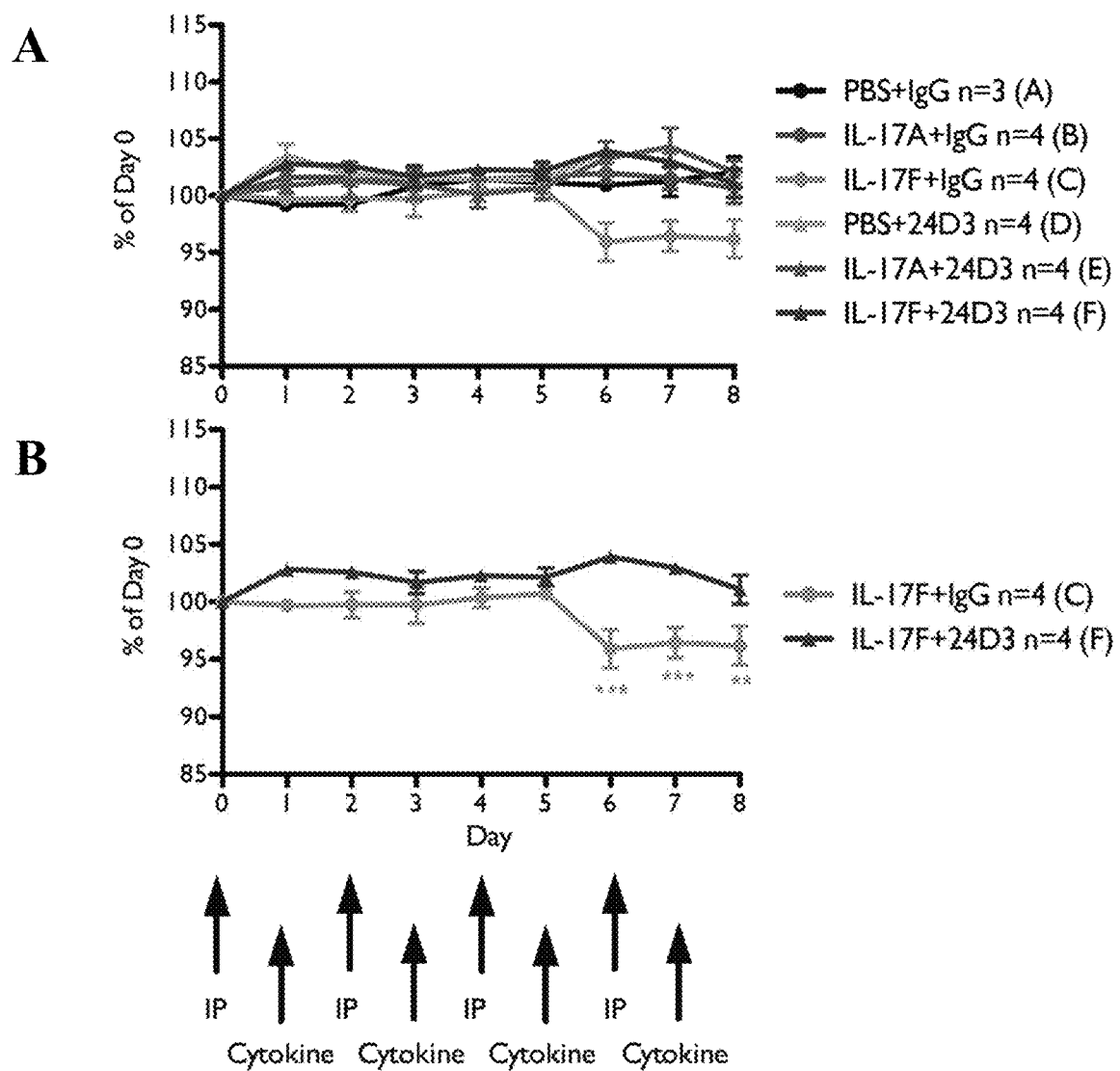

FIG. 40: CytoEar experiment—Monitoring body weight of the animals tested for reduction of ear inflammation phenotype by treatment with the exemplary anti-IL-17 antibody 24D3 of the present invention. (A) Experimental results overview. (B) Preliminary data suggest a possible effect of the treatment based on a weight difference observed in groups C and F.

Figure 41:
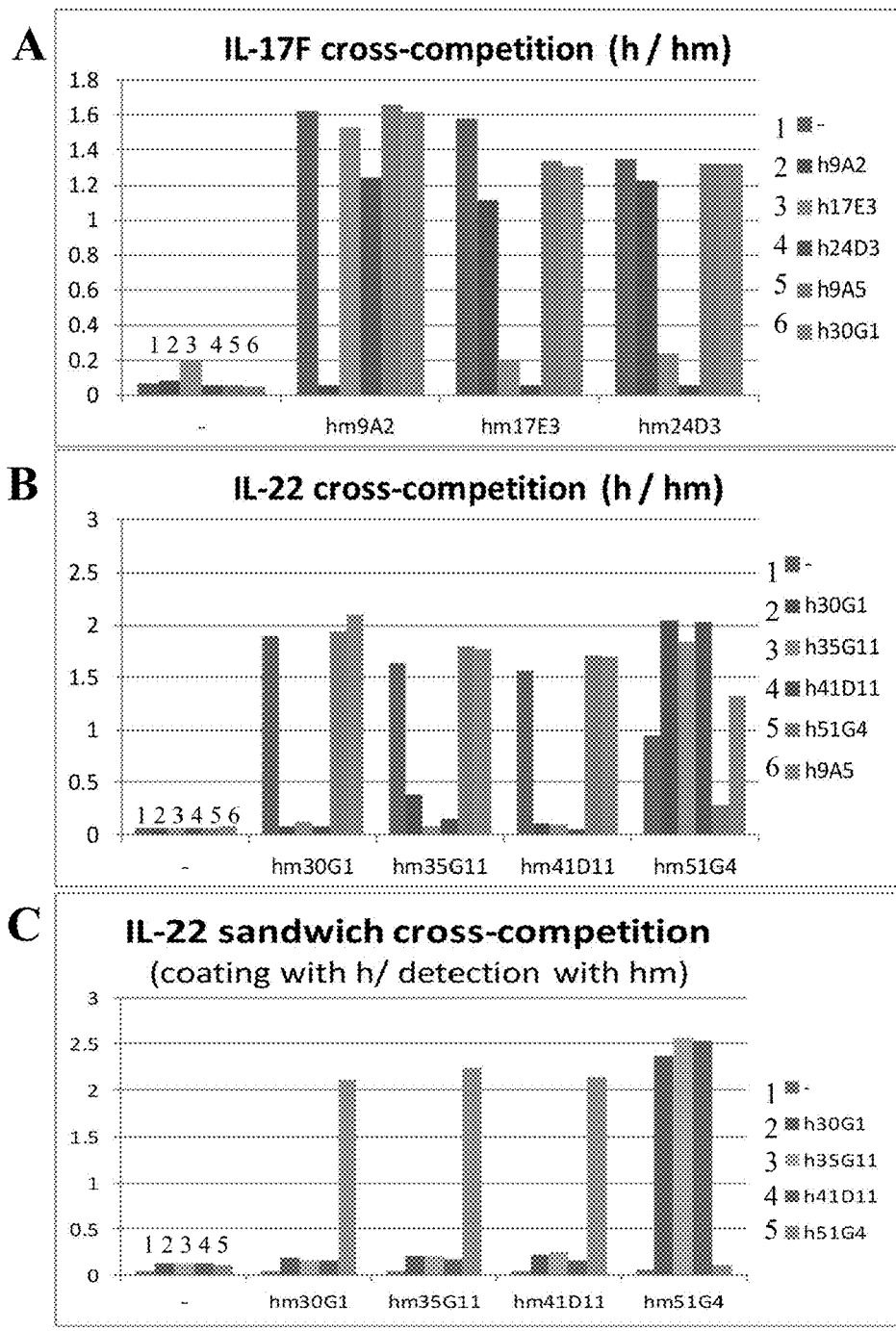

FIG. 41: Epitope mapping. Differential binding of exemplary IL-17 and aIL-22 MABs of the present invention to distinct binding sites. Cross-competition experiments show that anti-IL-17 antibodies 17E3 and 24D3 compete against each other but not against antibody 9A2 indicating a different binding site for the latter (A). Similarly, anti-IL-22 antibodies 30G1, 35G11 and 41D11 compete against each other but not against antibody 51G4, indicating as well two binding sites, one for the first group of antibodies and a second for antibody 51 G4 (B). The results for the exemplary anti-IL-22 antibodies of the present invention have been verified by sandwich ELISA experiments (C). Antibody 9A5 is a MAGEA3 specific antibody which is non-reactive with IL-17 and IL-22 and used herein as negative control (A, B).

Figure 42:
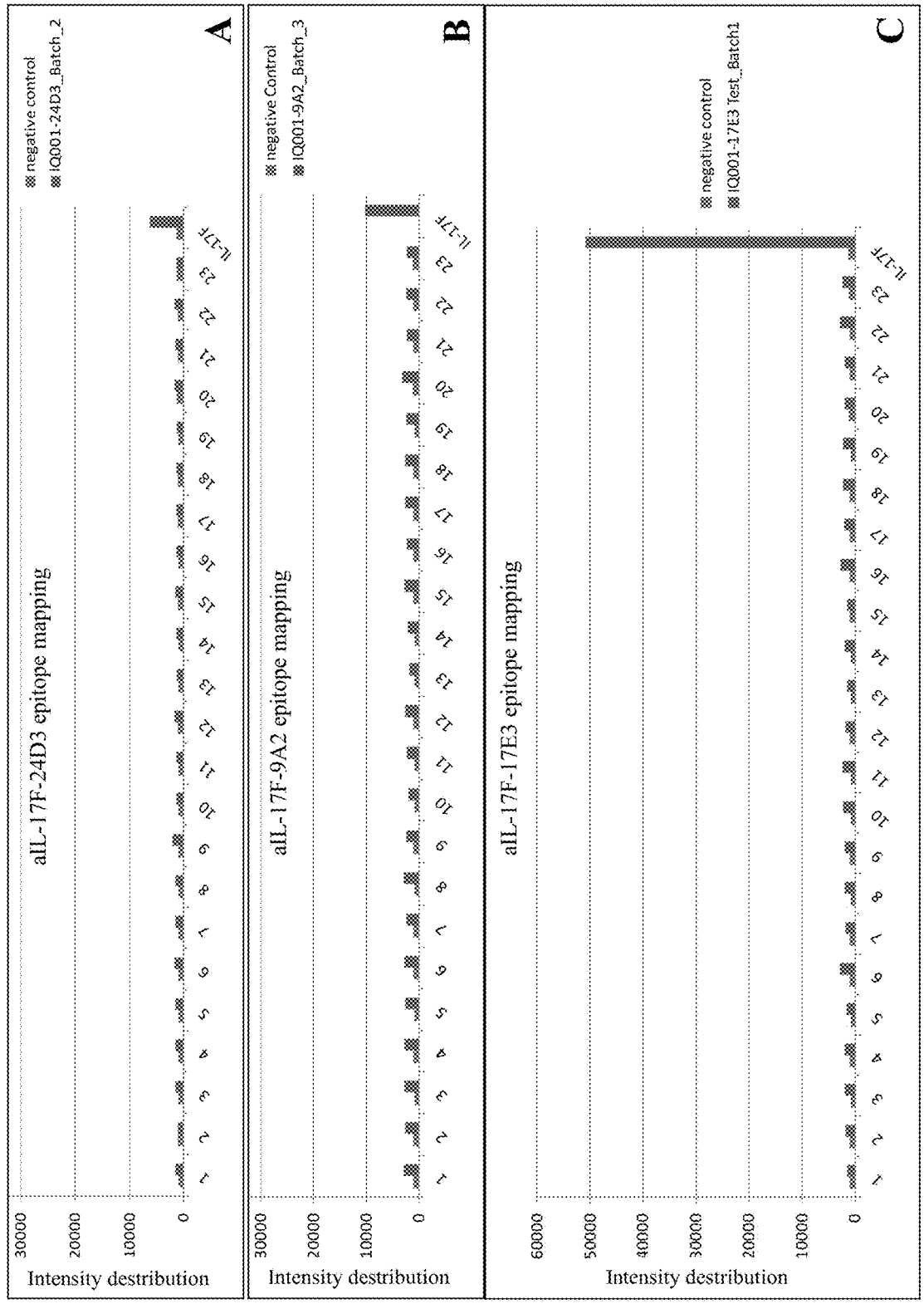

FIG. 42: Results of the PepStar™ analysis of the binding regions of MABs to their respective antigens—IL17F. Binding to overlapping 20mer peptides (15 amino acid overlap) spotted on microarray is shown covering full-length IL-17F including all known variants with full-length IL-17F as last column The low signal strength observed in respect of the binding to the full length antigen does not necessarily correlate to a lack of binding, since the low signal strength or lack of signal may also occur due to the orientation and use of surface lysines to immobilize the antigen. However, observed binding to full-length IL-17F suggests a preferential binding of the exemplary antibodies 24D3 (A), 9A2 (B) and 17E3 (C) to conformational epitopes. X-axis from left to right: Peptides numbered 1 to 23 and full-length IL-17F FIG. 43: Results of the PepStar™ analysis of the binding regions of MABs to their respective antigens—IL-22. All antibodies show very weak binding patterns to microarray bound peptides indicating failure to recognize linear peptides derived from their specific antigen. Observed low signal strength may have the same causes as indicated in FIG. 42. All tested anti-Il-22 antibodies appear to bind preferentially to conformational epitopes. Preliminary binding results are shown for anti-IL-22 antibodies: (A) 30G1, (B) 35G11, (C) 41D11 and (D) 51G4. X-axis from left to right: Peptides numbered 1 to 27 and full-length IL-22. Y-axis—Intensity distribution from 10000 to 60000 in 10000 steps.

Figure 44:
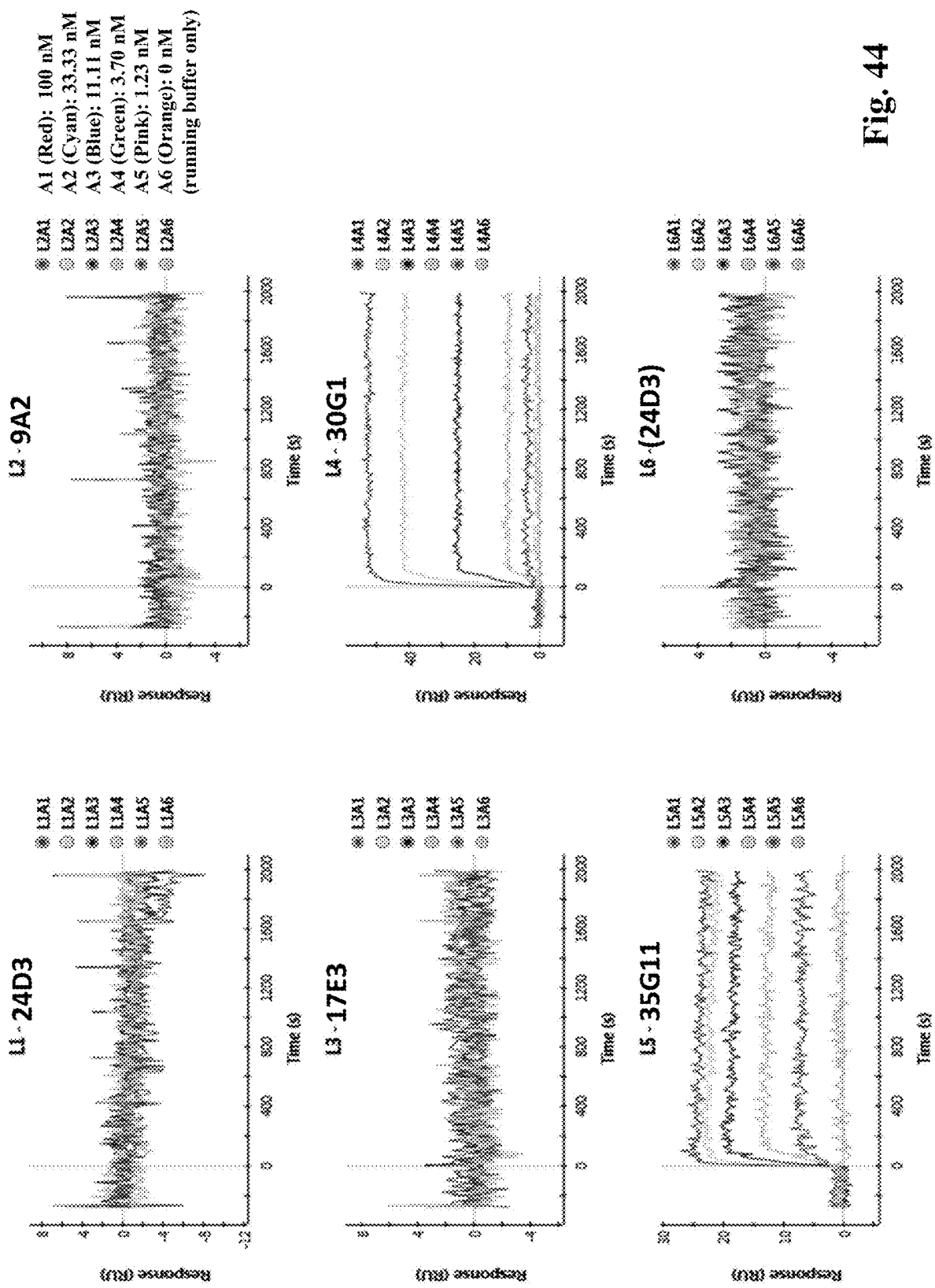

FIG. 44: Results of ProteOn XPR36 based analysis of antibody affinities. Injection of IL-22 in concentrations of A1: 100 nM, A2: 33.33 nM, A3: 11.11 nM A4: 3.70 nM A5: 1.23 nM and A6: 0 nM (running buffer only). Identifiers A1-A6 are preceded by prefixes L1 to L6 (LA1 etc.). Same concentrations were used in the following FIGS. 45-46. Data was referenced using the interspot regions of the sensor chip. Surfaces coated with exemplary aIL-22 antibodies of the present invention 30G1 and 35G11 show specific, concentration dependent binding reactions of the ligand.

FIG. 45: Detailed analysis of the sensorgrams concerning the binding of IL-22 to the aIL-22 30G1 antibody of the present invention. (A) Overlayed graphs for the *Langmuir* fit and experimental data of the binding reaction indicate a good fit to 1.1 *Langmuir* model. Residuals plot (B) shows a random scatter with the magnitude of the noise level indicating a good residual fit. Table below the figures shows the kinetic parameters derived from the fitted curves for the association ($k_a$), dissociation ($k_d$), $R_{max}$ and the calculated dissociations constant KD.

FIG. 46: Detailed analysis of the sensorgrams concerning the binding of IL-22 to the aIL-22 35G11 antibody of the present invention as described in FIG. 45.

Figure 47:
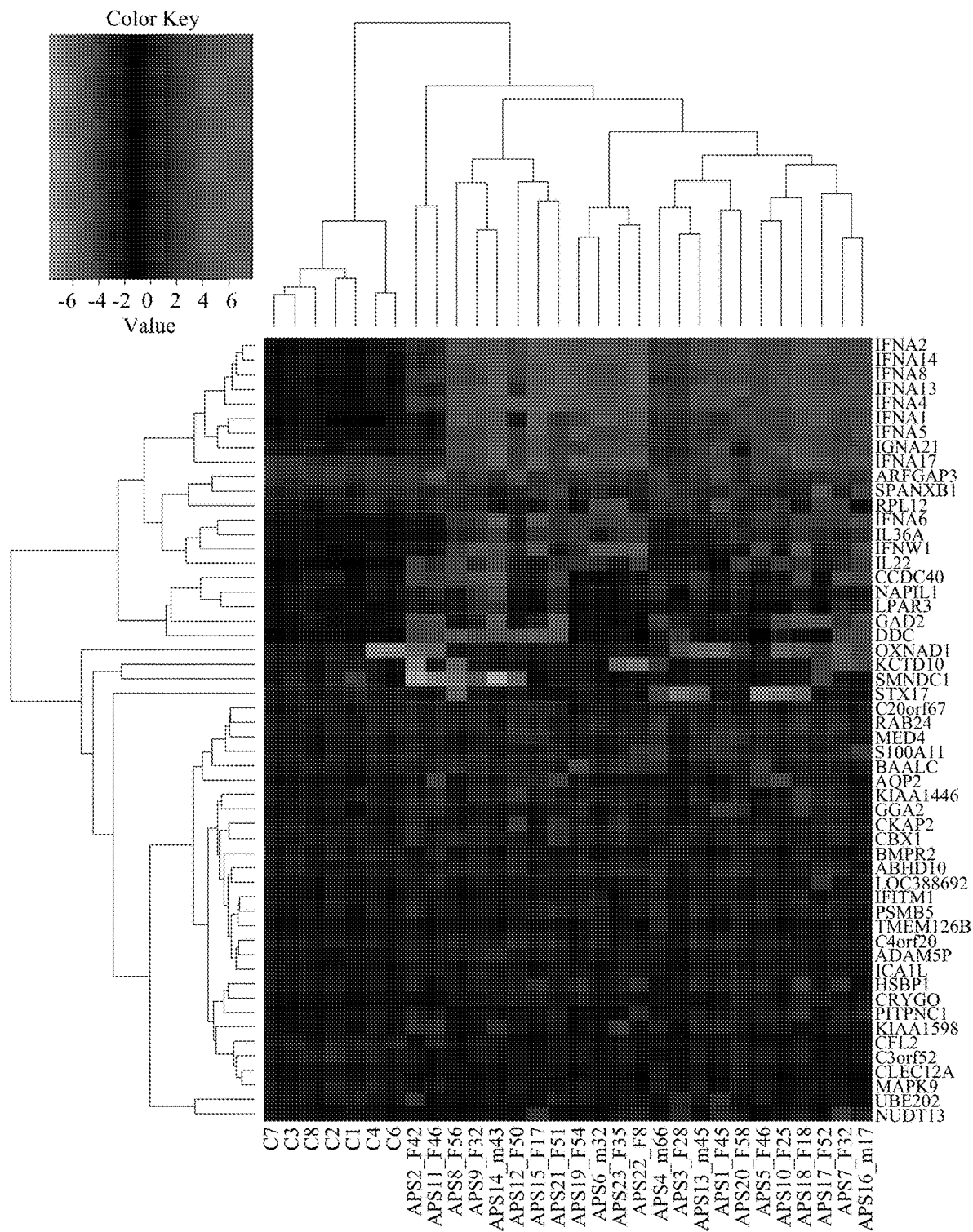

FIG. 47: Antibody response on the protein array assessed for the whole sample set. Hierarchical clustering with logarithmic normalized data using 30 samples and up to 54 measurements for each sample. The missing values (0 probe contains them) have been omitted in distance calculation. The distance metric is euclidian. Clustering is done using agglomerative clustering with average linkage.

Figure 48:
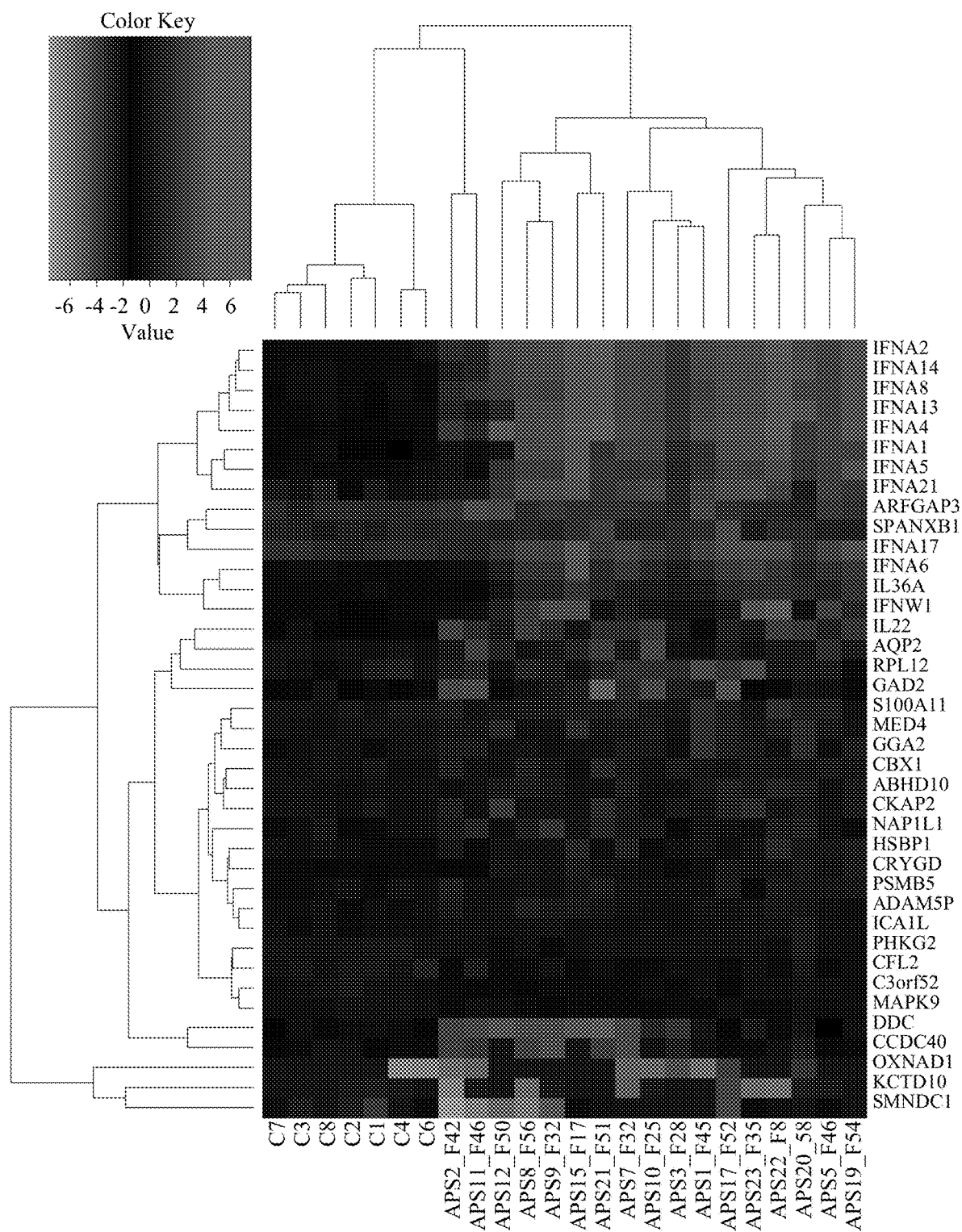

FIG. 48: Clustering with logarithmic normalized data for female patients. Hierarchical clustering using 24 samples and up to 39 measurements for each sample. The missing values (0 probe contains them) have been omitted in distance calculation. The distance metric is euclidian. Clustering is done using agglomerative clustering with complete linkage.

Figure 49:
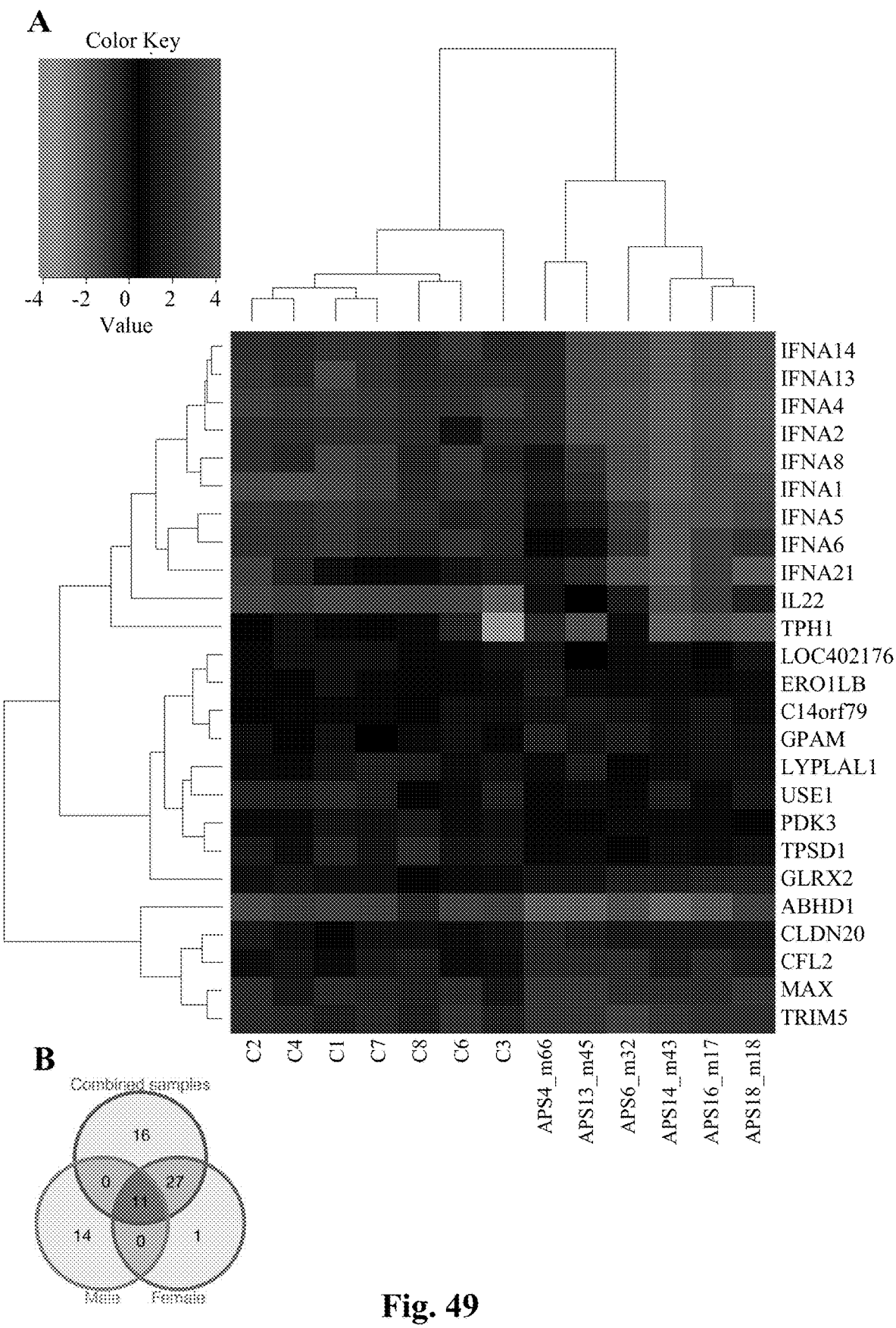

FIG. 49: (A) Clustering with logarithmic normalized data for male patients. Hierarchical clustering using 13 samples and up to 25 measurements for each sample. The missing values (0 probe contains them) have been omitted in distance calculation. The distance metric is euclidian. Clustering is done using agglomerative clustering with average linkage. (B) Intersections of sets: combined samples, Female and Male.

FIG. 50: Schematic representation of a general preferred process for isolating and producing recombinant human monoclonal antibodies derived from human memory B cells obtained from patients which are affected with an impaired central and/or peripheral tolerance or loss of self-tolerance, in particular APECED/APS1 patients secreting IgG antibodies that bind and/or neutralize human autoantigens comprising the methods of the present invention for providing short term oligoclonal cultures of antibody-secreting cells.

DETAILED DESCRIPTION OF THE INVENTION

The present invention generally relates to a method of isolating monoclonal autoantibodies with a desired antigen specificity, wherein a B cell expressing the monoclonal antibody is isolated from a sample obtained from a mammal which is affected with an impaired central and/or peripheral tolerance or loss of self-tolerance, which is a disorder typically associated with a disrupted or deregulated genesis of self-tolerance.

The principle attempt of cloning human antibodies is known in the art: see. e.g., Traggiai et al. describing an efficient method to make human monoclonal antibodies from memory B cells, which are capable of neutralization of SARS coronavirus in Nature Medicine (Traggiai et al., Nat. Med. 10 (2004), 871-875), and international applications WO2008/081008, WO2010/069603 and WO2008/110372 describing the cloning of human antibodies, in particular human antibodies recognizing beta-amyloid peptide, alpha synuclein and NY-ESO protein, a tumor specific antigen. In all these approaches as well as in other previous attempts healthy volunteers or patients have been used as the source of the human antibodies suffering from the disease caused by the infectious agent or associated with one particular antigen but having an unusual stable and mild disease state as indication of the presence of protective autoantibodies.

This approach suffers from the drawback that in principle for each antigen of interest a corresponding patient pool has to be identified producing an appropriate antibody such patients however may not always be available. Furthermore, though the antibodies so identified may be protective in those patients from whom they have been isolated they may be not effective or may even do not recognize the antigen in different patient populations, for example due to the presence of different neoepitopes. Furthermore, for some disorders or clinical pictures such as indicated hereinabove the respective antigen or group of antigens may not be known yet.

In this context, experiments performed in accordance with the present invention surprisingly revealed that APECED/APS1 patients display an auto-immunosome, i.e an autoantibody profile which in its variety is outstanding and represents a broad spectrum of binding molecules specific for proteins prone to invoke an autoimmune response and/or potentially associated to disorders related to an undesired autoimmune response. Thus, the provision of molecule members of the auto-immunosome identified in accordance with the present invention may pave the way for novel targets and means for therapeutic intervention and diagnosis of such disorders. APS1 is a rare autoimmune disease caused by mutations in the Autoimmune Regulator (AIRE) gene. The AIRE protein governs the expression in medullary thymic epithelium of many peripheral self-antigens (e.g., insulin) that are presented by MHC to tolerise developing thymocytes. In APS1, AIRE mutations cause aberrant negative selection, which enables autoreactive T cells to escape to the periphery.

The spectrum of clinical features in APS1 is extremely variable, but usually with several autoimmune disorders of endocrine tissues. The defining APS1 triad comprises chronic mucocutaneous candidiasis, hypoparathyroidism and adrenal failure (Perheentupa, Endocrinol. Metab. Clin. North Am. 31 (2002), 295-320). Other clinical conditions seen in APECED patients include thyroid autoimmune diseases, diabetes mellitus, gonadal failure, vitiligo, alopecia, chronic hepatitis, chronic gastritis and pernicious anemia and different forms other gastrointestinal symptoms. Importantly, although the patients presented with several clinical symptoms and diseases of autoimmune origin, a survey of numerous patient reports revealed that they did not present with some common diseases of autoimmune or inflammatory origin. Thus, the biological activity of the autoantibodies subject to this invention and developed uniquely in APECED patients, is consistent with the observation that these autoantibodies protect from the following diseases:

lupus erythematosus (all subtypes);
Sjögren's syndrome;
scleroderma (localized or systemic);
Multiple Sclerosis (MS) and other autoimmune neurological diseases;
Rheumatoid arthritis;
Psoriasis;
gluten intolerance (celiac disease);
inflammatory bowel disease (IBD);
Bullous autoimmune skin diseases (pemphigus; pemphigoid);
Cancer, except for oral cancer; and
allergic diseases like atopic eczema, asthma, allergic rhinitis, allergic conjunctivitis.

Another thymus-associated disorder which surprisingly has been found with similar high titre autoantibodies is thymoma, a tumor of thymic epithelial cells, often associated with the autoimmune disease myasthenia gravis (MG), where apparently due to the disturbed function of the thymus cells, negative selection of autoantibodies can be impaired in a similar manner as in APS1. Of all thymoma cases, 30-45% of patients have MG. Additional associated autoimmune conditions include pure red cell aplasia and Good's syndrome (thymoma with combined immunodeficiency and hypogammaglobulinemia). Other reported disease associations are with acute pericarditis, Addison's disease, agranulocytosis, alopecia areata, ulcerative colitis, Cushing's disease, hemolytic anemia, limbic encephalopathy, myocarditis, nephrotic syndrome, panhypopituitarism, pernicious anemia, polymyositis, rheumatoid arthritis, sarcoidosis, scleroderma, sensorimotor radiculopathy, stiff person syndrome, systemic lupus erythematosus and thyroiditis.

In view of the findings of the present invention, which will be also described further below but without intending to be bound by theory, the present inventors hypothesized that the high titer and diverse profile of autoantibodies observed in associated disorders, in particular APECED/APS1 patients is due to an impaired central and/or peripheral tolerance and loss of self-tolerance, respectively, leading to an humoral immune response including both, i.e. "autoagressive" autoantibodies which may be responsible for the susceptibility of such patients to infections such as candidasis but at the same time produce "protective" antibodies which provide a sort of autovaccine against common disorders of autoimmune or inflammatory origin as well as neoplastic diseases such as cancer. In addition, experiments performed within the scope of the present invention surprisingly revealed that autoantibodies observed in APECED patients which seem to be responsible for suppressing an appropriate immune response against candida infection at the same time have therapeutic utility in the treatment of chronic inflammatory and immunological diseases; see Examples 5, 6 and 12.

In accordance with the present invention the hypothesis could be substantiated by screening the sera of APECED/APS1 patients not only for autoantibodies against mediators of immune response such as interferons and interleukins for which the presence of autoantibodies had already been described but also to antigens which are associated with metabolic disorders, vascular function, neurodegenerative diseases and tumors. Those experiments surprisingly revealed that APECED/APS1 patients also produce autoantibodies which otherwise would be rather expected in for example tumor patients with a stable clinical course of the disease because of the presence of autoantibodies against tumor cells or proteins mediating neoplastic growth of the cells.

In particular, in accordance with the present invention protein microarray (ProtoArray®; Invitrogen, Carlsbad USA) have been screened against sera of APECED/APS1 patients and identified a complete set of auto-antigens as many as 3000, which may also be referred to as "AutoImmunosome"; see Example 7 and Tables 1 to 13. In particular, sera from 23 APECED patients and 7 healthy control subjects were tested against the protein array with in total 9000 recombinant proteins. Antibody activity of the APECED sera compared to controls was positive against 3000 target antigens. As demonstrated in the Examples, experiments performed in accordance with the present invention also confirmed that known auto-antigen candidates showed sero-reactivity.

Further experiments performed in accordance with the present invention were successful in cloning autoantibodies to selected autoantigens, i.e. IL-17F and IL-22; see Example 2. In particular, a method for cloning autoantibodies of desired specificity, i.e. against any of the identified autoantigen of the mentioned AutoImmunosome is disclosed, thereby providing the first time a common "Mab-AutoImmunosome", i.e. a complete set of auto-antibodies and thus reservoir for antibodies and binding molecules useful for therapy and diagnosis of autoimmune disorders as well as diseases caused by or associated with the aberrant expression or presence of autoantigens.

Hitherto, APECED/APS1 patients were known to show a broad seroreactivity which however could also be assumed to result from a rather unspecific immune response and thus polyclonal antibodies without any particular pronounced biological activity, specificity and affinity. This is particular true for the patient pool preferably selected in accordance with the present invention and illustrated in the Examples, wherein the patients do not only suffer from symptoms known from the clinical picture of common autoantibody disorders but from a general poor physical and/or psychological state of health indicated by enamel defects in teeth, nail and hair abnormalities, loss of skin pigment (vitiligo), loss of hair (alopecia), mental depression.

Hence, it was thus surprising that despite the rather severe state of health of the APECED/APS1 patients they nevertheless provide a source for highly specific neutralizing monoclonal antibodies such as illustrated for the anti-IL-17F and IL-22 antibodies in the Examples and even more surprisingly a reservoir for monoclonal autoantibodies to very many autoantigens.

In this context, since APECED/APS1 patients display a humoral response against mediators of the immune response such as interferon (IFN) alpha/omega and interleukin IL-17 A/F and IL-22, in one embodiment of the present invention monoclonal antibodies are isolated from B cells obtained from such patients for use in the therapy or diagnosis of chronic inflammatory and immunological disorders such as but not limited to chronic inflammatory diseases such as Acne vulgaris: Arthritis such as Gouty arthritis, Systemic lupus erythematosus (SLE), Osteoarthritis, Psoriatic arthritis, Rheumatoid arthritis (RA); Asthma-Celiac disease: Crohn's disease (CD); Chronic prostatitis: Dermatitis; Diabetes mellitus Type 1; Glomerulonephritis; Hypersensitivities: Myocarditis; Multiple sclerosis; Inflammatory bowel diseases: Pelvic inflammatory disease; Polymyositis; Psoriasis (PS); Sarcoidosis; Vasculitis; Interstitial cystitis, Familial Mediterranean fever (FMF), Pyogenic arthritis, pyoderma gangrenosum, acne (PAPA), Cryopyrin-associated periodic syndromes (CAPS), Hyper IgD syndrome (HIDS), Adult and juvenile Still disease, Schnitzler syndrome, TNF receptor-associated periodic syndrome (TRAPS), Blau syndrome; Sweet syndrome, Deficiency in IL-1 receptor antagonist (DIRA) Recurrent idiopathic pericarditis, Macrophage activation syndrome (MAS), Urticarial vasculitis, Antisynthetase syndrome, Relapsing chondritis, Behqet disease, Erdheim-Chester syndrome (histiocytosis), Synovitis, acne, pustulosis, hyperostosis, osteitis (SAPHO). Rheumatoid arthritis, Periodic fever, aphthous stomatitis, pharyngitis, adenitis syndrome (PFAPA), Urate crystal arthritis (gout), Type 2 diabetes, Smoldering multiple myeloma, Postmyocardial cinfarction heart failure, Osteoarthritis or in inflammation occuring due to reperfusion injury or transplant rejection, or in the treatment of diseases associated with a disrupted or deregulated genesis of self-tolerance, such as APS1.

In this context, it is noted that despite similarities in clinical condition, there is a clear distinction between those caused by mutation in gene involved in autoimmune regulation and/or development such as the aire gene, and the solitary components of the diseases, such as Addison's disease and diabetes mellitus that are caused by joint activity of environmental factors affecting individuals with so called risk-HLA haplotypes. For example, APS1, with its mucocutaneous candidiasis, hypoparathyroidism, and Addison's disease, is a monogenic disorder resulting from mutations of the autoimmune regulator gene (AIRE) while in contrast, APS2, similar to most common autoimmune disorders, is a polygenic disease with the dominant susceptibility locus on chromosome 6 within the major histocompatibility complex (MHC). APS2 was reported to be associated with the class I human leukocyte antigen (HLA) allele B8. With the discovery of class II HLA alleles, and their strong association with type 1 diabetes, and linkage disequilibrium of HLA-DR3 with HLA-B8, it was assumed that the association of HLA-B8 with Addison's disease was predominantly due to its association with HLA-DR3 and DQB1*0201, as is the case for type 1 diabetes and celiac disease; for review see, e.g., Baker et al., J. Clin. Endocrinol. Metab. 95 (2010), E263-E270.

While samples of patients with an autoimmune disorder due to risk-HLA haplotype and polygenic disorder, respectively, may be used in accordance with the present invention, samples of patients are preferably used, who suffer from such disorder because of one or more mutation(s) in on particular gene such as the Autoimmune Regulator (AIRE) or the forkhead box protein 3 (FOXP3) gene.

As explained above and demonstrated in the Examples, the concept underlying the present invention has been demonstrated with B cell samples from patients suffering from APECED/APS1, i.e. a rare monogenic autoimmune disease caused by mutations in the AIRE gene. In this context, the use of B cell samples from patients suffering from a monogenic disorder responsible for the impaired central and/or peripheral tolerance or loss of self-tolerance is advantageous and preferred over samples from for example patients suffering from polygenic disorders such as APS2 or from thymoma since because being monogenic the clinical picture of the disorder is quite reliable among those patients and does allow easy reproducibility of the method of the present invention. Furthermore, monogenic disorders more easily allow the generation of corresponding animal models such as mice, for example by inducing substantially the same mutation in the corresponding gene such as AIRE.

Accordingly, in one preferred embodiment of the method of the present invention the disorder of the patient providing the biological sample is monogenic and, preferably a disorder associated with at least one mutation of the Autoimmune Regulator (AIRE) gene; see also supra. Alternatively, or in addition the monogenic disorder may be associated with at least one mutation in the forkhead box protein 3 (FOXP3) gene: see also infra. Nevertheless, while the method of the present invention is preferably performed with B cell samples obtained from patients affected with a monogenic disorder, under specific circumstances, thymoma patients may be used as an equivalent source for the B cells expressing the antibody of interest, in particular if displaying an aire-deficient phenotype. However, since varying in humoral immune response due to the nature of tumors in accordance with the present invention it is preferred to select mammals which are not suffering from any disorder associated with tumors, such as thymoma.

In some instances, it may be desirable to provide a monoclonal autoantibody from a mammal other than human, for example as research tool in animal experiments or for the purposes of preclinical studies in animal models of given disease. Therefore, in one embodiment of the method of the present invention the mammal is not human but an animal, preferably an animal commonly used in laboratory investigations and animal trials such as dog, cat, horse, preferably rodents such rat, gerbil and mice. Most preferably, the non-human animal is a mouse, preferably an AIRE or FOXP3 deficient mouse (AIRE: Ramsey et al., *Hum. Mol. Genet.* 11 (2002), 397-409: Kuroda et al., *J. Immunol.* 174 (2005), 1862-1870: FOXP3: Brunkow et al., *Nat. Genet.* 27 (2001), 68-73; Wildin et al., *Nature Genetics* 27, (2001) 18-20). As postulated in the present application and meanwhile confirmed by Kärner et al. in *Clin. Exp. Immunol.* (2012); doi: 10.1111/cei.12024, the disclosure content of which is incorporated herein by reference, aire-deficient mice develop Abs (Antibodies) binding and neutralizing Th17-related cytokines as APECED patients do, substantiating a pathogenetic link with AIRE-deficiency in humans and mice. In particular, neutralizing autoantibodies to IL-17A in aged aire-deficient BALB/c mice were found characteristic to both, human and mouse AIRE-deficiency states.

Nevertheless, as illustrated in the Examples, preferably the mammal in the method of the present invention is a human patient, preferably a patient suffering from an autoimmune disorder which is autoimmune polyendocrinopathy-candidiasis-ectodermal dystrophy (APECED) or immune dysregulation, polyendocrinopathy, enteropathy, X-linked (IPEX). IPEX (immunodysregulation polyendocrinopathy enteropathy X-linked syndrome) is a rare X-linked recessive disease resulting in aggressive autoimmunity and early death which is described in more detail in the "Definitions and Embodiments" section below. In case of APECED the mammal typically suffers from one or more symptoms selected from the group consisting of chronic mucocutaneous candidiasis (CMC), hypoparathyroidism and autoimmune adrenal insufficiency (Addison's disease); see also supra.

As illustrated in the Examples, according to the method of the present invention the sample for isolating the antibody of interest comprises or consists of peripheral blood mononuclear cells (PBMC) and serum for the detection of possible antibody reactivities. The sample derived from the subject may either be directly used for, e.g., testing seroreactivity against one or more of the desired antigen(s) or may be further processed, for example enriched for B lymphocytes. In particular, it is preferred that the sample comprises or is derived from B cells that produce the antibody of interest, most preferably memory B-cells.

In principle, B-cells producing antibodies can be immortalized and antibodies can be cloned thereof as described in detail in section "B-cell immortalization" below. However, in the preferred embodiment, the method of the present invention does not comprise the step of immortalization of B-cells. Rather, as described in the Examples, memory B cells are isolated from peripheral blood monocytic cells derived from the peripheral blood of voluntary subjects and are cultured under conditions allowing only a definite life span of the B cells, typically no more than 1 to 2 weeks until singling out the cells from B cell cultures which are reactive against the desired antigen subsequently followed by RT-PCR of single sorted cells for obtaining the immunoglobulin gene repertoire for said antibody; see also the Examples, in particular Example 2.

As indicated in the Examples, the memory B cells were first stimulated with a first polyclonal B cell activator, i.e. by incubation with EBV containing supernatant obtained from B95-8 cells and then separated by seeding in a different medium with a second polyclonal B cell activator, i.e. CpG2006.

In fact, during experiments performed within the scope of the present invention it turned out that previous methods aiming at B cell immortalization for providing a B cell clone producing the antibody of interest such as those described in international application WO 2004/076677 do not work quite well if at all for B cells of patients suffering from APECED or other autoimmune diseases. Without intending to be bound by theory, it is believed that this is because that due to the impaired tolerance or loss of self-tolerance of the immune system, B cells, in particular those which are of interest in accordance with the present invention, have been pre-activated or triggered through signaling pathway otherwise which induces or is associated with the induction of apoptosis for which reason those cells have only a limited life span and are no longer effectively amenable to immortalization, at least not under the conditions hitherto reported for EBV-mediated immortalization. In view of the findings made in experiments performed in accordance with the present invention but without intending to be bound by theory it is believed that the simultaneous occurrence of cytokine and anti-cytokine antibodies such as observed in APECED/APS1 patients will lead to immune complex formation which could bind to B cells and activate them, thus explaining an activated state of B cells from APS1 patients and their vulnerability to senescence.

However, as illustrated in the Examples and mentioned above, in accordance with the present invention a method is provided to isolate the human antibodies by treating and culturing the memory B cells under short term oligoclonal culture conditions allowing only a definite life span of the B cells during activation with subsequent oligo or single cell harvesting of oligoclonal cultures producing the antibody of interest and cloning the cDNA of the variable region of the antibody. A schematic representation of the preferred method for isolating the human antibodies of the present invention is illustrated in FIG. 50.

Accordingly, in a preferred embodiment and particular aspect, the present invention relates to a method of producing a human antibody or binding fragment thereof with desired antigen specificity characterized by isolating B cells from short term oligoclonal cultures of activated B cells that secrete antibodies of IgG isotype comprising the following steps in the sequence:
(a) selecting B cells that express antibodies against a protein of interest from one or more biological samples;
(b) stimulating the selected cells with a first polyclonal B cell activator under cell culture conditions;
(c) separating the cells from said activator;
(d) activating the stimulated cells with a second polyclonal B cell activator under cell culture conditions:
(e) screening the activated cells that express IgG isotype antibodies of interest and preferably;
(e') single-cell harvesting of oligoclonal cultures producing the antibody of interest;
(f) sequencing and/or cloning the cDNA of at least the variable light and heavy chain regions and optionally constant region of the antibody of interest.

The term "oligoclonal culture" refers to a culture of cells producing the antibody of interest derived from one or a few cells that have been activated. Preferably, the oligoclonal culture is derived from one single B cell, which may also be referred to as "B cell clone". As mentioned above, and unless stated otherwise, the terms "oligoclonal" and "clone" do not imply or refer to immortalized cells. As illustrated in the Examples, the biological sample is preferably derived from peripheral blood mononuclear cells of a patient whose serum has been screened for the presence of auto-antibodies against the protein of interest.

Typically, the B cells that express antibodies against a protein of interest are selected on the basis of the expression of at least one B cell-surface membrane marker such as preferably CD22. However, in addition or alternatively the B cells are selected on the basis of their binding to the antigen using for example ELISPOT.

Preferably, the B cells are memory B cells, in particular human memory B cells and are depleted from IgM and/or IgD isotypes already before exposure to the first polyclonal activator, for example by FACS using appropriate B cell-surface membrane marker specific antibodies: see also the Examples.

The antibody-producing cells are isolated, stimulated, and proliferated according to the methods of the present invention in bulk cultures for a variable number of hours (e.g. from 1 up to 6 hours, or less preferred for longer periods of time such as 6 to 12 hours) before being subdivided into several pools of about 10 cells per culture for stimulation by the second polyclonal activator, each representing a population of cells, that are cultured separately (e.g. 96-, 384- or 1536 well plates). The bulk, polyclonal population of cells maintained in cell culture conditions may be tested using the assays performed already on sera to select the donor, or any other assay relevant for future use of the cells, in order to confirm the presence of cells. Moreover, some aliquots of the polyclonal population of cells may be put in vials and stored as frozen cells (as normally done for established mammalian cell lines), to be thawed and cultured again later. In this context, it is intended that the same culture supernatant can be tested on several different antigens, possibly all the antigens against which serum reactivity of the biological samples have been determined, e.g., in a protoarray.

Aliquots of the cell culture supernatant can be screened for their binding and/or functional activity in a high throughput manner, in order to identify the positive well(s) presenting the desired activity, possibly using a dose-response analysis with serially diluted culture supernatants or partially purified antibody preparations (e.g. obtained by affinity chromatography on protein A columns) in parallel experiments. Optionally, the positive pools of cells (i.e. those showing the desired antigen specificity and/or biological activity) can be then used to generate a new series of pools of cells to further restrict the screening to the level of a single cell culture(s) and consequently isolate the cDNA of the antibody variable regions form the selected cell secreting a monoclonal antibody having the desired specificity and activity, at least at the level of the initial screening assay. The selected monoclonal antibodies should be then re-evaluated using other more demanding functional assays and characterized at the level of isotype and of $V_H/V_L$ sequence, after isolating them using the recombinant DNA technologies applicable on B cells.

As further illustrated in the Examples, the first polyclonal B cell activator is preferably Epstein-Barr virus (EBV) and/or the second polyclonal B cell activator is preferably a CpG-based oligonucleotide.

Though EBV and CpG, in particular CpG2006 (ODN 2006 according to Hartmann et al., J. Immunol. 164 (2000), 1617-1624) are used as the preferred first and second polyclonal B cell activator, respectively, other polyclonal B cell activators are known to the person skilled in the art; see, e.g., European patent EP 1 974 020 B1, in particular for the first polyclonal B cell activator in accordance with the present invention at page 13, paragraph [0115] to page 14, paragraph [0126], the disclosure content of which is incorporated herein by reference and for the second polyclonal B cell activator such as TLR agonists with similar properties as CpG at page 12, paragraph [0096] to page 13, paragraph [0104], in particular CpG2006 illustrated by SEQ ID NO: 1 in paragraph [0177], and European patent EP 1 597 280 B1 at page 5, paragraphs [0014] to [0022], the disclosure content of which is incorporated herein by reference.

In this context, it is noted that though EBV has been used in the prior art for immortalizing B cells, EBV and like viral immortalizing agents have dual activities, i.e. besides the capability of immortalizing B cells under appropriate cell culture conditions to also independently activate the B cells inducing both proliferation and Ig secretion. This early function of EBV is distinct from its late function of immortalizing B cell lines as shown by Tsuchiyama et al., Hum. Antibodies 8 (1997), 43-47. Accordingly, the present invention only makes use of the early function as a polyclonal B cell activator of EBV and of similar viral immortalizing agents but not of the late function as a transforming virus capable of generating immortalized B cell lines that can be maintained in cell culture for several months, thereby only providing and using short term oligoclonal cultures of activated B cells with limited life span as further described below. Making use of only the early function of EBV and like agents can be accomplished by adjusting the time of culturing the cells in the presence of EBV only to the extent necessary to achieve a stimulation of the cells, i.e. proliferation of the cells and antibody secretion, with subsequent separation of the cells from EBV and like agents or vice versa.

As further turned out in the experiments performed within the scope of the present invention and illustrated in the Examples, the presence of a cytokine such as interleukin-2 (IL-2) as taught in European patent EP 1 974 020 B1 and EP 1 597 280 B1 or other costimulatory molecules such transferrin is not necessary. Rather, it turned out that in the method of the present invention the presence of cytokines in the B cell culture have substantially no beneficial effects, probably because of the mentioned preactivation or signaling in the B cells. Accordingly, in a preferred embodiment of the method of the present invention the culture conditions in step (b) and/or step (d) do not comprise a cytokine.

Typically, the stimulation of the selected cells with the first polyclonal B cell activator lasts less than 8 hours, preferably less than 6 hours and in the particular preferred embodiment of the method of the present invention the selected cells in step (b) are stimulated for about three to five hours.

After activation, the B cells are separated from the first polyclonal B cell activator in step (c), wherein the activator is removed for example by diluting off or washing out. In this context, experiments performed in accordance with the present invention confirmed that the presence of the first polyclonal B cell activator is indeed no longer necessary by ensuring the total removal of any thereof using multiple washing steps before subjecting the stimulated cells to the second polyclonal B cell activator. Nevertheless, for the purposes of the method of the present invention it is usually efficient to remove the first polyclonal B cell activator by diluting off, i.e. seeding the B cells in fresh culture medium. Thus, the cell culture subjected to the first polyclonal B cell activator may be placed in fresh culture media containing the second polyclonal activator thereby diluting the medium with the first polyclonal activator to a maximum of about 10%, preferably 5%, more preferably to 1%, and most preferably substantially below 1%, for example 0.5%, 0.1% or less.

Typically, during the culture in the presence of the second polyclonal activator the B cells are seeded at low concentration of cells per culture, for example in wells of microtiter culture plate. Preferably, the concentration of cells per well is 5 to 20, more preferably 5 to 15 and most preferably 10.

As mentioned hereinbefore and illustrated in the Examples, in step (d) the stimulated B cells are cultured in the presence of the second polyclonal B cell activator such as CpG no more than one to two weeks until singling out the cells from the B cell cultures which are reactive against the desired antigen. In a preferred embodiment of the method of the present invention, the transferred selected cells are exposed in step (d) to the second polyclonal activator for about eight to fourteen days. Preferably, in step (d) and/or (e) the cells are cultured under oligoclonal conditions with about ten cells per well in eight to fourteen days short term cultures.

Though the above described method of the present invention of isolating and culturing B cells in the method of the present invention for isolating and producing a human monoclonal antibody of interest is advantageous and thus preferred, the person skilled in the art nevertheless may use alternative means and methods such as those described in the prior art even though they may be less efficient and may provide not as many B cell clones producing the antibody of interest as the preferred method disclosed herein.

Further methods of isolating human monoclonal antibodies using methods based on hybridoma technology, clonal expansion of peripheral B cells, single-cell PCR, phage display, yeast display and mammalian cell display are known to the person skilled in the art and are reviewed for example in Beerli and Rader, *Landes Bioscience* 2 (2010), 365-378. A method of efficient generation of monoclonal antibodies from single human B cells by single cell RT-PCR and expression vector cloning is described by Tiller et al., in *J. Immunol. Methods* 329 (2008), 112-124.

Figure 1:
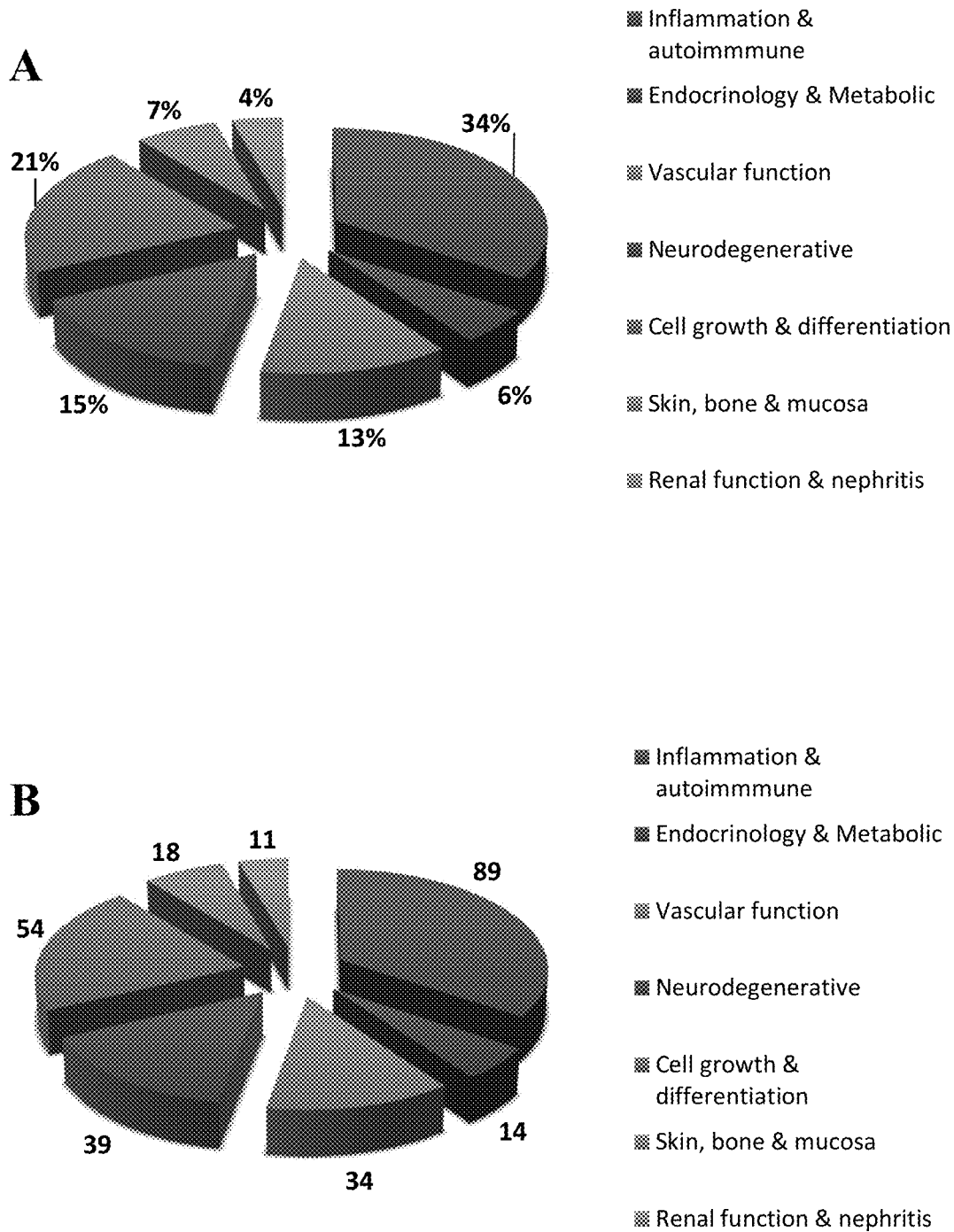
FIG. 1: A: APS1 patient seroreactivity (as a percentage of total shown number of reactivities that have been measured in at least one patient) against extracellular proteins that have been implicated in physiological functioning of tissues or pathophysiology of human disease.

According to the present invention, samples taken from individuals are tested individually or combined in a batch for seroreactivity against antigens of interest with techniques known in the art, such as ELISA: see also the Examples. The samples can be tested for seroreactivity against a particular antigen or against several antigens, at once or sequentially, wherein the antigens can be chosen as to represent particular groups of molecules. Said groups of molecules may be chosen, depending of, e.g., the involvement of the molecules in a particular biological process such as development, differentiation, adult tissue maintenance or disease. In one embodiment of the present invention the samples display substantially the same seroreactivity against a panel of antigens comprising at least one member of secreted or transmembrane proteins involved in inflammation, an autoimmune disorder, cell growth and differentiation, muscular function and neurodegeneration as indicated in tables 1 to 14 and FIGS. 1 to 4. Preferably, the sample or pool of samples for obtaining the antibody in accordance with the method of the present invention displays a seroreactivity substantially the same as shown in FIG. 1.

Preferably, the antibody to be isolated in accordance with the method of the present invention is selected based on the frequency of antibody response, strength of binding and/or antibody titer in the protoarray assay, and preferably for its potential physiological effect. For example, if seroreactivity is observed for >10% of the samples of the subjects to a given target protein the putative monoclonal antibody may be decided to be further pursued. Preferably, >20%, more preferably >30%, still more preferably 40%, still more preferably >50%, particularly preferred >75% and most preferably >90% of the samples of the different subjects show seroreactivity against the desired target antigen. Typically, the sample pool comprises at least samples from 10 different subjects, more preferably at least 15 subjects and most preferably at least 20 subjects. In view of the findings of the present invention seroreactivity of the samples corresponds with the rare clinical conditions found for the subjects such as for APECED patients; see also supra.

On the other hand, the use of samples obtained from patients suffering from a monogenic autoimmune disorder described above, in particular APECED as the preferred embodiment of the present invention provides the additional advantage that because of the defined phenotype and symptoms the corresponding patients are clearly defined but nevertheless produce a diversity of antibodies due to individual difference in genetic background, development, environment and challenge to infectious agents. For this reason, a pool of samples from the patients are tested in order to determine and isolate an antibody which is specifically produced only by one patient or patients with a particular condition, which otherwise may not be obtained when testing individuals only. Accordingly, in one preferred embodiment of the method of the present invention, a pool of samples from patients is tested for seroreactivity to the antigen of interest. After the pool of samples has been tested seroreactive to the desired antigen, a corresponding pool may be further processed for isolating the desired antibody or the sample pool may be reduced in order to identify the patient(s) whose sample actually contributed to the seroreactivity of the sample pool. The subgroup of patients from whom a corresponding pool is generated may be selected depending on different clinical status criteria of the patients, such as gender, age, quantity and/or severity of the disease's symptoms. As exemplary shown in Example 16, a gender difference in antibody response could be observed in the proteoarray data obtained from APECED patients. As indicated in Table 28, several antibodies could be obtained specifically from female or from male patients only. Furthermore, from these differentially expressed antibodies, substantially no antibodies against soluble proteins could be observed in male patients. Therefore, in one embodiment the method of the present invention for isolating a monoclonal antibody with desired antigen specificity is provided, wherein the antibody is specifically isolated from a subject with an impaired central and/or peripheral tolerance or loss of self-tolerance which has been selected depending on different clinical status criteria, such as gender, age, quantity and/or severity of the disease's symptoms. In one embodiment the subject is selected depending on its gender. i.e. the antibodies are isolated from male or female subjects only.

As described in the appended Examples the antibodies isolated in accordance with the method of the present invention preferably recognize a conformational epitope. Hence, this is a further advantage of the method of the present invention in that due to the fact that the humoral immune response has been elicited against the native antigen in its physiologic and cellular environment typically autoantibodies are produced and can be isolated which recognize a conformational epitope of the antigen due to its presentation in context for example with other cellular components, presentation on a cell surface membrane and/or binding to a receptor. In contrast, conventional methods of generating monoclonal antibodies such as mouse monoclonals, humanized versions thereof or antibodies obtained from phage display typically employ an antigenic fragment of the target protein for immunizing an non-human mammal and detection, respectively, upon which usually antibodies are obtained which recognize linear epitopes or conformational epitopes limited to a two-dimensional structure of the immunogen rather than the presence of the native protein in its physiological and cellular context. Accordingly, it is prudent to expect that the autoantibodies isolated in accordance with the method of the present invention are unique in terms of their epitope specificity. Therefore, the present invention also relates to antibodies and like-binding molecules which display substantially the same binding specificity as the autoantibodies isolated in accordance with the method of the present invention. Such antibodies can be easily tested by for example competitive ELISA or more appropriately in a cell based neutralization assay using an autoantibody and a monoclonal derivative, respectively, thereof of the present invention as a reference antibody and the immunological tests described in the Examples or otherwise known to the person skilled in the art.

As further illustrated in the Examples, the autoantibodies isolated in accordance with the method of the present invention preferably from human donors, preferably recognize only the human antigen or at least preferentially over the corresponding antigen from other species such as mice. Therefore, in one embodiment of the present invention, the desired antibody is specific for the species it is derived from, in particular human antigen and preferably does not substantially recognize the corresponding antigen of another species such as of murine origin, for example mice in case of a human antibody. Binding characteristics such as specificity and affinity of the antibodies of the present invention have been tested in several experimental assays as described in detail in the Examples 7, 8, 11, 13 and 14. Further indications could be obtained from in vivo experimental data within the tests of therapeutic potential of exemplary antibodies of the present invention, e.g., in induced psoriasis-like skin inflammation (Example 6) and in induced ear inflammation (Example 12). In this connection, specificity towards human IL-17F of the exemplary anti-IL-17 antibody 24D3 of the present invention could be confirmed by its observed therapeutic effect in the ear inflammation experiments induced by human IL-17F injections and described in Example 12, and the lack of a significant effect in the IMQ induced psoriasis-like skin inflammation, as shown in Example 7 (no significant effect on the inflammation mediated by murine IL-17F). In comparison, the mouse cross-reactive exemplary anti-IL-22 antibody 30G1 has shown a therapeutic effect therein, by reducing clinical symptoms of IMQ-induced psoriasiform lesions.

In addition, as illustrated in Example 9 in APECED related autoantigens coiled-coil structures are more frequently present than in the antigen repertoire of a healthy volunteer. The coiled-coil structure is a structural motif where 2-7 a-helices are coiled together, most commonly dimers and trimers. It contains a repeated pattern of heptad repeat HxxHCxC (H-hydrophobic; C-charged aa). Coiled-coil domain proteins are mostly intracellular enzymes. Exemplary proteins comprising coild-coil domains which have been found as APECED related autoantigens in the proteoarray assay of the present invention are identified in Table 21 in Example 9 and the Protoarray results in concern of two of them in FIG. 31 (CCDC40 and NAPIL). In one embodiment, the antibody of the present invention recognizes an antigen which displays a coiled-coil structure.

As has been further demonstrated for the antibodies isolated in accordance with the method of the present invention, they are capable of neutralizing the biological activity of their target protein. In this context, the term "neutralizing" means that the antibody of the present invention is capable of intervening with the biological activity of its target protein in a biochemical or cell-based assay as can be evaluated by performing the respective assay in the presence of the subject antibody of the present invention, wherein the biological activity of the target protein is reduced concomitantly with increasing level of the antibody of the present invention subjected to the assay compared to the biological activity of the protein without the presence of the antibody of the present invention and in the presence of a compound for example a control antibody which is known to leave the biological activity of the target protein unaffected in kind. Such biochemical and in vitro based assay can also be performed using a reference antibody known to be capable of neutralizing the biological activity of the target protein such as has been shown for the anti-IL-17 and IL-22 antibody of the present invention and subjecting the candidate antibody to the test sample, wherein either an additive neutralizing effect may be observed resulting from the combined activity of the reference and candidate antibody or a competition of the candidate antibody and reference antibody is observed which may be determined by labelling either antibody. In addition, though the method of the present invention is particular suitable for isolating autoantibodies against endogenous proteins and cellular structures, it nevertheless is also possible to obtain autoantibodies that provide effective antiviral immunity. Thus, in a preferred embodiment of the present invention, the antibody obtained by the method of the present invention is capable of neutralizing the biological activity of its antigen, e.g., IL-17 and IL-22.

As illustrated in the Examples, the method of the present invention typically comprises the steps of:

(i) purifying B-cells or B-memory cells from a sample which has been identified to contain antibodies of the desired specificity: and
(ii) culturing a B-cell and isolating the monoclonal antibody; or preferably
(iii) obtaining the immunoglobulin gene repertoire for said antibodies from said B-cells or B-memory cells; and
(iv) using said repertoire to express said antibodies or an antigen-binding fragment in a host cell and isolating the monoclonal antibody or an antigen-binding fragment thereof.

More specifically, the above-identified method of the present invention in step (iii) comprises the steps of:
(iv) obtaining mRNA from said B cells or memory B cells:
(v) obtaining cDNA from the mRNA of step (iv); and
(vi) using a primer extension reaction to amplify from said cDNA the fragments corresponding to the heavy chains (HC) and the kappa light chains (LC) of said antibodies.

Methods of producing clones of an immortalized human B cell and B memory lymphocyte, comprising the step of transforming human B memory lymphocytes using Epstein Barr Virus (EBV) in the presence of a polyclonal B cell activator are summarized in international application WO2004/076677 and are described in more detail in "B-cell immortalization" section further below. However, initial attempts at the cellular cloning of identified antigen-specific EBV-transformed human memory B cells had not been successful suggesting that the majority of cells are not transformed and not immortalized. Therefore, RT-PCR of single sorted cells is preferably employed for obtaining the immunoglobulin gene repertoire for said antibody; see also the Examples. Another method of obtaining human antibodies using inter alia single cell RT-PCR is described for example in the international application WO2008/110372, the disclosure content of which is incorporated herein by reference, in particular the Supplementary Methods section and Example 2. In addition, an improved method for producing a clone of an immortalized human B memory lymphocyte, comprising the step of inducing or enhancing telomerase activity in the B lymphocyte in the presence of a polyclonal B cell activator is described in international application WO2010/003529, the disclosure content of which is incorporated herein by reference.

The antibodies or antigen-binding fragments, e.g., peptides, polypeptides or fusion proteins of the present invention may be provided, as indicated above, by expression in a host cell or in an in vitro cell-free translation system, for example. To express the peptide, polypeptide or fusion protein in a host cell, the nucleic acid molecule encoding said peptide, polypeptide or fusion protein may be inserted into appropriate expression vector, i.e. a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., *Molecular Cloning., A Laboratory Manual* (1989), and Ausubel et al., *Current Protocols in Molecular Biology* (1989); see also the sections "Polynucleotides" and "Expressions" further below and literature cited in the Examples section for further details in this respect.

A suitable host cell for expression of the product may be any prokaryotic or eukaryotic cell: e.g., bacterial cells such as *E. coli* or *B. subtilis*, insect cells (baculovirus), yeast cells, plant cell or an animal cell. For efficient processing, however, mammalian cells are preferred. Typical mammalian cell lines useful for this purpose include CHO cells, HEK 293 cells, COS cells and NSO cells.

Seroreactivity against a variety of antigens has been found in the APS1 patients, which were analyzed according to known or putative pathophysiological functions and narrowed down to therapeutically interesting secreted or membrane bound/associated compounds as indicated in Tables 1 to 13 as molecules of interest within the present invention. In a further set of experiments, additional data concerning a variety of antigens has been found in respect of APS1-patients and in respect of APS2- and IPEX-patients: see Example 17 and Tables 29 to 31. In one embodiment of the method of the present invention, the antigen is selected from the group consisting of extracellular proteins and proteins, polysaccharides, lipopolyproteins and lipopolysaccharides, which are secreted, associated or attached to a membrane or transmembranous. However, in principle the method of the present invention is capable of providing autoantibodies against any desired antigen. This is because, as already explained before the subjects preferably used in accordance with the invention, i.e. those whose impaired central and/or peripheral tolerance or loss of self-tolerance is caused by a particular genotype, i.e. a monogenic autoimmune disorder due to the general responsiveness of their humoral immune response on the one hand and their exposure to different internal and external stimuli and conditions, respectively, comprising predisposition for an inherited disorder, toxins, infections, age-related disorders and the like on the other hand provide a pool of autoantibodies ranging from autoantibodies common to most if not all subjects to autoantibodies which are specific for an individual disease or condition. For autoantibodies commonly found in the pool of samples in one embodiment of the method of the present invention the antigen is selected from the group consisting of leukotrienes, lymphokines, cytokines, interleukins, interferons and chemokines.

Another interesting class of antigen target for autoantibodies are tripartite motif-containing proteins (TRIMs) which have emerged as having key roles in antiviral immunity either as viral restriction factors or as regulators of pathways downstream of viral RNA and DNA sensors, and the inflammasome. In particular, in view of the role of inflammasome hyperactivation in the pathogenesis of a range of autoinflammatory disorders, it is prudent to expect that antibodies identified in accordance with the method of the present invention against these targets provide useful tools for therapeutic intervention and the treatment of diseases associated with inflammasome activity. Accordingly, in one embodiment the antigen to which the autoantibody to be isolated in accordance with the method of the present invention shows seroreactivity belong to the so-called TRIM family members which typically contain an amino-terminal RING domain (which is critical for E3 ligase activity), a central B box and coiled-coil domain and a variable carboxyl-terminal domain, which is important for substrate interaction: for review, see, e.g., Jefferies et al, Nature 11 (2011), 617-625, the disclosure content of which is incorporated herein by reference, in particular Table 1 at page 619 regarding TRIM involvement in autoimmune and autoinflammatory disorders and the references cited therein.

Furthermore, regarding non-human animal models for use in the method of the present invention it is also conceived to expose a subject animal such as AIRE deficient mice to a external stimuli such as a test compound, radiation, abiotic or biotic stress and the like and to isolate an autoantibody specific to said external stimuli. To the extent that such expose is in conformity with the law of ethics and morality, the method of the present invention may be similar performed with human subjects, for example in order to identify and isolate stress-specific autoantibodies or autoantibodies evoked in response to food or medicaments.

The isolated antibodies of the present invention may of course not be applied as such to a patient, but usually have to be pharmaceutically formulated to ensure, e.g., their stability, acceptability and bioavailability in the patient. Therefore, in one embodiment, the method of of the present invention is provided, further comprising the step of admixing the isolated monoclonal antibody with a pharmaceutically acceptable carrier. Pharmaceutically acceptable carriers will be described in detail further below.

As described above, the present invention is based on the finding that mammals suffering from a disorder associated with a disrupted or deregulated genesis of autoimmunity, due to, e.g., mutations in the AIRE gene, constantly produce high titers of specific antibodies against several molecules of interest. In this respect, according to the present invention, B-cells producing said antibodies are isolated from such mammals. Therefore, in one embodiment a B-cell as defined hereinabove is provided, preferably characterized by at least one mutation in the AIRE gene.

As a measure to obtain a stable and permanent source of binding molecules of the present invention, heterologous genes encoding these binding molecules may be isolated by direct cloning, PCR amplification, or artificial synthesis and introduced and expressed in suitable host cells or organisms. In one embodiment, it is thus also an object of the present invention to provide a method for preparing a recombinant cell, comprising the steps of:
(i) preparing a B-cell clone by the method of the present invention, as described above:
(ii) obtaining nucleic acid from the B-cell clone that encodes an antibody of interest; and
(iii) inserting the nucleic acid into an expression host in order to permit expression of the antibody of interest in that host.

In another embodiment, a method for preparing a recombinant cell is provided, comprising the steps of:
(i) preparing a B-cell clone by the method of the present invention, as described above:
(ii) sequencing nucleic acid from the B-cell clone that encodes an antibody of interest; and
(iii) using the sequence information from step (ii) to prepare nucleic acid for inserting into an expression host in order to permit expression of the antibody of interest in that host.

Host cells as described above may be used as well in the preceding two methods and as described in detail in the "Host" section of this specification. In this respect, in one embodiment the above two methods are provided, where the expression host is a yeast cell, a plant cell or an animal cell. Besides the recombinant cells, in one embodiment it is also within the scope of the present invention to provide a method for preparing a nucleic acid molecule that encodes an antibody of interest, comprising the steps of:
(i) preparing a B-cell clone obtained by the method of the present invention, as described above;
(ii) sequencing nucleic acid and/or obtaining from the B-cell clone nucleic acid that encodes the antibody of interest.

In one embodiment, it is an object of the present invention also to provide a method for preparing an antibody for pharmaceutical use or as target for therapeutic intervention, comprising the steps of:
(i) selecting a B-cell that produces an antibody of interest by the method of the present invention, as described above:
(ii) obtaining and/or sequencing nucleic acid that encodes the antibody of interest from the selected B-cell;
(iii) inserting the nucleic acid into or using the nucleic acid to prepare an expression host that can express the antibody of interest;
(iv) culturing or sub-culturing the expression host under conditions where the antibody of interest is expressed; and, optionally,
(v) purifying the antibody of interest.

In respect of the above described methods for production of the respective antibody of interest, in one embodiment the present invention provides a method, wherein the nucleic acid is manipulated between above steps (ii) and (iii) to introduce restriction sites, to change codon usage, and/or to add or optimize transcription and/or translation regulatory sequences.

In an alternative embodiment of the method of the present invention, seroreactive autoantibodies form the patients' samples are produced by a method in accordance with international application WO92/13065 comprising (a) administering lymphocytes from a donor individual as defined above to immunodeficient mammals, (b) after a period of time sufficient to permit reconstitution of immune cells in at least one of said mammals, selecting a reconstituted mammal producing the desired autoantibodies, (c) immortalizing B-lymphocytes of the selected mammal before or after isolating lymphocytes therefrom, and (d) culturing the immortalized B-lymphocytes under conditions permitting their production of the desired autoantibodies and recovering the resulting autoantibodies and recovering the resulting autoantibodies from the culture.

In a further alternative embodiment of the method of the present invention, autoantibodies may be purified from intravenous immunoglobulin preparations (IVIg) obtained from the patients sample using affinity chromatography on a ligand bound to a solid support such as described in European patent application EP 1 394 183 A1, the disclosure content of which is incorporated herein by reference.

As explained above, it was within the scope of the present invention to provide binding molecules binding specifically particular antigens of interest. In respect of such a binding molecule, the present invention further provides an antibody or antigen-binding fragment thereof obtainable by the method of the present invention, as described above and in Examples in detail. In a particularly preferred embodiment, this antibody is a human antibody. In one embodiment of the present invention, the antibody is directed against (i) interleukin-17A (IL-17A) and/or interleukin-17F (IL-17F); (ii) interleukin-22 (IL-22); or (iii) an IL-17A/IL-17F heterodimer.

As demonstrated in appended Examples 4 and 6, binding molecules. i.e. antibodies have been identified and cloned, which display particularly high in vitro neutralizing activity with low inhibitory concentrations (IC50) for tested cytokines IL-17F and IL-22. In this respect, in one embodiment of the present invention antibodies are provided with a high affinity for their respective target molecules, e.g. IL-17 or IL-22, showing an ED50 at concentrations below 100 ng/ml, preferably below 10 ng/ml. For more details in respect of the binding affinity of the antibodies of the present invention see, e.g., section "Binding characteristics" further below.

The present invention exemplifies such binding molecules, i.e. antibodies and binding fragments thereof, which may be characterized by comprising in their variable region, i.e. binding domain at least one complementarity determining region (CDR) of the $V_H$ and/or $V_L$ of the variable region comprising the amino acid sequence depicted in FIG. 15 of ($V_H$) (SEQ ID NOs: 7, 15, 23, 31, 39, 47, 55) and ($V_L$) (SEQ ID NOs: 9, 17, 25, 33, 41, 49, 57)—see the exemplary CDR sequences underlined in FIG. 15. However, as discussed in the following the person skilled in the art is well aware of the fact that in addition or alternatively CDRs may be used, which differ in their amino acid sequence from those indicated in FIG. 15 by one, two, three or even more amino acids, in particular in case of CDR2 and CDR3. Thus, in one embodiment the antibody or antigen-binding fragment of the present invention is provided comprising in its variable region at least one complementarity determining region (CDR) of the $V_H$ and/or $V_L$ of the variable region comprising any one of the amino acid sequences depicted in
(a) FIG. 15 ($V_H$) (SEQ ID NOs: 7, 15, 23, 31, 39, 47, 55); and
(b) FIG. 15 ($V_L$) (SEQ ID NOs: 9, 17, 25, 33, 41, 49, 57).

Furthermore, in one embodiment, the antibody or antigen-binding fragment of the present invention comprises an amino acid sequence of the $V_H$ and/or $V_L$ region as depicted in FIG. 15. Alternatively, the antibody of the present invention is an antibody or antigen-binding fragment thereof, which competes for binding to the IL-17 or the IL-22 antibody with at least one of the antibodies having the $V_H$ and/or $V_L$ region as depicted in FIG. 15 or as encoded by the corresponding nucleic acids as indicated in Table 17.

Hence, the present invention generally relates to an antibody, preferably human antibody and antigen-binding fragment thereof having one or more of the above-described functional properties comprising in its variable region
(a) at least one complementarity determining region (CDR) of the $V_H$ and/or $V_L$ variable region amino acid sequences depicted in
   (i) FIG. 15 ($V_H$) (SEQ ID NOs: 7, 15, 23, 31, 39, 47, 55); and
   (ii) FIG. 15 ($V_L$) (SEQ ID NOs: 9, 17, 25, 33, 41, 49, 57);
(b) an amino acid sequence of the $V_H$ and/or $V_L$ region as depicted in FIG. 15:
(c) at least one CDR consisting of an amino acid sequence derived from (a) resulted from a partial alteration of any one of the amino acid sequences of (a);
(d) a heavy chain and/or light variable region comprising an amino acid sequence derived from (b) resulted from a partial alteration of the amino acid sequence of (b);
(e) at least one CDR comprising an amino acid sequence derived from (a) with at least 80% identity to any one of the amino acid sequences of (a);
(f) an amino acid sequence derived from (b) with at least 60% identity to the amino acid sequence of (b).

In order to provide fully human antibodies and native Fab fragments thereof, the human antibody of the present invention preferably further comprises a $C_H$ and/or $C_L$ constant region comprising an amino acid sequence selected from the $C_H$ and $C_L$ amino acid sequences set forth in Table 17 (SEQ ID NOs.: 11, 13, 19, 21, 27, 29, 35, 37, 43, 45, 51, 53, 59, 61) or an amino acid sequence derived thereof with at least 60% identity.

In case of a derived sequence, said sequence shows at least 60% identity, more preferably (in the following order) at least 70%, at least 75%, at least 80%, at least 85%, at least 90%, and most preferably 95%, at least 96-99%, or even 100% identity to a sequence of the group consisting of those sequences referred to above and identified in the Sequence Listing. The percent identity between two sequences is a function of the number of identical positions shared by the sequences, taking into account the number of gaps, and the length of each gap, which need to be introduced for optimal alignment of the two sequences. The comparison of sequences and determination of percent identity between two sequences can be accomplished using a mathematical algorithm, which is well known to those skilled in the art. The identities referred to herein are to be determined by using the BLAST programs as further referred to herein infra.

As explained above, these antibodies may be murine as well, however, humanized, xenogeneic, or chimeric human-murine antibodies being preferred and in particular fully human antibodies for therapeutic applications. An antigen-binding fragment of the antibody can be, for example, a single chain Fv fragment (scFv), a F(ab') fragment, a F(ab) fragment, an F(ab')2 fragment or an single domain antibody fragment (sdAB).

As mentioned in a preferred embodiment the present invention relates to substantially fully human antibodies, preferably IgG including at least the constant heavy chain I ($C_H1$) and the corresponding light chain of the constant region, i.e. γ-1, γ-2, γ-3 or γ-4 in combination with lamda or kappa. In a particular preferred embodiment the nucleotide and amino acid sequences of those constant regions isolated for the subject antibodies illustrated in the Examples are used as depicted in Table 17 below and in SEQ ID NOs: 10-13, 18-21, 26-29, 34-37, 42-45, 50-53 and 58-61.

In accordance with the above, in one embodiment the present invention also provides a polynucleotide encoding at least the variable region of one immunoglobulin chain of the antibody or antigen-binding fragment of the present invention. Typically, said variable region encoded by the polynucleotide comprises at least one complementarity determining region (CDR) of the $V_H$ and/or $V_L$ of the variable region of the said antibody. Variable and constant regions of antibodies are described in more detail in the section "IgG structure" below. In a preferred embodiment of the present invention, the polynucleotide comprises, consists essentially of, or consists of a nucleic acid having a polynucleotide sequence of the $V_H$ or $V_L$ region of an antibody of the present invention as depicted in Table 17 below. In this respect, the person skilled in the art will readily appreciate that the polynucleotides encoding at least the variable domain of the light and/or heavy chain may encode the variable domain of either immunoglobulin chains or only one of them.

TABLE 17

Nucleotide and amino acid sequences of the variable and constant regions (V_H, V_L, C_H, C_L) of IL-17A, IL17F or IL-22 specific antibodies of the present invention.
IL-17F specific antibody 9A2: IgG1, kappa (VH3; G1m17; VK1, Km3).
IL-17F and IL-17A specific antibody 17E3: IgG1, kappa (VH1, G1m17, VK1, Km3). IL-17F specific antibody 24D3: IgG1, lambda (VH3, G1m17; VL3), IL-22 specific antibody 30G1: IgG1, kappa (VH3, G1m17, VK3, Km3 or Km1, 2). IL-22 specific antibody 35G11: IgG4, lambda (VH7, IGHG4*01; VL1); 35G11-C_L; at positions 211-213 TAC may be as well TAT, both coding for Tyr. IL-22 specific antibody 41D11: IgG1, lambda (VH4, G1m3 L410F; VL4). IL-22 specific antibody 51G4: IgG2, lambda (VH1, IGHG2*01; VL3); 41D11-C_H: positions 877-879 of the nucleotide sequence may be ctc instead of ttc and position 293 of the corresponding amino acid sequence may be Leu instead of Phe (underlined). Underlined, bold nucleotides or amino acids indicate the CDR coding regions in the variable chain sequence. Underlined, italic nucleotides indicate sequences in the constant chain sequences which have not been sequenced but obtained from database.

| Antibody | Nucleotide and amino acid sequences of variable heavy (VH) and variable light |
|---|---|
| 9A2-V_H | GAGGTGCAATTGGAGGAGTCTGGCGGAGGCTTGGTTCAGCCTGGAGGGTCCCT GAGACTCTCCTGTGCAGCCTCTGGATTCCCCTTCAGCAACTATGAAATGAATT GGGTCCGCCAGGCTCCCGGGAAGGGACTGGAGTGGATTTCATACATTAGTGTG AGCGGTGGTCCCGCTCACTACGCAGACTCTGTGAAGGGCCGATTCACCATTTC CAGAGACGACGCCACAAAGTCACTGTTTCTGCAAATGAACCGCCTGAGAGCCG ACGACACGGCAGTTTATTACTGTGTGCGCCGCGAATATGTCACTGGCCGCAAT TACAACTACTACCCCTACATGGACGTCTGGGGCACTGGGACCACGGTCACCGT CTCCCCA SEQ ID NO: 6 |
| 9A2-V_H | EVQLEESGGGLVQPGGSLRLSCAASGFPFSNYEMNWVRQAPGKGLEWISYISV SGGPAHYADSVKGRFTISRDDATKSLFLQMNRLRADDTAVYYCVRREYVTGRN YNYYPYMDVWGTGTTVTVSP SEQ ID NO: 7 |
| 9A2-V_L kappa-type | GACATCCAGATGACCCAGTCTCCGTCCTCCCTGTCTGCTTCTGTTGGGGACAG AGTCACCATCACTTGCCGGGCAAGTCAGACCATAAGTGATTATTTAAATTGGT ACCAGCACAAACCAGGGGAAGCCCCTAAACTCCTAATCTATTCTGCATCCACC TTGCAACGTGGGGTGCCTTCACGGTTCAGTGGCAGTGGATCTGGGACAGATTT CGTTTTCACCATTAGTAGTCTGCAGTCTGATGATTTTGCGACTTACTACTGTC AACAGACTTCCAGTACCGCCCTCACTTTCGGCGAGGGACCAAGGTGGAGGTC AAA SEQ ID NO: 8 |
| 9A2-V_L kappa-type | DIQMTQSPSSLSASVGDRVTITCRASQTISDYLNWYQHKPGEAPKLLIYSAST LQRGVPSRFSGSGSGTDFVFTISSLQSDDFATYYCQQTSSTALTFGGGTKVEV K SEQ ID NO: 9 |
| 9A2-C_H | GCCTCCACCAAGGGCCCATCGGTCTTCCCCCTGGCACCCTCCTCCAAGAGCAC CTCTGGGGGCACAGCGGCCCTGGGCTGCCTGGTCAAGGACTACTTCCCCGAAC CGGTGACGGTGTCGTGGAACTCAGGCGCCCTGACCAGCGGCGTGCACACCTTC CCGGCTGTCCTACAGTCCTCAGGACTCTACTCCCTCAGCAGCGTGGTGACCGT GCCCTCCAGCAGCTTGGGCACCCAGACCTACATCTGCAACGTGAATCACAAGC CCAGCAACACCAAGGTGGACAAGAAAGTTGAGCCCAAATCTTGTGACAAAACT CACACATGCCCACCGTGCCCAGCACCTGAACTCCTGGGGGGACCGTCAGTCTT CCTCTTCCCCCCAAAACCCAAGGACACCCTCATGATCTCCCGGACCCCTGAGG TCACATGCGTGGTGGTGGACGTGAGCCACGAAGACCCTGAGGTCAAGTTCAAC TGGTACGTGGACGGCGTGGAGGTGCATAATGCCAAGACAAAGCCGCGGGAGGA GCAGTACAACAGCACGTACCGTGTGGTCAGCGTCCTCACCGTCCTGCACCAGG ACTGGCTGAATGGCAAGGAGTACAAGTGCAAGGTCTCCAACAAAGCCCTCCCA GCCCCCATCGAGAAAACCATCTCCAAAGCCAAAGGGCAGCCCCGAGAACCACA GGTGTACACCCTGCCCCCATCCCGGGATGAGCTGACCAAGAACCAGGTCAGCC TGACCTGCCTGGTCAAAGGCTTCTATCCCAGCGACATCGCCGTGGAGTGGGAG AGCAATGGGCAGCCGGAGAACAACTACAAGACCACGCCTCCCGTGCTGGACTC CGACGGCTCCTTCTTCCTCTACAGCAAGCTCACCGTGGACAAGAGCAGGTGGC AGCAGGGGAACGTCTTCTCATGCTCCGTGATGCATGAGGCTCTGCACAACCAC TACACGCAGAAGAGCCTCTCCCTGTCTCCGGGTAAATGA SEQ ID NO: 10 |
| 9A2-C_H | ASTKGPSVFPLAPSSKSTSGGTAALGCLVKDYFPEPVTVSWNSGALTSGVHTF PAVLQSSGLYSLSSVVTVPSSSLGTQTYICNVNHKPSNTKVDKKVEPKSCDKT HTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVYTLPPSRDELTKNQVSLTCLVKGFYPSDIAVEWE SNGQPENNYKTTPPVLDSGSFFLYSKLTVDKSRWQQGNVFSCSVMHEALHNH YTQKSLSLSPGK SEQ ID NO: 11 |
| 9A2-C_L kappa-type | CGAACTGTGGCTGCACCATCTGTCTTCATCTTCCCGCCATCTGATGAGCAGTT GAAATCTGGAACTGCCTCTGTTGTGTGCCTGCTGAATAACTTCTATCCCAGAG AGGCCAAAGTACAGTGGAAGGTGGATAACGCCCTCCAATCGGGTAACTCCCAG GAGAGTGTCACAGAGCAGGACAGCAAGGACAGCACCTACAGCCTCAGCAGCAC CCTGACGCTGAGCAAAGCAGACTACGAGAAACACAAAGTCTACGCCTG*C*GAAG |

TABLE 17-continued

Nucleotide and amino acid sequences of the variable and constant regions (V_H, V_L, C_H, C_L) of IL-17A, IL17F or IL-22 specific antibodies of the present invention.
IL-17F specific antibody 9A2: IgG1, kappa (VH3; G1m17; VK1, Km3).
IL-17F and IL-17A specific antibody 17E3: IgG1, kappa (VH1, G1m17, VK1, Km3). IL-17F specific antibody 24D3: IgG1, lambda (VH3, G1m17; VL3), IL-22 specific antibody 30G1: IgG1, kappa (VH3, G1m17, VK3, Km3 or Km1, 2). IL-22 specific antibody 35G11: IgG4, lambda (VH7, IGHG4*01; VL1); 35G11-C_L: at positions 211-213 TAC may be as well TAT, both coding for Tyr. IL-22 specific antibody 41D11: IgG1, lambda (VH4, G1m3 L410F; VL4). IL-22 specific antibody 51G4: IgG2, lambda (VH1, IGHG2*01; VL3); 41D11-C_H: positions 877-879 of the nucleotide sequence may be ctc instead of ttc and position 293 of the corresponding amino acid sequence may be Leu instead of Phe (underlined). Underlined, bold nucleotides or amino acids indicate the CDR coding regions in the variable chain sequence. Underlined, italic nucleotides indicate sequences in the constant chain sequences which have not been sequenced but obtained from database.

| Antibody | Nucleotide and amino acid sequences of variable heavy (VH) and variable light |
|---|---|
| | TCACCCATCAGGGCCTGAGCTCGCCCGTCACA*AAGAGCTTCAACAGGGGAGAG* *TGTTAG* SEQ ID NO: 12 |
| 9A2-C_L kappa-type | RTVAAPSVFIFPPSDEQLKSGTASVVCLLNNFYPREAKVQWKVDNALQSGNSQ ESVTEQDSKDSTYSLSSTLTLSKDAYEKHKVYACEVTHQGLSSPVTKSFNRGE C SEQ ID NO: 13 |
| 17E3-V_H | CAGGTGCAACTGGTCCAGTCTGGGGCTGAAGTGGCGAAGCCTGGGGCCTCAGT GAGACTTTCCTGCAAGGCGTCTGGATTCAGTTTTATCAAGTATTATATGCACT GGGTGCGACAGGCCCCTGGACAAGGGCTTGAGTGGATGGGGGTCATCGAGCCC ACCGGTGGTGGCACAAGCTCCGCACAGAAGTTCCGAGACAGAGTCACCCTGAG CAGGGACACGTCCACGGCCACTGTCCATTTGGAAGTGAGTAGGCTGACTCTTG AGGACACGGGCATTTATTTCTGTGTGAGAGACTCCATATATTGTAAACATGGG ACCTGTCATCGGACTGTGATCGATGCTTTTGACATTTGGGGCCAAGGGACGGC GGTCACCGTCTCTTCA SEQ ID NO: 14 |
| 17E3-V_H | QVQLVQSGAEVKAPGASVRLSCKASGFSFIKYYMHWVRQAPGQGLEWMGVIEP TGGGTSSAQKFRDRVTLSRDTSTATVHLEVSRLTLEDTGIYFCVRDSIYCKHG TCHRTVIDAFDIWGQGTAVTVSS SEQ ID NO: 15 |
| 17E3-V_L kappa-type | GACATCCAGATGACCCAGTCTCCATCCTCCCTGTCTGCATCAGTAGGAGACCG AGTCACCATCACTTGCCGGTCAAGTCAGGACATAAAAAATGATTTAGCCTGGT ATCAGCAGAAGCCAGGAAAAGCCCCTGAGCGCCTGATCTATGCTGCATCCAAT TTGCAGAGTGGGGTCCCATCAAGGTTCAGCGGCAGTGGCTCTGGGACAGAATT CAGTCTTACAATCAGTGGCCTGCAGCCTGAAGATTTTGCAACTTATTACTGTCTACAGCATAATAGTTACCCTCTGCTCACTTTCGGCGGAGGGACCAAGGTGGAG ATCAAA SEQ ID NO: 16 |
| 17E3-C_L kappa-type | DIQMTQSPSSLSASVGDRVTITCRSSQDIKNDLAWYQQKPGKAPERLIYAASN LQSGVPSRFSGSGSGTEFSLTISGLQPEDFATYYCLQHNSYPLLTFGGGTKVE IK SEQ ID NO: 17 |
| 17E3-C_H | GCCTCCACCAAGGGCCCATCGGTCTTCCCCCTGGCACCCTCCTCCAAGAGCAC CTCTGGGGGCACAGCGGCCCTGGGCTGCCTGGTCAAGGACTACTTCCCCGAAC CGGTGACGGTGTCGTGGAACTCAGGCGCCCTGACCAGCGGCGTGCACACCTTC CCGGCTGTCCTACAGTCCTCAGGACTCTACTCCCTCAGCAGCGTGGTGACCGT GCCCTCCAGCAGCTTGGGCACCCAGACCTACATCTGCAACGTGAATCACAAGC CCAGCAACACCAAGGTGGACAAGAAAGTTGAGCCCAAATCTTGTGACAAAACT CACACATGCCCACCGTGCCCAGCACCTGAACTCCTGGGGGGACCGTCAGTCTT CCTCTTCCCCCCAAAACCCAAGGACACCCTCATGATCTCCCGGACCCCTGAGG TCACATGCGTGGTGGTGGACGTGAGCCACGAAGACCCTGAGGTCAAGTTCAAC TGGTACGTGGACGGCGTGGAGGTGCATAATGCCAAGACAAAGCCGCGGGAGGA GCAGTACAACAGCACGTACCGTGTGGTCAGCGTCCTCACCGTCCTGCACCAGG ACTGGCTGAATGGCAAGGAGTACAAGTGCAAGGTCTCCAACAAAGCCCTCCCA GCCCCCATCGAGAAAACCATCTCCAAAGCCAAAGGGCAGCCCCGAGAACCACA GGTGTACACCCTGCCCCCATCCCGGGATGAGCTGACCAAGAACCAGGTCAGCC TGACCTGCCTGGTCAAAGGCTTCTATCCCAGCGACATCGCCGTGGAGTGGGAG AGCAATGGGCAGCCGGAGAACAACTACAAGACCACGCCTCCCGTGCTGGACTC CGACGGCTCCTTCTTCCTCTACAGCAAGCTCACCGTGGACAAGAGCAGGTGGC AGCAGGGGAACGTCTTCTCATGCTCCGTGATGCATGAGGCTCTGCACAACCAC TACACGCAGAAGAGCCTCTCCCTGTCTCCGGGTAAATGA SEQ ID NO: 18 |
| 17E3-C_H | ASTKGPSVFPLAPSSKSTSGGTAALGCLVKDYFPEPVTVSWNSGALTSGVHTF PAVLQSSLGYSLSSVVTVPSSSLGTQTYICNVNHKPSNTKVDKKVEPKSCDKT HTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALP |

TABLE 17-continued

Nucleotide and amino acid sequences of the variable and constant regions (V$_H$, V$_L$, C$_H$, C$_L$) of IL-17A, IL17F or IL-22 specific antibodies of the present invention.
IL-17F specific antibody 9A2: IgG1, kappa (VH3, G1m17; VK1, Km3). IL-17F and IL-17A specific antibody 17E3: IgG1, kappa (VH1, G1m17, VK1, Km3). IL-17F specific antibody 24D3: IgG1, lambda (VH3, G1m17; VL3), IL-22 specific antibody 30G1: IgG1, kappa (VH3, G1m17, VK3, Km3 or Km1, 2). IL-22 specific antibody 35G11: IgG4, lambda (VH7, IGHG4*01; VL1); 35G11-C$_L$; at positions 211-213 TAC may be as well TAT, both coding for Tyr. IL-22 specific antibody 41D11: IgG1, lambda (VH4, G1m3 L410F; VL4). IL-22 specific antibody 51G4: IgG2, lambda (VH1, IGHG2*01; VL3); 41D11-C$_H$: positions 877-879 of the nucleotide sequence may be ctc instead of ttc and position 293 of the corresponding amino acid sequence may be Leu instead of Phe (underlined). Underlined, bold nucleotides or amino acids indicate the CDR coding regions in the variable chain sequence. Underlined, italic nucleotides indicate sequences in the constant chain sequences which have not been sequenced but obtained from database.

| Antibody | Nucleotide and amino acid sequences of variable heavy (VH) and variable light |
|---|---|
| | APIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNH YTQKSLSLSPGK SEQ ID NO: 19 |
| 17E3-C$_L$ kappa-type | CGAACTGTGGCTGCACCATCTGTCTTCATCTTCCCGCCATCTGATGAGCAGTT GAAATCTGGAACTGCCTCTGTTGTGTGCCTGCTGAATAACTTCTATCCCAGAG AGGCCAAAGTACAGTGGAAGGTGGATAACGCCCTCCAATCGGGTAACTCCCAG GAGAGTGTCACAGAGCAGGACAGCAAGGACAGCACCTACAGCCTCAGCAGCAC CCTGACGCTGAGCAAAGCAGACTACGAGAAACACAAAGTCTACGCCTGCGAAG TCACCCATCAGGGCCTGAGCTCGCCCGTCACA*AAGAGCTTCAACAGGGGAGAG TGTTAG* SEQ ID NO: 20 |
| 17E3-C$_L$ kappa-type | RTVAAPSVFIFPPSDEQLKSGTASVVCLLNNFYPREAKVQWKVDNALQSGNSQ ESVTEQDSKDSTYSLSSTLTLSKDAYEKHKVYACEVTHQGLSSPVTKSFNRGE C SEQ ID NO: 21 |
| 24D3-V$_H$ | GAGGTGAAGTTGGAGGAGTCTGGGGGAGACCTGGTAAAGCCTGGGGGGTCTCT TAGACTCTCCTGTGTAGCCTCTGGATTCACTTTCGGCACCGCCTGGATGAGCT GGGTCCGCCAGGCTCCAGGGAAGGGGCTGGAGTGGGTTGGCCGTATTAGCAAC AAAGACACTGGTGGGAGAATAGACTACGCCGCACCCGTGAGAGGCAGATTCGC CATCTCAAGAGATGATTCGAAAGCCACCCTGTTTCTGCAAATGAACAGCCTGA AAACCGAGGACACAGCCGTGTATTTTTGTACTACAAATTTTTACGATGTTTTG ACTGGTGATCATGTTGACTATTGGGGCCAGGGAACCGTGGTCGTCGTCTCCTC A SEQ ID NO: 22 |
| 24D3-V$_H$ | EVKLEESGGDLVKPGGSLRLSCVASGFTFGTAWMSWVRQAPGKGLEWVGRISN KDTGGRIDYAAPVRGRFAISRDDSKATLFLQMNSLKTEDTAVYFCTTNFYDVL TGDHVDYWGQGTVVVVSS SEQ ID NO: 23 |
| 24D3-V$_L$ lambda-type | TCCTATGAGCTGACACAGCCACCCTCGGTGTCAGTGTCCCCAGGAGAGACGGC CAGGATCCCCTGCTCTGGAGAAACATTGCCAAAGAAACTTGTTTATTGGTATC AGCAGAAGCCAGGCCAGGCCCCTGTATTGATGATTTATAAAGACAGTGAGAGG CCCTCACGAATATCTGAGCGATTCTCTGGCTCCAACTCAGGGACAATGGCCTC CTTGACCATCAGTGGAGTCCAGGCAGAAGACGAGGCTGACTATTACTGTCAAA CATCAGACAGCAGTGGTGTGGTTTTCGGCGGAGGGACCAAGTTGACCGTCTTA SEQ ID NO: 24 |
| 24D3-V$_L$ lambda-type | SYELTQPPSVSVSPGETARIPCSGETLPKKLVYWYQQKPGQAPVLMIYKDSER PSRISERFSGSNSGTMASLTISGVQAEDEADYYCQTSDSSGVVFGGGTKLTVL SEQ ID NO: 25 |
| 24D3-C$_H$ | GCCTCCACCAAGGGCCCATCGGTCTTCCCCCTGGCACCCTCCTCCAAGAGCAC CTCTGGGGGCACAGCGGCCCTGGGCTGCCTGGTCAAGGACTACTTCCCCGAAC CGGTGACGGTGTCGTGGAACTCAGGCGCCCTGACCAGCGGCGTGCACACCTTC CCGGCTGTCCTACAGTCCTCAGGACTCTACTCCCTCAGCAGCGTGGTGACCGT GCCCTCCAGCAGCTTGGGCACCCAGACCTACATCTGCAACGTGAATCACAAGC CCAGCAACACCAAGGTGGACAAGAAAGTTGAGCCCAAATCTTGTGACAAAACT CACACATGCCCACCGTGCCCAGCACCTGAACTCCTGGGGGGACCGTCAGTCTT CCTCTTCCCCCCAAAACCCAAGGACACCCTCATGATCTCCCGGACCCCTGAGG TCACATGCGTGGTGGTGGACGTGAGCCACGAAGACCCTGAGGTCAAGTTCAAC TGGTACGTGGACGGCGTGGAGGTGCATAATGCCAAGACAAAGCCGCGGGAGGA GCAGTACAACAGCACGTACCGTGTGGTCAGCGTCCTCACCGTCCTGCACCAGG ACTGGCTGAATGGCAAGGAGTACAAGTGCAAGGTCTCCAACAAAGCCCTCCCA GCCCCCATCGAGAAAACCATCTCCAAAGCCAAAGGGCAGCCCCGAGAACCACA GGTGTACACCCTGCCCCCATCCCGGGATGAGCTGACCAAGAACCAGGTCAGCC TGACCTGCCTGGTCAAAGGCTTCTATCCCAGCGACATCGCCGTGGAGTGGGAG AGCAATGGGCAGCCGGAGAACAACTACAAGACCACGCCTCCCGTGCTGGACTC CGACGGCTCCTTCTTCCTCTACAGCAAGCTCACCGTGGACAAGAGCAGGTGGC |

TABLE 17-continued

Nucleotide and amino acid sequences of the variable and constant
regions (V$_H$, V$_L$, C$_H$, C$_L$) of IL-17A, IL17F or IL-22 specific
antibodies of the present invention.
IL-17F specific antibody 9A2: IgG1, kappa (VH3; G1m17; VK1, Km3).
IL-17F and IL-17A specific antibody 17E3: IgG1, kappa (VH1, G1m17,
VK1, Km3). IL-17F specific antibody 24D3: IgG1, lambda (VH3,
G1m17; VL3), IL-22 specific antibody 30G1: IgG1, kappa (VH3, G1m17,
VK3, Km3 or Km1, 2). IL-22 specific antibody 35G11: IgG4, lambda
(VH7, IGHG4*01; VL1); 35G11-C$_L$; at positions 211-213 TAC may be as
well TAT, both coding for Tyr. IL-22 specific antibody 41D11: IgG1,
lambda (VH4, G1m3 L410F; VL4). IL-22 specific antibody 51G4: IgG2,
lambda (VH1, IGHG2*01; VL3); 41D11-C$_H$: positions 877-879 of the
nucleotide sequence may be ctc instead of ttc and position 293 of
the corresponding amino acid sequence may be Leu instead of Phe
(underlined). Underlined, bold nucleotides or amino acids indicate
the CDR coding regions in the variable chain sequence. Underlined,
italic nucleotides indicate sequences in the constant chain
sequences which have not been sequenced but obtained from database.

| Antibody | Nucleotide and amino acid sequences of variable heavy (VH) and variable light |
|---|---|
|  | AGCAGGGGAACGTCTTCTCATGCTCCGTGATGCATGAGGCTCTGCACAACCAC TACACGCAGAAGAGCCTCTCCCTGTCTCCGGGTAAATGA SEQ ID NO: 26 |
| 24D3-C$_H$ | ASTKGPSVFPLAPSSKSTSGGTAALGCLVKDYFPEPVTVSWNSGALTSGVHTF PAVLQSSGLYSLSSVVTVPSSSLGTQTYICNVNHKPSNTKVDKKVEPKSCDKT HTCPPVPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHEALHNH YTQKSLSLSPGK SEQ ID NO: 27 |
| 24D3-C$_L$ lambda-type | GGTCAGCCCAAGGCTGCCCCCTCGGTCACTCTGTTCCCGCCCTCCTCTGAGGA GCTTCAAGCCAACAAGGCCACACTGGTGTGTCTCATAAGTGACTTCTACCCGG GAGCCGTGACAGTGGCCTGGAAGGCAGATAGCAGCCCCGTCAAGGCGGGAGTG GAGACCACCACACCCTCCAAACAAAGCAACAACAAGTACGCGGCCAGCAGCTA TCTGAGCCTGACGCCTGAGCAGTGGAAGTCCCACAGA*AGCTACAGCTGCCAGG TCACGCATGAAGGGAGCACCGTGGAGAAGACAGTGGCCCCTACAGAATGTTCA TAG* SEQ ID NO: 28 |
| 24D3-C$_L$ lambda-type | GQPKAAPSVTLFPPSSEELQANKATLVCLISFDYPGAVTVAWKADSSPVKAGV ETTTPSKQSNNKYAASSYLSLTPEQWKSHRSYSCQVTHEGSTVEKTVAPTECS SEQ ID NO: 29 |
| 30G1-V$_H$ | GAGGTGCAGCTGTTGGAATCGGGGGGAGGCTTGGTTCAGCCGGGGGGGTCCCT GAGACTCTCCTGTGCAGCCTCTGGATTCACCTTTAGTACCTATGCCATGAGTT GGGTCCGCCAGGCTCCAGGGAAGGGGCTGGAGTGGGTCTCAACTATAACTAGC AGTGGTGGTGCCACTTACCACGCAGACTCCGTGAAGGGCCGGCTCACCATCTC CAGAGACAATTCCAAGAACACGCTGTATTTGGAGATGAACAGCCTGAGAGTCG AGGACACGGCCGTCTATTACTGTGCGAAAGATTGGGGAAGAACGGTTTATGCG GTGATCAAGGACCTTGACATCTGGGGCCAGGGAACCCTGGTCACCGTCTCCTC A SEQ ID NO: 30 |
| 30G1-V$_H$ | EVQLLESGGGLVQPGGSLRLSCAASGFTFSTYAMSWVRQAPGKGLEWVSTITS SGGATYHADSVKGRLTISRDNSKNTLYLEMNSLRVEDTAVYYCAKDWGRTVYA VIKDLDIWGQGTLTVTSS SEQ ID NO: 31 |
| 30G1-V$_L$ kappa-type | GAAATTGTGATGACACAGTCTCCAGCCATCCTGTCTGTGTCTCCAGGGGAAAG AGCCACCCTCTCCTGCAGGGCCAGTCAGAGTGTTAGCAACTACTTAGCCTGGT TCCAACAAAGCCTGGCCAGGCTCCCAGGCTCCTCATCTATGACACATCTAAG AGGGCCACTGGCACCCCCGCCAGGTTCAGTGGCAGTGGGTCTGGGACAGACTT CACTCTCACCATCAGCAGCCTAGAGCCTGAAGATTTTGCAGTTTATTTCTGTC AGCAGCGTAGCGACTGGCCTCAGTACACTTTTGGCCAGGGGACCAAACTGGAG ATCAAA SEQ ID NO: 32 |
| 30G1-V$_L$ kappa-type | EIVMTQSPAILSVSPGERATLSCRASQSVSNYLAWFQQKPGQAPRLLIYDTSK RATGTPARFSGSGSGTDFTLTISSLEPEDFAVYFCQQRSDWPQYTFGQGTKLE IK SEQ ID NO: 33 |
| 30G1-C$_H$ | GCCTCCACCAAGGGCCCATCGGTCTTCCCCCTGGCACCCTCCTCCAAGAGCAC CTCTGGGGGCACAGCGGCCCTGGGCTGCCTGGTCAAGGACTACTTCCCCGAAC CGGTGACGGTGTCGTGGAACTCAGGCGCCCTGACCAGCGGCGTGCACACCTTC CCGGCTGTCCTACAGTCCTCAGGACTCTACTCCCTCAGCAGCGTGGTGACCGT GCCCTCCAGCAGCTTGGGCACCCAGACCTACATCTGCAACGTGAATCACAAGC CCAGCAACACCAAGGTGGACAAGAAAGTTGAGCCCAAATCTTGTGACAAAACT CACACATGCCCACCGTGCCCAGCACCTGAACTCCTGGGGGGACCGTCAGTCTT CCTCTTCCCCCCAAAACCCAAGGACACCCTCATGATCTCCCGGACCCCTGAGG TCACATGCGTGGTGGTGGACGTGAGCCACGAAGACCCTGAGGTCAAGTTCAAC TGGTACGTGGACGGCGTGGAGGTGCATAATGCCAAGACAAAGCCGCGGGAGGA |

TABLE 17-continued

Nucleotide and amino acid sequences of the variable and constant regions (V$_H$, V$_L$, C$_H$, C$_L$) of IL-17A, IL17F or IL-22 specific antibodies of the present invention.
IL-17F specific antibody 9A2: IgG1, kappa (VH3, G1m17; VK1, Km3).
IL-17F and IL-17A specific antibody 17E3: IgG1, kappa (VH1, G1m17, VK1, Km3). IL-17F specific antibody 24D3: IgG1, lambda (VH3, G1m17; VL3), IL-22 specific antibody 30G1: IgG1, kappa (VH3, G1m17, VK3, Km3 or Km1, 2). IL-22 specific antibody 35G11: IgG4, lambda (VH7, IGHG4*01; VL1); 35G11-C$_L$: at positions 211-213 TAC may be as well TAT, both coding for Tyr. IL-22 specific antibody 41D11: IgG1, lambda (VH4, G1m3 L410F; VL4). IL-22 specific antibody 51G4: IgG2, lambda (VH1, IGHG2*01; VL3); 41D11-C$_H$: positions 877-879 of the nucleotide sequence may be ctc instead of ttc and position 293 of the corresponding amino acid sequence may be Leu instead of Phe (underlined). Underlined, bold nucleotides or amino acids indicate the CDR coding regions in the variable chain sequence. Underlined, italic nucleotides indicate sequences in the constant chain sequences which have not been sequenced but obtained from database.

| Antibody | Nucleotide and amino acid sequences of variable heavy (VH) and variable light |
|---|---|
|  | GCAGTACAACAGCACGTACCGTGTGGTCAGCGTCCTCACCGTCCTGCACCAGG<br>ACTGGCTGAATGGCAAGGAGTACAAGTGCAAGGTCTCCAACAAAGCCCTCCCA<br>GCCCCCATCGAGAAAACCATCTCCAAAGCCAAAGGGCAGCCCCGAGAACCACA<br>GGTGTACACCCTGCCCCCATCCCGGGATGAGCTGACCAAGAACCAGGTCAGCC<br>TGACCTGCCTGGTCAAAGGCTTCTATCCCAGCGACATCGCCGTGGAGTGGGAG<br>AGCAATGGGCAGCCGGAGAACAACTACAAGACCACGCCTCCCGTGCTGGACTC<br>CGACGGCTCCTTCTTCCTCTACAGCAAGCTCACCGTGGACAAGAGCAGGTGGC<br>AGCAGGGGAACGTCTTCTCATGCTCCGTGATGCATGAGGCTCTGCACAACCAC<br>TACACGCAGAAGAGCCTCTCCCTGTCTCCGGGTAAATGA SEQ ID NO: 34 |
| 30G1-C$_H$ | ASTKGPSVFPLAPSSKSTSGGTAALGCLVKDYFPEPVTVSWNSGLATSGVHTF<br>PAVLQSSGLYSLSSVVTVPSSSLGTQTYICNVNHKPSNTKVDKKVEPKSCDKT<br>HTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALP<br>APIEKTISKAKGQPREPQVYTLPPSRDELTKNQVSLTCLVKGFYPSDIAVEWE<br>SNGQPENNYKTTPPVLDSDGSFFLYSKLTVDKSRWQQGNVFSCSVMHEALHNH<br>YTQKSLSLSPGK SEQ ID NO: 35 |
| 30G1-C$_L$<br>kappa-type | CGAACTGTGGCTGCACCATCTGTCTTCATCTTCCCGCCATCTGATGAGCAGTT<br>GAAATCTGGAACTGCCTCTGTTGTGTGCCTGCTGAATAACTTCTATCCCAGAG<br>AGGCCAAAGTACAGTGGAAGGTGGATAACGCCCTCCAATCGGGTAACTCCCAG<br>GAGAGTGTCACAGAGCAGGACAGCAAGGACAGCACCTACAGCCTCAGCAGCAC<br>CCTGACGCTGAGCAAAGCAGACTACGAGAAACACA*AAGTCTACGCCTGCGAAG*<br>*TCACCCATCAGGGCCTGAGCTCGCCCGTCACAAAGAGCTTCAACAGGGGAGAG*<br>*TGTTAG* SEQ ID NO: 36 |
| 30G1-C$_L$<br>kappa-type | RTVAAPSVFIFPPSDEQLKSGTASVVCLLNNFYPREAKVQWKVDNALQSGNSQ<br>ESVTEQDSKDSTYSLSSTLTLSKADYEKHKVYACEVTHQGLSSPVTKSFNRGE<br>C SEQ ID NO: 37 |
| 35G11-V$_H$ | CAGGTGCAGCTGGTTCAATCTGGGTCTGAGTTGAGGAGGCCTGGGGCCTCAGT<br>GAACATTTCCTGCAAGGCTTCTGGTTACGGCTTCAATACTTATGCTATGAATT<br>GGGTGCGACAGGCCCCTGGACAAGGGCCTGAGTGGATGGGATGGATCAACACC<br>GACACTGGGGACCCAACGTACGCCCAGGGGTTCACGGGACGGTTTGCCTTCTT<br>CTTGGACACGTCTGCCAGCACGGCATTTCTGCAGATCACTCGCCTAACGGGTG<br>AGGACACTGCCGTGTATTTCTGTGCGAGAACTCGGAACAACTGGAACGGCGTT<br>TACTATCACTACTCCGGTTTGGACGTCTGGGGCCAAGGGACCACGGTCACCGT<br>CTCCTCA SEQ ID NO: 38 |
| 35G11-V$_H$ | QVQLVQSGSELRRPGASVNISCKASGYGFNTYAMNWVRQAPGQGPEWMGWINT<br>DTGDPTYAQGFTGRFAFFLDTSASTAFLQITRLTGEDTAVYFCARTRNNWNGV<br>YYHYSGLDVWGQGTTVTVSS SEQ ID NO: 39 |
| 35G11-V$_L$<br>lambda-type | CAGTCTGTGCTGACTCAGCCTCCCTCTGCGTCTGGGACCCCCGGGCAGACGGT<br>CACCATCTCCTGTTCTGGAAGCAGCCCCAACCTCGGAGACAATTATGTATACT<br>GGTACCACCAAGTCCCAGGAACGGCCCCCAAACTCCTCATTTTTAGGAATACT<br>CAGCGGCCCTCAGGGGTCACTGACCGATTCTCTGGCTCCAAGTATGGCACCTC<br>AGCCTCCTGGCCATAAGTGATCTCCGGTCCGACGATGAAGGTGATTTTTACT<br>GTGCTTCGTGGGATGACCGCCTGAGTCGTCTGGTGTTCGGCGGAGGGACCAAG<br>CTGACCGTCCTA SEQ ID NO: 40 |
| 35G11-V$_L$<br>lambda-type | QSVLTQPPSASGTPGQTVTISCSGSSPNLGDNYVYWYHQVPGTAPKLLIFRNT<br>QRPSGVTDRFSGSKYGTSASLAISDLRSDDEGDFYCASWDDRLSRLVFGGGTK<br>LTVL SEQ ID NO: 41 |
| 35G11-C$_H$ | GCTTCCACCAAGGGCCCATCCGTCTTCCCCCTGGCGCCCTGCTCCAGGAGCAC<br>CTCCGAGAGCACAGCCGCCCTGGGCTGCCTGGTCAAGGACTACTTCCCCGAAC<br>CGGTGACGGTGTCGTGGAACTCAGGCGCCCTGACCAGCGGCGTGCACACCTTC |

TABLE 17-continued

Nucleotide and amino acid sequences of the variable and constant regions (V$_H$, V$_L$, C$_H$, C$_L$) of IL-17A, IL17F or IL-22 specific antibodies of the present invention.
IL-17F specific antibody 9A2: IgG1, kappa (VH3, G1m17; VK1, Km3). IL-17F and IL-17A specific antibody 17E3: IgG1, kappa (VH1, G1m17, VK1, Km3). IL-17F specific antibody 24D3: IgG1, lambda (VH3, G1m17; VL3), IL-22 specific antibody 30G1: IgG1, kappa (VH3, G1m17, VK3, Km3 or Km1, 2). IL-22 specific antibody 35G11: IgG4, lambda (VH7, IGHG4*01; VL1); 35G11-C$_L$; at positions 211-213 TAC may be as well TAT, both coding for Tyr. IL-22 specific antibody 41D11: IgG1, lambda (VH4, G1m3 L410F; VL4). IL-22 specific antibody 51G4: IgG2, lambda (VH1, IGHG2*01; VL3); 41D11-C$_H$: positions 877-879 of the nucleotide sequence may be ctc instead of ttc and position 293 of the corresponding amino acid sequence may be Leu instead of Phe (underlined). Underlined, bold nucleotides or amino acids indicate the CDR coding regions in the variable chain sequence. Underlined, italic nucleotides indicate sequences in the constant chain sequences which have not been sequenced but obtained from database.

| Antibody | Nucleotide and amino acid sequences of variable heavy (VH) and variable light |
|---|---|
| | CCGGCTGTCCTACAGTCCTCAGGACTCTACTCCCTCAGCAGCGTGGTGACCGT GCCCTCCAGCAGCTTGGGCACGAAGACCTACACCTGCAACGTAGATCACAAGC CCAGCAACACCAAGGTGGACAAGAGAGTTGAGTCCAAATATGGTCCCCCATGC CCATCATGCCCAGCACCTGAGTTCCTGGGGGGACCATCAGTCTTCCTGTTCCC CCCAAAACCCAAGGACACTCTCATGATCTCCCGGACCCCTGAGGTCACGTGCG TGGTGGTGGACGTGAGCCAGGAAGACCCCGAGGTCCAGTTCAACTGGTACGTG GATGGCGTGGAGGTGCATAATGCCAAGACAAAGCCGCGGGAGGAGCAGTTCAA CAGCACGTACCGTGTGGTCAGCGTCCTCACCGTCCTGCACCAGGACTGGCTGA ACGGCAAGGAGTACAAGTGCAAGGTCTCCAACAAAGGCCTCCCGTCCTCCATC GAGAAAACCATCTCCAAAGCCAAAGGGCAGCCCCGAGAGCCACAGGTGTACAC CCTGCCCCCATCCCAGGAGGAGATGACCAAGAACCAGGTCAGCCTGACCTGCC TGGTCAAAGGCTTCTACCCCAGCGACATCGCCGTGGAGTGGGAGAGCAATGGG CAGCCGGAGAACAACTACAAGACCACGCCTCCCGTGCTGGACTCCGACGGCTC CTTCTTCCTCTACAGCAGGCTAACCGTGGACAAGAGCAGGTGGCAGGAGGGGA ATGTCTTCTCATGCTCCGTGATGCATGAGGCTCTGCACAACCACTACACACAG AAGAGCCTCTCCCTGTCTCTGGGTAAATGA SEQ ID NO: 42 |
| 35G11-C$_H$ | ASTKGPSVFPLAPCSRSTSESTAALGCLVKDYFPEPVTVSWNSGALTSGVHTF PAVLQSSGLYSLSSVVTVPSSSLGTKTYTCNVDHKPSNTKVDKRVESKYGPPC PSCPAPEFLGGPSVFLFPPKPKDTLMISRTPEVTCVVVDVSQEDPEVQFNWYV DGVEVHNAKTKPREEQFNSTYRVVSVLTVLHQDWLNGKEYKCKVSNKGLPSSI EKTISKAKGQPREPQVYTLPPSQEEMTKNQVSLTCLVKGFYPSDIAVEWESNG QPENNYKTTPPVLDSDGSFFLYSRLTVDKSRWQEGNVFSCSVMHEALHNHYTQ KSLSLSLGK SEQ ID NO: 43 |
| 35G11-C$_L$ lambda-type | GGTCAGCCCAAGGCTGCCCCCTCGGTCACTCTGTTCCCGCCCTCCTCTGAGGA GCTTCAAGCCAACAAGGCCACACTGGTGTGTCTCATAAGTGACTTCTACCCGG GAGCCGTGACAGTGGCCTGGAAGGCAGATAGCAGCCCCGTCAAGGCGGGAGTG GAGACCACCACACCCTCCAAACAAAGCAACAACAAGTACGCGGCCAGCAGCTA CCTGAGCCTGACGCCTGAGCAGTGGAAGTCCCACAGA*AGCTACAGCTGCCAGG TCACGCATGAAGGGAGCACCGTGGAGAAGACAGTGGCCCCTACAGAATGTTCA TAG* SEQ ID NO: 44 |
| 35G11-C$_L$ lambda-type | GQPKAAPSVTLFPPSSEELQANKATLVCLISDFYPGAVTVAWKADSSPVKAGV ETTTPSKQSNNKYAASSYLSLTPEQWKSHRSYSCQVTHEGSTVEKTVAPTECS SEQ ID NO: 45 |
| 41D11-V$_H$ | CAGGTGCAACTACATGAGTCGGGCCCAGGACTGGTGAAGCCTTCGGAGACCCT GTCCGTAACCTGCAGTCTCTCTGGTGGCTCCATCAGTAGTAGTAGTCACCTGT GGGCCTGGATCCGCCAGCCCCAGAGAAGGGACTGGAATATATCGGGCGTATT CATTATAGGGGCAGTGTGTCCTACAATCCGTCCCTCAAGAGTCGCGCCGCCAT TTCCGTCGACACGGCCAAGAACCAGTTCTCCCTGACGTTGAGTGCTGTGACCG CCGCAGACACGTCTTTTTATTACTGTGCGAGACTGGACATGGGGGCAATAGAC AAGTGGGGCCAGGGAACCCTGGTCATCGTCTCCTCA SEQ ID NO: 46 |
| 41D11-V$_H$ | QVQLHESGPGLVKPSETLSVTCSLSGGSISSSSHLWAWIRQPPEKGLEYIGRI HYRGSVSYNPSLKSRAAISVDTAKNQFSLTLSAVTAADTSFYYCARLDMGAID KWGQGTLVIVSS SEQ ID NO: 47 |
| 41D11-V$_L$ lambda-type | CAGCCTGTGCTGACTCAATCGCCCTCTGCCTCTGCCTCCCTGGGAGCCTCGAT CAAACTCACCTGCACTCTGAGCAGTGGACACAGCAACTACGACATCGCTTGGC ATCAACAGCAGTCGGGGAAGGGCCCTCGATTCTTGATGAGAGTTAACAATGGT GGAAGCCACAACAAGGGGGACGGGATCCCTGATCGTTTCTCAGGCTCCAGCTC TGGGGCAGAGCGCTACCTCACAATCTCCAGTCTCCAGTCTGAGGATGAGGCTG ACTATTATTGTCAGACATGGGGCACTGGCACTCATGTCTTCGGCACTGGGACT AAGGTCACCGTCCTG SEQ ID NO: 48 |

TABLE 17-continued

Nucleotide and amino acid sequences of the variable and constant
regions (V$_H$, V$_L$, C$_H$, C$_L$) of IL-17A, IL17F or IL-22 specific
antibodies of the present invention.
IL-17F specific antibody 9A2: IgG1, kappa (VH3; G1m17; VK1, Km3).
IL-17F and IL-17A specific antibody 17E3: IgG1, kappa (VH1, G1m17,
VK1, Km3). IL-17F specific antibody 24D3: IgG1, lambda (VH3,
G1m17; VL3), IL-22 specific antibody 30G1: IgG1, kappa (VH3, G1m17,
VK3, Km3 or Km1, 2). IL-22 specific antibody 35G11: IgG4, lambda
(VH7, IGHG4*01; VL1); 35G11-C$_L$; at positions 211-213 TAC may be as
well TAT, both coding for Tyr. IL-22 specific antibody 41D11: IgG1,
lambda (VH4, G1m3 L410F; VL4). IL-22 specific antibody 51G4: IgG2,
lambda (VH1, IGHG2*01; VL3); 41D11-C$_H$: positions 877-879 of the
nucleotide sequence may be ctc instead of ttc and position 293 of
the corresponding amino acid sequence may be Leu instead of Phe
(underlined). Underlined, bold nucleotides or amino acids indicate
the CDR coding regions in the variable chain sequence. Underlined,
italic nucleotides indicate sequences in the constant chain
sequences which have not been sequenced but obtained from database.

| Antibody | Nucleotide and amino acid sequences of variable heavy (VH) and variable light |
|---|---|
| 41D11-V$_L$ lambda-type | QPVLTQSPSASASLGASIKLTCTLSSGHSNYDIAWHQQQSGKGPRFLMRVNNG GSHNKGDGIPDRFSGSSSGAERYLTISSLQSEDEADYYCQTWGTGTHVFGTGT KVTVL SEQ ID NO: 49 |
| 41D11-C$_H$ | GCCTCCACCAAGGGCCCATCGGTCTTCCCCCTGGCACCCTCCTCCAAGAGCAC CTCTGGGGGCACAGCGGCCCTGGGCTGCCTGGTCAAGGACTACTTCCCCGAAC CGGTGACGGTGTCGTGGAACTCAGGCGCCCTGACCAGCGGCGTGCACACCTTC CCGGCTGTCCTACAGTCCTCAGGACTCTACTCCCTCAGCAGCGTGGTGACCGT GCCCTCCAGCAGCTTGGGCACCCAGACCTACATCTGCAACGTGAATCACAAGC CCAGCAACACCAAGGTGGACAAGAGAGTTGAGCCCAAATCTTGTGACAAAACT CACACATGCCCACCGTGCCCAGCACCTGAACTCCTGGGGGGACCGTCAGTCTT CCTCTTCCCCCCAAAACCCAAGGACACCCTCATGATCTCCCGGACCCCTGAGG TCACATGCGTGGTGGTGGACGTGAGCCACGAAGACCCTGAGGTCAAGTTCAAC TGGTACGTGGACGGCGTGGAGGTGCATAATGCCAAGACAAAGCCGCGGGAGGA GCAGTACAACAGCACGTACCGTGTGGTCAGCGTCCTCACCGTCCTGCACCAGG ACTGGCTGAATGGCAAGGAGTACAAGTGCAAGGTCTCCAACAAAGCCCTCCCA GCCCCCATCGAGAAAACCATCTCCAAAGCCAAAGGGCAGCCCCGAGAACCACA GGTGTACACCCTGCCCCCATCCCGGGAGGAGATGACCAAGAACCAGGTCAGCC TGACCTGCCTGGTCAAAGGCTTCTATCCCAGCGACATCGCCGTGGAGTGGGAG AGCAATGGGCAGCCGGAGAACAACTACAAGACCACGCCTCCCGTGCTGGACTC CGACGGCTCCTTCTTCCTCTATAGCAAGTTCACCGTGGACAAGAGCAGGTGGC AGCAGGGGAACGTCTTCTCATGCTCCGTGATGCATGAGGCTCTGCACAACCAC TACACGCAGAAGAGCCTCTCCCTGTCCCCGGGTAAATGA SEQ ID NO: 50 |
| 41D11-C$_H$ | ASTKGPSVFPLPASSKSTSGGTAALGCLVKDYFPEPVTVSWNSGALTSGVHTF PAVLQSSGLYSLSSVVTVPSSSLGTQTYICNVNHKPSNTKVDKRVEPKSCDKT HTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVYTLPPSREEMTKNQVSLTCLVKGFYPSDIAVEWE SNGQPENNYKTTPPVLDSDGSFFLYSKFTVDKSRWQQGNVFSCSVMHEALHNH YTQKSLSLSPGK SEQ ID NO: 51 |
| 41D11-C$_L$ lamdga-type | GGTCAGCCCAAGGCCAACCCCACTGTCACTCTGTTCCCGCCCTCCTCTGAGGA GCTCCAAGCCAACAAGGCCACACTAGTGTGTCTGATCAGTGACTTCTACCCGG GAGCTGTGACAGTGGCCTGGAAGGCAGATGGCAGCCCCGTCAAGGCGGGAGTG GAGACCACCAAACCCTCCAAACAGAGCAACAACAAGTACGCGGCCAGCAGCTA CCTGAGCCTGACGCCCGAGCAGTGGAAGTCCCACAGA*AGCTACAGCTGCCAGG TCACGCATGAAGGGAGCACCGTGGAGAAGACAGTGGCCCCTACAGAATGTTCA TAG* SEQ ID NO: 52 |
| 41D11-C$_L$ lambda-type | KQPKANPTVTLFPPSSEELQANKATLVCLISDFYPGAVTVAWKADGSPVKAGV ETTKPSKQSNNKYAASSYLSLTPEQWKSHRSYSCQVTHEGSTVEKTVAPTECS SEQ ID NO: 53 |
| 51G4-V$_H$ | *GAGGTGCAGCTGGTGCAG*TCTGGGGCTGAGGTGAAGAAGCCTGGGGCCTCAGT GAAGGTTTCATGTAAAACTTCTGGATACAAATTCGCTCTCTATGATATTCATT GGGTGCGCCAGGCCCCCGGACAAGGGCTTGAGTGGATGGGCTGGATCAACGCT GCCAATGGTGACACAGAATATTCACAGAAGTTTGAGGGCAGAGTCACCATTAC CAGGGACACATCGGCGACTACAGTCTACATGGAGTTGAACAGTCTGACATATG GCGACACGGCCGTGTACTACTGTGCGAGAGAGGAAGGTCTCTACAACTGGTTC GACCCCTGGGGCCAGGGAACC*CTGGTCACCGTCTCCTCA* SEQ ID NO: 54 |
| 51G4-V$_H$ | EVQLVQSGAEVKKPGASVKVSCKTSGYKFALYDIHWVRQAPGQGLEWMGWINA ANGDTEYSQKFEGRVTITRDTSATTVYMELNSLTYGDTAVYYCAREEGLYNWF DPWGQGTLVTSS SEQ ID NO: 55 |

TABLE 17-continued

Nucleotide and amino acid sequences of the variable and constant regions (V$_H$, V$_L$, C$_H$, C$_L$) of IL-17A, IL17F or IL-22 specific antibodies of the present invention.
IL-17F specific antibody 9A2: IgG1, kappa (VH3; G1m17; VK1, Km3). IL-17F and IL-17A specific antibody 17E3: IgG1, kappa (VH1, G1m17, VK1, Km3). IL-17F specific antibody 24D3: IgG1, lambda (VH3, G1m17; VL3), IL-22 specific antibody 30G1: IgG1, kappa (VH3, G1m17, VK3, Km3 or Km1, 2). IL-22 specific antibody 35G11: IgG4, lambda (VH7, IGHG4*01; VL1); 35G11-C$_L$; at positions 211-213 TAC may be as well TAT, both coding for Tyr. IL-22 specific antibody 41D11: IgG1, lambda (VH4, G1m3 L410F; VL4). IL-22 specific antibody 51G4: IgG2, lambda (VH1, IGHG2*01; VL3); 41D11-C$_H$: positions 877-879 of the nucleotide sequence may be ctc instead of ttc and position 293 of the corresponding amino acid sequence may be Leu instead of Phe (underlined). Underlined, bold nucleotides or amino acids indicate the CDR coding regions in the variable chain sequence. Underlined, italic nucleotides indicate sequences in the constant chain sequences which have not been sequenced but obtained from database.

| Antibody | Nucleotide and amino acid sequences of variable heavy (VH) and variable light |
|---|---|
| 51G4-V$_L$ | *TCCTATGAGCTGACACAG*GACCCTGCTGTGTCTGTGGCCTTGGGACAGACAGT CAGGATCACATGCCAAGGAGACAGCCTCAGAATCTATTATGCAAACTGGTACC AGCAGAAGCCAGGACAGGCCCCTGTTCTTGTCATCTATGGTAAAAGCAACCGG CCCTCAGGGATCCAGACCGATTCTCTGCCTCCAGCTCAGGAAACACAGCTTC CTTGACCATCACTGGGGCTCAGGCGGAAGATGAGGCTGACTATTACTGTAACT CCCGGGACAGCAGTGATAAGCATCCCGTGCCTTTCGGCGGGGGGACCAAGCTG ACCGTCCTA SEQ ID NO: 56 |
| 51G4-V$_L$ | SYELTQDPAVSVALGQTVRITCQGDSLRIYYANWYQQKPGQAPVLVIYGKSNR PSGIPDRFSASSSGNTASLTITGAQAEDEADYYCNSRDSSDKHPVPFGGGTKL TVL SEQ ID NO: 57 |
| 51G4-C$_H$ | *GCCTCCACCAAGGGCCCATCGGTCTTCCCCCTGGCGCCCTGCTCCAGG*AGCAC CTCCGAGAGCACAGCGGCCCTGGGCTGCCTGGTCAAGGACTACTTCCCCGAAC CGGTGACGGTGTCGTGGAACTCAGGTGCTCTGACCAGCGGCGTGCACACCTTC CCAGCTGTCCTACAGTCCTCAGGACTCTACTCCCTCAGCAGCGTGGTGACCGT GCCCTCCAGCAACTTCGGCACCCAGACCTACACCTGCAACGTAGATCACAAGC CCAGCAACACCAAGGTGGACAAGACAGTTGAGCGCAAATGTTGTGTCGAGTGC CCACCGTGCCCAGCACCACCTGTGGCAGGACCGTCAGTCTTCCTCTTCCCCCC AAAACCCAAGGACACCCTCATGATCTCCCGGACCCCTGAGGTCACGTGCGTGG TGGTGGACGTGAGCCACGAAGACCCCGAGGTCCAGTTCAACTGGTACGTGGAC GGCGTGGAGGTGCATAATGCCAAGACAAAGCCACGGGAGGAGCAGTTCAACAG CACGTTCCGTGTGGTCAGCGTCCTCACCGTTGTGCACCAGGACTGGCTGAACG GCAAGGAGTACAAGTGCAAGGTCTCCAACAAAGGCCTCCCAGCCCCCATCGAG AAAACCATCTCCAAAACCAAAGGGCAGCCCCGAGAACCACAGGTGTACACCCT GCCCCCATCCCGGGAGGAGATGACCAAGAACCAGGTCAGCCTGACCTGCCTGG TCAAAGGCTTCTACCCCAGCGACATCGCCGTGGAGTGGGAGAGCAATGGGCAG CCGGAGAACAACTACAAGACCACACCTCCCATGCTGGACTCCGACGGCTCCTT CTTCCTCTACAGCAAGCTCACCGTGGACAAGAGCAGGTGGCAGCAGGGGAACG TCTTCTCATGCTCCGTGATGCATGAGGCTCTGCACAACCACTACACGCAGAAG AGCCTCTCCCTGTCTCCGGGTAAATGA SEQ ID NO: 58 |
| 51G4-C$_H$ | ASTKGPSVFPLAPCSRSTSESTAALGCLVKDYFPEPVTVSWNSGALTSGVHTF PAVLQSSGLYSLSSVVTVPSSNFGTQTYTCNVDHKPSNTKVDKTVERKCCVEC PPCPAPPVAGPSVFLFPPKPKDTLMISRTPEVTCVVVDVSHEDPEVQFNWYVD GVEVHNAKTKPREEQFNSTFRVVSVLTVVHQDWLNGKEYKCKVSNKGLPAPIE KTISKTKGQPREPQVYTLPPSREEMTKNQVSLTCLVKGFYPSDIAVEWESNGQ PENNYKTTPPMLDSDGSFFLYSKLTVDKSRWQQGNVFSCSVMHEALHNHYTQK SLSLSPGK SEQ ID NO: 59 |
| 51G4-C$_L$ | AGTCAGCCCAAGGCTGCCCCCTCGGT*CACTCTGTTCCCGCCCTCCTCTGAGGA GCTTCAAGCCAACAAGGCCACACTGGTGTGTCTCATAAGTGACTTCTACCCGG GAGCCGTGACAGTGGCCTGGAAGGCAGATAGCAGCCCCGTCAAGGCGGGAGTG GAGACCACCACACCCTCCAAACAAAGCAACAACAAGTACGCGGCCAGCAGCTA TCTGAGCCTGACGCCTGAGCAGTGGAAGTCCCACAGAAGCTACAGCTGCCAGG TCACGCATGAAGGGAGCACCGTGGAGAAGACAGTGGCCCCTACAGAATGTTCA TAG* SEQ ID NO: 60 |
| 51G4-C$_L$ | SQPKAAPSVTLFPPSSEELQANKATLVCLISDFYPGAVTVAWKADSSPVKAGV ETTTPSKQSNNKYAASSYLSLTPEQWKSHRSYSCQVTHEGSTVEKTVAPTECS SEQ ID NO: 61 |

The person skilled in the art will readily appreciate that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously have substantially the same or similar binding properties as the antibody described in the appended examples. The person skilled in the art will readily appreciate that using the variable domains or CDRs described herein antibodies can be constructed according to methods known in the art, e.g., as described in European patent applications EP 0 451 216 A1 and EP 0 549 581 A1. Furthermore, the person skilled in the art knows that binding affinity may be enhanced by making amino acid substitutions within the CDRs or within the hypervariable loops (Chothia and Lesk, *J. Mol. Biol.* 196 (1987), 901-917) which partially overlap with the CDRs as defined by Kabat. Thus, the present invention also relates to antibodies wherein one or more of the mentioned CDRs comprise one or more, preferably not more than two amino acid substitutions. Preferably, the antibody of the invention comprises in one or both of its immunoglobulin chains two or all three CDRs of the variable regions as set forth in SEQ ID NOs: 7, 9, 15, 17, 23, 25, 31, 33, 39, 41, 47, 49, 55 or 57 or indicated in FIG. 15.

The polynucleotide of the invention encoding the above described antibody may be, e.g., DNA, cDNA, RNA or synthetically produced DNA or RNA or a recombinantly produced chimeric nucleic acid molecule comprising any of those polynucleotides either alone or in combination. In a preferred embodiment a vector comprising the above polynucleotide is provided, optionally in combination with said polynucleotide which encodes the variable region of the other immunoglobulin chain of said antibody. Such vectors may comprise further genes such as marker genes which allow for the selection of said vector in a suitable host cell and under suitable conditions.

Preferably, the polynucleotide of the invention is operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally associated or heterologous promoter regions.

In this respect, the person skilled in the art will readily appreciate that the polynucleotides encoding at least the variable domain of the light and/or heavy chain may encode the variable domains of both immunoglobulin chains or one chain only.

Likewise, said polynucleotides may be under the control of the same promoter or may be separately controlled for expression. Possible regulatory elements permitting expression in prokaryotic host cells comprise, e.g., the $P_L$, lac, trp or tac promoter in *E. coli*, and examples for regulatory elements permitting expression in eukaryotic host cells are the AOX1 or GAL1 promoter in yeast or the CMV-, SV40-, RSV-promoter, CMV-enhancer, SV40-enhancer or a globin intron in mammalian and other animal cells.

Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the polynucleotide of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including a C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3 (Invitrogen), or pSPORT1 (GIBCO BRL).

Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the immunoglobulin light chains, heavy chains, light/heavy chain dimers or intact antibodies, binding fragments or other immunoglobulin forms may follow; see, Beychok, *Cells of Immunoglobulin Synthesis*, Academic Press, N.Y., (1979).

Furthermore, the present invention relates to vectors, particularly plasmids, cosmids, viruses and bacteriophages used conventionally in genetic engineering that comprise a polynucleotide encoding the antigen or preferably a variable domain of an immunoglobulin chain of an antibody of the invention; optionally in combination with a polynucleotide of the invention that encodes the variable domain of the other immunoglobulin chain of the antibody of the invention. Preferably, said vector is an expression vector and/or a gene transfer or targeting vector.

Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, *Molecular Cloning A Laboratory Manual*, Cold Spring Harbor Laboratory (1989) N.Y. and Ausubel, *Current Protocols in Molecular Biology*, Green Publishing Associates and Wiley Interscience, N.Y. (1994). Alternatively, the polynucleotides and vectors of the invention can be reconstituted into liposomes for delivery to target cells. The vectors containing the polynucleotides of the invention (e.g., the heavy and/or light variable domain(s) of the immunoglobulin chains encoding sequences and expression control sequences) can be transferred into the host cell by well known methods, which vary depending on the type of cellular host. For example, calcium chloride transfection is commonly utilized for prokaryotic cells, whereas calcium phosphate treatment or electroporation may be used for the transformation of other cellular hosts; see Sambrook, supra.

In respect to the above, the present invention furthermore relates to a host cell comprising said polynucleotide or vector. Said host cell may be a prokaryotic or eukaryotic cell. The polynucleotide or vector of the invention which is present in the host cell may either be integrated into the genome of the host cell or it may be maintained extrachromosomally. The host cell can be any prokaryotic or eukaryotic cell, such as a bacterial, insect, fungal, plant, animal or human cell; suitable host cells and methods for production of the antibodies of the present invention are described in more detail in the section "Host cells" below.

The binding molecules, antibodies or fragments thereof may be directly used as a therapeuticum. However, in one embodiment the antibody or antigen-binding fragment which is provided by the present invention, is detectably labeled or attached to a drug, wherein the detectable label is selected from the group consisting of an enzyme, a radioisotope, a fluorophore, a peptide and a heavy metal. Labeled antibodies or antigen-binding fragments of the present invention may be used to detect specific targets in vivo or in vitro including "immunochemistry/immunolabeling" like assays in vitro. In vivo they may be used in a manner similar to nuclear medicine imaging techniques to detect tissues, cells, or other material expressing the antigen of interest. Labels, their use in diagnostics and their coupling to the binding molecules of the present invention are described in more detail in section "labels and diagnostics" further below.

The antibodies of the present invention are isolated from animals or humans affected by an autoimmune disorder. By binding to endogenous molecules, e.g., proteins as enlisted in tables 1 to 14 or in tables 29-31, some of them can be used in treatment of tumor or neurodegenerative diseases. On the other hand antibodies identified in the present invention may be involved in eliciting inflammation or severely impair the immune system of the affected individual, which is associated with, e.g., symptoms observed in APECED patients as described in more detail hereinbefore and below. Therefore, it is a further aspect of the present invention, to extinguish or at least relieve the pathological reactions of subjects suffering from autoimmune disorders by providing means and measures to minimize the number of auto-antibodies and/or their effects in a diseased human patient or animal. Therefore, in one embodiment the present invention also provides an anti-idiotypic antibody of an autoantibody of the present invention. A similar effect may be obtained by application of competitive antigens, sequestering and preventing thereby the binding of the autoantibodies to their respective targets. Thus, in one embodiment the present invention also relates to a synthetic peptide or peptide-based compound comprising an epitope specifically recognized by an autoantibody of the present invention, i.e. isolated according to the methods of the present invention.

As already indicated above, the present invention also relates to the anti-idiotypic antibody or the peptide or peptide-based compound of the present invention for use in the treatment of a disorder as defined above, i.e. a disorder associated with a disrupted or deregulated genesis of self-tolerance. These isolated antibodies or fragments thereof of the present invention can be used as immunogens to generate a panel of monoclonal anti-idiotypes. For suitable methods for the generation of anti-idiotypic antibodies see Raychadhuri et al., J. Immunol. 137 (1986), 1743 and for T-cells see Ertl et al., J. Exp. Med 159 (1985), 1776. The anti-idiotypic antibodies will be characterized with respect to the expression of internal image and non-internal image idiotopes using standard-assays routinely practiced in the art as described in detail by Raychaudhuri et al., J. Immunol. 137 (1986), 1743. If an anti-idiotipic antibody structurally mimics the antigen of the antibody it is binding to or bound by, it is called the "internal image" of the antigen.

Methods of providing molecules which mimic an idiotype of an autoimmune disease-associated auto-antibody (autoantibodies) are described in the art; see, e.g., international application WO03/099868, the disclosure content of which incorporated herein by reference. For example, such method may comprise the following steps: (a) providing autoantibodies in accordance with the method of the present invention; (b) binding the autoantibodies to a solid phase to form an affinity matrix; (c) contacting pooled plasma or B cells comprising immunoglobulins with the affinity matrix followed by removal of unbound plasma components; (d) eluting bound immunoglobulins, being anti-Idiotypic antibodies (anti-Id) to autoantibodies, from the matrix: (e) providing a molecular library comprising a plurality of molecule members: and (e) contacting the anti-Id with the molecular library and isolating those bound molecules which are bound by the anti-Id, the bound molecules being molecules which mimic an idiotype of autoantibodies. A method of isolating idiotypic autoantibodies in disclosed in international application WO2010/136196, the disclosure content of which incorporated herein by reference, which describes immunoglobulin preparations containing natural polyclonal IgG-reactive antibodies (Abs) isolated from normal human serum (NHS), for the treatment of autoimmune diseases and immune system disorders. The IgG-reactive Abs potently neutralize disease-associated or pathogenic autoantibodies present in sera of patients suffering from autoimmune diseases, by binding to their antigenic determinants located either within or near (e.g. overlapping with) the antigen combining sites.

Moreover, the present invention also relates to compositions comprising the aforementioned antibody or antigen-binding fragment, the polynucleotide, the vector, the cell, the anti-idiotypic antibody or the peptide or peptide-based compound. In one embodiment the composition is a pharmaceutical composition and further comprises a pharmaceutically acceptable carrier. Pharmaceutically acceptable carriers, administration routes and dosage regimen can be taken from corresponding literature known to the person skilled in the art and are described as well in more detail in sections "Pharmaceutical carriers" and "Dosage regimen" further below.

Besides biochemical and cell based in vitro assays therapeutic utility of the antibody of the present invention can be validated in appropriate animal models such as for psoraris, IBD, candidasis; see Examples 5 and 6 and for Inflammatory bowel disease IBD (DSS colitis) model in Wirtz et al, Nature Protocols 2 (2007), 541-546; for a Psoriasis (Imiquimod) model in van der Fits et al, J Immunol 182 (2009), 5836-5845; for a multiple sclerosis (Experimental Autoimmune Encephalomyelitis (EAE)) model in Miller, S. D. and Karpus, W. J., Current Protocols in Immunology. 78 (2007), 15.1.1-15.1.18 and at http://hookelabs.com/products/eae/: for a rheumatoid arthritis (Collagen-induced arthritis) model in Julia J Inglis et al, Nature Protocols 3 (2008), 612-618.

In one embodiment the pharmaceutical composition further comprises an additional agent useful for treating an inflammation or an autoimmune disorder, selected from the group consisting of Non-Steroidal Antiinflammatory Drugs (NSAIDs), Corticosteroids, Anti-Histamines and combinations thereof. In addition or alternatively, in a further embodiment the pharmaceutical composition further comprises an additional agent useful for treating an inflammation related disease, selected from the group consisting of immunosuppressive and anti-inflammatory or "anti-rheumatic" drugs.

In another embodiment, the composition is a diagnostic composition and further comprises reagents conventionally used in immuno- or nucleic acid based diagnostic methods.

Furthermore, the present invention provides the aforementioned antibody or antigen-binding fragment, the anti-idiotypic antibody or the peptide or peptide-based compound for use in treating or preventing the progression of an inflammatory or an autoimmune disorder; for the amelioration of symptoms associated with inflammation or an autoimmune disorder; for diagnosing or screening a subject for the presence or for determining a subject's risk for developing inflammation or an autoimmune disorder.

In this respect several application routes may be used. In one embodiment of the present invention the aforementioned antibody or antigen-binding fragment, the anti-idiotypic antibody or peptide or peptide-based compound is provided, which is designed to be administered intravenously, intramuscularly, subcutaneously, intraperitoneally, intranasally, parenterally or as an aerosol.

Due to the multitude of molecules suitable in treatment of, e.g., disorders associated with inflammation, the present invention also provides several methods of treatment of such disorders. In one embodiment a method of treating a disorder associated with an inflammation or an autoimmune disorder is provided, which method comprises administering to a subject in need thereof a therapeutically effective amount of the aforementioned antibody or antigen-binding fragment, the anti-idiotypic antibody or the peptide or peptide-based compound.

In one embodiment of this method said disorder is selected from the group consisting of Acne vulgaris; Arthritis such as Gouty arthritis, Systemic lupus erythematosus (SLE), Osteoarthritis, Psoriatic arthritis, Rheumatoid arthritis; Asthma; Celiac disease: Chronic prostatitis; Dermatitis: Diabetes mellitus Type 1; Glomerulonephritis; Hypersensitivities; Myocarditis; Multiple sclerosis: Inflammatory bowel diseases: Pelvic inflammatory disease; Polymyositis; Psoriasis; Sarcoidosis; Vasculitis; APS1: Interstitial cystitis or the inflammation occurs due to reperfusion injury or transplant rejection; see supra.

Furthermore, in one embodiment the present invention relates to a method of diagnosing and/or treating a disorder related to an inflammation or an autoimmune disorder comprising administering to a subject a therapeutically effective amount of a ligand binding molecule comprising:
(i) at least one CDR of the aforementioned antibody or antigen-binding fragment; or
(ii) at least one aforementioned anti-idiotypic antibody and/or peptide or peptide-based compound.

Treatment methods based on the use of only one monoclonal antibody specific for an epitope of a particular antigen, which is related or causing a disease may suffer from several shortcomings. For example, difficulties and probably inefficiency of treatment may stem from the multiplicity of the pathogenic mechanisms causing a specific disorder requiring targeting of several antigens simultaneously. Furthermore, the inherent diversity of the patient population has to be taken into account concerning, e.g., polymorphism, heterogeneity of glycosylation or slight denaturation of a given antigen, either in different or in one patient which may lead to a decreased binding efficiency of the monoclonal antibody used at least. Some of these shortcomings may be circumvented by, e.g., pretreatment screenings to determine whether the antigen is immunologically relevant to the patients intended to be treated and whether there are any epitope changes in the particular patients. However, such screenings are often omitted either due to treatment urgency or to cost restraints. Therefore, the present invention further relates to methods based on the application of more than one type of a binding molecule at once to a patient. These binding molecules may specifically bind to one antigen at different epitopes or each of the binding molecules applied binds specifically another disease related antigen. In case the binding molecules of the present invention are directed (bind specifically) towards one antigen, their binding specificity is directed towards distinct epitopes of said antigen. The use of such cocktails is in particular envisaged for the treatment of patients suffering from autoimmune disorders such as APS1, who in view of the presence of autoantibodies against about 3000 endogenous antigens are often not amenable to monotherapy with one particular antibody. In such cases, combination therapy with two or more monoclonal antibodies and/or peptides and peptide-based compounds of the present invention with the same or different antigen specificity are expected to achieve at least some relief of the symptoms.

Therefore, in one embodiment a further method of treating a disorder is provided comprising administering to a subject a therapeutically effective amount of a cocktail consisting essentially of at least two, three, four, five and more components selected from the groups consisting of:
an antibody or antigen-binding fragment thereof of the present invention specifically binding an antigen from the group of secreted or transmembrane proteins involved in inflammation, an autoimmune disorder, cell growth and differentiation, muscular function and neurodegeneration as indicated in tables 1 to 14 and 29 to 31 and FIGS. 1 to 4; and/or
an anti-idiotypic antibody of the present invention, and/or from a peptide or peptide-based compound of the present invention, which peptide or peptide-based compound comprises an epitope specifically recognized by an antibody or antigen-binding fragment thereof of the present invention.

In another embodiment the present invention relates to a kit for the diagnosis of a disorder which is accompanied with the presence of a disorder-associated protein as defined in any one of the peptides claimed, said kit comprising the aforementioned antibody or antigen-binding fragment, the anti-idiotypic antibody or the peptide or peptide-based compound, the polynucleotide, the vector or the cell, optionally with reagents and/or instructions for use. Associated with the kits of the present invention, e.g., within a container comprising the kit can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The compositions, i.e. kits of the present invention are of course particularly suitable for the diagnosis, prevention and treatment of a disorder which is accompanied with the presence of a inflammation-associated antigen defined above, in particular applicable for the treatment of diseases as mentioned above.

In another embodiment the present invention relates to a diagnostic composition comprising any one of the above described binding molecules, antibodies, antigen-binding fragments, peptides or peptide-based compounds, polynucleotides, vectors or cells of the invention and optionally suitable means for detection such as reagents conventionally used in immuno or nucleic acid based diagnostic methods. The antibodies of the invention are, for example, suited for use in immunoassays in which they can be utilized in liquid phase or bound to a solid phase carrier. Examples of immunoassays which can utilize the antibody of the invention are competitive and non-competitive immunoassays in either a direct or indirect format. Examples of such immunoassays are the radioimmunoassay (RIA), the sandwich (immunometric assay), flow cytometry and the Western blot assay. The antigens and antibodies of the invention can be bound to many different carriers and used to isolate cells specifically bound thereto. Examples of well known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds: see also the embodiments discussed hereinabove.

In this context, the present invention also relates to means specifically designed for this purpose. For example, a protein- or antibody-based array may be used, which is for example loaded with either antigens derived from the mentioned disorder-associated protein and containing the inflammation-associated antigen in order to detect autoantibodies which may be present in patients suffering from a autoimmune diseases, in particular arthritis, type I diabetes or APECED/APS1, or with antibodies or equivalent antigen-binding molecules of the present invention which specifically recognize any one of those inflammation-associated antigens. Design of microarray immunoassays is summarized in Kusnezow et al., *Mol. Cell Proteomics* 5 (2006), 1681-1696. Accordingly, the present invention also relates to microarrays loaded with binding molecules or antigens identified in accordance with the present invention.

Definitions and Embodiments

Unless otherwise stated, a term as used herein is given the definition as provided in the *Oxford Dictionary of Biochemistry and Molecular Biology*, Oxford University Press, 1997, revised 2000 and reprinted 2003. ISBN 0 19 850673 2.

It is to be noted that the term "a" or "an" entity refers to one or more of that entity, for example, "an antibody," is understood to represent one or more antibodies. As such, the terms "a" (or "an"), "one or more." and "at least one" can be used interchangeably herein.

The term "neutralizing" and "neutralizing antibody", respectively, is used as common in the art in that an antibody is meant that reduces or abolishes at least some biological activity of an antigen or of a living microorganism. For example, an anti-IL-17F antibody of the present invention is a neutralizing antibody, if, in adequate amounts, it abolishes the cytokine activity for example in an assay as described in the Examples. Neutralization is commonly defined by 50% inhibitory concentrations (IC 50) and can be statistically assessed based on the area under the neutralization titration curves (AUC). For tumor diseases neutralization can be assessed for example by determining inhibition of tumor growth. For example, it is known that oncogenic grafts-induced secretion of interleukin-6 is required for tumorgenesis and that anti-IL-6 antibodies may be used for corresponding cancer therapy; see, e.g. Ancrile et al., "*Genes and development*" 21 (2007), 1714-1719. Neutralization of an infectious agent such as a virus is defined as the loss of infectivity through reaction of the virus or its target cell, for example by blocking the receptor of the virus resulting in the reduction of infected cells which can be easily determined in appropriate cell-based assays known by the person skilled in the art. Other biological activities which may be "neutralized" by the antibody of the present invention can be easily ascertained by the person skilled in the art.

Central and Peripheral Tolerance

Self-tolerance is the process whereby the immune system does not respond to an antigen that is a constituent of that organism. Self-tolerance is achieved by death or inactivation of self-reactive T and B-cells, which may occur as part of central tolerance in a central (generative) immune organ (thymus or bone marrow) or as peripheral tolerance in what are most commonly regarded as secondary immune tissues (e.g. spleen, lymph node, intestine). Self-tolerance is a central feature of the normal immune system. Failure to establish and/or maintain self-tolerance leads to autoimmunity, which may result in autoimmune diseases that have severe health implications for the host organism.

Central tolerance is a form of self-tolerance that is induced in central immune organs such as the thymus and bone marrow. In the process of central tolerance, newly developed T and B-cells recognizing self-antigens are rendered non-reactive to self antigens by cell death, by other forms of inactivation, or by developmental conversion to immunosuppressive regulatory lymphocytes. Central tolerance for T-cells is induced in the thymus, where developing thymocytes (T-cells in thymus) that recognize self-peptide-MHC complexes with high affinity are mostly deleted. Central tolerance for B-cells is induced in the bone marrow. During their differentiation in thymus and bone marrow, T- and B-cells rearrange their genomic regions respectively containing T-cell receptor and B-cell receptor genes. The somatic gene rearrangement, also called V(D)J recombination, generates a diversity of T-cell receptors and antibodies. This diversity is the basis for T and B-cell clonal repertoires. After V(D)J recombination, maturing T- and B-cells are capable of antigen recognition. Recognition of antigen at this stage can lead to negative selection that eliminates or alters developing T- and B-cells whose antigen receptors bind strongly to self-antigens present in generative immune organs. Both T and B-cells are susceptible to negative selection within a short period after T-cell receptors and B-cell receptors, respectively, are first expressed on cell surface.

T- and B-cells can develop central tolerance towards those antigens that are present in generative immune organs. In the bone marrow, B cells develop tolerance to ubiquitously expressed, bone-marrow specific antigens and to antigens imported by the blood circulation. In the thymus, thymic medullary epithelial cells can express many hundreds of self-antigens that are presented to developing T-cells. The gene responsible for the broad expression of self-antigens in thymic medullary epithelial cells is AIRE (autoimmune regulator). AIRE activates multiple tissue specific genes that normally are expressed only in particular peripheral organs such as insulin in pancreatic Langerhans islands. In the absence of the functional AIRE gene, antigens are not presented, T cells are not inactivated, and autoimmunity to self-antigens develops, leading to pathology in APECED patients and in Aire deficient mice.

Central tolerance is distinct from peripheral tolerance in that it occurs while cells are still present in the generative immune organs, prior to export into the periphery, while peripheral tolerance is generated after the cells reach the periphery.

Peripheral tolerance is a form of self-tolerance where T and B-cells do not respond to antigens in peripheral tissues. Peripheral tolerance is induced by recognition of antigens without necessary co-stimulatory signals for lymphocyte activation or in the presence of co-inhibitory signals or by repeated and persistent stimulation by these antigens. Peripheral tolerance includes immunological ignorance where self-reactive lymphocytes are not activated because the antigens are expressed in immunoprivileged tissues, which are not under direct immune surveillance such as brain, eye, testis and foetus. Peripheral tolerance also includes the suppression of autoreactive cells by regulatory T cells.

AIRE expression has been reported outside the thymus, in a small population of AIRE-expressing cells in the lymph nodes. Thus, AIRE may play a significant role in self-tolerance via the deletion of autoreactive T cells in periphery. Rare AIRE expressing cells in the lymph nodes share some characteristics with thymic medullary epithelial cells as they act as professional antigen-presenting cells and express tissue-specific antigens. Despite this, the set of AIRE-regulated tissue specific antigens in lymph nodes has little overlap with thymic AIRE-regulated antigens. The lack of overlap suggests that there may be a different order of AIRE-dependent transcriptional regulation of tissue specific antigen expression between the thymus and the lymph nodes.

Another important gene in the induction of tolerance is foxp3. This encodes a transcription factor that induces a immunosuppressive, regulatory fate in T lymphocytes that engage self-antigen in the thymus, and possibly also in the periphery. Failure to encode a functional foxp3 gene is a characteristic of IPEX patients that as a consequence, also suffer widespread autoimmune disease.

Peptides and Polypeptides:

The term "peptide" is understood to include the terms "polypeptide" and "protein" (which, at times, may be used interchangeably herein) and any amino acid sequence such as those of the heavy and light chain variable region as well as constant region of the present invention within its meaning. Similarly, fragments of proteins and polypeptides are also contemplated and may be referred to herein as "peptides". Nevertheless, the term "peptide" preferably denotes an amino acid polymer including at least 5 contiguous amino acids, preferably at least 10 contiguous amino acids, more preferably at least 15 contiguous amino acids, still more preferably at least 20 contiguous amino acids, and particularly preferred at least 25 contiguous amino acids. In addition, the peptide in accordance with present invention typically has no more than 100 contiguous amino acids, preferably less than 80 contiguous amino acids and more preferably less than 50 contiguous amino acids.

As used herein, the term "polypeptide" is intended to encompass a singular "polypeptide" as well as plural "polypeptides" such as antibodies of the present invention, and refers to a molecule composed of monomers (amino acids) linearly linked by amide bonds (also known as peptide bonds). The term "polypeptide" refers to any chain or chains of two or more amino acids, and does not refer to a specific length of the product. Thus, "peptides." "dipeptides," "tripeptides, "oligopeptides," "protein," "amino acid chain," or any other term used to refer to a chain or chains of two or more amino acids, are included within the definition of "polypeptide," and the term "polypeptide" may be used instead of, or interchangeably with any of these terms.

The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Nevertheless, the term "polypeptide" preferably denotes an amino acid polymer including at least 100 amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

"Recombinant peptides, polypeptides or proteins" refer to peptides, polypeptides or proteins produced by recombinant DNA techniques, i.e. produced from cells, microbial or mammalian, transformed by an exogenous recombinant DNA expression construct encoding the fusion protein including the desired peptide. Proteins or peptides expressed in most bacterial cultures will typically be free of glycan. Proteins or polypeptides expressed in yeast may have a glycosylation pattern different from that expressed in mammalian cells.

Also included as polypeptides of the present invention are fragments, derivatives, analogs and variants of the foregoing polypeptides and any combination thereof. The terms "fragment," "variant," "derivative" and "analog" include peptides and polypeptides having an amino acid sequence sufficiently similar to the amino acid sequence of the natural peptide. The term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 1006%, identical are defined herein as sufficiently similar. Preferably, variants will be sufficiently similar to the amino acid sequence of the preferred peptides of the present invention, in particular to antibodies or antibody fragments, or to synthetic peptide or peptide-based compound comprising epitopes recognized by the antibodies of the present invention or fragments, variants, derivatives or analogs of either of them. Such variants generally retain the functional activity of the peptides of the present invention, i.e. are bound by the antibodies of the present invention. Variants include peptides that differ in amino acid sequence from the native and wt peptide, respectively, by way of one or more amino acid deletion(s), addition(s), and/or substitution(s). These may be naturally occurring variants as well as artificially designed ones.

The terms "fragment," "variant," "derivative" and "analog" when referring to antibodies or antibody polypeptides of the present invention include any polypeptides which retain at least some of the antigen-binding properties of the corresponding native binding molecule, antibody, or polypeptide. Fragments of polypeptides of the present invention include proteolytic fragments, as well as deletion fragments, in addition to specific antibody fragments discussed elsewhere herein. Variants of antibodies and antibody polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions or additions. Derivatives of binding molecules of the present invention, e.g., antibodies and antibody polypeptides of the present invention, are polypeptides which have been altered so as to exhibit additional features not found on the native polypeptide. Examples include fusion proteins. Variant polypeptides may also be referred to herein as "polypeptide analogs". As used herein a "derivative" of a binding molecule or fragment thereof, an antibody, or an antibody polypeptide refers to a subject polypeptide having one or more residues chemically derivatized by reaction of a functional side group. Also included as "derivatives" are peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine: and ornithine may be substituted for lysine.

Anti-Idiotypic Antibodies:

The term "anti-idiotypic antibodies" when referring to antibodies or other binding molecules includes molecules which bind to the unique antigenic peptide sequence located on an antibody's variable region near or at the antigen binding site, inhibiting by this a specific immune response by otherwise caused by the given auto-antibody. In an analogous manner synthetic peptide or peptide-based compound comprising an epitope specifically recognized by an antibody of the present invention may be used.

Anti-idiotypic antibodies may be obtained in a similar fashion as other antibodies. The particular anti-idiotypic antibody is detected by any sort of cross-linking, either by agglutination (in turbidimetric or nephelometric assays), precipitation (radial immunodiffusion), or sandwich immunoassays such as ELISAs. U.S. patent application No. 20020142356 provides a method for obtaining anti-idiotypic monoclonal antibody populations directed to an antibody that is specific for a high-concentration, high-molecular-weight target antigen wherein said anti-idiotypic antibody populations have a wide range of binding affinities for the selected antibody specific to said target antigen and wherein a subset of said anti-idiotypic antibody populations can be selected having the required affinity for a particular application.

U.S. patent application No. 20020142356 describes a competitive immunoassay of an antigen using an antibody as coat and an anti-idiotypic antibody as detection or vice-versa. Other references disclosing use of an anti-idiotypic antibody as a surrogate antigen include Losman et al., Cancer Research, 55 (1995) (23 suppl. S):S5978-S5982; Becker et al., J. of Immunol. Methods 192 (1996), 73-85: Baral et al., International J. of Cancer, 92 (2001), 88-95; and Kohen et al., Food and Agriculture Immunology, 12 (2000)), 193-201. Use of anti-idiotypic antibodies in treatment of diseases or against parasites is known in the art; see, e.g., in Sacks et al., J. Exper. Medicine, 155 (1982), 1108-1119.

Determination of Similarity and/or Identity of Molecules:

"Similarity" between two peptides is determined by comparing the amino acid sequence of one peptide to the sequence of a second peptide. An amino acid of one peptide is similar to the corresponding amino acid of a second peptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos, EMBO J. 8 (1989), 779-785. For example, amino acids belonging to one of the following groups represent conservative changes or substitutions: -Ala, Pro, Gly, Gln, Asn, Ser, Thr; -Cys, Ser, Tyr, Thr; -Val, Ile, Leu, Met, Ala, Phe; -Lys, Arg, His; -Phe, Tyr, Trp, His; and -Asp, Glu.

The determination of percent identity or similarity between two sequences is preferably accomplished using the mathematical algorithm of Karlin and Altschul (1993) Proc. Natl. Acad. Sci USA 90: 5873-5877. Such an algorithm is incorporated into the BLASTn and BLASTp programs of Altschul et al. (1990) J. Mol. Biol. 215: 403-410 available at NCBI (http://www.ncbi.nlm.nih.gov/blast/Blast.cge).

The determination of percent identity or similarity is performed with the standard parameters of the BLASTn and BLASTp programs.

BLAST polynucleotide searches are performed with the BLASTn program.

For the general parameters, the "Max Target Sequences" box may be set to 100, the "Short queries" box may be ticked, the "Expect threshold" box may be set to 10 and the "Word Size" box may be set to 28. For the scoring parameters the "Match/mismatch Scores" may be set to 1,-2 and the "Gap Costs" box may be set to linear. For the Filters and Masking parameters, the "Low complexity regions" box may not be ticked, the "Species-specific repeats" box may not be ticked, the "Mask for lookup table only" box may be ticked, and the "Mask lower case letters" box may not be ticked.

BLAST protein searches are performed with the BLASTp program. For the general parameters, the "Max Target Sequences" box may be set to 100, the "Short queries" box may be ticked, the "Expect threshold" box may be set to 10 and the "Word Size" box may be set to "3". For the scoring parameters the "Matrix" box may be set to "BLOSUM62", the "Gap Costs" Box may be set to "Existence: 11 Extension:", the "Compositional adjustments" box may be set to "Conditional compositional score matrix adjustment". For the Filters and Masking parameters the "Low complexity regions" box may not be ticked, the "Mask for lookup table only" box may not be ticked and the "Mask lower case letters" box may not be ticked.

Polynucleotides:

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding a binding molecule, an antibody, or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit ß-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picomaviruses (particularly an internal ribosome entry site, or IRES, also referred to as a CITE sequence).

In other embodiments, a polynucleotide of the present invention is RNA, for example, in the form of messenger RNA (mRNA), small hairpin RNA (shRNA), small interfering RNA (siRNA) or any other RNA product.

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full-length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse ß-glucuronidase.

Expression:

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., small interfering RNA (siRNA), a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

A variety of expression vector/host systems may be utilized to contain and express polynucleotide sequences. These include, but are not limited to, microorganisms such as bacteria transformed with recombinant bacteriophage, plasmid, or cosmid DNA expression vectors: yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

To express the peptide, polypeptide or fusion protein (hereinafter referred to as "product") in a host cell, a procedure such as the following can be used. A restriction fragment containing a DNA sequence that encodes said product may be cloned into an appropriate recombinant plasmid containing an origin of replication that functions in the host cell and an appropriate selectable marker. The plasmid may include a promoter for inducible expression of the product (e.g., pTrc (Amann et al, *Gene* 69 (1988), 301 315) and pETI Id (Studier et al., *Gene Expression Technology: Methods in Enzymology* 185, Academic Press, San Diego, Calif. (1990), 60 89). The recombinant plasmid may be introduced into the host cell by, for example, electroporation and cells containing the recombinant plasmid may be identified by selection for the marker on the plasmid. Expression of the product may be induced and detected in the host cell using an assay specific for the product.

In some embodiments, the DNA that encodes the product/peptide may be optimized for expression in the host cell. For example, the DNA may include codons for one or more amino acids that are predominant in the host cell relative to other codons for the same amino acid.

Alternatively, the expression of the product may be performed by in vitro synthesis of the protein in cell-free extracts which are also particularly suited for the incorporation of modified or unnatural amino acids for functional studies; see also infra. The use of in vitro translation systems can have advantages over in vivo gene expression when the over-expressed product is toxic to the host cell, when the product is insoluble or forms inclusion bodies, or when the protein undergoes rapid proteolytic degradation by intracellular proteases. The most frequently used cell-free translation systems consist of extracts from rabbit reticulocytes, wheat germ and *Escherichia coli*. All are prepared as crude extracts containing all the macromolecular components (70S or 80S ribosomes, tRNAs, aminoacyl-tRNA synthetases, initiation, elongation and termination factors, etc.) required for translation of exogenous RNA. To ensure efficient translation, each extract must be supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors known in the art ($Mg^{2+}$, $K^+$, etc.). Appropriate transcription/translation systems are commercially available, for example from Promega Corporation, Roche Diagnostics, and Ambion, i.e. Applied Biosystems (Anderson, C. et al., *Meth. Enzymol.* 101 (1983), 635-644; Arduengo, M. et al. (2007), *The Role of Cell-Free Rabbit Reticulocyte Expression Systems in Functional Proteomics* in, Kudlicki, Katzen and Bennett eds., *Cell-Free Expression* Vol. 2007. Austin, Tx: *Landes Bioscience*, pp. 1-18: Chen and Zubay, *Meth. Enzymol.* 101 (1983), 674-90; Ezure et al., *Biotechnol. Prog.* 22 (2006), 1570-1577).

Host Cells:

In respect of the present invention, host cell can be any prokaryotic or eukaryotic cell, such as a bacterial, insect, fungal, plant, animal or human cell. Preferred fungal cells are, for example, those of the genus *Saccharomyces*, in particular those of the species *S. cerevisiae*. The term "prokaryotic" is meant to include all bacteria which can be transformed or transfected with a DNA or RNA molecules for the expression of an antibody of the invention or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and preferably mammalian cells, most preferably HEK 293, NSO, CSO and CHO cells. Depending upon the host employed in a recombinant production procedure, the antibodies or immunoglobulin chains encoded by the polynucleotide of the present invention may be glycosylated or may be non-glycosylated. Antibodies of the invention or the corresponding immunoglobulin chains may also include an initial methionine amino acid residue. A polynucleotide of the invention can be used to transform or transfect the host using any of the techniques commonly known to those of ordinary skill in the art. Furthermore, methods for preparing fused, operably linked genes and expressing them in. e.g., mammalian cells and bacteria are well-known in the art (Sambrook, *Molecular Cloning: A Laboratory Manual*, Cold Spring Harbor Laboratory. Cold Spring Harbor, N.Y., 1989). The genetic constructs and methods described therein can be utilized for expression of the antibody of the invention or the corresponding immunoglobulin chains in eukaryotic or prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. Suitable source cells for the DNA sequences and host cells for immunoglobulin expression and secretion can be obtained from a number of sources, such as the American Type Culture Collection ("Catalogue of Cell Lines and Hybridomas," Fifth edition (1985) Rockville, Md., U.S.A., which is incorporated herein by reference). Furthermore, transgenic animals, preferably mammals, comprising cells of the invention may be used for the large scale production of the antibody of the invention.

The transformed hosts can be grown in fermentors and cultured according to techniques known in the art to achieve optimal cell growth. Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like; see, Scopes. "*Protein Purification*", Springer Verlag, N.Y. (1982). The antibody or its corresponding immunoglobulin chain(s) of the invention can then be isolated from the growth medium, cellular lysates, or cellular membrane fractions. The isolation and purification of the, e.g., recombinantly expressed antibodies or immunoglobulin chains of the invention may be by any conventional means such as, for example, preparative chromatographic separations and immunological separations such as those involving the use of monoclonal or polyclonal antibodies directed, e.g., against the constant region of the antibody of the invention. It will be apparent to those skilled in the art that the antibodies of the invention can be further coupled to other moieties for, e.g., drug targeting and imaging applications. Such coupling may be conducted chemically after expression of the antibody or antigen to site of attachment or the coupling product may be engineered into the antibody or antigen of the invention at the DNA level. The DNAs are then expressed in a suitable host system, and the expressed proteins are collected and renatured, if necessary.

Substantially pure immunoglobulins of at least about 90 to 95% homogeneity are preferred, and 98 to 99% or more homogeneity most preferred, for pharmaceutical uses. Once purified, partially or to homogeneity as desired, the antibodies may then be used therapeutically (including extracorporally) or in developing and performing assay procedures.

The present invention also involves a method for producing cells capable of expressing an antibody of the invention or its corresponding immunoglobulin chain(s) comprising genetically engineering cells with the polynucleotide or with the vector of the invention. The cells obtainable by the method of the invention can be used, for example, to test the interaction of the antibody of the invention with its antigen.
ELISA-Assays:

Enzyme-linked immunosorbent assays (ELISAs) for various antigens include those based on colorimetry, chemiluminescence, and fluorometry. ELISAs have been successfully applied in the determination of low amounts of drugs and other antigenic components in plasma and urine samples, involve no extraction steps, and are simple to carry out. ELISAs for the detection of antibodies to protein antigens often use direct binding of short synthetic peptides to the plastic surface of a microtitre plate. The peptides are, in general, very pure due to their synthetic nature and efficient purification methods using high-performance liquid chromatography. A drawback of short peptides is that they usually represent linear, but not conformational or discontinuous epitopes. To present conformational epitopes, either long peptides or the complete native protein is used. Direct binding of the protein antigens to the hydrophobic polystyrene support of the plate can result in partial or total denaturation of the bound protein and loss of conformational epitopes. Coating the plate with an antibody, which mediates the immobilization (capture ELISA) of the antigens, can avoid this effect.

However, frequently, overexpressed recombinant proteins are insoluble and require purification under denaturing conditions and renaturation, when antibodies to conformational epitopes are to be analyzed. See, for example, U.S. patent application No. 20030044870 for a generic ELISA using recombinant fusion proteins as coat proteins.
Binding Molecules:

A "binding molecule" as used in the context of the present invention relates primarily to antibodies, and fragments thereof, but may also refer to other non-antibody molecules that bind to the "molecules of interest" of the present invention as enlisted in tables 1 to 14 and 28 to 31 wherein the molecules of interest are proteins, peptides, polysaccharides, lipopolyproteins and lipopolysaccharides, for example, but not limited to leukotrienes, lymphokines and cytokines, e.g., interleukins and interferons. The molecules of interest of the present invention will be defined in further detail within the description of the particular embodiments of the present invention below. The binding molecules of the present invention include but are not limited to hormones, receptors, ligands, major histocompatibility complex (MHC) molecules, chaperones such as heat shock proteins (HSPs) as well as cell-cell adhesion molecules such as members of the cadherin, intergrin, C-type lectin and immunoglobulin (Ig) superfamilies. Thus, for the sake of clarity only and without restricting the scope of the present invention most of the following embodiments are discussed with respect to antibodies and antibody-like molecules which represent the preferred binding molecules for the development of therapeutic and diagnostic agents.
Antibodies:

The terms "antibody" and "immunoglobulin" are used interchangeably herein. An antibody or immunoglobulin is a molecule binding to a molecule of interest of the present invention as defined hereinabove and below, which comprises at least the variable domain of a heavy chain, and normally comprises at least the variable domains of a heavy chain and a light chain. Basic immunoglobulin structures in vertebrate systems are relatively well understood: see, e.g., Harlow and Lane, Antibodies: A Laboratory Manual, (Cold Spring Harbor Laboratory Press, 2nd ed. 1988). The terms "binds" and "recognizes" are used interchangeably in respect of the binding affinity of the binding molecules of the present invention, e.g., antibodies.

Any antibody or immunoglobulin fragment which contains sufficient structure to specifically bind to the molecules of interest, as defined hereinabove and below, is denoted herein interchangeably as a "binding molecule", "binding fragment" or an "immunospecific fragment."

Antibodies or antigen-binding fragments, immunospecific fragments, variants, or derivatives thereof of the invention include, but are not limited to, polyclonal, monoclonal, multispecific, human, humanized, primatized, murinized or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to antibodies disclosed herein). ScFv molecules are known in the art and are described, e.g., in U.S. Pat. No. 5,892,019. In this respect, antigen-binding fragment of the antibody can be as well domain antibodies (dAb) also known as single domain antibodies (sdAB) or Nanobodies™ (Ablynx, Gent, Belgium), see. e.g., De Haard et al., *J. Bacteriol.* 187 (2005), 4531-4541: Holt et al., *Trends Biotechnol.* 21 (2003), 484-490. As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgE, IgM, IgD, IgA, and IgY, respectively. The immunoglobulin subclasses (isotypes) e.g., IgG1, IgG2, IgG3, IgG4, IgA1, etc. are well characterized and are known to confer functional specialization. Immunoglobulin or antibody molecules of the invention can be of any type (e.g., IgG. IgE, IgM, IgD. IgA, and IgY), class (e.g., IgG1, IgG2, IgG3, IgG4, IgA1, IgA2, etc.) or subclass of immunoglobulin molecule. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules.

With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region. As evident from the classification of the exemplary anti-IL-17A, IL-17F and IL-22 antibodies of the present invention enlisted in Table 17 above, such as the IL-22 specific antibodies 30G1 of the IgG1 class and 35G11 of the class IgG4, dominant subtypes of the antibodies of the present invention appear to be IgG1 and IgG4, possibly implicating regulatory T-cell responses and/or epithelia in their initiation in these AIRE-deficiency states. These findings are confirmed by the classification of corresponding autoantibodies found in the AIRE-deficient mice described by Kärner et al., in Clin. Exp. Immunol. (2012); doi: 10.1111/cei.12024, the disclosure content of which is incorporated herein by reference. Accordingly, in a preferred embodiment of the present invention, the human antibodies of the present invention are of the IgG type, in particular IgG1 or IgG4.

IgG Structure:

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region: the CH3 and CL domains actually comprise the carboxy-terminus of the heavy and light chain, respectively.

As indicated above, the variable region allows the antibody to selectively recognize and specifically bind epitopes on antigens. That is, the $V_L$ domain and $V_H$ domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the $V_H$ and $V_L$ chains. Any antibody or immunoglobulin fragment which contains sufficient structure to specifically bind to a molecule of interest of the present invention is denoted herein interchangeably as a "binding fragment" or an "immunospecific fragment."

In naturally occurring antibodies, an antibody comprises six hypervariable regions, sometimes called "complementarity determining regions" or "CDRs" present in each antigen-binding domain, which are short, non-contiguous sequences of amino acids that are specifically positioned to form the antigen-binding domain as the antibody assumes its three dimensional configuration in an aqueous environment. The "CDRs" are flanked by four relatively conserved "framework" regions or "FRs" which show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined; see, "Sequences of Proteins of Immunological Interest," Kabat. E., et al., U.S. Department of Health and Human Services, (1983); and Chothia and Lesk, J. Mol. Biol. 196 (1987), 901-917, which are incorporated herein by reference in their entireties.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia and Lesk, J. Mol. Biol. 196 (1987), 901-917, which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 16 as a comparison. The exact residue numbers which encompass a particular CDR will vary depending on the sequence and size of the CDR. Those skilled in the art can routinely determine which residues comprise a particular hypervariable region or CDR of the human IgG subtype of antibody given the variable region amino acid sequence of the antibody.

TABLE 16

CDR Definitions[1]

|  | Kabat | Chothia |
| --- | --- | --- |
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 16 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein. "Kabat numbering" refers to the numbering system set forth by Kabat et al., *U.S. Dept. of Health and Human Services*. "Sequence of Proteins of Immunological Interest" (1983). Unless otherwise specified, references to the numbering of specific amino acid residue positions in an antibody or antigen-binding fragment, variant, or derivative thereof of the present invention are according to the Kabat numbering system, which however is theoretical and may not equally apply to every antibody of the present invention. For example, depending on the position of the first CDR the following CDRs might be shifted in either direction.

In one embodiment, the antibody of the present invention is not IgM or a derivative thereof with a pentavalent structure. Particular, in specific applications of the present invention, especially therapeutic use, IgMs are less useful than IgG and other bivalent antibodies or corresponding binding molecules since IgMs due to their pentavalent structure and lack of affinity maturation often show unspecific cross-reactivities and very low affinity.

In a particularly preferred embodiment, the antibody of the present invention is not a polyclonal antibody, i.e. it substantially consists of one particular antibody species rather than being a mixture obtained from a plasma immunoglobulin sample.

Antibody Fragments, Animalization:

Antibody fragments, including single-chain antibodies, may comprise the variable region(s) alone or in combination with the entirety or a portion of the following: hinge region, CH1, CH2, and CH3 domains. Also included in the invention are fragments binding to a molecule of interest of the present invention, said fragments comprising any combination of variable region(s) with a hinge region, CH1, CH2, and CH3 domains. Antibodies or immunospecific fragments thereof of the present invention equivalent to the monoclonal antibodies isolated in accordance with the method of the present invention, in particular to the human monoclonal antibodies may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

In a particularly preferred embodiment of the present invention, the antibodies are naturally occurring human monoclonal antibodies or binding fragments, derivatives and variants thereof cloned from human subjects, which bind specifically to the molecules of the present invention, as defined in detail below, in Tables 1 to 14, 28 to 31, FIGS. 1 to 4 and in the Examples.

Optionally, the framework region of the human antibody is aligned and adopted in accordance with the pertinent human germ line variable region sequences in the database; see, e.g., Vbase (http://vbase.mrc-cpe.cam.ac.uki) hosted by the MRC Centre for Protein Engineering (Cambridge, UK). For example, amino acids considered to potentially deviate from the true germ line sequence could be due to the PCR primer sequences incorporated during the cloning process. Thus, in accordance with the present invention the terms "human monoclonal antibody", "human monoclonal autoantibody", "human antibody" and the like are used to denote binding molecule which binds a molecule of interest of the present invention, which is of human origin, i.e. which has been isolated from a human cell such as a B cell or hybridoma thereof or the cDNA of which has been directly cloned from mRNA of a human cell, for example a human memory B cell. A human antibody is still "human" even if amino acid substitutions are made in the antibody. e.g., to improve binding characteristics.

Antibodies derived from human immunoglobulin libraries or from animals transgenic for one or more human immunoglobulins and that do not express endogenous immunoglobulins, as described infra and, for example in, U.S. Pat. No. 5,939,598 by Kucherlapati et al., are denoted human-like antibodies in order distinguish them from truly human antibodies of the present invention.

For example, the paring of heavy and light chains of human-like antibodies such as synthetic and semi-synthetic antibodies typically isolated from phage display do not necessarily reflect the original paring as it occurred in the original human B cell. Accordingly Fab and scFv fragments obtained from recombinant expression libraries as commonly used in the prior art can be considered as being artificial with all possible associated effects on immunogenicity and stability.

In contrast, the present invention provides isolated affinity-matured antibodies from selected human subjects, which are characterized by their therapeutic utility and their tolerance in man.

Grafted Antibodies (Equivalents)

The invention also relates to grafted antibodies (interchangeably referred to as equivalents) containing CDRs derived from the antibodies of the present invention, such as IL-17 and IL-22 antibodies, respectively. Such grafted CDRs include animalized antibodies, in which CDRs from the antibodies of the present invention have been grafted or in which a CDR containing one or more amino acid substitutions is grafted. The CDRs can be grafted directly into a human framework or an antibody framework from animal origin as indicated above. If desired, framework changes can also be incorporated by generating framework libraries. The optimization of CDRs and/or framework sequences can be performed independently and sequentially combined or can be performed simultaneously, as described in more detail below.

To generate grafted antibodies donor CDRs of the antibodies of the present invention are grafted onto an antibody acceptor variable region framework. Methods for grafting antibodies and generating CDR variants to optimize activity have been described previously (see, e.g., international patent applications WO 98/33919: WO 00/78815: WO 01/27160). The procedure can be performed to achieve grafting of donor CDRs and affinity reacquisition in a simultaneous process. The methods similarly can be used, either alone or in combination with CDR grafting, to modify or optimize the binding affinity of a variable region. The methods for conferring donor CDR binding affinity onto an acceptor variable region are applicable to both heavy and light chain variable regions and as such can be used to simultaneously graft and optimize the binding affinity of an antibody variable region.

The donor CDRs can be altered to contain a plurality of different amino acid residue changes at all or selected positions within the donor CDRs. For example, random or biased incorporation of the twenty naturally occurring amino acid residues, or preselected subsets, can be introduced into the donor CDRs to produce a diverse population of CDR species. Inclusion of CDR variant species into the diverse population of variable regions allows for the generation of variant species that exhibit optimized binding affinity for a predetermined antigen. A range of possible changes can be made in the donor CDR positions. Some or all of the possible changes that can be selected for change can be introduced into the population of grafted donor CDRs. A single position in a CDR can be selected to introduce changes or a variety of positions having altered amino acids can be combined and screened for activity.

One approach is to change all amino acid positions along a CDR by replacement at each position with, for example, all twenty naturally occurring amino acids. The replacement of each position can occur in the context of other donor CDR amino acid positions so that a significant portion of the CDR maintains the authentic donor CDR sequence, and therefore, the binding affinity of the donor CDR. For example, an acceptor variable region framework, either a native or altered framework, can be grafted with a population of CDRs containing single position replacements at each position within the CDRs. Similarly, an acceptor variable region framework can be targeted for grafting with a population of CDRs containing more than one position changed to incorporate all twenty amino acid residues, or a subset of amino acids. One or more amino acid positions within a CDR, or within a group of CDRs to be grafted, can be altered and grafted into an acceptor variable region framework to generate a population of grafted antibodies. It is understood that a CDR having one or more altered positions can be combined with one or more other CDRs having one or more altered positions, if desired.

A population of CDR variant species having one or more altered positions can be combined with any or all of the CDRs which constitute the binding pocket of a variable region. Therefore, an acceptor variable region framework can be targeted for the simultaneous incorporation of donor CDR variant populations at one, two or all three recipient CDR locations in a heavy or light chain. The choice of which CDR or the number of CDRs to target with amino acid position changes will depend on, for example, if a full CDR grafting into an acceptor is desired or whether the method is being performed for optimization of binding affinity.

Another approach for selecting donor CDR amino acids to change for conferring donor CDR binding affinity onto an antibody acceptor variable region framework is to select known or readily identifiable CDR positions that are highly variable. For example, the variable region CDR3 is generally highly variable. This region therefore can be selectively targeted for amino acid position changes during grafting procedures to ensure binding affinity reacquisition or augmentation, either alone or together with relevant acceptor variable framework changes.

Murinized Antibodies:

An example of antibodies generated by grafting, as described above, are murinized antibodies. As used herein, the term "murinized antibody" or "murinized immunoglobulin" refers to an antibody comprising one or more CDRs from a human antibody of the present invention; and a human framework region that contains amino acid substitutions and/or deletions and/or insertions that are based on a mouse antibody sequence. The human immunoglobulin providing the CDRs is called the "parent" or "acceptor" and the mouse antibody providing the framework changes is called the "donor". Constant regions need not be present, but if they are, they are usually substantially identical to mouse antibody constant regions, i.e. at least about 85-90%, preferably about 95% or more identical. Hence, in some embodiments, a full-length murinized human heavy or light chain immunoglobulin contains a mouse constant region, human CDRs, and a substantially human framework that has a number of "murinizing" amino acid substitutions. Typically, a "murinized antibody" is an antibody comprising a murinized variable light chain and/or a murinized variable heavy chain. For example, a murinized antibody would not encompass a typical chimeric antibody. e.g., because the entire variable region of a chimeric antibody is non-mouse. A modified antibody that has been "murinized" by the process of "murinization" binds to the same antigen as the parent antibody that provides the CDRs and is usually less immunogenic in mice, as compared to the parent antibody.

Antibody Fragments:

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain: a polypeptide chain comprising a CH1 domain, at least a portion of a hinge domain, and a CH2 domain: a polypeptide chain comprising a CH1 domain and a CH3 domain: a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody or diabody.

In another embodiment, the antibodies, or antigen-binding fragments, variants, or derivatives thereof disclosed herein are composed of a single polypeptide chain such as scFvs and are to be expressed intracellularly (intrabodies) for potential in vivo therapeutic and diagnostic applications.

The heavy chain portions of a binding polypeptide for use in the diagnostic and treatment methods disclosed herein may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

Thus, as also exemplified in the Examples, in one embodiment the constant region of the antibody of the present invention or part thereof, in particular the CH2 and/or CH3 domain but optionally also the CH1 domain is heterologous to the variable region of the native human monoclonal antibody isolated in accordance with the method of the present invention. In this context, the heterologous constant region(s) are preferably of human origin in case of therapeutic applications of the antibody of the present invention but could also be of for example rodent origin in case of animal studies; see also the Examples.

As used herein, the term "light chain portion" includes amino acid sequences derived from an immunoglobulin light chain. Preferably, the light chain portion comprises at least one of a $V_L$ or $C_L$ domain.

As previously indicated, the subunit structures and three dimensional configuration of the constant regions of the various immunoglobulin classes are well known. As used herein, the term "$V_H$ domain" includes the amino terminal variable domain of an immunoglobulin heavy chain and the term "CH1 domain" includes the first (most amino terminal) constant region domain of an immunoglobulin heavy chain. The CH1 domain is adjacent to the $V_H$ domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains; see Roux et al., *J. Immunol.* 161 (1998), 4083.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the terms "linked", "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

Epitopes:

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, a peptide or polypeptide epitope recognized by antibodies of the present invention contains a sequence of at least 4, at least 5, at least 6, at least 7, more preferably at least 8, at least 9, at least 10, at least 15, at least 20, at least 25, or between about 15 to about 30 contiguous or non-contiguous amino acids of a molecule of interest of the present invention as defined in Tables 1 to 14, 28-31, FIGS. 1 to 4 and in the Examples.

Binding Characteristics:

By "binding" or "recognizing", used interchangeably herein, it is generally meant that a binding molecule, e.g., an antibody binds to a predetermined epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D". Unrelated epitopes are usually part of a nonspecific antigen (e.g., BSA, casein, or any other specified polypeptide), which may be used for the estimation of the binding specificity of a given binding molecule. In this respect, term "specific binding" refers to antibody binding to a predetermined antigen with a $K_D$ that is at least twofold less than its $K_D$ for binding to a nonspecific antigen. The term "highly specific" binding as used herein means that the relative $K_D$ of the antibody for the specific target epitope is at least 10-fold less than the $K_D$ for binding that antibody to other ligands.

Where present, the term "immunological binding characteristics," or other binding characteristics of an antibody with an antigen, in all of its grammatical forms, refers to the specificity, affinity, cross-reactivity, and other binding characteristics of an antibody.

By "preferentially binding", it is meant that the binding molecule, e.g., antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, a binding molecule, e.g., an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, a binding molecule, e.g., an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

A binding molecule, e.g., an antibody or antigen-binding fragment, variant, or derivative disclosed herein may be said to bind a molecule of interest of the present invention, a fragment or variant thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. More preferably, an antibody of the invention may be said to bind a molecule of interest of the present invention or a fragment or variant thereof with an off rate (k(off)) less than or equal to $5 \times 10^{4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{--1}$, $10^{-6}$ sec$^{-1}$, $5 \times 10^{-7}$ sec$^{-1}$ or $10^{-7}$ sec$^{-1}$.

A binding molecule, e.g., an antibody or antigen-binding fragment, variant, or derivative disclosed herein may be said to bind a molecule of interest of the present invention or a fragment or variant thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. More preferably, an antibody of the invention may be said to bind a molecule of interest of the present invention or a fragment or variant thereof with an on rate (k(on)) greater than or equal to $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

A binding molecule, e.g., an antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of a binding molecule, e.g., an immunoglobulin molecule: see, e.g., Harlow et al., *Antibodies: A Laboratory Manual*. Cold Spring Harbor Laboratory Press, 2nd ed. (1988) at pages 27-28. As used herein, the term "avidity" refers to the overall stability of the complex between a population of immunoglobulins and an antigen, that is, the functional combining strength of an immunoglobulin mixture with the antigen: see, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity. The affinity or avidity of an antibody for an antigen can be determined experimentally using any suitable method; see, for example, Berzofsky et al., "Antibody-Antigen Interactions" In *Fundamental Immunology*, Paul, W. E., Ed., Raven Press New York, N Y (1984), Kuby, *Janis Immunology*, W. H. Freeman and Company New York, N.Y. (1992), and methods described therein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

Binding molecules, e.g., antibodies or antigen-binding fragments, variants or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Binding molecules, e.g., antibodies or antigen-binding fragments, variants or derivatives thereof of the invention may also be described or specified in terms of their binding affinity to a molecule of interest of the present invention. Preferred binding affinities include those with a dissociation constant or $K_D$ less than $5 \times 10^{-2}$ M, $10^{-2}$M, $5 \times 10^{-3}$M, $10^{-3}$M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M. Typically, the antibody binds with a dissociation constant ($K_D$) of $10^{-7}$ M or less to its predetermined antigen. Preferably, the antibody binds its cognate antigen with a dissociation constant ($K_D$) of $10^{-9}$ M or less and still more preferably with a dissociation constant ($K_D$) of $10^{-11}$ M or less.

Modifications of Antibodies:

The immunoglobulin or its encoding cDNAs may be further modified. Thus, in a further embodiment the method of the present invention comprises any one of the step(s) of producing a chimeric antibody, humanized antibody, single-chain antibody, Fab-fragment, bispecific antibody, fusion antibody, labeled antibody or an analog of any one of those. Corresponding methods are known to the person skilled in the art and are described, e.g. in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to the same epitope as that of any one of the antibodies provided by the present invention (Schier, *Human Antibodies Hybridomas* 7 (1996), 97-105; Malmborg, *J. Immunol. Methods* 183 (1995), 7-13). The production of chimeric antibodies is described, for example, in international application WO89/09622. Methods for the production of humanized antibodies are described in, e.g., European application EP-A1 0 239 400 and international application WO90/07861. Further sources of antibodies to be utilized in accordance with the present invention are so-called xenogeneic antibodies. The general principle for the production of xenogeneic antibodies such as human antibodies in mice is described in, e.g., international applications WO91/10741, WO94/02602, WO96/34096 and WO 96/33735. As discussed above, the antibody of the invention may exist in a variety of forms besides complete antibodies: including, for example, Fv, Fab and F(ab)$_2$, as well as in single chains; see e.g. international application WO88/09344.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook. *Molecular Cloning A Laboratory Manual*, Cold Spring Harbor Laboratory (1989) N.Y. and Ausubel, *Current Protocols in Molecular Biology*, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as a label or a drug. Antigen binding molecules generated this way may be used for drug localization to cells expressing the appropriate surface structures of the diseased cell and tissue, respectively. This targeting and binding to cells could be useful for the delivery of therapeutically or diagnostically active agents and gene therapy/gene delivery. Molecules/particles with an antibody of the invention would bind specifically to cells/tissues expressing the particular antigen of interest, and therefore could have diagnostic and therapeutic use.

Samples:

As used herein, the term "sample" refers to any biological material obtained from a subject or patient. In one aspect, a sample can comprise blood, cerebrospinal fluid ("CSF"), or urine. In other aspects, a sample can comprise whole blood, plasma, mononuclear cells enriched from peripheral blood (PBMC) such as lymphocytes (i.e. T-cells, NK-cell or B-cells), monocytes, macrophages, dendritic cells and basophils; and cultured cells (e.g., B-cells from a subject). A sample can also include a biopsy or tissue sample including tumor tissue. In still other aspects, a sample can comprise whole cells and/or a lysate of the cells. In one embodiment a sample comprises peripheral blood mononuclear cells (PBMC). Samples can be collected by methods known in the art.

Identification and Isolation of B-Cells:

Identification of B-cells specific for the particular molecules of interest of the present invention, as enlisted in Tables 1 to 14, and as exemplary shown for IL17 or IL-22 and molecular cloning of antibodies displaying specificity of interest as well as their recombinant expression and functional characterization can be generally performed as described in particular in Example 2. A method for identification of B-cells expressing the antibodies of the specificity of interest and molecular cloning of antibodies displaying specificity of interest as well as their recombinant expression and functional characterization is provided within this application. As described in detail below, in one embodiment of the present invention cultures of single or oligoclonal B-cells are cultured and the supernatant of the culture, which contains antibodies produced by said B-cells is screened for presence and affinity of new antibodies specific for a molecule of interest of the present invention, such as molecules enlisted in Tables 1 to 14, and described in the Examples, or in particular molecules involved in inflammation or related to an autoimmune disease in a subject, e.g., IL17 or IL-22 therein. In another embodiment, not B-cells cultures but patient sera are first screened for the presence of autoantibodies against a molecule of interest and then those with high titer are selected for peripheral blood mononuclear cells isolation; see Example 2. The screening process comprises screening for binding on fragments, peptides or derivates of the particular molecule of interest. Subsequently the antibody for which binding is detected or the cell producing said antibody are isolated; see Example 3. Thus, a preliminary screen can be done on a panel of candidate donors, using samples containing antibody secreting cells (such as total peripheral blood or serum). In particular, mononuclear cells can be isolated from blood or lymphatic tissues using standard separation techniques for isolating peripheral blood mononuclear cells (PBMCs), such as gradient centrifugation. After and/or before this separation step, the samples of sera (or plasma), cell culture supernatants, or cells (obtained from different patients, from different tissues, and/or at different time points) can be prescreened using standard technologies for detecting the presence of antibodies and antibody-secreting cells (e.g. ELISA, BIACORE, Western blot, FACS, SERPA, antigen arrays, neutralization of viral infection in a cell culture system, or ELISPOT assays). The literature provides several examples of these technologies showing, for example, the use of ELISPOT for characterizing the immune response in vaccinated donors (Crotty et al., Immunol Meth. 286 (2004), 111-122), the use of antigen microarrays as diagnostic tools for newly infected patients (Mezzasoma et al., Clin Chem. 48 (2002), 121-130, and other technologies for measuring antigen-specific immune responses (Kem et al., Trends Immunol. 26 (2005), 477-484).

B-Cell Immortalization:

B-cells producing antibodies may be immortalized, e.g., by infection with viruses such as the oncogenic Epstein-Barr virus (EBV; Sugimoto et al., *Cancer Res.* 64 (2004), 3361-3364; Counter et al., *J. Virol.* 68 (1994), 3410-3414) or long term repeated CD40 ligand/IL-4 stimulation (Wiesner et al., *PLoS ONE*, 3 (2008), e1464.). Methods of producing clones of an immortalized human B cell and a B memory lymphocyte, comprising the step of transforming human B memory lymphocytes using Epstein Barr Virus (EBV) in the presence of a polyclonal B cell activator are summarized in international application WO2004/076677. This international application also describes methods for obtaining a nucleic acid sequence that encodes an antibody of interest, comprising the steps of preparing an immortalized B cell clone and obtaining/sequencing nucleic acid from the B cell clone that encodes the antibody of interest and further inserting the nucleic acid into or using the nucleic acid to prepare an expression host that can express the antibody of interest, culturing or sub-culturing the expression host under conditions where the antibody of interest is expressed and, optionally, purifying the antibody of interest. It goes without saying that the nucleic acid may be manipulated in between to introduce restriction sites, to change codon usage, and/or to add or optimize transcription and/or translation regulatory sequences. All these techniques are state of the art and can be performed by the person skilled in the art without undue burden. For example, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Once the genetic material is available, design of analogs as described above which retain both their ability to bind the desired target is straightforward. Methods for the cloning of antibody variable regions and generation of recombinant antibodies are known to the person skilled in the art and are described, for example, in Gilliland et al., *Tissue Antigens* 47 (1996), 1-20: Doenecke et al., *Leukemia* 11 (1997), 1787-1792.

Diseases and Disorders:

Unless stated otherwise, the terms "disorder" and "disease" are used interchangeably herein. The term "autoimmune disorder" as used herein is a disease or disorder arising from and directed against an individual's own tissues or organs or a co-segregate or manifestation thereof or resulting condition therefrom. Autoimmune diseases are primarily caused by dysregulation of adaptive immune responses and autoantibodies or autoreactive T cells against self structures are formed. Nearly all autoimmune diseases have an inflammatory component, too. Autoinflammatory diseases are primarily inflammatory, and some classic autoinflammatory diseases are caused by genetic defects in innate inflammatory pathways. In autoinflammatory diseases, no autoreactive T cells or autoantibodies are found. In many of these autoimmune and autoinflammatory disorders, a number of clinical and laboratory markers may exist, including, but not limited to, hypergammaglobulinemia, high levels of autoantibodies, antigen-antibody complex deposits in tissues, benefit from corticosteroid or immunosuppressive treatments, and lymphoid cell aggregates in affected tissues. Without being limited to a theory regarding B-cell mediated autoimmune disorder, it is believed that B cells demonstrate a pathogenic effect in human autoimmune diseases through a multitude of mechanistic pathways, including autoantibody production, immune complex formation, dendritic and T-cell activation, cytokine synthesis, direct chemokine release, and providing a nidus for ectopic neo-lymphogenesis. Each of these pathways may participate to different degrees in the pathology of autoimmune diseases.

As used herein, an "autoimmune disorder" can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease that can affect multiple organ systems (for example, systemic lupus erythematosus (SLE), rheumatoid arthritis, polymyositis, autoimmune polyendocrinopathy syndrome type 1 (APS1)/autoimmune polyendocrinopathy-candidiasis-ectodermal dystrophy (APECED) etc. Preferred such diseases include autoimmune rheumatologic disorders (such as, for example, rheumatoid arthritis, Sjogren's syndrome, scleroderma, lupus such as SLE and lupus nephritis, polymyositis/dermatomyositis, cryoglobulinemia, anti-phospholipid antibody syndrome, and psoriatic arthritis), autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis (MS), opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, atopic dermatitis, urticaria, pemphigus group diseases, bullous pemphigoid diseases, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, autoimmune thyroid disease (e.g., Graves' disease and thyroiditis)) and diseases affecting the generation of autoimmunity such as autoimmune polyendocrinopathy syndrome type 1 (APS1)/autoimmune polyendocrinopathy-candidiasis-ectodermal dystrophy (APECED) Myasthenia Gravis (MG/Thymoma. Preferred diseases include, for example, RA, IBD, including Crohn's disease and ulcerative colitis, ANCA-associated vasculitis, lupus, MS, Sjogren's syndrome, Graves' disease, IDDM, pernicious anemia, thyroiditis, and glomerulonephritis, and APS1. Still more preferred are RA, IBD, lupus, and MS, and more preferred RA and IBD, and most preferred RA.

Specific examples of other autoimmune disorders as defined herein, which in some cases encompass those listed above, include, but are not limited to, arthritis (acute and chronic, rheumatoid arthritis including juvenile-onset rheumatoid arthritis and stages such as rheumatoid synovitis, gout or gouty arthritis, acute immunological arthritis, chronic inflammatory arthritis, degenerative arthritis, type II collagen-induced arthritis, infectious arthritis. Lyme arthritis, proliferative arthritis, psoriatic arthritis, Still's disease, vertebral arthritis, osteoarthritis, arthritis chronica progrediente, arthritis deformans, polyarthritis chronica primaria, reactive arthritis, menopausal arthritis, estrogen-depletion arthritis, and ankylosing spondylitis/rheumatoid spondylitis), autoimmune lymphoproliferative disease, inflammatory hyperproliferative skin diseases, psoriasis such as plaque psoriasis, gutatte psoriasis, pustular psoriasis, and psoriasis of the nails, atopy including atopic diseases such as hay fever and Job's syndrome, atopic dermatitis, allergic and toxic contact dermatitis (acute and chronic), exfoliative dermatitis, allergic dermatitis, hives, dermatitis herpetiformis, nummular dermatitis, seborrheic dermatitis, non-specific dermatitis, x-linked hyper IgM syndrome, allergic intraocular inflammatory diseases, urticarias such as chronic allergic urticaria and chronic idiopathic urticaria, cold urticarial, including chronic autoimmune urticaria, myositis, polymyositis/dermatomyositis, juvenile dermatomyositis, toxic epidermal necrolysis, scleroderma (including local and systemic forms of scleroderma), multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, gastrointestinal inflammation, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, autoimmune hematological disorders, graft-versus-host disease, angioedema such as hereditary angioedema, cranial nerve damage as in meningitis, herpes gestationis, pemphigoid group diseases, pempgihus group disease, gestationis, pruritis scroti, autoimmune premature ovarian failure, sudden hearing loss due to an autoimmune condition, IgE-mediated diseases such as anaphylaxis and allergic and atopic rhinitis, various forms of asthma, Chronic Obstructive Pulmonary Disease (COPD), encephalitis such as Rasmussen's encephalitis and limbic and/or brainstem encephalitis, uveitis, such as anterior uveitis, acute anterior uveitis, granulomatous uveitis, non-granulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN (RPGN), proliferative nephritis, autoimmune polyglandular endocrine failure, balanitis including balanitis circumscripta plasmacellularis, balanoposthitis, erythema annulare centrifugum, erythema dyschromicum perstans, evthema multiform, granuloma annulare, lichen nitidus, lichen sclerosus et atrophicus, lichen simplex chronicus, lichen spinulosus, lichen planus, epidermolytic hperkeratosis, premalignant keratosis (e.g., actinic keratosis), pyoderma gangrenosum, allergic conditions and responses, food allergies, drug allergies, insect allergies, rare allergic disorders such as various forms of mastocytosis, allergic reaction, eczema including allergic or atopic eczema, asteatotic eczema, dyshidrotic eczema, pustulosis palmoplantaris, vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-0 blood groups during pregnancy, chronic pulmonary inflammatory disease, autoimmune myocarditis, leukocyte adhesion deficiency, lupus erythematosus (LE), both chronic and acute cutaneous forms (like chronic cutaneous LE (CCLE), discoid lupus erythematosus (DLE). Subacute cutaneous LE (SCLE)) and systemic forms (like SLE), including lupus nephritis, lupus cerebritis, pediatric lupus, non-renal lupus, extra-renal lupus, neonatal lupus syndrome (NLE), juvenile onset (Type I) diabetes mellitus, including pediatric IDDM, adult onset diabetes mellitus (Type II diabetes), autoimmune diabetes, idiopathic diabetes insipidus, diabetic retinopathy, diabetic nephropathy, diabetic colitis, diabetic large-artery disorder, immune responses associated with acute and delayed hypersensitivity mediated by cytokines and T-lymphocytes, tuberculosis, sarcoidosis, granulomatosis including lymphomatoid granulomatosis, agranulocytosis, vasculitides (including large-vessel vasculitis such as polymyalgia rheumatica and giant-cell (Takayasu's) arteritis, medium-vessel vasculitis such as Kawasaki's disease and polyarteritis nodosa/periarteritis nodosa, immuno vasculitis, CNS vasculitis, cutaneous vasculitis, hypersensitivity vasculitis, necrotizing vasculitis such as fibrinoid necrotizing vasculitis and systemic necrotizing vasculitis, A CA-negative vasculitis, and ANCA-associated vasculitis such as Churg-Strauss syndrome (CSS), Wegener's granulomatosis, and microscopic polyangiitis), leukocytoclastic vasculitis, temporal arteritis, aplastic anemia, autoimmune aplastic anemia. Coombs positive anemia, Diamond Blackfan anemia, hemolytic anemia or immune hemolytic anemia including autoimmune hemolytic anemia (AIHA), pernicious anemia (anemia pemiciosa). Addison's disease, pure red cell anemia or aplasia (PRCA). Factor VIII deficiency, hemophilia A, autoimmune neutropenia(s), cytopenias such as pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, motoneuritis, allergic neuritis, Beliefs disease/syndrome, Castleman's syndrome, Goodpasture's syndrome, Reynaud's syndrome, Sjogren's syndrome, Stevens-Johnson syndrome, pemphigoid or pemphigus such as pemphigoid bullous, cicatricial (mucous membrane) pemphigoid, skin pemphigoid, pemphigus vulgaris, paraneoplastic pemphigus, pemphigus foliaceus, pemphigus mucus-membrane pemphigoid, and pemphigus erythematosus, epidermolysis bullosa acquisita, ocular inflammation, preferably allergic ocular inflammation such as allergic conjunctivis, linear IgA bullous disease, autoimmune-induced conjunctival inflammation, autoimmune polyendocrinopathies, Reiter's disease or syndrome, thermal injury due to an autoimmune condition, preeclampsia, an immune complex disorder such as immune complex nephritis, antibody-mediated nephritis, neuroinflammatory disorders, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP), post-transfusion purpura (PTP), heparin-induced thrombocytopenia, and autoimmune or immune-mediated thrombocytopenia including, for example, idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, Grave's eye disease (ophthalmopathy or thyroid-associated ophthalmopathy), polyglandular syndromes such as autoimmune polyglandular syndromes, for example, type I (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant-cell hepatitis, chronic active hepatitis or autoimmune chronic active hepatitis, pneumonitis such as lymphoid interstitial pneumonitis (LIP), bronchiolitis obliterans (non-transplant) vs. NSIP, Guillain-Barre syndrome. Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia such as mixed cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, keratitis such as Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory nmopathy, focal or segmental or focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia areata, alopecia totalis. CREST syndrome (calcinosis, Raynaud's phenomenon, esophageal dysmotility, sclerodactyly, and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, fibrosing mediastinitis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis (systemic inflammatory response syndrome (SIRS)), endotoxemia, pancreatitis, thyroxicosis, parvovirus infection, rubella virus infection, post-vaccination syndromes, congenital rubella infection. Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant-cell polymyalgia, chronic hypersensitivity pneumonitis, conjunctivitis, such as vernal catarrh, keratoconjunctivitis sicca, and epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders (cerebral vascular insufficiency) such as arteriosclerotic encephalopathy and arteriosclerotic retinopathy, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica (sympathetic ophthalmitis), neonatal ophthalmitis, optic neuritis, orchitis granulomatosa, pancreatitis, polyradiculitis *acuta*, pyoderma gangrenosum, Quervain's thyreoiditis, acquired spenic atrophy, non-malignant thymoma, lymphofollicular thymitis, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, autoimmune polyendocrinopathies, oophoritis, primary myxedema, autoimmune atrophic gastritis, rheumatic diseases, mixed connective tissue disease, nephrotic syndrome, insulitis, polyendocrine failure, autoimmune polyglandular syndromes, including polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, allergic sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, spondyloarthropathies, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism such as chronic arthrorheumatism, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, and endometriosis.

Monogenic Disorders

APECED

TABLE 32

APECED manifestations and associated autoantibodies

| Manifestation and autoantibody targets | Prevalence (%) |
|---|---|
| Hypoparathyroidism [a] | 85 |
| NACHT leucine-rich-repeat protein 5 (NALP5) | 32-49 |
| calcium-sensing receptor (CaSR) | 86[b] |
| Addison's disease | 78 |
| steroid 17-α-hydroxylase (P450c17) | 44 |
| steroid 21-hydroxylase (P450c21) | 60-66 |
| side chain cleavage enzyme (P450scc) | 38-52 |
| Ovarian failure | 60 |
| P450scc and P450c17 | |
| Diabetes mellitus | 13 |
| islet antigen-2 (IA-2) | 7 |
| glutamic acid decarboxylase (GAD65)[c] | 27-36 |
| Hypothyroidism | 14 |
| thyroglobulin (TG) | 15-18 |
| thyroid peroxidase (TPO) | 21-36 |
| Testicular failure | 8 |
| testis-specific gene 10 protein (TSGA10)[c] | 8 |
| Hypopituitarism | 5 |
| tudor domain containing protein 6 (TDRD6) | 49 |
| Gastritis/pernicious anemia | 20 |
| intrinsic factor (IF) | 15-30 |
| Autoimmune hepatitis | 18 |
| aromatic L-amino acid decarboxylase (AADC) | 39-51 |
| cytochrome P450 1A2 (P450 1A2) | 8 |
| Intestinal dysfunction | 22 |
| tryptophan hydroxylase (TPH) | 48 |
| histidine decarboxylase (HDC) | 37 |
| Alopecia | 39 |
| tyrosine hydroxylase (TH) | 44 |
| Vitiligo | 27 |
| SOX9/SOX10 | 15-22 |
| Rash with fever | 14 |
| Lung manifestations | rare |
| potassium channel-regulating protein (KCNRG) | 6 |
| Tubulointerstitial nephritis | 9 |
| Asplenia | 20 |
| Keratoconjunctivitis | 22 |
| Dental enamel dysplasia | 77 |
| Nail dystropy | 50 |

TABLE 33

Prevalences of autoantibodies specific for cytokines in APECED and thymoma patients.

| Autoantibodies to | APECED | Prevalence (%) in thymoma/MG |
|---|---|---|
| IFN-ω | 100 | 60 |
| IFN-α | 95 | 70 |
| IFN-β | 22 | rare |
| IFN-λ | 14 | rare |
| IL-22 | 91 | 5-10 |
| IL-17F | 75 | 5-10 |
| IL-17A | 41 | 5-10 |

IPEX:

Immunodysregulation polyendocrinopathy enteropathy X-linked syndrome (IPEX) is a rare X-linked recessive disease. In 25% of males with clinical phenotype, mutations in the FOXP3 gene (forkhead box P3: member of the forkhead/winged-helix family of transcriptional regulators) could be found, however data has been presented (Owen et al., J. Clin. Endocrinol. Metab. 2003:88:6034-6039) suggesting that at least one additional autosomal locus possibly from the same pathway might be involved leading to a dysfunction of FOXP3 since in several cases without an identified mutation, lowered expression or low numbers of FOXP3-expressing cells were detected (Torgerson, unpublished results-GeneReviews; NCBI Bookshelf). IPEX syndrome can be taken as a prototype of a disease caused by a defect in peripheral tolerance. Mutations in the FoxP3 gene lead to suppression of regulatory T-cells and subsequent hyper activation of auto aggressive T-cells and autoantibody formations. Clinical findings include a basic clinical triad (Powell et al., J. Pediatr. 100 (1982), 731-737; Ochs et al., Immunol. Rev. 203 (2005), 156-164) comprising:

Endocrinopathy with most commonly type 1 diabetes mellitus or autoimmune thyroid disease leading to hypothyroidism or hyperthyroidism (Wildin et al., J. Med. Genet. 39 (2002), 537-545: Gambineri et al., J. Allergy Clin. Immunol. 122(2008), 1105-1112)

Enteropathy with chronic watery diarrhea

Dermatitis with eczema most common, nail dystrophy, erythroderma, psoriasiform lesions, and alopecia universalis also reported Without treatment, most patients die within first 12 to 24 months of life, immunosuppressive regimens and bone marrow transplantation prolong survival but not beyond the second or third decade of life in milder disease cases (Powell et al., J. Pediatr. 100 (1982); Kobayashi et al, J. Med. Genet. 38 (2001), 874-876; Levy-Lahad and Wildin, J. Pediatr. 138 (2001), 577-580; Taddio et al., Eur. J. Pediair. 166 (2007), 1195-1197).

Thymoma:

Thymoma is a tumor of the thymus gland and located in the upper mediastinum, just behind the sternum. It is the most common tumor of the anterior mediastinum, and originates from the epithelial cells from the thymus. The tumor can originate both from the cortical as well as medullary epithelial cells or it can contain cells originating from both of these cell types.

Based on histology, the tumor can be divided in these categories:

Type A if the epithelial cells have an oval or fusiform shape; (less lymphocyte count)

Type B if they have an epithelioid shape (Type B has three subtypes B1 (lymphocyte-rich), B2 (cortical) and B3 (epithelial).)

Type AB if the tumor contains a combination of both cell types.

(Dadmanesh et al., Chest Surg Clin N Am 11 (2001), 407-420)

One third to half of the tumors are symptomless and the most common symptoms are caused by compression of adjacent organs by expanding tumor. A small portion of the thymomas is malignant, showing local invasion but metastases are rare.

An important feature of the thymoma is the various systemic diseases associated with this tumor. Most of these thymoma-associated conditions are linked to autoimmunity. The most well know is the relatively rare neuromuscular disease Myasthenia gravis, which is caused by autoantibodies to the acetylcholine receptors, located at postsynaptic neuromuscular junction. These antibodies block the effect of the neurotransmitter acetylcholine and thus will cause muscular fatigue. Close to half (30-45%) or patients with thymoma have myasthenia gravis. Other autoimmune diseases associated with thymoma are acute pericarditis, Addison's disease (adrenocortical failure) alopecia areata, ulcerative colitis, hemolytic anemia, pernicious anemia, rheumatoid arthritis, scleroderma, systemic lupus erythematosis and thyroiditis.

Labels and Diagnostics:

Labeling agents can be coupled either directly or indirectly to the antibodies or antigens of the invention. One example of indirect coupling is by use of a spacer moiety. Furthermore, the antibodies of the present invention can comprise a further domain, said domain being linked by covalent or non-covalent bonds. The linkage can be based on genetic fusion according to the methods known in the art and described above or can be performed by, e.g., chemical cross-linking as described in, e.g., international application WO94/04686. The additional domain present in the fusion protein comprising the antibody of the invention may preferably be linked by a flexible linker, advantageously a polypeptide linker, wherein said polypeptide linker comprises plural, hydrophilic, peptide-bonded amino acids of a length sufficient to span the distance between the C-terminal end of said further domain and the N-terminal end of the antibody of the invention or vice versa. The therapeutically or diagnostically active agent can be coupled to the antibody of the invention or an antigen-binding fragment thereof by various means. This includes, for example, single-chain fusion proteins comprising the variable regions of the antibody of the invention coupled by covalent methods, such as peptide linkages, to the therapeutically or diagnostically active agent. Further examples include molecules which comprise at least an antigen-binding fragment coupled to additional molecules covalently or non-covalently include those in the following non-limiting illustrative list. Traunecker, *Int. J. Cancer Surp. SuDP* 7 (1992), 51-52, describe the bispecific reagent janusin in which the Fv region directed to CD3 is coupled to soluble CD4 or to other ligands such as OVCA and IL-7. Similarly, the variable regions of the antibody of the invention can be constructed into Fv molecules and coupled to alternative ligands such as those illustrated in the cited article. Higgins, *J. Infect. Disease* 166 (1992), 198-202, described a hetero-conjugate antibody composed of OKT3 cross-linked to an antibody directed to a specific sequence in the V3 region of GP120. Such hetero-conjugate antibodies can also be constructed using at least the variable regions contained in the antibody of the invention methods. Additional examples of specific antibodies include those described by Fanger, *Cancer Treat. Res.* 68 (1993), 181-194 and by Fanger, *Crit. Rev. Immunol.* 12 (1992), 101-124. Conjugates that are immunotoxins including conventional antibodies have been widely described in the art. The toxins may be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers, *Seminars Cell. Biol.* 2 (1991), 59-70 and by Fanger, *Immunol. Today* 12 (1991), 51-54.

The above described fusion protein may further comprise a cleavable linker or cleavage site for proteinases. These spacer moieties, in turn, can be either insoluble or soluble (Diener et al., *Science* 231 (1986), 148) and can be selected to enable drug release from the antigen at the target site. Examples of therapeutic agents which can be coupled to the antibodies and antigens of the present invention for immunotherapy are chemokines, homing molecules, drugs, radioisotopes, lectins, and toxins. The drugs with which can be conjugated to the antibodies and antigens of the present invention depend on the disease context in which the conjugated molecules are intended to be used. For example, antibodies specific for targets useful in treatment of tumor diseases can be conjugated to compounds which are classically referred to as anti-neoplastic drugs such as mitomycin C, daunorubicin, and vinblastine. In using radioisotopically conjugated antibodies or antigens of the invention for, e.g., tumor immunotherapy, certain isotopes may be more preferable than others depending on such factors as leukocyte distribution as well as stability and emission. Depending on the autoimmune response, some emitters may be preferable to others. In general, α and β particle emitting radioisotopes are preferred in immunotherapy. Preferred are short range, high energy α emitters such as $^{212}$Bi. Examples of radioisotopes which can be bound to the antibodies or antigens of the invention for therapeutic purposes are $^{125}$I, $^{131}$I, $^{90}$Y, $^{67}$Cu, $^{212}$Bi, $^{212}$At, $^{211}$Pb, $^{47}$Sc, $^{109}$Pd and $^{188}$Re. Other therapeutic agents which can be coupled to the antibody or antigen of the invention, as well as ex vivo and in vivo therapeutic protocols, are known, or can be easily ascertained, by those of ordinary skill in the art. Non-limiting examples of suitable radionuclides for labeling are $^{198}$Au, $^{212}$Bi, $^{11}$C, $^{14}$C, $^{57}$Co, $^{67}$Cu, $^{18}$F, $^{67}$Ga, $^{68}$Ga, $^{3}$H, $^{197}$Hg, $^{166}$Ho, $^{111}$In, $^{113m}$In, $^{123}$I, $^{125}$I, $^{127}$I, $^{131}$I, $^{111}$In, $^{177}$Lu, $^{177}$Lu, $^{15}$O, $^{13}$N, $^{32}$P, $^{33}$P, $^{203}$Pb, $^{186}$Re, $^{188}$Re, $^{105}$Rh, $^{97}$Ru, $^{35}$S, $^{153}$Sm and $^{99m}$Tc. Other molecules suitable for labeling are a fluorescent or luminescent dye, a magnetic particle, a metal, and a molecule which may be detected through a secondary enzymatic or binding step such as an enzyme or peptide tag. Commercial fluorescent probes suitable for use as labels in the present invention are listed in the Handbook of Fluorescent Probes and Research Products, 8th Edition, the disclosure contents of which are incorporated herein by reference. Magnetic particles suitable for use in magnetic particle-based assays (MPAs) may be selected from paramagnetic, diamagnetic, ferromagnetic, ferrimagnetic and superpara-magnetic materials.

General methods in molecular and cellular biochemistry useful for diagnostic purposes can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996). Reagents, detection means and kits for diagnostic purposes are available from commercial vendors such as Pharmacia Diagnostics, Amersham, Bio-Rad, Stratagene, Invitrogen, and Sigma-Aldrich as well as from the sources given any one of the references cited herein, in particular patent literature.

Treatment and Drugs:

As used herein, the terms "treat" or "treatment" refer to both therapeutic treatment and prophylactic or preventative measures, wherein the object is to prevent or slow down (lessen) an undesired physiological change or disorder, such as the development of an autoimmune and/or autoinflammatory disease. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented.

If not stated otherwise the term "drug," "medicine," or "medicament" are used interchangeably herein and shall include but are not limited to all (A) articles, medicines and preparations for internal or external use, and any substance or mixture of substances intended to be used for diagnosis, cure, mitigation, treatment, or prevention of disease of either man or other animals; and (B) articles, medicines and preparations (other than food) intended to affect the structure or any function of the body of man or other animals; and (C) articles intended for use as a component of any article specified in clause (A) and (B). The term "drug," "medicine," or "medicament" shall include the complete formula of the preparation intended for use in either man or other animals containing one or more "agents." "compounds", "substances" or "(chemical) compositions" as and in some other context also other pharmaceutically inactive excipients as fillers, disintegrants, lubricants, glidants, binders or ensuring easy transport, disintegration, disaggregation, dissolution and biological availability of the "drug," "medicine," or "medicament" at an intended target location within the body of man or other animals, e.g., at the skin, in the stomach or the intestine. The terms "agent," "compound" or "substance" are used interchangeably herein and shall include, in a more particular context, but are not limited to all pharmacologically active agents, i.e. agents that induce a desired biological or pharmacological effect or are investigated or tested for the capability of inducing such a possible pharmacological effect by the methods of the present invention.

Examples of "anti-rheumatic drugs" and immunosuppressive drugs include chloroquine, hydroxycloroquine, myocrisin, auranofm, sulfasalazine, methotrexate, leflunomide, etanercept, infliximab (plus oral and subcutaneous methotrexate), adalimumab etc., azathioprine, D-penicilamine, gold salts (oral), gold salts (intramuscular), minocycline, cyclosporine including cyclosporine A and topical cyclosporine, tacrolimus, mycophenolate mofetil, cyclophosphamide, staphylococcal protein A (Goodyear and Silverman, J. Exp. Med., 197 (2003), 125-39), including salts and derivatives thereof, etc.

Examples of "non-steroidal anti-inflammatory drugs" or "NSAIDs" include aspirin, acetylsalicylic acid, ibuprofen and ibuprofen retard, fenoprofen, piroxicam, flurbiprofen, naproxen, ketoprofen, naproxen, tenoxicam, benorylate, diclofenac, naproxen, nabumetone, indomethacin, ketoprofen, mefenamic acid, diclofenac, fenbufen, azapropazone, acemetacin, tiaprofenic acid, indomethacin, sulindac, tolmetin, phenylbutazone, diclofenac and diclofenac retard, cyclooxygenase (COX)-2 inhibitors such as GR 253035, MK966, celecoxib (CELEBREX®; 4-(5-(4-methylphenyl)-3-(trifluoromethyl)-1H-pyrazol-1-yl), benzenesulfon-amide and valdecoxib (BEXTRA®), and meloxicam (MOBIC®), including salts and derivatives thereof, etc. Preferably, they are aspirin, naproxen, ibuprofen, indomethacin, or tolmetin. Such NSAIDs are optionally used with an analgesic such as codenine, tramadol, and/or dihydrocodinine or narcotic such as morphine.

By "subject" or "individual" or "animal" or "patient" or "mammal," is meant any subject, particularly a mammalian subject, e.g., a human patient, for whom diagnosis, prognosis, prevention, or therapy is desired.

Pharmaceutical Carriers:

Pharmaceutically acceptable carriers and administration routes can be taken from corresponding literature known to the person skilled in the art. The pharmaceutical compositions of the present invention can be formulated according to methods well known in the art: see for example *Remington: The Science and Practice of Pharmacy* (2000) by the University of Sciences in Philadelphia. ISBN 0-683-306472, *Vaccine Protocols.* 2nd Edition by Robinson et al., Humana Press, Totowa, N.J., USA. 2003; Banga *Therapeutic Peptides and Proteins: Formulation. Processing, and Delivery Systems.* 2nd Edition by Taylor and Francis. (2006), ISBN: 0-8493-1630-8. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods. Aerosol formulations such as nasal spray formulations include purified aqueous or other solutions of the active agent with preservative agents and isotonic agents. Such formulations are preferably adjusted to a pH and isotonic state compatible with the nasal mucous membranes. Pharmaceutical compositions for oral administration, such as single domain antibody molecules (e.g., "Nanobodies™") etc are also envisaged in the present invention. Such oral formulations may be in tablet, capsule, powder, liquid or semi-solid form. A tablet may comprise a solid carrier, such as gelatin or an adjuvant. Formulations for rectal or vaginal administration may be presented as a suppository with a suitable carrier; see also O'Hagan et al., *Nature Reviews. Drug Discovery* 2(9) (2003), 727-735. Further guidance regarding formulations that are suitable for various types of administration can be found in *Remington's Pharmaceutical Sciences*, Mace Publishing Company, Philadelphia, Pa., 17th ed. (1985) and corresponding updates. For a brief review of methods for drug delivery see Langer, *Science* 249 (1990), 1527-1533.

Dosage Regimen:

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg (or of nucleic acid for expression or for inhibition of expression in this range); however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as anti-tumor agents and cytotoxic drugs, depending on the intended use of the pharmaceutical composition.

In addition, co-administration or sequential administration of other agents may be desirable. A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

Preferably, the therapeutic agent in the composition is present in an amount sufficient for preventing inflammation or suppression of the immune response.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, *TIBTECH* 12 (1994), 352-364.

The above disclosure generally describes the present invention. Unless otherwise stated, a term as used herein is given the definition as provided in the *Oxford Dictionary of Biochemistry and Molecular Biology*, Oxford University Press, 1997, revised 2000 and reprinted 2003. ISBN 0 19 850673 2. Several documents are cited throughout the text of this specification. Full bibliographic citations may be found at the end of the specification immediately preceding the claims. The contents of all cited references (including literature references, issued patents, published patent applications as cited throughout this application and manufacturer's specifications, instructions, etc) are hereby expressly incorporated by reference: however, there is no admission that any document cited is indeed prior art as to the present invention.

A more complete understanding can be obtained by reference to the following specific examples which are provided herein for purposes of illustration only and are not intended to limit the scope of the invention.

EXAMPLES

The Examples 1 to 17 which follow and corresponding FIGS. 1 to 50 further illustrate the invention, but should not be construed to limit the scope of the invention in any way. Detailed descriptions of conventional methods, such as those employed herein can be found in the cited literature: see also "*The Merck Manual of Diagnosis and Therapy*" Seventeenth Ed. ed. by Beers and Berkow (Merck & Co., Inc., 2003).

The practice of the present invention will employ, unless otherwise indicated, conventional techniques of cell biology, cell culture, molecular biology, transgenic biology, microbiology, recombinant DNA, and immunology, which are within the skill of the art.

Methods in molecular genetics and genetic engineering are described generally in the current editions of Molecular Cloning: A Laboratory Manual, (Sambrook et al., (1989) *Molecular Cloning: A Laboratory Manual*, 2nd ed., Cold Spring Harbor Laboratory Press); DNA Cloning, Volumes I and II (Glover ed., 1985); *Oligonucleotide Synthesis* (Gait ed., 1984); *Nucleic Acid Hybridization* (Hames and Higgins eds. 1984); *Transcription And Translation* (Hames and Higgins eds. 1984); *Culture Of Animal Cells* (Freshney and Alan, Liss. Inc., 1987); *Gene Transfer Vectors for Mammalian Cells* (Miller and Calos, eds.); *Current Protocols in Molecular Biology and Short Protocols in Molecular Biology*, 3rd Edition (Ausubel et al., eds.); and *Recombinant DNA Methodology* (Wu, ed., Academic Press). *Gene Transfer Vectors For Mammalian Cells* (Miller and Calos, eds., 1987. Cold Spring Harbor Laboratory); *Methods In Enzymology*. Vols. 154 and 155 (Wu et al., eds.); *Immobilized Cells And Enzymes* (IRL Press, 1986); *Perbal, A Practical Guide To Molecular Cloning* (1984); the treatise, *Methods In Enzymology* (Academic Press, Inc., N.Y.); *Immunochemical Methods In Cell And Molecular Biology* (Mayer and Walker, eds., Academic Press, London, 1987); *Handbook Of Experimental Immunology*, Volumes I-IV (Weir and Blackwell, eds., 1986). Reagents, cloning vectors, and kits for genetic manipulation referred to in this disclosure are available from commercial vendors such as BioRad, Stratagene. Invitrogen, and Clontech. General techniques in cell culture and media collection are outlined in Large Scale Mammalian Cell Culture (Hu et al., *Curr. Opin. Biotechnol.* 8 (1997), 148); Serum-free Media (Kitano, *Biotechnology* 17 (1991), 73); Large Scale Mammalian Cell Culture (*Curr. Opin. Biotechnol.* 2 (1991), 375); and Suspension Culture of Mammalian Cells (Birch et al., *Bioprocess Technol.* 19 (1990), 251.

Material and Methods

Patients Selection and Disease Associations of the Invention

The group of 33 Finnish APECED patients studied for the autoantibodies and serving as the source for specific B-lymphocyte cloning in respect of the present invention have the following features. Of the patients, 21 were female and 12 male, the mean age being 38 yrs (females 38.3 yrs; males 37.8 yrs). The mean age at $1^{st}$ symptoms of APECED had been 6.2 yrs. The mean weight of the men was 69.75 kg and of the women 59.4 kg. These 33 patients responded to a questionnaire on their clinical symptoms. As general symptoms, 30% of the patients experienced fever periods and 67% experienced asthenia. 30 of the patients donated blood and their sera were analyzed by ELISA as shown in FIGS. 6 to 10. Sera of 23 of these patients and of 7 healthy control persons (C1 to C7) were selected for protoarray screening.

Organ-Specific Symptoms and Diseases

The organ-specific symptoms and diseases in APECED patients, as a consequence of the AIRE gene defect, have been previously described and the tissue-specific autoantigens are mostly known (Betterle et al., *J. Clin. Endocrinol. Metab.* 83 (1998) 1049-1055: Husebye, E. S., Perheentupa et al., *J. Intern. Med.* 265 (2009), 514-529; Soderbergh et al., *J. Clin. Endocrinol. Metab.* 89 (2004), 557-562: Uibo et al., *J. Clin. Endocrinol. Metab.* 78 (1994), 323-328). The present patient cohort presented with organ-specific autoimmune symptoms as follows (known autoantigen in parentheses): Addison's disease in 81% (adrenal gland 21 hydroxylase; 17alpha-hydroxylase; side chain cleavage enzyme (SCC)), concomitant hypoparathyroidism in 79% (parathyroid, NALP5 (NACHT leucin rich repeat protein 5) and hypothyroidism in 45% (thyroperoxydase; Thyroglobuline). Twelve of the latter 15 patients also had hypoparathyroidism and Addison's disease. Infertility was recorded in 30% (testicular/ovarian insufficiency/atrophy in 1 male and in 10 females; 17alpha-hydroxylase and SCC), asplenia in 24%, HypophysialiGH deficiency in 18% (mostly male: Tudor domain containing protein 6 (TDRD6)), diabetes mellitus in 12% (pancreatic GAD65: Insuline: Tyrosine phosphatase IA2), Pernicious anemia in 12% (stomach mucosa, Intrinsic factor, gastric parietal cell as autoantigens), Autoimmune hepatitis in 9% (AntiLKMI+but different antigens: cytochrome P450 1A2, P450 2A6, P450 1A1, P450 2B6) and Nephritis in 90/o (all female).

Hair loss had occurred in 42% (less in women), alopecia in 33% (less in women; possible autoantigen is Tyrosine hydroxylase). Vitiligo was present in 15% (Anti-melanocytes: SOX 9; SOX 10: AADC)

Clinical Manifestations of Unknown Origin:

The APECED patients also have ectodermal deficiencies whose pathophysiology is as yet unknown. Such were in the present patient cohort tooth dystrophy (72%) and nail dystrophy (33%). Eye infections were found in 64%, dry eyes in 79% and photosensitivity in 55%.

Intestinal symptoms, mostly functional and malabsorption, are common in the present APECED cohort. Episodes of abdominal pain were reported by 56%, episodes of diarrhea in 39%, Episodes of constipation by 39% and 18% had abdominal pain+diarrhea+constipation. Retrostemal pain/high dysphagia was reported by 33%.

Since IL-7 expression by enterocytes is essential for extrathymic development of TCR-gamma delta cells in situ within the intestinal epithelium and for organization of mucosal lymphoid tissue (Laky et al, JEM 2000), the patient's anti-IL7 autoantibodies or autoantibodies directed against the ET-converting enzyme 1 (ECE1) are likely to contribute to the observed intestinal symptoms.

Diseases NOT Found in APECED Patients i.e. Protection Against these Diseases

The anti-cytokine and anti-chemokine and other autoantibodies (see Table 2 to Table 14) developed uniquely in APECED patients, and mostly identified for the first time in this study, are likely to protect the patient from the following diseases:

Non-Organ Specific Diseases of Autoimmune and Autoinflammatory Origin NOT Found in the Present APECED Patients:

Lupus erythematosus; Sjogren's syndrome: scleroderma (localized or systemic); antiphospholipid syndrome: Multiple Sclerosis (MS); Rheumatoid arthritis. In Finland, the national prevalence of RA is 0.8%: Psoriasis. In Finland, the national prevalence of psoriasis is 2-4%; gluten intolerance (celiac disease). In Finland, the national prevalence of celiac disease is 2%: inflammatory bowel diseases (IBD); Bullous auto-immune skin diseases (pemphigus: pemphigoid); Goodpasture syndrome; Hemolytic anaemia; Auto-immune thrombopenia, acquired haemophilia; Auto-immune neuropathy Without indending of being bound to theory, it is prudent to expect that the human antibodies, naturally elicited in APECED patients as identified herein and protective against the above diseases are as follows:
- anti-interferon antibodies: protective against lupus erythematosus.
- anti-IL17: protective against psoriasis and inflammatory bowel disease (IBD)
- anti-IL-5, IL-7 (thymus, skin, intestine), IL-10. IL-11: protective against atopic diseases
- anti-IL-10 antibodies: may be used to enhance antitumor immune response (in various types of cancer)
- anti-IL-7 antibodies: protective against human T-cell acute lymphoblastic leukemias
- anti-IL-28, IL-29: produced widely, esp. DC, antiviral and cytostatic, target epithelial cells and hepatocytes, upregul. TLR 2 an 3, TLR-induced IL-12
- anti-CCL-17, CCL-22 (expressed by eosinophiles, basal cells, Th-2): protective against asthma, RA, CNS inflammation.
- anti-IL-17 A/F, IL-22, also CCL-20 and anti-IL-36: protect against psoriasis Allergic Diseases The incidence of allergic diseases is decreased in APECED patients and we propose this is due, in part, to the autoantibodies naturally elicited in APECED patients and targeting the central inflammatory mediator pathways in allergic diseases. In Finland, the prevalence of various allergic diseases in the general population are as follows: atopic eczema: (AE) prevalence in children 15-20% and 25-30% of the adults have experienced AE at some time during their lifetime. While in the APECED patient cohort, atopic eruption was found in only 12% of the cases, nasal allergy in 12%, ocular allergy in 15%, airway allergy/Asthma in 10% and contact allergy in 6%. The autoantibodies found in accordance with the present invention and which are directed against CCL17, CCL, 19, CCL21 and CCL22 are protective against the allergic manifestations, since e.g. CCL17 and CCL22 are known to be upregulated in AE (ref), and likewise CCL19, CCL21 in asthma: iBALT (infection/chronic infection).

Microbe Infections

APECED patients with the aforementioned autoimmune response are not vulnerable to common microbe infections except for mucous membrane overgrowth of *candida* yeast. The present patient cohort presented with ungula (nails) *Candida* infection in 27%, ungula dystrophy associated with nail infection in 50%, Oral candidiasis (confirmed) in 64%, Oesophageal candidiasis in 30% (most had also oral candidiasis), Gingivitis in 36%.

Cancer

Cancer, except for oral squamous cell cancer, is rare in APECED. In the patient cohort tested within the experiments underlying the present invention, oral cancer was found in 9% of the patients. The patients' autoantibodies against CRLF3, CCL7, CCL20, CCL22 and CCL17 may be protective in this context.

Mutation Analysis of the AIRE Gene:

Genotyping of the respective mutations in the AIRE (APECED) gene is performed as described in international application WO99/15559 in Example 2 at pages 12 to 13, the disclosure content of which is incorporated herein by reference in its entirety. In particular, for the mutation analysis the DNA samples are purified from periferal blood mononuclear cells from patients with APECED and from suspected carriers of APECED and from normal healthy controls (according to Sambrook et al. 1989, *Molecular*

*Cloning. A Laboratory Manual*. CSH Press) and subjected to PCR using primers specific for all identified exons.

For sequencing the mutated exons, PCR fragments, 6F/6R in exon 6 and 49300F/49622R in exon 2, are amplified by PCR with the following conditions: 95° C. for 9 min., 35 cycles of 94° C. for 30 sec, 60° C. for 30 sec and 72° C. for 30 sec, and 94° C. for 3 min., 35 cycles of 94° C. for 30 sec, 60° C. for 30 25 sec, and 68° C. for 30 sec, respectively. The PCR products are sequenced using specific primers:

```
                                        (SEQ ID NO. 1)
6F:         5'-TGCAGGCTGTGGGAACTCCA-3'

(SEQ ID NO. 2)
6R:         5'-AGAAAAAGAGCTGTACCCTGTG-3'

(SEQ ID NO. 3)
3R:         5'-TGCAAGGAAGAGGGGCGTCAGC-3'

(SEQ ID NO. 4)
49300F:     5'-TCCACCACAAGCCGAGGAGAT-3'
and (SEQ ID NO. 5)
49622R:     5'-ACGGGCTCCTCAAACACCACT-3'.
```

For a confirmation of the mutations in exons 2 and 6 of the AIRE gene, an restriction enzyme analysis PCR amplification products of the respective regions is performed, as described in Example 3 of international application WO99/15559 at page 13, line 5 bridging to page 14, line 13, the disclosure content of which is incorporated herein by reference.

Protoarray Chips:

Invitrogen protoarray chips for seroactivity testing: The ProtoArray® Human Protein Microarray v5.0 slides (Invitrogen) were blocked and then probed with a 1:500 dilution of each serum sample diluted in PBST buffer. Arrays were then incubated 90 minutes at 4° C. with gently agitation. After incubation, the slides were washed five times in PBST buffer. An Alexa Fluor® 647-conjugated goat anti-human IgG antibody diluted in PBST buffer was then added to each array and allowed to incubate with gentle shaking at 4° C. for 90 minutes. After incubation, the secondary antibody was removed, arrays were washed as described above and dried by spinning. Finally, arrays were scanned using an Axon GenePix 4000B fluorescent microarray scanner.

Memory B Cell Culture

Memory B cells were isolated from human peripheral blood monocytic cells derived from the peripheral blood of voluntary Finnish patients with Autoimmune polyendocrinopathy candidiasis ectodermal dystrophy (APECED, OMIM 240300), also called autoimmune polyendocrine syndrome type 1 (APS1) with a one step protocol using phycoerythrin-conjugated mAb anti-human IgD, APC-conjugated mAbs anti-human IgM, CD3, CD56, CD8 and FITC-conjugated mAb anti human CD22 (Becton Dickinson, Basel, Switzerland). Cell sorting was carried out using a MoFlo XDP cell sorter (Beckman Coulter). CD22-positive- and IgM-, IgD-negative B cells were then incubated with EBV containing supernatant obtained from B95-8 cells (in B cell medium containing RPMI 1640 supplemented with 10% fetal calf serum) for 3 to 5 hours (preferably 3.5 hours). Cells were seeded at 10 cells per well in IMDM medium supplemented with CpG 2006 on 30.000 irradiated feeder PBL prepared from voluntary donors. After 8-14 days of culture the conditioned medium of memory B cell culture was screened for the presence of antigen of interest-specific (e.g., IL-17, IL-22) antibodies by ELISA.

IL-17, IL-22 ELISA 96 well microplates (Costar, USA) were coated with human IL-17A, or IL-17F (both from BioLegend), or IL-22 (ImmunoTools). Plates were washed with PBS-T and blocked 1 h at room temperature with PBS containing 2% BSA (Sigma, Buchs, Switzerland). Patient sera. B cell conditioned medium, or recombinant antibody preparations were incubated for 2 h at room temperature. Binding of human IgG to the antigen of interest was determined using a horseradish peroxidase conjugated goat anti human Fc-gamma-specific antibody (Jackson ImmunoResearch, Europe Ltd., Cambridgeshire, UK) followed by measurement of the HRP activity using a TMB substrate solution (TMB, Sigma, Buchs, Switzerland).

Example 1: Isolation of Human Peripheral Blood Mononuclear Cells (PBMC) from APECED/APS1 Patients As starting material for the cloning of fully human antibodies, human lymphocytes were used obtained from the peripheral blood of 23 voluntary Finnish patients with Autoimmune polyendocrinopathy candidiasis ectodermal dystrophy (APECED. OMIM 240300), also called autoimmune polyendocrine syndrome type 1 (APS1). These volunteers were recruited for the blood donation through the Finnish APECED and Addison patient association. All patients gave their written informed consent and the study has been approved by the Medicine Ethical Review Board of the Joint Authority of Helsinki and Uusimaa hospital district. APECED is an autosomal recessive disorder caused by mutations in the AIRE (autoimmune regulator) gene, located on chromosome 21 (21q22.3) and APECED is prevalent in Finland (1/25,000) because of a founder effect. APECED patients present with various endocrine autoimmune dysfunctions including mainly adrenal failure and hypoparathyroidism, but also variously hypogonadism, diabetes mellitus, thyroiditis and hypophysitis. Other main symptoms are chronic mucocutaneous candidiasis, alopecia and vitiligo (see also supra). Since a strong correlation between the antigen-specific IgG levels in the serum and the frequency of antigen-specific B cells in the memory pool of peripheral blood mononuclear cells has been reported (Bemasconi et al. 2002, Lanzavecchia et al. 2006), patient sera were first screened for the presence of autoantibodies against the proteins of interest (like IFN, IL-17, IL-22) and then those APECED cases with high titer (>1:5000) were selected for peripheral blood mononuclear cell (PBMC) isolation as follows. Heparinized peripheral blood was obtained and diluted with two volumes of 1×PBS at RT, and the cells were overlayed on Lympholyte H, centrifuged at 2000 rpm (805 rcf) at RT for 20 minutes. The cells were harvested at interphase, mixed in washing buffer fill, centrifuged at 1,500 rpm (453 rcf) for 15 min at 4° C. and resuspended by gentle flicking, with 10 ml WB. Thereinafter the cells were centrifuged at 1,000 rpm (201 rcf), 10 min at 4° C. and washed once more with WB. The cells were then resuspended gently in appropriate volume of FBS on ice. FBS was added to adjust volume to have 20 mio/ml whereafter 1 volume of freezing medium (80% FBS (Hyclone. Thermo Scientific and 20%0/DMSO, #154938, Sigma) was slowly added while stirring, resuspended and aliquoted into cryovials kept on ice. The cryovials were placed in Mr. Frosty box and transferred to −80° C. freezer for a maximum of 5 days before further processing as described in Example 2. Alternatively the cryovials were stored in liquid nitrogen.

Example 2: Molecular Cloning of Human Antibodies Specific to IL-17 or IL-22

Preferably, antibodies specific to IL-17 or IL-22 were isolated by molecular cloning of immunoglobulin genes obtained from single-cell sorted cells derived from short term oligoclonal cultures of activated memory B cells producing the antibodies of interest.

Memory B cells were isolated from PBMC derived from the peripheral blood of voluntary Finnish patients with APECED with a one step protocol using phycoerythrin-conjugated mAb anti-human IgD, APC-conjugated mAbs anti-human IgM, CD3, CD56, CD8 and FITC-conjugated mAb anti human CD22 (Becton Dickinson, Basel, Switzerland). Cell sorting was carried out using a MoFlo XDP cell sorter (Beckman Coulter). CD22-positive- and IgM-, IgD-negative B cells were stimulated with EBV containing supernatant obtained from B95-8 cells (in B cell medium containing RPMI 1640 supplemented with 10% fetal calf serum). Cells were seeded in IMDM medium supplemented with CpG 2006 at 10 cells per well on 30.000 irradiated feeder PBMC prepared from voluntary donors. After 10-14 days stimulation, culture supernatants were screened for the presence of antibodies specific for the target of interest (e.g. IL17, IL-22). The screening process comprised screening for binding on fragments, peptides or derivates of the particular molecule of interest, e.g., by ELISA. Subsequently the antibody for which binding is detected or the cell producing said antibody is isolated.

Single cells obtained from IL-17/IL-22-reactive memory B cell cultures are deposited into a 96 well PCR plate, containing first strand buffer (Invitrogen. LuBioScience, Switzerland). cDNA is prepared using Random hexamer primer (Invitrogen, LuBioScience, Switzerland). PCR amplification of immunoglobulin heavy and light chain variable regions is performed according to standard protocols (Wardemann et al., *Science* 301, 2003, 1374-1377). Immunoglobulin heavy and light chain variable regions are amplified using a nested PCR approach. 1st round PCR is performed with primers specific for the IgG constant region and primer mixes specific for all signal peptides of heavy and light chain Ig variable region families (Wardemann et al., *Science* 301, 2003, 1374-1377). Subsequently, nested PCR is performed using primer mixes specific for the immunoglobulin J-regions and the 5' region of framework 1 of heavy and light chain Ig variable region families. Sequence analysis is carried out to identify the individual antibody clones present in the selected B-cell culture. Subsequently, the Ig-variable heavy- and light regions of each antibody clone are cloned into expression vectors providing the constant regions of human IgG1, human Ig-Kappa or human Ig-Lambda. Upon co-transfection of the Ig-heavy- and light expression vectors into HEK 293 cells the antibody clones are produced. Identification of the antibody clone presumably responsible for the IL-17/IL-22-reactivity of the parental B cell culture is performed upon re-screening of the recombinant antibody clones in IL-17/IL-22- and control ELISA.

In order to identify and to correct primer encoded sequence mismatches in the Ig-variable region, a further PCR amplification using a semi-nested protocol is performed with 2 primer pairs specific for a conserved region of the Ig-heavy- and light chain constant regions as 3'-primers and primer mixes specific for the Ig-signal peptides as 5'-primers. PCR products are cloned into TOPO™ vector (Invitrogen, LuBioScience, Luceme, Switzerland). Sequence determination of the complete Ig-variable region is carried out and the information is used to design specific primers for the cloning of the authentic human antibody sequence into antibody expression vectors. This approach allows the identification of the complete antibody sequence of the Ig-variable region as it occurred in the patient. This sequence is used for recombinant production of these antibodies which are then used in the subsequent characterization steps.

Example 3: Antibody Production and Purification

Transient gene expression of human antibodies is achieved upon transfection of antibody expression vectors into 293-T human embryonic kidney cells or Chinese Hamster Ovary cells (CHO) using the Polyethylenimine Transfection method (PEI, Polyscience Warrington, USA). After transfection cells are cultured in serum free medium (OPTI-MEM I supplemented with GlutaMAX-I Gibco). Supernatants are collected after 3-6 days of culture and IgG is purified using protein A columns (GE HealthCare. Sweden) on a fast protein liquid chromatography device (FPLC) (GE HealthCare, Sweden).

Example 4: In Vitro Cell-Based Neutralizing Assays

The neuralizing assays are carried out on cell lines that respond to the studied cytokine, i.e. carry the necessary receptor. The ligand binding to receptor activates a corresponding signaling pathway, translocation of transcription factors to the nucleus and upregulate responder gene transcription, translation and if applicable product secretion. The cytokine concentration used is selected from the beginning of the linear part of the dose-response curve to maximize the sensitivity of the assay. To test the neutralizing capacity of antibodies the optimal concentration of the target cytokine is preincubated with serial dilutions of serum, supernatant or purified antibody samples. The results are expressed as titer or concentration of antibody that show the value half-way between the positive and negative controls.

IL-22 Neutralizing Assay

Serial dilutions of serum samples, culture supernatants or purified antibodies are co-incubated with 0.5 ng/ml of IL-22 in 96-well tissue culture plate at 37° C. Colo205 cell line is added after 2 hours of co-incubation at $3 \times 10^4$ cells/well in RPMI-1640 with 10% heat inactivated FBS. After incubation at 37° C. for 16-20 h, supernatants are collected and analyzed for IL-10 production by ELISA. Results are estimated from graphs of ELISA absorbances as the serum or supernatant titer or antibody concentration yielding a value half-way between the positive and negative controls. ED50s are defined as the concentration or titer needed to halve the cytokine activity of the test sample.

IL-17A Neutralizing Assay

1BR.3.G human skin fibroblast cells are seeded at $1 \times 10^4$ cells/well in which IL-17-A (2 ng/ml) had been pre-exposed to serially diluted serum, supernatant or antibody samples for 2 h in DMEM with 10% inactivated FBS. After incubation at 37° C. for 16-20 h, supernatants are collected and analyzed for growth-related oncogene (GRO)-α production by ELISA. Results are estimated from graphs of ELISA absorbances as the serum or supernatant titer or antibody concentration yielding a value half-way between the positive and negative controls. ED50s are defined as the concentration or titer needed to halve the cytokine activity of the test sample.

IL-17F Neutralizing Assay

NCTC 2544 keratinocytes are pre-treated with TNF-α (0.1 ng/ml) in DMEM with 10% inactivated FBS for 3 hours. Serial dilutions of serum samples, culture supernatants or purified antibodies are co-incubated with 10 ng/ml of IL-17F in 96-well tissue culture plate at 37° C. Keratinocytes are added after 2 hours of co-incubation at $1\times10^4$ cells/well. After incubation at 37° C. for 16-20 h, supernatants are collected and analyzed for growth-related oncogene (GRO)-α production by ELISA. Results are estimated from graphs of ELISA absorbances as the serum or supernatant titer or antibody concentration yielding a value half-way between the positive and negative controls. ED50s are defined as the concentration or titer needed to halve the cytokine activity of the test sample.

IL-17A'IL-17F Heterodimer Neutralizing Assay

NCTC 2544 keratinocytes are pre-treated with TNF-α (0.1 ng/ml) in DMEM with 10% inactivated FBS for 3 hours. Serial dilutions of serum samples, culture supernatants or purified antibodies are co-incubated with 5 ng/ml of IL-17A/IL-17F heterodimer in 96-well tissue culture plate at 37° C. Keratinocytes are added after 2 hours of co-incubation at $1\times10^4$ cells/well. After incubation at 37° C. for 16-20 h, supernatants are collected and analyzed for growth-related oncogene (GRO)-α production by ELISA. Results are estimated from graphs of ELISA absorbances as the serum or supernatant titer or antibody concentration yielding a value half-way between the positive and negative controls. ED50s are defined as the concentration or titer needed to halve the cytokine activity of the test sample.

Example 5: Validation of Subject Antibodies

1. Protocol for Imiquimod-Induced Psoriasis-Like Skin Inflammation in Selected Animal Models Mouse models were used to assay the effect of APECED-derived anti-IL-17, anti-IL-22 autoantibodies and other APECED-derived autoantibodies upon imiquimod-induced psoriasis-like skin inflammation. C57Bl/6 mice were dorsal back-shaved under anaesthesia 48-72 hours prior to treatment. 24 hours prior to or post imiquimod application, mice were intraperitoneally injected with anti-IL-17, anti-IL-22 and other APECED-derived autoantibodies, with further doses at 2-day intervals. Control mice were injected with human Ig control. Treated mice received a daily topical dose of 62.5 mg of commercially available IMQ cream (5%) (Aldara: 3M Pharmaceuticals) for 5 consecutive days. Control mice were treated with Vaseline. Mice were scored daily using an objective scoring system based on the clinical Psoriasis Area and Severity Index (PASI). Erythema, scaling, and thickening were scored independently on a scale from 0 to 4: 0, none; 1, slight; 2, moderate; 3, marked: 4, very marked. Spleens were weighed, and lymph node-derived T cells stimulated overnight for analysis by flow cytometry.

2. Inducing EAE in Aire Deficient Mice, Co-Treated with Anti-IL-7 and Anti-IFN Antibodies The Aire$^{-/-}$ mouse model, in which the Aire protein coding potential is disrupted, which would be predicted to precipitate autoimmunity, was used to investigate the potentially protective effects of anti-IL-17, anti-IFN, and other auto-antibodies derived from APECED patients upon EAE (experimental allergic encephalomyelitis) induction by MOG$_{35-55}$ CFA emulsion (immunogenic Myelin oligodendrocyte glycoprotein peptide fragment that induces an autoimmune destruction of MOG-expressing nerve cells; complete Freund's adjuvant). For example, complete Freunds adjuvant (CFA) emulsion pre-filled syringes containing 1 mg MOG$_{35-55}$/mL emulsion and 2 mg killed *Mycobacterium tuberculosis* H37Ra/mL emulsion were used in this respect. Aire$^{-/-}$ and wild-type control female mice were pre-treated 24 hours prior to the onset of EAE induction with intraperitoneal injection of antibodies (e.g., anti-IL-7 and anti-IFN antibodies), with further doses at 2-day intervals. Control mice were injected with control immunoglobulin. 24 hours post initial antibody administration, minimally stressed (at least 7 days acclimatization, static cages, quiet environment) Aire$^{-/-}$ and wild-type control female mice were injected subcutaneously (upper and lower back) with MOG$_{35-55}$ CFA emulsion to instigate EAE. Within 2 hours, treated mice were injected intraperitoneally with pertussis toxin to exarcerbate EAE induction, with a further subcutaneous pertussis toxin dose administrated at 22-26 hours. EAE induction was scored at 7 days post initiation and beyond using the standard Hooke Lab clinical observation scale, scoring the severity of the EAE phenotype on a 0-5 scale. A 0 scored phenotype represents no obvious changes, ranging to a scored 5 phenotype indicating complete hind and front leg paralysis.

3. Protocol for Inducing EAE in Mouse Models

A mouse model was used to investigate the effect of anti-IL-17, anti-IL-22 and other APECED-derived autoantibodies upon EAE induction by MOG$_{35-55}$ (immunogenic MOG peptide that precipitates an autoimmune destruction of MOG-expressing nerve cells) CFA emulsion. Aire$^{-/-}$ and wild-type control female mice were pre-treated 24 hours prior to the onset of EAE induction with intraperitoneal injection of anti-IL-17, anti-IL-22 antibodies, with further doses at 2-day intervals. Control mice were injected with Ig control. 24 hours post initial antibody administration, minimally stressed (at least 7 days acclimatization, static cages, quiet environment) Aire$^{-/-}$ and wild-type control female mice were injected subcutaneously (upper and lower back) with MOG$_{35-55}$ CFA emulsion to instigate EAE. Within 2 hours, treated mice were injected intraperitoneally with pertussis toxin to exarcerbate EAE induction, with a further subcutaneous pertussis toxin dose administrated at 22-26 hours. EAE induction was scored at 7 days post initiation and subsequently using the standard Hooke Lab clinical observation scale, scoring the severity of the EAE phenotype on a 0-5 scale. A 0 scored phenotype represents no obvious changes, ranging to a scored 5 phenotype indicating complete hind and front leg paralysis.

4. Protocol for Inducing Collagen-Induced Arthritis in Mouse Models

A mouse model was used to investigate the effect of anti-IL-17, anti-IL-22 and other APECED-derived autoantibodies upon the induction of collagen-induced arthritis (CIA). C57Bl/6 mice were pre-treated with intraperitoneally injected APECED-derived autoantibodies 24 hours prior to CIA induction, with further doses at 2-day intervals (Ig used as control). Collagen-induced arthritis was instigated with intradermal injection (2× injections at base of tail) of chicken type II collagen (prepared 1:1 with CFA) extracted from chicken sternum cartilage. A further boost of chicken type II collagen 1:1 IFA was injected intradermally at 14 days post induction. Mice were monitored and scored for arthritis every day starting 2 weeks following primary immunisation, with typical arthritis onset occurring between 3 and 6 weeks post immunisation, and was scored either by clinical monitoring (scoring of hind paw swelling using calipers), measurement of anti-collagen antibodies (ELISA using collagen coated plates), T-cell responses (T-cell proliferation in response to chicken collagen as determined using [3H] thymidine incorporation) or cytokine ELISA.

5. Protocol for Inducing DSS Colitis in Mouse Models

Mouse models were used to assay the effect of anti-IL-17, anti-IL-22 and other APECED-derived autoantibodies upon the induction of DSS colitis. C57Bl/6 mice were pre-treated with intraperitoneally injected APECED-derived autoantibodies 24 hours prior to DSS colitis induction, with further doses at 2-day intervals. Chronic DSS colitis was induced by cycles of drinking water containing 2% DSS for 5 days, followed by 14 days autoclaved drinking water without DSS; repeated for 3 cycles. Control mice received only autoclaved drinking water. DSS-induced colitis induction and severity was measured by histological evaluation (hematoxylin and eosin staining on paraffin sections), full thickness organ culture (with collection of supernatants at 24 hours for cytokine analysis) or direct tissue sampling for qPCR or immunoblotting. Mice subjected to DSS-induced colitis were also weighed daily to determine the degree of weight loss, as colitis is strongly associated with wasting disease.

The efficacy of human-derived antibodies against cytokines or other relevant molecules will also be assessed by the effects of such antibodies, e.g. anti-IL-17F and anti-IL-22 on inflammation in human tissue grafted into immuno-deficient strains of mice, such as was described by Sagoo et al., Sci Transl Med 3 (2011):83ra42.

Example 6: Results of Imiquimod-Induced Psoriasis-Like Skin Inflammation

In mice topically treated with Imiquimod to induce psoriasis-like skin inflammation (see FIG. 16 for experimental timelines and treatment scheme), APECED derived 30G1 anti-IL-22 [HD-MAB] antibodies significantly reduce Psoriasis Area and Severity Index (PASI) scores relative to control IgG antibodies. Erythema (redness), scaling, and thickening (hardness) were scored independently on a scale from 0 to 4: 0, none; 1, slight; 2, moderate; 3, marked; 4, very marked. As can be seen in FIGS. 17, 18, 20-22, Imiquimod treatment induces psoriasis-like skin inflammation as measured by PASI scores of Erythema (redness), scaling and skin thickening (hardness) relative to mice treated with control antibodies. Mice treated with anti-IL-22 HDMABs of the present invention, such as the exemplary 30G1 antibody, showed a decrease in both the cumulative and individual scores of measurements when compared to mice treated with control IgG (compare data indicated by solid lines (IgG+IMQ) vs. data indicated by dotted lines (aIL22+IMQ) in FIGS. 17, 18, 20, and the back skin showing extended lesions and red skin areas (spots) of animals treated with IgG+IMQ in FIGS. 20-21 (B) with a lack or smaller extension of such lesions on backs of animals treated with 30G1 anti-IL-22 and IMQ in FIGS. 20-21 (C) and IgG+IMQ versus aIL22+IMQ entries in Tables 18 and 19 below). Furthermore, flow cytometric analysis of lymph node derived T cells showed a reduced state of effector activation in anti-IL-22 HDMAB-treated mice compared with mice treated with control IgG.

Following 5 days of imiquimod treatment, mice treated with control human IgG displayed mean clinical scores of: redness=3.75 (scored 0-4), hardness=3 and scales=2.25, while mice treated with IMQ and anti-IL-22 30G1 antibody had scores of redness=1.75, hardness=1.75 and scales=2; see Tables 18 and 19 below. These appear to be significant differences. IgG IMQ treated mice also displayed increased skin thickness compared to anti-IL-22 IMQ treated mice.

TABLE 18

Redness clinical scores in BL6 mice over 5 day time course (blind scored on scale 0-4) Vas = Vaseline, IMQ = Imiquimod

|  |  | Day 0 | Day 1 | Day 2 | Day 3 | Day 4 | Day 5 |
| --- | --- | --- | --- | --- | --- | --- | --- |
| IgG + Vas | IgG + Vas 1 | 0 | 0 | 0 | 0 | 0 | 0 |
| IgG + Vas | IgG + Vas 2 | 0 | 0 | 0 | 0 | 0 | 0 |
| IgG + Vas | IgG + Vas 3 | 0 | 0 | 0 | 0 | 0 | 0 |
| IgG + IMQ | IgG + IMQ 1 | 0 | 0 | 0 | 2 | 3 | 4 |
| IgG + IMQ | IgG + IMQ 2 | 0 | 0 | 1 | 1 | 3 | 3 |
| IgG + IMQ | IgG + IMQ 3 | 0 | 0 | 1 | 3 | 4 | 4 |
| IgG + IMQ | IgG + IMQ 4 | 0 | 0 | 0 | 2 | 4 | 4 |
| aIL22 + Vas | aIL22 + Vas 1 | 0 | 0 | 0 | 0 | 0 | 0 |
| aIL22 + Vas | aIL22 + Vas 2 | 0 | 0 | 0 | 0 | 0 | 0 |
| aIL22 + Vas | aIL22 + Vas 3 | 0 | 0 | 0 | 0 | 0 | 0 |
| aIL22 + IMQ | aIL22 + IMQ 1 | 0 | 0 | 0 | 1 | 2 | 2 |
| aIL22 + IMQ | aIL22 + IMQ 2 | 0 | 0 | 1 | 2 | 2 | 2 |
| aIL22 + IMQ | aIL22 + IMQ 3 | 0 | 0 | 0 | 1 | 1 | 1 |
| aIL22 + IMQ | aIL22 + IMQ 4 | 0 | 0 | 0 | 2 | 2 | 2 |

TABLE 19

Hardness clinical scores in BL6 mice over 5 day time course (blind scored on scale 0-4)

|  |  | Day 0 | Day 1 | Day 2 | Day 3 | Day 4 | Day 5 |
| --- | --- | --- | --- | --- | --- | --- | --- |
| IgG + Vas | IgG + Vas 1 | 0 | 0 | 0 | 0 | 0 | 0 |
| IgG + Vas | IgG + Vas 2 | 0 | 0 | 0 | 0 | 0 | 0 |
| IgG + Vas | IgG + Vas 3 | 0 | 0 | 0 | 0 | 0 | 0 |
| IgG + IMQ | IgG + IMQ 1 | 0 | 0 | 1 | 2 | 3 | 3 |
| IgG + IMQ | IgG + IMQ 2 | 0 | 0 | 1 | 2 | 3 | 3 |

TABLE 19-continued

Hardness clinical scores in BL6 mice over 5 day time course (blind scored on scale 0-4)

|  |  | Day 0 | Day 1 | Day 2 | Day 3 | Day 4 | Day 5 |
|---|---|---|---|---|---|---|---|
| IgG + IMQ | IgG + IMQ 3 | 0 | 0 | 1 | 2 | 4 | 3 |
| IgG + IMQ | IgG + IMQ 4 | 0 | 0 | 1 | 2 | 4 | 3 |
| aIL22 + Vas | aIL22 + Vas 1 | 0 | 0 | 0 | 0 | 0 | 0 |
| aIL22 + Vas | aIL22 + Vas 2 | 0 | 0 | 0 | 0 | 0 | 0 |
| aIL22 + Vas | aIL22 + Vas 3 | 0 | 0 | 0 | 0 | 0 | 0 |
| aIL22 + IMQ | aIL22 + IMQ 1 | 0 | 0 | 1 | 2 | 2 | 2 |
| aIL22 + IMQ | aIL22 + IMQ 2 | 0 | 0 | 1 | 2 | 2 | 2 |
| aIL22 + IMQ | aIL22 + IMQ 3 | 0 | 0 | 1 | 1 | 2 | 1 |
| aIL22 + IMQ | aIL22 + IMQ 4 | 0 | 0 | 0 | 2 | 2 | 2 |

Both IgG and anti-IL-22 (30G1) treated mice displayed fever symptoms by Day 2 of time course, and increased spleen size at day 5 (see FIG. 27). However, at Day 1, the fever symptoms in anti-IL-22-treated mice were much less than in mice treated with control human IgG. This data indicates that anti-IL-22 antibodies of the present invention, as shown, e.g., in respect of antibody 30G1 reduce the severity of the clinical symptoms of imiquimod-induced psoriaform lesions in C57.BL/6 mice.

Wherein treatment with anti-IL-22 30G1 antibody showed therapeutic effect in the treated mice indicating the cross-reactivity of this antibody towards murine in addition to human antigens, experiments performed analogously with human specific anti-IL-17 exemplary antibody 24D3 had no effect on imiquimod-induced psoriasiform lesions validating the specificity of the 24D3 antibody towards the human antigen.

Furthermore, to investigate possible therapeutic effectiveness of anti-IL-22 antibodies of the present invention, exemplary antibody 30G1 was tested in imiquimod-induced psoriasis assay with antibody administration both pre and post imiquimod induction and in a second experiment only post the induction (see FIG. 33 for experimental timelines and treatment scheme).

APECED derived 30G1 anti-IL-22 antibody significantly reduces Psoriasis Area and Severity Index (PASI) scores relative to control IgG antibodies if administrated either pre or post IMQ-treatment. Mice treated with anti-IL-22 HDMABs of the present invention, such as the exemplary 30G1 antibody, showed a decrease of skin thickness as an indicator of skin thickness scores relative to control IgG antibodies when compared to mice treated with control IgG in both situations of prophylactic and therapeutic treatment; see skin thickness measurements shown in FIG. 38A (pre) for the prophylactic and FIG. 38B for the therapeutic treatment, 24 hours post IMQ induction. The therapeutic effect was further validated in a second experiment with an increased number of animals (see FIG. 35 for experimental timelines and treatment scheme). Mice treated with anti-IL-22 HDMABs of the present invention, such as the exemplary 30G1 antibody, showed a decrease in both the cumulative and individual scores of measurements when compared to mice treated with control IgG; see FIGS. 36 and 37. The therapeutic effect of the mouse cross-reactive, exemplary anti-IL-22 antibody 30G1 was also tested in concern of its dose-dependency in IMQ-induced psoriasis. Three different doses—200 μg, 20 μg and 2 μg—were administered post IMQ-induction and skin erythema and hardness of the plaques were evaluated as described hereinbefore. As can be seen in FIG. 38, treatment with exemplary anti-IL-22 antibody 30G1 shows indications of dose dependence in individual and cumulative scores, proving less effective when titrated down to 1/100 of the initial dose.

Thereafter, additional screens are performed, such as optical coherence tomography (OCT) imaging for epidermal thickness measurements (Morsy et al., Arch. Dermatol. Res. 302 (2010), 105-111: Phillips et al., J. Biomed. Opt. 16 (2011), 040503), RNA isolation from the animal skin and gene expression analysis in the samples for, e.g., identification of the disease-specific patterns of tissue inflammatory responses. Furthermore, FACS analysis is performed on skin single cell suspensions, whole blood or sera isolated from the animals, for sorting and/or phenotypic characterization of different cell types such as psoriatic dermal DC (dendritic cells) or peripheral blood mononuclear cell populations.

Example 7: Data Analysis of Seroactivities Identified in APECED/APS1 Patients

The following Tables 2 to 13 of seroreactivities have been identified in 23 APECED/APS1 patients following the application of their sera to Protoarray chips (Invitrogen). The data provided by Invitrogen on seroreactivity (excel spreadsheet) was taken as the basis for the following analysis:

Raw data for each protein spot was re-calculated relative to the respective cut-off (background) value. The result is termed "fold-difference" compared to background.

Filter #1: The fold-difference was then filtered by selecting only those values greater than 5-times above background.

Filter #2: The list of >5× seroreactivities was then reviewed on the basis of whether the proteins are (a) secreted (b) membrane-bound or (c) cytosolic.

With few exceptions, cytosolic proteins were excluded from further analysis.

Following filters 1 & 2, the remaining 372 seroreactivities (Tables 2 to 13), were then analyzed according to know n or putative pathophysiological functions. The resulting lists are provided in this document and consist in general of molecules involved in pathophysiological indications as enlisted in Table 1.

TABLE 1

Summary of 372 seroreactivities from ProtoArray analysis

| Pathophysiological implication | Number of antigens proving seropositive |
|---|---|
| Autoimmune & inflammatory conditions | 89 |
| Endocrinology & metabolic disorders | 14 |
| Vascular function | 34 |
| Neurodegenerative diseases | 39 |
| Oncology, cell growth & differentiation | 54 |
| Skin, bone & mucosal medical conditions | 18 |

TABLE 1-continued

Summary of 372 seroreactivities from ProtoArray analysis

| Pathophysiological implication | Number of antigens proving seropositive |
|---|---|
| Renal function, nephritis | 11 |
| Cell adhesion | 24 |
| Synapse-located proteins | 26 |
| Lipid layers | 27 |
| Protein degradation | 10 |
| Cellular counterparts of viral proteins | 26 |

TABLE 2

Autoimmune & Inflammatory conditions

| # of Pts | Description |
|---|---|
| 23 | interferon, alpha 8 (IFNA8) |
| 22 | Interferon alpha-14 |
| 22 | Interferon alpha-4 |
| 22 | interferon, alpha 2 (IFNA2) |
| 21 | Interferon alpha-1/13 |
| 20 | interferon, alpha 1 (IFNA1) |
| 20 | interleukin 22 (IL22) |
| 17 | interferon, alpha 5 (IFNA5) |
| 16 | interferon, alpha 6 (IFNA6) |
| 14 | interferon, alpha 21 (IFNA21) |
| 11 | interferon, omega 1 (IFNW1) |
| 6 | interleukin 15 (IL15), transcript variant 3 |
| 6 | Interleukin-1 family member 6 |
| 5 | cytokine receptor-like factor 3 (CRLF3) |
| 5 | NKG2-E type II integral membrane protein |
| 5 | S100 calcium binding protein A7A (S100A7A) |
| 4 | fibroblast growth factor 12 (FGF12), transcript variant 1 |
| 4 | interferon, alpha 16 (IFNA16) |
| 4 | interleukin 17A (IL17A) |
| 4 | interleukin 32 (IL32) |
| 3 | chemokine (C-C motif) ligand 26 (CCL26) |
| 3 | cystatin F (leukocystatin) (CST7) |
| 3 | tumor necrosis factor (ligand) superfamily, member 14 (TNFSF14), transcript variant 2 |
| 3 | Tumor necrosis factor receptor superfamily member 6 |
| 3 | interleukin 23, alpha subunit p19 (IL23A) |
| 3 | LYNX 1 |
| 3 | Recombinant Human Stromal Cell derived Factor-1a (SDF-1a) |
| 3 | S100 calcium binding protein A7 (S100A7) |
| 3 | selectin P ligand (SELPLG) |
| 2 | C-X-C motif chemokine 9 |
| 2 | CD300 molecule-like family member g (CD300LG) |
| 2 | CD40 molecule, TNF receptor superfamily member 5 (CD40) |
| 2 | chemokine (C-X-C motif) ligand 5 (CXCL5) |
| 2 | colony stimulating factor 1 (macrophage) (CSF1), transcript variant 1 |
| 2 | interferon induced transmembrane protein 1 (9-27) (IFITM1) |
| 2 | interferon induced transmembrane protein 2 (1-8D) (IFITM2) |
| 2 | interferon induced transmembrane protein 3 (1-8U) (IFITM3) |
| 2 | EDA 2R |
| 2 | IFI 30 |
| 2 | interleukin 1, beta (IL1B) |
| 2 | interleukin 12A (natural killer cell stimulatory factor 1, cytotoxic lymphocyte maturation factor 1, p35) (IL12A) |
| 2 | interleukin 32 (IL32), transcript variant 2 |
| 2 | Interleukin-1 alpha |
| 2 | killer cell immunoglobulin-like receptor, three domains, X1 (KIR3DX1) |
| 2 | small inducible cytokine subfamily E, member 1 (endothelial monocyte-activating) (SCYE1) |
| 1 | C-C motif chemokine 24 |
| 1 | calumenin (CALU) |
| 1 | CD53 molecule (CD53) |
| 1 | CD74 molecule, major histocompatibility complex, class II invariant chain (CD74) |
| 1 | chemokine (C-C motif) ligand 28 (CCL28), transcript variant 1 |
| 1 | chemokine (C-X-C motif) ligand 14 (CXCL14) |
| 1 | chemokine (C-X-C motif) ligand 2 (CXCL2) |
| 1 | Eotaxin |
| 1 | Interferon-induced transmembrane protein 3 |
| 1 | interferon, kappa (IFNK) |
| 1 | interleukin 1 family, member 8 (eta) (IL1F8), transcript variant 2 |
| 1 | interleukin 11 receptor, alpha (IL11RA), transcript variant 1 |
| 1 | interleukin 17 receptor E (IL17RE) |
| 1 | interleukin 2 (IL2) |
| 1 | interleukin 20 receptor beta (IL20RB) |
| 1 | interleukin 21 (IL21) |
| 1 | interleukin 26 (IL26) |
| 1 | interleukin 4 (IL4), transcript variant 1 |
| 1 | Interleukin-1 family member 10 |
| 1 | Interleukin-24 |
| 1 | Interleukin-6 |
| 1 | S100 calcium binding protein A11 (S100A11) |
| 1 | S100 calcium binding protein A14 (S100A14) |
| 1 | S100 calcium binding protein A16 (S100A16) |
| 1 | S100 calcium binding protein A2 (S100A2) |
| 1 | T cell receptor gamma variable 9, mRNA (cDNA clone MGC: 90486 IMAGE: 5755352), complete cds |
| 1 | tumor necrosis factor (ligand) superfamily, member 13b (TNFSF13B) |
| 1 | tumor necrosis factor (ligand) superfamily, member 15 (TNFSF15) |
| 1 | tumor necrosis factor (ligand) superfamily, member 8 (TNFSF8) |
| 1 | tumor necrosis factor (TNF superfamily, member 2) (TNF) |
| 1 | tumor necrosis factor receptor superfamily, member 19 (TNFRSF19), transcript variant 2 |
| 1 | advanced glycosylation end product-specific receptor (AGER), transcript variant 1 |
| 1 | fibromodulin (FMOD) |
| 1 | G protein-coupled receptor 77 (GPR77) |
| 1 | Gremlin-1 |
| 1 | histamine receptor H1 (HRH1), transcript variant 4 |
| 1 | killer cell lectin-like receptor subfamily D, member 1 (KLRD1), transcript variant 1 |
| 1 | killer cell lectin-like receptor subfamily G, member 1 (KLRG1) |
| 1 | KIT ligand (KITLG), transcript variant b |
| 1 | Macrophage stimulating protein receptor |
| 1 | oncostatin M (OSM) |
| 1 | pro-platelet basic protein (chemokine (C-X-C motif) ligand 7) (PPBP) |
| 1 | SLAM family 8 |

TABLE 3

Endocrinology and Metabolic conditions

| # of Pts | Description |
|---|---|
| 3 | gastric intrinsic factor (vitamin B synthesis) (GIF) |
| 3 | ghrelin/obestatin preprohormone (GHRL) |
| 2 | chorionic gonadotropin, beta polypeptide (CGB) |
| 2 | CFHR2 |
| 2 | G protein-coupled receptor 78 (GPR78) |
| 2 | Growth hormone 1 |
| 2 | proopiomelanocortin (POMC), transcript variant 2 |
| 2 | thyroid hormone receptor, alpha (v-erb-a) oncogene homolog, avian |
| 2 | Urocortin-3 |
| 1 | chorionic somatomammotropin hormone 1 (placental lactogen) (CSH1) |
| 1 | neuromedin B (NMB) |
| 1 | neuropeptide Y receptor Y2 (NPY2R) |
| 1 | Thyroid hormone receptor alpha |
| 1 | thyroid hormone receptor, alpha (v-erb-a) oncogene homolog, avian) variant 1 |

TABLE 4

Vascular function

| # of Pts | Description |
|---|---|
| 7 | fms-related tyrosine kinase 1 (FLT1) |
| 7 | Malcavernin |
| 5 | endothelin converting enzyme 1 (ECE1) |
| 5 | Recombinant human VEGF |
| 5 | vasohibin 1 (VASH1) |
| 4 | angiopoietin 1 (ANGPT1) |
| 4 | angiotensin II receptor-associated protein (AGTRAP) |
| 4 | relaxin/insulin-like family peptide receptor 3 (RXFP3) |
| 3 | endothelin 2 (EDN2) |
| 2 | endothelin receptor type B (EDNRB), transcript variant 1 |
| 2 | ephrin receptor B4 (EPHB4) |
| 2 | EGF-like domain-containing protein 7 |
| 2 | fibroblast growth factor 16 (FGF16) |
| 2 | Plasminogen activator inhibitor 2 |
| 2 | urotensin 2 domain containing |
| 1 | endothelial differentiation, sphingolipid G-protein-coupled receptor, 3 (EDG3) |
| 1 | endothelin 3 (EDN3) |
| 1 | endothelin converting enzyme 2 (ECE2), transcript variant 3 |
| 1 | Endothelin-1 |
| 1 | ephrin receptor B4 (EPHB4) |
| 1 | Vasohibin-2 |
| 1 | adrenomedullin (ADM) |
| 1 | AHSG |
| 1 | Angiogenic factor with G patch and FHA domains 1 |
| 1 | angiopoietin-like 7 (ANGPTL7) |
| 1 | Ephrin type-B receptor 1 |
| 1 | fibroblast growth factor 1 (acidic) (FGF1), transcript variant 1 |
| 1 | fms-related tyrosine kinase 4 (FLT4), transcript variant 2 |
| 1 | matrix metallopeptidase 19 (MMP19), transcript variant 1 |
| 1 | Nostrin |
| 1 | syndecan 1 (SDC1) |
| 1 | Tafazzin |
| 1 | thrombomodulin |
| 1 | tissue factor pathway inhibitor 2 (TFPI2) |

TABLE 5

Neurodegenerative diseases

| # of Pts | Description |
|---|---|
| 7 | Ermin |
| 6 | Calpastatin |
| 5 | GABA(A) receptor-associated protein like 1 (GABARAPL1) |
| 5 | Synphilin-1 |
| 4 | ataxin 3 (ATXN3) |
| 4 | presenilin 1 (Alzheimer disease 3) (PSEN1) |
| 3 | chloride channel 2 (CLCN2) |
| 3 | huntingtin interacting protein 1 (HIP1) |
| 3 | myelin-associated oligodendrocyte basic protein (MOBP) |
| 2 | ninjurin 2 (NINJ2) |
| 2 | Paralemmin-2 |
| 2 | colony stimulating factor 1 receptor, formerly McDonough feline sarcoma viral (v-fms) oncogene homolog (CSF1R) |
| 2 | Amyotrophic lateral sclerosis 2 chromosomal region candidate gene 4 protein |
| 2 | cystatin B (stefin B) (CSTB) |
| 2 | Huntingtin-interacting protein 1-related protein |
| 2 | myelin associated glycoprotein (MAG), transcript variant 2 |
| 2 | neurensin 1 (NRSN1) |
| 2 | Parkin co-regulated gene protein |
| 2 | roundabout, axon guidance receptor, homolog 3 (*Drosophila*) (ROBO3) |
| 2 | serum amyloid A4, constitutive (SAA4) |
| 1 | paralemmin 2 (PALM2) |
| 1 | Cerebellin-4 |
| 1 | Ataxin-7-like protein 3 |
| 1 | endothelial differentiation, sphingolipid G-protein-coupled receptor, 1 (EDG1) |
| 1 | Parkinson disease (autosomal recessive, early onset) 7 (PARK7) |

TABLE 5-continued

Neurodegenerative diseases

| # of Pts | Description |
|---|---|
| 1 | amyloid beta (A4) precursor protein (peptidase nexin-II, Alzheimer disease) |
| 1 | amyotrophic lateral sclerosis 2 (juvenile) (ALS2) |
| 1 | DBI 1 |
| 1 | glutamate receptor, ionotropic, N-methyl D-aspartate-like 1A (GRINL1A), transcript variant 1 |
| 1 | Huntingtin-interacting protein M |
| 1 | Kalirin |
| 1 | Myelin protein zero-like protein 1 |
| 1 | neuritin 1 (NRN1) |
| 1 | Neuroplastin |
| 1 | ninjurin 1 (NINJ1) |
| 1 | Noelin |
| 1 | paralemmin (PALM) |
| 1 | prepronociceptin (PNOC) |
| 1 | transthyretin (prealbumin, amyloidosis type I) (TTR) |

TABLE 6

Oncology, Cell Growth and Differentiation

| # of Pts | Description |
|---|---|
| 7 | epidermal growth factor receptor (v-erb-b) (EGFR) |
| 7 | PDGFA associated protein 1 (PDAP1) |
| 6 | melanoma antigen family B, 2 (MAGEB2) |
| 6 | SPANX family, member B1 (SPANXB1) |
| 5 | Melanoma-associated antigen 3 |
| 4 | Melanoma-associated antigen 2 |
| 4 | Serologically defined colon cancer antigen 3 |
| 4 | SPANX family, member C (SPANXC) |
| 3 | antigen p97 (melanoma associated) transcript variant 2 |
| 3 | fibroblast growth factor 13 (FGF13), transcript variant 1B |
| 3 | fibroblast growth factor binding protein 2 (FGFBP2) |
| 3 | leukemia inhibitory factor (cholinergic differentiation factor) (LIF) |
| 3 | melanoma antigen family A, 12 (MAGEA12) |
| 3 | Podoplanin |
| 3 | Prostate stem cell antigen |
| 3 | TIMP 1 |
| 2 | B melanoma antigen 2 |
| 2 | cancer/testis antigen family 45, member A1 (CT45A1), mRNA. |
| 2 | activin A receptor, type IB (ACVR1B), transcript variant 1 |
| 2 | Activin receptor type-2B |
| 2 | Growth factor receptor-bound protein 7 |
| 2 | Melanoma-associated antigen 2 |
| 2 | platelet-derived growth factor beta polypeptide (v-sis) variant 1 |
| 2 | TIMP 4 |
| 2 | X antigen family, member 2 (XAGE2) |
| 1 | cancer/testis antigen CT45-3 (CT45-3) |
| 1 | Ephrin receptor A3 (EPHA3), transcript variant 1 |
| 1 | ephrin-A1 (EFNA1) |
| 1 | epidermal growth factor receptor (v-erb-b), avian) (EGFR) |
| 1 | epidermal growth factor receptor (v-erb-b)) (EGFR) |
| 1 | melanoma antigen family H, 1 (MAGEH1) |
| 1 | activin A receptor, type IC (ACVR1C) |
| 1 | ALK tyrosine kinase receptor |
| 1 | EGF-like repeats and discoidin I-like domains 3 (EDIL3) |
| 1 | EGF-like-domain, multiple 8 (EGFL8) |
| 1 | EGF-like, fibronectin type III and laminin G domains variant 4 |
| 1 | fibroblast growth factor 12 (FGF12) |
| 1 | fibroblast growth factor 13 (FGF13), transcript variant 1A |
| 1 | Fibroblast growth factor 18 |
| 1 | fibroblast growth factor binding protein 1 (FGFBP1) |
| 1 | Fibroblast growth factor receptor 4 |
| 1 | fibroblast growth factor receptor substrate 3 (FRS3) |
| 1 | follistatin (FST), transcript variant FST344 |
| 1 | G antigen 4 |
| 1 | G antigen 7 (GAGE7) |
| 1 | growth factor, augmenter of liver regeneration (ERV1 homolog) |
| 1 | leukocyte-associated immunoglobulin-like receptor 1 variant a |
| 1 | mucin-like 1 (MUCL1) |

TABLE 6-continued

Oncology, Cell Growth and Differentiation

| # of Pts | Description |
|---|---|
| 1 | MPP1 |
| 1 | P antigen family, member 2 (prostate associated) (PAGE2) |
| 1 | Proto-oncogene tyrosine-protein kinase receptor ret |
| 1 | ret proto-oncogene (RET), transcript variant 4 |
| 1 | Tesmin |
| 1 | trefoil factor 2 (spasmolytic protein 1) (TFF2) |

TABLE 7

Skin, bone and mucosal medical conditions

| # of Pts | Description |
|---|---|
| 5 | sciellin (SCEL) |
| 5 | Suprabasin |
| 5 | Tyrosine-protein kinase transmembrane receptor ROR2 |
| 4 | odontogenic, ameloblast asssociated (ODAM) |
| 3 | Vitamin D receptor |
| 2 | ectodysplasin A2 receptor (EDA2R) |
| 2 | Keratin 15 |
| 2 | Keratinocyte growth factor |
| 1 | Defensin-5 |
| 1 | Parathyroid related protein |
| 1 | Bone morphogenetic protein 3b |
| 1 | bone morphogenetic protein 7 (osteogenic protein 1) (BMP7) |
| 1 | bone morphogenetic protein 8a, mRNA (cDNA clone IMAGE: 7939588), complete cds. |
| 1 | CLCF1 |
| 1 | fibroblast growth factor 10 (FGF10) |
| 1 | osteoclast stimulating factor 1 (OSTF1) |
| 1 | osteoglycin (OGN), transcript variant 1 |
| 1 | Tff2 |

TABLE 8

Renal function & nephritis

| # of Pts | Description |
|---|---|
| 20 | tubulointerstitial nephritis antigen-like 1 (TINAGL1) |
| 4 | aquaporin 2 (collecting duct) (AQP2) |
| 3 | arginine vasopressin-induced 1 (AVPI1) |
| 2 | platelet-derived growth factor receptor, alpha polypeptide (PDGFRA); |
| 1 | aquaporin 8 (AQP8) |
| 1 | aquaporin 8 (AQP8) |
| 1 | beta 2 microglobulin |
| 1 | CFHR 1 |
| 1 | platelet-derived growth factor receptor, alpha polypeptide (PDGFRA); |
| 1 | platelet-derived growth factor receptor, alpha polypeptide (PDGFRA); |
| 1 | Uromodulin |

TABLE 9

Cell adhesion

| # of Pts | Description |
|---|---|
| 10 | ladinin 1 (LAD1) |
| 4 | Ezrin |
| 3 | Fibronectin 1 |
| 3 | gap junction protein, beta 5 (GJB5) |

TABLE 9-continued

Cell adhesion

| # of Pts | Description |
|---|---|
| 3 | glycoprotein IX (platelet) (GP9) |
| 3 | Nephrocystin-1 |
| 3 | symplekin (SYMPK) |
| 3 | vitronectin (VTN) |
| 2 | integrin beta 3 binding protein (beta3-endonexin) (ITGB3BP) |
| 2 | beta sarcoglycan |
| 2 | dermatopontin (DPT) |
| 2 | EGF-containing fibulin-like extracellular matrix protein 1 (EFEMP1), transcript variant 2 |
| 2 | integrin-linked kinase-associated serine/threonine phosphatase 2C (ILKAP) |
| 1 | Gap junction alpha-4 protein |
| 1 | Gap junction beta-2 protein |
| 1 | gap junction protein, alpha 10, 59 kDa (GJA10) |
| 1 | gap junction protein, beta 4 (GJB4) |
| 1 | gap junction protein, beta 7 (GJB7) |
| 1 | integrin beta 1 binding protein 3 (ITGB1BP3) |
| 1 | Integrin-linked protein kinase |
| 1 | latrophilin 1 (LPHN1), transcript variant 2 |
| 1 | MPP 7 |
| 1 | uroplakin 3A (UPK3A) |
| 1 | uroplakin 3B (UPK3B), transcript variant 2 |

TABLE 10

Synapse-located proteins

| # of Pts | Description |
|---|---|
| 14 | syntaxin binding protein 1 |
| 9 | secretogranin III (SCG3) |
| 9 | SNAP 25 transcript variant 1 |
| 5 | syntaxin 3 (STX3) |
| 5 | SNAP23 |
| 4 | Neuropilin and tolloid-like protein 2 |
| 4 | Syntaxin-1B |
| 4 | Syntaxin-2 |
| 3 | syntaxin binding protein 5 |
| 3 | Syntaxin-10 |
| 2 | potassium voltage-gated channel, shaker-related subfamily, beta member 3 (KCNAB3) |
| 2 | potassium voltage-gated channel, shaker-related subfamily, member 2 (KCNA2) |
| 2 | complexin 1 (CPLX1) |
| 2 | complexin 2 (CPLX2), transcript variant 2 |
| 2 | Copine-6 |
| 2 | Secretagogin |
| 2 | synaptobrevin 1 |
| 2 | synaptotagmin IX (SYT9) |
| 1 | KCTD6 |
| 1 | KCTD7 |
| 1 | potassium inwardly-rectifying channel, subfamily J, member 15 (KCNJ15), transcript variant 2 |
| 1 | sodium channel, voltage-gated, type II, beta (SCN2B) |
| 1 | syntaxin binding protein 1 |
| 1 | Synaptobrevin 2 |
| 1 | Synaptotagmin I (SYT1) |
| 1 | synaptotagmin VI (SYT6) |
| 1 | Syndecan-1 |
| 1 | copine II (CPNE2) |
| 1 | gamma-aminobutyric acid (GABA) A receptor, alpha 4 (GABRA4) |
| 1 | gamma-aminobutyric acid (GABA) A receptor, epsilon (GABRE) |
| 1 | syntaxin 11 (STX11) |
| 1 | syntaxin 5 (STX5) |

TABLE 11

Lipid layers

| # of Pts | Description |
|---|---|
| 5 | annexin A11 (ANXA11), transcript variant a |
| 2 | Apolipoprotein A-I-binding protein |
| 2 | Apolipoprotein L2 |
| 2 | apolipoprotein O-like (APOOL) |
| 2 | potassium channel, subfamily K, member 5 (KCNK5) |
| 2 | Potassium channel tetradimerization 6 |
| 1 | apolipoprotein C-IV (APOC4) |
| 1 | apolipoprotein H (beta-2-glycoprotein I) (APOH) |
| 1 | annexin A10 (ANXA10) |
| 1 | annexin A2 (ANXA2) |
| 1 | annexin A2 (ANXA2) |
| 1 | flotillin 2 (FLOT2) |
| 3 | annexin A2 (ANXA2), transcript variant 3 |
| 1 | Endothelial lipase |
| 1 | Plasmolipin |
| 1 | lipocalin 1 (tear prealbumin) (LCN1) |
| 1 | phospholipase B1 (PLB1) |
| 1 | phospholipase C, delta 4 (PLCD4) |
| 1 | Phospholipase D1 |

TABLE 12

Protein degradation

| # of Pts | Description |
|---|---|
| 4 | PEX12 |
| 3 | let M2 |
| 3 | Secernin-3 |
| 2 | kallikrein 1 (KLK1) |
| 1 | Kallikrein-1 |
| 1 | Kallikrein-6 |
| 1 | kallikrein-related peptidase 13 (KLK13) |
| 1 | kallikrein-related peptidase 2 (KLK2), transcript variant 3 |
| 1 | kallikrein-related peptidase 6 (KLK6), transcript variant A |
| 1 | Myeloblastin |

TABLE 13

Cellular counterparts of viral proteins

| # of Pts | Description |
|---|---|
| 8 | v-rel nuclear factor of kappa light polypeptide gene enhancer in B-cells 3, p65 (RELA) |
| 6 | v-abl (ABL1), transcript variant a |
| 4 | v-abl (ABL1), transcript variant a |
| 4 | v-abl (arg, Abelson-related gene) (ABL2), transcript variant a |
| 4 | v-ets erythroblastosis virus E26 oncogene homolog 2 (avian) (ETS2) |
| 3 | v-akt murine thymoma viral oncogene homolog 1 (AKT1) |
| 3 | v-ets erythroblastosis virus E26 oncogene homolog 1 (avian) (ETS1) |
| 2 | v-abl (ABL1), transcript variant a |
| 2 | v-akt murine thymoma viral oncogene homolog 2 (AKT2) |
| 2 | v-akt (protein kinase B, gamma) (AKT3), transcript variant 2 |
| 2 | v-crk sarcoma virus CT10 oncogene homolog (avian)-like (CRKL) |
| 2 | v-ets erythroblastosis virus E26 oncogene homolog (avian) (ERG), transcript variant 2 |
| 2 | v-fos FBJ murine osteosarcoma viral oncogene homolog (FOS) |
| 2 | v-raf murine sarcoma viral oncogene homolog B1 (BRAF) |
| 2 | HIV-1 Rev binding protein (HRB) |
| 1 | v-abl (ABL1), transcript variant a |
| 1 | v-abl (ABL1), transcript variant a |
| 1 | v-akt (protein kinase B, gamma) (AKT3), transcript variant 1 |
| 1 | v-erb-b2 oncogene homolog (ERBB2), transcript variant 2 |
| 1 | v-kit Hardy-Zuckerman 4 (KIT), transcript variant 1 |
| 1 | v-raf murine sarcoma 3611 viral oncogene homolog (ARAF) |
| 1 | v-raf-1 murine leukemia viral oncogene homolog 1 (RAF1) |
| 1 | v-ral B (ras related; GTP binding protein) (RALB) |
| 1 | HIV-1 Rev binding protein-like (HRBL) |
| 1 | HIV-1 Tat interacting protein, 60 kDa (HTATIP) |
| 1 | HIV-1 Tat interacting protein, 60 kDa (HTATIP), transcript variant 2 |

TABLE 24

Localization of exemplary coiled-coil protein encoding gene sequences on human chromosomes. UniGene/EntrezGene - Database identification numbers of the respective proteins, EnsemblChr. - localization of the respective gene sequence on a human chromosome as indicated in the Ensembl-Database with the detailed localization on the chromosome indicated in basepairs in the Start/End columns. Strand - localization of the gene on the sense (1) or antisense/complementary strand (−1) of the chromosome.

| Gene Name | UniGene | Entrez Gene | Description | Ensembl Chr. | Start (bp) | End (bp) | Strand |
|---|---|---|---|---|---|---|---|
| AFAP1L2 | Hs.501106 | 84632 | Actin filament associated protein 1-like 2 | 10 | 116044575 | 116154505 | −1 |
| ANKRD13A | Hs.528703 | 88455 | Ankyrin repeat domain 13A | 12 | 108921618 | 108961614 | 1 |
| APPL1 | Hs.476415 | 26060 | Adaptor protein, phosphotyrosine interaction, PH domain and leucine zipper containing 1 | 3 | 57236805 | 57282539 | 1 |
| ARGLU1 | Hs.508644 | 55082 | Hypothetical protein FLJ10154 | 13 | 105992022 | 106018513 | −1 |
| ARHGEF1 | Hs.631550 | 9138 | Rho guanine nucleotide exchange factor (GEF) 1 | 19 | 47079106 | 47103437 | 1 |
| ASZ1 | Hs.352412 | 136991 | Ankyrin repeat, SAM and basic leucine zipper domain containing 1 | 7 | 116790512 | 116854779 | −1 |

TABLE 24-continued

Localization of exemplary coiled-coil protein encoding gene sequences on human chromosomes.
UniGene/EntrezGene - Database identification numbers of the respective proteins,
EnsemblChr. - localization of the respective gene sequence on a human chromosome
as indicated in the Ensembl-Database with the detailed localization on the
chromosome indicated in basepairs in the Start/End columns. Strand - localization
of the gene on the sense (1) or antisense/complementary strand (−1) of the chromosome.

| Gene Name | UniGene | Entrez Gene | Description | Ensembl Chr. | Start (bp) | End (bp) | Strand |
|---|---|---|---|---|---|---|---|
| ATF6 | Hs.492740 | 22926 | Activating transcription factor 6 | 1 | 160194974 | 160199592 | 1 |
| BBX | Hs.124366 | 56987 | Bobby sox homolog (Drosophila) | 3 | 108724480 | 109007396 | 1 |
| C10orf118 | Hs.159066 | 55088 | Chromosome 10 open reading frame 118 | 10 | 115871964 | 115924354 | −1 |
| C10orf80 | Hs.253576 | 159686 | Chromosome 10 open reading frame 80 | 10 | 106103513 | 106204855 | 1 |
| C3orf44 | Hs.147128 | 131831 | Chromosome 3 open reading frame 44 | 3 | 151860367 | 151904432 | −1 |
| C6orf65 | Hs.582993 | 221336 | Chromosome 6 open reading frame 65 | 6 | 56928047 | 57000099 | 1 |
| CCDC12 | Hs.631918 | 151903 | Coiled-coil domain containing 12 | 3 | 46938225 | 46993242 | −1 |
| CCDC25 | Hs.445512 | 55246 | Coiled-coil domain containing 25 | 8 | 27646756 | 27686089 | −1 |
| CCDC40 | Hs.202542 | 55036 | Coiled-coil domain containing 40 | 17 | 75625033 | 75689007 | 1 |
| CEP290 | Hs.150444 | 80184 | Centrosomal protein 290 kDa | 12 | 86966922 | 87060124 | −1 |
| CHCHD6 | Hs.518119 | 84303 | Coiled-coil-helix-coiled-coil-helix domain containing 6 | 3 | 127908884 | 127910183 | 1 |
| CORO2A | Hs.113094 | 7464 | Coronin, actin binding protein, 2A | 9 | 99926299 | 99994743 | −1 |
| CRLF3 | Hs.370168 | 51379 | Cytokine receptor-like factor 3 | 17 | 26133852 | 26175826 | −1 |
| DBNL | Hs.436500 | 28988 | Drebrin-like | 3 | 10265372 | 10297900 | 1 |
| FAM133A | Hs.110069 | 286499 | Family with sequence similarity 133, member A | X | 92815861 | 92853917 | 1 |
| FAM76B | Hs.288304 | 143684 | Family with sequence similarity 76, member B | 11 | 95141765 | 95162429 | −1 |
| FOSL2 | Hs.220971 | 2355 | FOS-like antigen 2 | 2 | 28469173 | 28493683 | 1 |
| GNL3L | Hs.654677 | 54552 | Guanine nucleotide binding protein-like 3 (nucleolar)-like | X | 54570464 | 54608698 | 1 |
| HDAC9 | Hs.196054 | 9734 | Histone deacetylase 9 | 7 | 18584321 | 19003509 | 1 |
| HELLS | Hs.655830 | 3070 | Helicase, lymphoid-specific | 8 | 29249539 | 29264104 | −1 |
| HIRIP3 | Hs.592046 | 8479 | HIRA interacting protein 3 | 16 | 29911818 | 29914888 | −1 |
| HOMER3 | Hs.410683 | 9454 | Homer homolog 3 (Drosophila) | 19 | 18901012 | 18912983 | −1 |
| KIAA0562 | Hs.509017 | 9731 | KIAA0562 | 1 | 3721204 | 3763657 | −1 |
| KIF20A | Hs.73625 | 10112 | Kinesin family member 20A | 5 | 137542586 | 137551303 | 1 |
| KIF3A | Hs.43670 | 11127 | Kinesin family member 3A | 5 | 132056222 | 132101164 | −1 |
| KIF3B | Hs.369670 | 9371 | Kinesin family member 3B | 20 | 30329128 | 30386468 | 1 |
| KLC3 | Hs.298079 | 147700 | Kinesin light chain 3 | 19 | 50535838 | 50546618 | 1 |
| MED4 | Hs.181112 | 29079 | Mediator complex subunit 4 | 13 | 47548093 | 47567268 | −1 |
| NAP1L1 | Hs.524599 | 4673 | Nucleosome assembly protein 1-like 1 | 12 | 74726227 | 74764717 | −1 |
| NFE2 | Hs.75643 | 4778 | Nuclear factor (erythroid-derived 2), 45 kDa | 1 | 226679169 | 226679649 | −1 |
| NRBF2 | Hs.449628 | 29982 | Nuclear receptor binding factor 2 | 10 | 64563056 | 64584789 | 1 |
| PHF11 | Hs.369039 | 51131 | PHD finger protein 11 | 13 | 48967817 | 49001118 | 1 |
| PIBF1 | Hs.441926 | 10464 | Progesterone immunomodulatory binding factor 1 | 10 | 16672616 | 16899468 | −1 |
| PKNOX2 | Hs.696454 | 63876 | PBX/knotted 1 homeobox 2 | 11 | 124539769 | 124808495 | 1 |
| RBM17 | Hs.498548 | 84991 | RNA binding motif protein 17 | 10 | 6171013 | 6198843 | 1 |

TABLE 24-continued

Localization of exemplary coiled-coil protein encoding gene sequences on human chromosomes.
UniGene/EntrezGene - Database identification numbers of the respective proteins,
EnsemblChr. - localization of the respective gene sequence on a human chromosome
as indicated in the Ensembl-Database with the detailed localization on the
chromosome indicated in basepairs in the Start/End columns. Strand - localization
of the gene on the sense (1) or antisense/complementary strand (−1) of the chromosome.

| Gene Name | UniGene | Entrez Gene | Description | Ensembl Chr. | Start (bp) | End (bp) | Strand |
|---|---|---|---|---|---|---|---|
| SCYL1 | Hs.238839 | 57410 | SCY1-like 1 (*S. cerevisiae*) | 11 | 65049124 | 65062758 | 1 |
| SEPT2 | Hs.335057 | 4735 | Septin 2 | 6 | 27941013 | 27941585 | 1 |
| SLU7 | Hs.435342 | 10569 | SLU7 splicing factor homolog (*S. cerevisiae*) | 18 | 59473412 | 59480119 | −1 |
| SMTNL2 | Hs.441709 | 342527 | Smoothelin-like 2 | 17 | 4434043 | 4458363 | 1 |
| SNCAIP | Hs.426463 | 9627 | Synuclein, alpha interacting protein (synphilin) | 5 | 121675719 | 121827693 | 1 |
| STX2 | Hs.437585 | 2054 | Syntaxin 2 | 12 | 129840102 | 129889764 | −1 |
| ZMYND11 | Hs.292265 | 10771 | Zinc finger, MYND domain containing 11 | 1 | 148161834 | 148166860 | −1 |
| TEKT2 | Hs.127111 | 27285 | Tektin 2 (testicular) | 1 | 36322263 | 36326462 | 1 |
| TLE3 | Hs.287362 | 7090 | Transducin-like enhancer of split 3 (E(sp1) homolog, *Drosophila*) | c6_QB | 31500463 | 31516090 | 1 |
| TRIM15 | Hs.591789 | 89870 | Tripartite motif-containing 15 | c6_CO | 30268170 | 30277650 | 1 |
| TRIM22 | Hs.501778 | 10346 | Tripartite motif-containing 22 | 11 | 5667495 | 5688668 | 1 |
| TRIM29 | Hs.504115 | 23650 | Tripartite motif-containing 29 | 11 | 119487205 | 119514073 | −1 |
| TRIM69 | Hs.489254 | 140691 | Tripartite motif-containing 69 | 15 | 42832407 | 42847317 | + |
| TTLL7 | Hs.445826 | 79739 | Tubulin tyrosine ligase-like family, member 7 | 1 | 84107645 | 84237421 | −1 |
| UBE2O | Hs.16130 | 63893 | Ubiquitin-conjugating enzyme E2O | 17 | 71897491 | 71960883 | −1 |
| USP47 | Hs.577256 | 55031 | Ubiquitin specific peptidase 47 | 11 | 11819546 | 11937448 | 1 |
| VAPA | Hs.699980 | 9218 | VAMP (vesicle-associated membrane protein)-associated protein A, 33 kDa | 13 | 78071237 | 78075696 | −1 |
| WTAP | Hs.446091 | 9589 | Wilms tumor 1 associated protein | 6 | 160068142 | 160097339 | 1 |

TABLE 14

Presence of auto-antibodies binding to indicated targets in APS1 patients shown by ELISA-assay

| Target | Synonym | Highest elisa titer (reciprocal) | Patients with this titer |
|---|---|---|---|
| IL-1 alpha | | 1 250 | APS1-2 |
| IL-1F6 | IL-36 alpha | 1 250 | APS1-5 |
| IL-1F9 | IL-36 gamma | 1 250 | APS1-7, -23 |
| IL-5 | | 6 250 | APS1-18 |
| IL-7 | | 1 250 | APS1-1, -3, -16 |
| IL-11 | | >250 | APS1-7 |
| IL-17A | CTLA-8 | 6 250 | APS1-13, -18, -20, -22 |
| IL-17F | | 6 250 | APS1-08, -13, -14, -16, -18 |
| IL-22 | | 31 250 | APS1-2, -10, -14, -16, -19, -22 |
| IL-32 alpha | | >4 000 | APS1-2, APS1-28 |
| IL-32 gamma | | >4 000 | APS1-2, APS1-28 |
| IFN-alpha 1beta | | 31 250 | APS1-08, -14, -15, -16, -17, -19, -22 |
| IFNA2 | | >128 000 | APS1-05, APS1-09, APS1-16, APS1-17, APS1-18, APS1-19, APS1-22. APS1-23, APS1-24, APS1-26, APS1-28 |

TABLE 14-continued

Presence of auto-antibodies binding to indicated targets in APS1 patients shown by ELISA-assay

| Target | Synonym | Highest elisa titer (reciprocal) | Patients with this titer |
|---|---|---|---|
| IFNA4 | | >135 000 | APS1-05, APS1-14, APS1-15, APS1-16, APS1-19, APS1-22, APS1-24, APS1-28 |
| IFNA14 | | >135 000 | APS1-07, APS1-08, APS1-09, APS1-10, APS1-14, APS1-15, APS1-16, APS1-17, APS1-18, APS1-19, APS1-20, APS1-21, APS1-22, APS1-23, APS1-24, APS1-26, APS1-27, APS1-28, APS1-30 |
| CCL2 | MCP-1 | >250 | APS1-2 |
| CCL13 | MCP-4 | >250 | APS1-4, APS1-5 |
| CCL4 | MIP-1-alpha | >250 | APS1-4 |
| CCL15 | MIP-5 | >250 | APS1-11, APS1-13, APS1-14 |
| CCL22 | MDC | >250 | APS1-6 |
| CCL25 | TECK | >250 | APS1-5, APS1-7 |
| CCL11 | Eotaxin | >250 | APS1-9, APS1-10, APS1-13 |
| CCL21 | Exodus2 | >250 | APS1-9, APS1-10 |
| CXCL9 | MIG | 12 800 | APS1-09 |
| CXCL10 | IP-10 | >4 000 | APS1-04 |
| CXCL11 | I-TAC | >4 000 | APS1-09 |
| Sclerostin | SOST | 6 400 | APS1-03, APS1-12 |
| BLyS | BAFF | >16 000 | APS1-05 |
| S100A7 | PSOR1 | 1 000 | APS1-17 |
| TMEFF2 | | 6 400 | APS1-05 |

TABLE 15

List of recombinant proteins used in the Elisa assays

| Target | Synonym | Provider | Catalog number | Source | Lyophilized from a solution containing | Comments |
|---|---|---|---|---|---|---|
| Asporin | ASPN | Novus Biologicals | H00054829-P01 | Wheat germ expression system | 50 mM Tris-HCl, 10 mM reduced Glutathione, pH 8.0 in the elution buffer | Human ASPN full-length ORF (AAH63114.1, 1 a.a. - 384 a.a.) recombinant protein with GST-tag at N-terminal. |
| BAFF | BLyS, CD257 | Immunotools | 11343430 | E. coli | PBS, pH 7.0 | |
| BAFF | BLyS, CD257 | R&D | 2149-BF-010/CF | mouse myeloma cell line, NS0-derived | | |
| CCL1 | I-309 | Immunotools | 11343843 | E. coli | no additives | |
| CCL2 | MCP-1 | Immunotools | 11343384 | E. coli | no additives | |
| CCL3 | MIP1-alpha | Immunotools | 11343204 | E. coli | no additives | |
| CCL4 | MIP1-beta | Immunotools | 11343223 | E. coli | no additives | |
| CCL7 | MCP-3 | Immunotools | 11343903 | E. coli | no additives | |
| CCL8 | MCP-2 | Immunotools | 11343893 | E. coli | no additives | |
| CCL11 | Eotaxin | Immunotools | 11343213 | E. coli | 20 mM PB, pH 7.4, 130 mM NaCl | |
| CCL13 | MCP-4 | Immunotools | 11343923 | E. coli | 20 mM PBS pH 7.4, 100 mM NaCl | |
| CCL15 | MIP-5 | Immunotools | 11343864 | E. coli | 20 mM PBS pH 7.4, 100 mM NaCl | |
| CCL16 | LEC/NCC-4 | Immunotools | 11344164 | E. coli | 20 mM PBS pH 7.4, 0.15M sodium chloride | |
| CCL17 | TARC | Immunotools | 11344504 | E. coli | 20 mM PBS, 150 mM NaCl, pH 7.4 | |
| CCL18 | MIP4 | Immunotools | 11343253 | E. coli | 20 mM PBS pH 7.4, 100 mM NaCl | |
| CCL19 | MIP-3 beta | Immunotools | 11343244 | E. coli | no additives | |
| CCL20 | MIP-3 alpha | Immunotools | 11343264 | E. coli | no additives | |
| CCL21 | Exodus-2 | Immunotools | 11343184 | E. coli | no additives | |
| CCL22 | MDC | Immunotools | 11344334 | E. coli | 20 mM PB, 500 mM NaCl, pH 7.4 | |
| CCL24 | Eotaxin-2 | Immunotools | 11344174 | E. coli | 20 mM PBS pH 7.4, 150 mM NaCl | |
| CCL25 | TECK | Immunotools | 11344374 | E. coli | 20 mM PBS pH 7.4, 150 mM NaCl | |
| CCL26 | Eotaxin-3 | R&D Systems | 346-E3-025CF | E. coli | 30% (v/v) acetonitrile, 0.1% (v/v) TFA | |
| CCCL26 | Eotaxin-3 | Creative Biomart | CCL26-72H | E. coli | | |

TABLE 15-continued

List of recombinant proteins used in the Elisa assays

| Target | Synonym | Provider | Catalog number | Source | Lyophilized from a solution containing | Comments |
|---|---|---|---|---|---|---|
| CCL28 | Mec | Immunotools | 11344204 | E. coli | 20 mM PBS pH 7.4, 150 mM NaCl | Concentration 500 ug/ml |
| CTLA-4 | | Immunotools | 11348025 | Sf9 cells | no additives | |
| CXCL1 | GRO-alpha | Immunotools | 11343704 | E. coli | no additives | |
| CXCL2 | GRO beta | Immunotools | 11343713 | E. coli | no additives | |
| CXCL3 | GRO-gamma | Immunotools | 11343723 | E. coli | no additives | |
| CXCL5 | ENA-78 | Immunotools | 11344344 | E. coli | no additives | |
| CXCL7 | NAP-2 | Immunotools | 11343393 | E. coli | no additives | |
| CXCL8 | IL-8 | Immunotools | 11340084 | E. coli | PBS, pH 7.4 | |
| CXCL9 | MIG | R&D Systems | 392-MG-010/CF | E. coli | no additives | |
| CXCL9 | MIG | BioLegend | 578108 | E. coli | no additives | |
| CXCL10 | IP-10 | Immunotools | 11343884 | E. coli | no additives | |
| CXCL10 | | Creative Biomart | CXCL10-08H | E. coli | Lyophilized from a 0.2 μm filtered concentrated (0.5 mg/ml) solution in 20 mM PB, pH 7.4, 50 mM NaCl | |
| CXCL11 | I-TAC | Immunotools | 11343374 | E. coli | no additives | |
| CXCL11 | I-TAC | Creative Biomart | CXCL11-09H | E. Coli | Lyophilized from a 0.2 μm filtered concentrated (0.5 mg/ml) solution in 20 mM PB, pH 7.4,100 mM NaCl. > 97% purity | |
| CXCL12a | SDF-1a | Immunotools | 11343363 | E. coli | no additives | |
| CXCL12b | SDF-1b | Immunotools | 11343933 | E. coli | no additives | |
| CXCL13 | BCA-1 | Immunotools | 11344184 | E. coli | 20 mM PBS, 150 mM NaCl pH 7.4 | |
| CXCL14 | BRAK | R&D Systems | 866-CX-025 | E. coli | PBS | Conc. 0.5 mg/ml |
| CXCL16 | | R&D Systems | 1164-CX/CF | Mouse myeloma cells, His-tag | EXTRACELLULAR DOMAIN aa49-224 | |
| CXCL16 | | R&D | 1164-CX/CF | mouse myeloma cell line, NS0-derived | Asn 49-Thr224 extracellular domain (AAH44930, sp1-29, transmembrane 206-226) | |
| HIP-1 protein | Huntigtin interacting protein | Novus Biologicals/Abnova | H00003092-P01 | E. coli, GST tag | | GST tag, WB ja ELISAan |
| IL-1alpha (IL1A) | IL1F1 | Immunotools | 11349013 | E. coli | 20 mM Tris-HCl pH 8, 5 mM MgCl2, 10% glycerol | |
| IL-1 beta | IL1F2 | Immunotools | 11340013 | E. coli | 25 mM phosphate buffer | |

TABLE 15-continued

List of recombinant proteins used in the Elisa assays

| Target | Synonym | Provider | Catalog number | Source | Lyophilized from a solution containing | Comments |
|---|---|---|---|---|---|---|
| (IL1B) | | | | | pH 7.1, 100 mM NaCl | |
| IL1F6 | IL-36 alpha | R&D Systems | 1078-IL-025/CF | E. coli | PBS, 500 mM NaCl, 0.05% (v/v) Tween 20, pH 7.4 | |
| IL1F6 | TL-36 alpha | R&D Systems | 1078-IL/CF | E. coli | PBS, 500 mM NaCl, 0.05% (v/v) Tween 20, pH 7.4 | |
| IL1F7 | FIL-1Z | R&D Systems | 1975-IL-025 | E. coli | PBS, 1 mM DTT | |
| IL1F8 | IL-36 beta | R&D Systems | 1099-IL-025/CF | E. coli | PBS | |
| IL1F9 | IL-36 gamma, IL-1H1 | R&D Systems | 2320-IL-025/CF | E. coli | PBS | |
| IL1F9 | IL-36 gamma, IL-1H1 | R&D Systems | 2320-IL/CF | E. coli | PBS | |
| IL1F10 | | ProSpec | CYT-012 | E. coli | | |
| IL2 | TCGF | Immunotools | 11340023 | E. coli | lyophilized after extensive dialysis against 0.17 mg sodium monobasic & 0.89 mg dibasic sodium phosphate buffer to a pH of 7.5. Reconstituted in 20 mM acetic acid. | |
| IL3 | | Immunotools | 11340033 | E. coli | PBS | |
| IL4 | BSF-1 | Immunotools | 11340043 | E. coli | 25 mM Tris-HCl pH 8.0 no additives | |
| IL5 | | Immunotools | 11340053 | E. coli | PBS pH 7.5, 0.25M NaCl | |
| IL6 | | Immunotools | 11340064 | E. coli | 25 mM sodiumphoshate, 200 mM NaCl, pH 6.5 | |
| IL7 | | Immunotools | 11340073 | E. coli | 20 mM PBS pH 7.4, 50 mM NaCl | |
| IL8 | CXCL-8 | Immunotools | 11340084 | E. coli | no additives | |
| IL9 | P40 | Immunotools | 11340093 | E. coli | 25 mM sodiumphoshate pH 6.5, 200 mM NaCl | Concentration 0.068 mg/ml |
| IL10 | CSIF(IL10A) | Immunotools | 11340103 | E. coli | no additives | |
| IL-11 | | Immunotools | 11340113 | E. coli | PBS, pH 7.4 | |
| IL-12 | | Immunotools | 11340123 | CHO cells | | Heterodimer, containing IL-12A (p35) + IL-12B (p40) subunits |
| IL13 | NC30 | Immunotools | 11340133 | E. coli | 50 mM Tris, 50 mM NaCl, pH 8.0 | |

TABLE 15-continued

List of recombinant proteins used in the Elisa assays

| Target | Synonym | Provider | Catalog number | Source | Lyophilized from a solution containing | Comments |
|---|---|---|---|---|---|---|
| IL15 | | Immunotools | 11340153 | E. coli | 5 mM Tris, pH 8.0 | |
| IL-17 | CTLA-8, IL-17A | Immunotools | 11340174 | E. coli | no additives | |
| IL17 | CTLA-8, IL-17A | Biolegend | 570506 | E. coli | | |
| IL-17C | | R&D Systems | 1234-IL-025/CF | E. coli | Acetonitrile and TFA, reconstituted at 100 µg/ml in sterile 4 mM HCl. | |
| IL-17 E | IL25 | R&D Systems | 1258-IL-025-CF | E. coli | 25 mM sodiumphosphate, 200 mM NaCl, pH 7.0 | |
| IL17F | | Immunotools | 11349174 | E. coli | | |
| IL17F | | Biolegend | 570606 | E. coli | no additives | |
| IL19 | | Immunotools | 11340193 | E. coli | no additives | |
| IL20 | | Immunotools | 11340203 | E. coli | 20 mM NaP, pH 7.5 | |
| IL21 | | Immunotools | 11340213 | E. coli | 25 mM sodiumphosphate, 200 mM NaCl, pH 6.0 | |
| IL-22 | | Immunotools | 11340223 | E. coli | | |
| IL23 | | Sino Biological Inc. | CT12-H08H | human cells | | IL-23 A & IL-12B heterodimer, conc. 0.25 mg/ml R&D Systems product has a C-terminal His-tag |
| IL-24 | | Immunotools | 11340243 | S. cerevisiae*, murine myeloma cell line | 50 ug BSA/1 mg IL-24 | |
| IL-24 | | R&D Systems | 1965-IL-025/CF | mouse myeloma cell line, NS0-derived | | |
| IL25 | IL-17E | R&D Systems | 1258-IL-025/CF | E. coli | 35% (v/v) acetonitrile, 0.1% (v/v) TFA | |
| IL26 | AK155 dimer | R&D Systems | 1870-II010/CF (dimer) | E. coli | 20 mM NaH2PO4, 700 mM NaCl, 10% (v/v) glycerol, pH 6.5 | Concentration 0.187 mg/ml |
| IL27 | | R&D Systems | 2526-IL-010/CF | murine myeloma cell line | PBS, 300 mM NaCl, pH 7.0 | C-terminal His-tag, concentration 0.155 mg/ml |
| IL-28A | | Immunotools | 11340284 | E. coli | no additives | |
| IL-29 | | Immunotools | 11340294 | E. coli | no additives | |
| IL-31 | | Immunotools | 11340312 | E. Coli | E. Coli Phosphate buff, NaCl | |
| IL-31 | | GenScript | Z02717 | E. coli | 50 mM sodium phosphate buffer pH 7.5 | |
| IL-32 α | | Immunotools | 11340323 | E. coli | PBS, 1 mM DTT, pH 7.0 | |
| IL-32 γ | | R&D Systems | 4690-IL-025/CF | E. coli | | |
| IL-32 γ | | R&D Systems | 4690-IL/CF | E. coli | | |
| IL-34 | | R&D Systems | 5265-IL-010/CF | mouse myeloma cell line, NS0-derived | PBS, 500 mM NaCl, pH 6.0 | C-terminal His-tag |

TABLE 15-continued

List of recombinant proteins used in the Elisa assays

| Target | Synonym | Provider | Catalog number | Source | Lyophilized from a solution containing | Comments |
|---|---|---|---|---|---|---|
| IL-35 alpha | IL1-F6 | R&D Systems | 1078-IL/CF | E. coli | | |
| IFN-alpha 1beta | | Immunotools | 11343596 | E. coli | 4% mannitol and 1% HSA | |
| IFN alpha 2beta | | Immunotools | 11343516 | E. coli | | |
| IFN-α4b | IFNA4 | Sino Biological | 10336-H01H | Human cells | | IFN-α4b/Fc Chimera (1.1.11) fused with hFcIgG1! IFN-alpha 2beta, 166 aa Conc. 100 ug/ml |
| IFNA2 | | ImmunoTools | 11343516 | E. coli | | |
| IFNA4 | | Abnova | H00003441-P01 | Wheat germ expression system | | |
| IFNA4 | | Novus Biologicals | H00003441-P01 | Wheat germ expression system | 50 mM Tris-HCl, 10 mM reduced Glutathione, pH 8.0 in elution buffer | ~26 kD N-terminal GST tag |
| IFNA4 | | Sino Biological | 10336-H08B | Baculovirus-Insect cells | | |
| IFNA5 | | Abnova | H00003442-P01 | Wheat germ expression system | | Conc. 80 ug/ml |
| IFNA6 | | Novus Biologicals | H00003443-P01 | Wheat germ expression system | | ~26 kD N-terminal GST tag |
| IFNA8 | | Novus Biologicals | H00003445-P01 | Wheat germ expression system | | ~26 kD N-terminal GST tag |
| IFNA14 | | Novus Biologicals | H00003448-P01 | Wheat germ expression system | 50 mM Tris-HCl, 10 mM reduced Glutathione, pH 8.0 in elution buffer | ~26 kD N-terminal GST tag |
| IFNA14 | | ATGen | ATGP1500 | E. Coli | Liquid. 20 mM Tris-HCl buffer (pH 8.0) containing 50% glycerol, 0.2M NaCl, 2 mM DTT | IFNA14, 24-189aa His-tag |
| IFN-omega 1 | | ProSpec | CYT-040 | E. coli | | |
| IFN,gamma | | Immunotools | 11343536 | E. coli | | |
| L-aminoacid decarboxylase | dopa decarboxylase, asi, aadc, ddc | Nordic Biosite | PAT-80291-1 | E. coli, his-tag | | |
| MIF | | Immunotools | 11344263 | E. coli | 10 mM sodium phosphate buffer, pH 7.5 | |

TABLE 15-continued

List of recombinant proteins used in the Elisa assays

| Target | Synonym | Provider | Catalog number | Source | Lyophilized from a solution containing | Comments |
|---|---|---|---|---|---|---|
| NGF | Nerve growth factor | Immunotools | 11343350 | CHO | | |
| NY-ESO-1 | | Thermo Scientific | RP-39227 | bacterially expressed | | 50 mM Tris-HCl, pH 7.5, with 10 mM L-glutathione (reduced) Nicholas |
| OSM | | Immunotools | 11344023 | *E. coli* | | |
| PDGF-AA | PDGF-1 | Immunotools | 11343683 | *E. coli* | 10 mM acetic acid | |
| Relaxin | | R&D | 6586-RN/CF | *E. coli*, Lyophilized from a 0.2 μm filtered solution in sodium acetate | | Asp25Ser53 (B chain) & Gln162Cys185, (A chain), P04090, full length mature is made of B chain 25-53 and A chain 162-185 |
| S100A7/P SOR1 | | Sino Biologicals | 11141-HNAE | *E. coli* | | 7xHis, N-term |
| S100A7/P SOR1 | | ATGen | ATGP0991 | *E. coli*, his-tag | | WB, Elisa |
| SCF | | Immunotools | 11344323 | insect cells | reconstituted in 10 mM acetic acid to a conc 0.1 mg/ml | |
| Sclerostin | | R&D Systems | 1406-ST/CF | NS0 cells, Lyophilized CF | | |
| SNAP25 | synaptosomal associated protein | Novus Biologicals/ Abnova | NBC1-18333 | *E. coli*, his-tag | | |
| SNCAIP | | Abnova | H00009627-P01 | Wheat germ expression system | 50 mM Tris-HCl, 10 mM reduced Glutathione, pH = 8.0 in the elution buffer. | Human SNCAIP full-length ORF (AAH94759.1, 1 a.a. - 603 a.a.) recombinant protein with GST-tag at N-terminal |
| SPG20 | | Origene/ BioNordika | TP307971 | Human HEK293 cells | Buffer: 10% glycerol, 100 mM glycine, 25 mM Tris-HCl, pH 7.3 | C-terminal Myc-DDK, conc. 0.229 ug/ml |
| STXBP1 | | Abnova | H00006812-P01 | Wheat germ expression system | 50 mM Tris-HCl, 10 mM reduced Glutathione, pH = 8.0 in the elutionbuffer. | Human STXBP1 full-length ORF (NP_003156.1, 1 a.a. - 603 a.a.) recombinant protein with GST-tag at N-terminal |
| TGF-beta1 | | Immunotools | 11343160 | Human 293 cells | 10 mM HCl, 50 ug BSA | |

TABLE 15-continued

List of recombinant proteins used in the Elisa assays

| Target | Synonym | Provider | Catalog number | Source | Lyophilized from a solution containing | Comments |
|---|---|---|---|---|---|---|
| TGF-beta3 | | Immunotools | 11343153 | E. coli | 20% ethanol, 0.12% acetic acid | |
| TINAGL1 | | Novus Biologicals | H00064129-P01 | Wheat germ expression system | Tris-HCl + Glutathione, pH 8.0 | Human TINAGL1 full-length ORF (AAH09048.1, 1 a.a. - 218 a.a.) recombinant protein with GST-tag at N-terminal |
| TMEFF-1 | tomoregulin-1 | Novus Biologicals | H00008577-P01 | Wheat germ expression system | | 26 kDA N-terminal GST-tag, not be tested for any functionality, conc. 120 ug/ml |
| TMEFF-2 | | Novus Biologicals | H00023671 | Wheat germ expression system | | ~26 kD N-terminal GST tag |
| TNF alpha | | Immunotools | 11343015 | E. coli | 20 mM PBS, pH 7.2, 10 mM NaCl | Concentration 500 ug/ml |
| TROY | | Novus Biologicals | H00055504-P01 | Wheat germ expression system | | Human TNFRSF19 full-length ORF (NP_683760.1, 1 a.a. - 417 a.a.) recombinant protein with GST-tag at N-terminal |
| VEGF | | Immunotools | 11343663 | E. coli | | |
| Villin 1 | | Novus Biologicals | H00007429-P01 | Wheat germ expression system | | Human VIL1 full-length ORF (AAH17303, 1 a.a. - 421 a.a.) recombinant protein with GST-tag at N-terminal. |

Example 8: Detection of cytokine specific antibodies in the serum of patients by ELISA ELISA (Enzyme linked immunosorbent assay) was used to test the presence and relative concentration of the various cytokine specific antibodies in the sera of the patients suffering from the genetic condition APECED (Autoimmune polyendocrinopathy candidiasis epidermal dysplasia, also called Autoimmune polyendocrinopathy type 1 (APS1). Altogether sera from 23 patients, presented by codes from APS1-1 to APS1-23 were used in the assays. Eight control sera were obtained from healthy laboratory personnel, age matched with the patients and coded as C1-C8. In addition, sera of 10 further patients, presented by codes from APS1-24 to APS1-33 were used in the assays as well.

Equipment

EIA/RIA PLATE (enzme-/radioimmunoassay), 96 well half-area plates, high binding flat bottom (Costar cat. 3690); Digital multi-channel pipette 50-1200 µl (Biohit, Helsinki, Finland); Digital multi-channel pipette 10-2501 (Biohit, Helsinki, Finland); Orbital shaker Elisa reader (Multiskan FC).

Reagents:

Peroxidase-conjugated Goat anti-human IgG Fc (Jackson cat. 109-035-098); Coating buffer (Carbonate-bicarbonate buffer, Sigma cat. C3041-50CAP); Washing buffer (Phosphate buffered saline with tween 20, pH 7.4 Sigma cat. P-3563); BSA, albumin, from bovine serum (Sigma cat. A7030-50G); Blocking buffer (2% BSA in phosphate buffered saline, pH 7.4); Dilution buffer (0.5% BSA in phosphate buffered saline, pH 7.4); 1-step ultra TMB-ELISA (Thermo cat. 34028); Stop reagent for TMP substrate (Sigma cat. S5814); 2M $H_2SO_4$ Test Antigens Recombinant cytokines, lymphokines, chemokines and other antigens were obtained from commercial sources: see table 14.

Procedure
- A solution of the test antigen is prepared in coating buffer at concentrations of 0.75, 1.0 or 2.0 µg/ml
- 30 µl of the antigen solution are added into each well of the 96 well Costar EIS/RIA plate and incubated at +4 C overnight (16 hours)
- The antigen solutions are removed and the plate washed three times with 150 µl/well of wash buffer.
- 100 µl/well 2% BSA/PBS blocking buffer are added and incubated for 2 hours at room temperature waving at 150 rpm.
- The blocking buffer solution is removed.
- 30 µl/well of patient sera are added and the plate incubated for two hours at room temperature by mixing at 150 rpm.
- The serum dilution of solutions is removed and the plate washed four times with 150 µl/well of wash buffer.
- 30 µl/well goat anti-human-HRP secondary antibody at a dilution of 1:50 000 0.5% BSA/PBS buffer is added and incubated for 1 h at room temperature by waving at 150 rpm.
- Secondary antibody is removed from the solutions and the plate is washed four times with 150 µl/well of wash buffer.
- 30 µl/well of room temperature TMB solution are added and incubated for 15 minutes at room temperature.
- Color development is stopped by adding 30 µl well of stop solution or 2M $H_2SO_4$ solution and the absorbances 450 nm are read in the ELISA reader.

Antibody Titer

The antibody titer is defined as the highest dilution (lowest concentration) of the test sera that gives an OD (optical density) value equal to or higher than three times the OD given by control serum at the same dilution. So far, test sera of patients as indicated in Table 14 have shown immunoreactivity to the respective indicated targets.

Example 9: Analysis of Statistical Aberrancies in Occurrence of Autoantigen Protein Types Analysis of the Protoarray data provided in the experiments of the present invention has shown that cellular localizations (see FIG. 32) of the proteins recognized by antibodies found in APECED patients are not evenly distributed. In addition, proteins related to different pathways are not equally represented as well, with specific pathways found over-represented; see also Table 1 above and Table 20 below.

TABLE 20

Representation of proteins relating to specific pathways in APECED patients.

| Over-represented pathways | | Under-represented pathways | |
|---|---|---|---|
| GO pathway | P-value | GO pathway | P-value |
| nucleus | 4.21e-21 | intrinsic to membrane | 1.93e-52 |
| nucleic acid binding | 1.12e-15 | membrane part | 1.01e-47 |
| gene expression | 1 15 14 | membrane | 3 00 34 |
| nuclear lumen | 2.82e-11 | receptor activity | 5.32e-13 |
| nucleic acid metabolism | 2.59e-10 | transmembrane receptor | 3.86e-12 |
| RNA metabolic process | 3.88e-10 | signal transducer activity | 8.13e-12 |
| DNA binding | 7.27e-10 | intrinsic plasma membrane | 3.28e-10 |

For a further analysis, occurrence of specific structural motifs in APECED related autoantigens has been assessed. The coiled-coil structure is a structural motif where 2-7 a-helices are coiled together, most commonly dimers and trimers. It contains a repeated pattern of heptad repeat HxxHCxC (H-hydrophobic: C-charged aa). Chromosomal localization of exemplary coiled-coil domain comprising proteins is indicated in Table 24.

The data obtained in the experiments of the present invention were analyzed as follows in concern of occurency of coiled-coil containing proteins. The fluorescence signals of Invitrogen Protoarray results of sera from 23 Finnish APECED patients and 7 healthy controls were used. The reactivities were listed according the P-value (as indicated by Invitrogen). The putative antigens recognized by at least 1 APECED patient sera with signal values at least 10-fold higher than cut-off value (provided by Invitrogen) were included (altogether 1797 proteins). From this list replicates (some proteins were on the array in duplicate or triplicat) were eliminated, including only those that had Swissprot accession numbers, and type 1 IFNs and IL-22 were excluded as nontypical autoantigens. The coiled-coil protein analysis was made with GeneTrail program (http://genetrail-.bioinf.uni-sb.de/—[49, 51] with default settings. The GeneTrail program was able to annotate (to find match with) 1517 unique human proteins. From Top1500 list 16.7% and from Top250 list 24.4% contained coiled-coil structure. An Top60 list of exemplary coiled-coil proteins recognized by the sera of APECED patients tested in the proteoarray assay of the present invention is indicated in Table 21 below, immunoreactivity for the exemplary CCDC40 (coiled-coil domain containing 40) and NAP1L1 (Nucleosome assembly protein 1-like 1) proteins is shown in FIG. 31 (column B, top and middle chart).

TABLE 21

Top60 list of exemplary coiled-coil proteins showing immunoreactivity in the Proteoarray assay of the present invention.

| Gene Name | Description |
|---|---|
| AFAP1L2 | Actin filament associated protein 1-like 2 |
| ANKRD13A | Ankyrin repeat domain 13A |
| APPL1 | Adaptor protein, phosphotyrosine interaction, PH domain and leucine zipper containing 1 |
| ARGLU1 | Hypothetical protein FLJ10154 |
| ARHGEF1 | Rho guanine nucleotide exchange factor (GEF) 1 |
| ASZ1 | Ankyrin repeat, SAM and basic leucine zipper domain containing 1 |
| ATF6 | Activating transcription factor 6 |
| BBX | Bobby sox homolog (Drosophila) |
| C10orf118 | Chromosome 10 open reading frame 118 |
| C10orf80 | Chromosome 10 open reading frame 80 |
| C3orf44 | Chromosome 3 open reading frame 44 |
| C6orf65 | Chromosome 6 open reading frame 65 |
| CCDC12 | Coiled-coil domain containing 12 |
| CCDC25 | Coiled-coil domain containing 25 |
| CCDC40 | Coiled-coil domain containing 40 |
| CEP290 | Centrosomal protein 290 kDa |
| CHCHD6 | Coiled-coil-helix-coiled-coil-helix domain containing 6 |
| CORO2A | Coronin, actin binding protein, 2A |
| CRLF3 | Cytokine receptor-like factor 3 |
| DBNL | Drebrin-like |
| FAM133A | Family with sequence similarity 133, member A |
| FAM76B | Family with sequence similarity 76, member B |
| FOSL2 | FOS-like antigen 2 |
| GNL3L | Guanine nucleotide binding protein-like 3 (nucleolar)-like |
| HDAC9 | Histone deacetylase 9 |
| HELLS | Helicase, lymphoid-specific |
| HIRIP3 | HIRA interacting protein 3 |
| HOMER3 | Homer homolog 3 (Drosophila) |
| KIAA0562 | KIAA0562 |
| KIF20A | Kinesin family member 20A |
| KIF3A | Kinesin family member 3A |
| KIF3B | Kinesin family member 3B |
| KLC3 | Kinesin light chain 3 |
| MED4 | Mediator complex subunit 4 |
| NAP1L1 | Nucleosome assembly protein 1-like 1 |
| NFE2 | Nuclear factor (erythroid-derived 2), 45 kDa |
| NRBF2 | Nuclear receptor binding factor 2 |
| PHF11 | PHD finger protein 11 |
| PIBF1 | Progesterone immunomodulatory binding factor 1 |
| PKNOX2 | PBX/knotted 1 homeobox 2 |
| RBM17 | RNA binding motif protein 17 |
| SCYL1 | SCY1-like 1 (S. cerevisiae) |
| SEPT2 | Septin 2 |
| SLU7 | SLU7 splicing factor homolog (S. cerevisiae) |
| SMTNL2 | Smoothelin-like 2 |
| SNCAIP | Synuclein, alpha interacting protein (synphilin) |
| STX2 | Syntaxin 2 |
| ZMYND11 | Zinc finger, MYND domain containing 11 |
| TEKT2 | Tektin 2 (testicular) |
| TLE3 | Transducin-like enhancer of split 3 (E(sp1) homolog, Drosophila) |
| TRIM15 | Tripartite motif-containing 15 |
| TRIM22 | Tripartite motif-containing 22 |
| TRIM29 | Tripartite motif-containing 29 |
| TRIM69 | Tripartite motif-containing 69 |
| TTLL7 | Tubulin tyrosine ligase-like family, member 7 |
| UBE2O | Ubiquitin-conjugating enzyme E2O |
| USP47 | Ubiquitin specific peptidase 47 |
| VAPA | VAMP (vesicle-associated membrane protein)-associated protein A, 33 kDa |
| WTAP | Wilms tumor 1 associated protein |

In comparison, all unique and SwissProt-annotated Protoarray proteins were analyzed in parallel; from these (7010 unique and Swissprot annotated) 12.5% of proteins contained coiled-coil structure (see Table 22 below).

TABLE 22

Enrichment of coiled-coil domains in APECED related autoantigens identified in the Invitrogen Protoarray assay of the present invention.

| | APECED (Top 250) | APECED (Top 1500) | Protoarray proteins |
|---|---|---|---|
| Coiled-coil domain | 24.4% | 16.7% | 12.5% |
| P-value | 7.5e−08 | 6.38e−08 | |

Without intending to be bound by theory, it can be concluded that the protein list recognized by APECED sera contains more proteins with coiled-coil structure than the list of all proteins on the Protoarray representing the distribution in healthy volunteers. In comparison, when regarding all human genome proteins—approximately 11.4% from 23253 proteins comprise coiled-coil structures, which is close to the list of all Protoarray proteins (12.5%). The data validates and extends earlier speculations regarding over-representation of coiled-coil structures in autoantigens; see Plotz P H. "The autoantibody repertoire: searching for order." Nat. Rev. Immunol. 3 (2003), 73-78 in that autoantigen proteins contain more often coiled-coil structures than randomly expected.

Example 10: Identification of the Major Ig Subclasses Neutralizing the Cytokines in APECED The following Materials and Methods, if not indicated otherwise or extended by additions, are or have been used in addition or alternatively to the corresponding methods described in the Examples above for experiments described in Examples 10 and 11. Substantially the same methods have been used and are described in detail for the investigation of anti-cytokine autoantibodies in aire-deficient mice for comparison with APECED patients by Karner et al. in Clin. Exp. Immunol. (2012); doi: 10.1111/cei.12024, the disclosure content of which is incorporated herein by reference.

Patients and Controls

Sera from patients which are affected with an impaired central and/or peripheral tolerance or loss of self-tolerance as defined herein above, e.g., from APECED, APS2 or IPEX patients, and from matched healthy controls are collected/stored in parallel at −20° C., at −80° C. or in liquid nitrogen until use. Immunoglobulins are isolated from patient and control sera as described in the above Examples. The diagnosis of diseases of genetic origin is confirmed by mutation analysis of the corresponding gene(s) and presence of autoantibodies known to be associated with given disease, e.g., APECED is confirmed by mutation analysis of AIRE genes and by the presence of autoantibodies against specific proteins associated with the disease, such as proteins as defined in Tables 32 or 33. Preferably, presence of highly prevalent autoantibodies is used as a marker, for example in case of APECED the presence of autoantibodies against to IFN-co is tested.

Purification of Immunoglobulins

Total IgG fractions are separated with fast protein liquid chromatography using Protein G Sepharose 4 Fast Flow (GE Healthcare, Biosciences, Little Chalfont. UK), concentrated and buffer-exchanged for PBS with iCon™ Concentrator 7 ml/20K tubes (Pierce Biotechnology, Inc., Rockford, Ill., USA). Total IgA is separated using Agarose-bound Jacalin lectin (Vector Laboratories Inc., Burlingame, Calif. USA) and dialyzed against 1×PBS using Spectra/Por Dialysis Membrane (MWCO 12-14 000) (Spectrum Laboratories, Inc., Rancho Dominguez, Calif., USA). Protein concentrations are determined with the Bio-Rad Protein Assay, based on the method of Bradford and using bovine gamma globulin as standard (Bio-Rad Laboratories Inc., Hercules, Calif., USA).

The purities of the isolated IgGs and IgAs are assessed by SDS-PAGE and Western blotting. The identity of the IgH bands is confirmed with specific Abs. IgG contamination in isolated IgA preparations is detected by immune-turbidimetry with Cobas Integra 400 Plus (Hoffmann-La Roche, Basel, Switzerland).

Western Blot

For testing for the presence of autoantibodies against a protein of interest in patient or control sera by Western Blot the following experimental procedure exemplary described for human IFN-α2 is used. Human IFN-α2 (PBL InterferonSource) is boiled 5 min in reducing sample buffer (3% SDS, 10% glycerol, 0.1 M DTT, 0.02% bromophenol blue and 6.25 mM Tris-HCl, pH 6.8), run in 12% SDS-PAGE and blotted onto PVDF filters. After blocking, strips of the filter are incubated with patient or control sera (1:100) or mouse anti-IFN-α2b antibody (1:1000, Abcam) followed by secondary antibodies (anti-human-HRP 1:100,000 and anti-mouse-HRP 1:30,000, Jackson ImmunoResearch Inc). Reaction is visualized by enhanced chemiluminescence (ECL) using the manufacturer's protocol (GE Healthcare).

Cell-Based Cytokine-Neutralization Assays

Antiviral neutralization assay (AVINA) is done as described previously [13]. Briefly, the human glioblastoma cell line 2D9 is pre-incubated with a diluted immunoregulatory cytokine of interest, e.g., IFN-α2a (Hoffmann-La Roche) or IFN-ω (Bender and Co., Vienna. Austria) preparations (10 laboratory units per ml) that had been pre-incubated for 2 h with serial dilutions of IgG or IgA samples (starting from 12.5 µg/ml). The cells are then challenged with encephalomyocarditis virus for 24 h, before staining with 0.05% amido black, fixed with 4% formaldehyde in acetic acid buffer, and washed with 0.15 ml of 0.05 M sodium hydroxide solution before absorbance is read at 620 nm.

Human IL-17A, IL-17F and IL-22 Neutralization Assays

The assays are carried out as described previously [19]. Briefly, for IL-17A, HFB4 human foreskin fibroblast cells (Schering-Plough Corporation, Reno, Nev. USA) are seeded at $1 \times 10^4$ cells/well in which IL-17A (2 ng/ml, R&D Systems Inc., Minneapolis, Minn., USA) had been pre-incubated with serially diluted IgG or IgA for 2 h. For IL-17F, NCTC 2544 keratinocytes (Interlab Cell Line Collection, Genova, Italy) preincubated with 0.1 ng/ml TNF (Biolegend, San Diego, Calif., USA) are used instead of HFB4. After incubation at 37° C. for 16-20 h, supernatants are collected and assayed by ELISA (R&D Systems) for CXCL1. For human IL-22, cell line Colo205 is used. Cells are seeded at $3 \times 10^4$ cells per well in which IL-22 (2 ng/ml, R&D Systems) had been pre-incubated with serially diluted patient sera or IgGs or IgAs for 2 h. After incubation at 37° C. for 24-30 h, supernatants are collected and analyzed for IL-10 by ELISA (R&D Systems Inc). Results from all the cytokine neutralization assays are estimated from graphs of ELISA absorbances as the $ED_{50}$-values—the concentration of Ig needed to halve the cytokine activity of the test sample—and represented graphically as cytokine neutralization units (NU) per µg of protein.

Constructs Encoding Luciferase (LUC) Fused to Fill-Length or Truncated Recombinant Protein of Interest Constructs encoding luciferase (LUC) fused to a full-length or truncated recombinant protein of interest can be generated as described in the following for two exemplary cytokines. An overview of all full-length and truncated human IFN-α2a and IL-22 proteins and the primer sequences used are given in Table 23 below.

Human IFN-α2a and IL-22 coding sequences were amplified by polymerase chain reaction (PCR) without the signal sequences. The PCR products were ligated into the BamHI/NotI site of pPK-CMV-F4 (PromoCell GmbH, Heidelberg; Germany) mammalian expression vector using T4 ligase (Invitrogen, Carlsbad, Calif. USA). All plasmids containing correct inserts (as confirmed by DNA sequencing) were propagated in *E. coli* NOVA XG cells, amplified, extracted and purified using conventional methods. Finally, HEK 293 cells were transfected with the plasmids; after 48 h the crude protein extracts were prepared using 1× passive lysis buffer (Promega, Madison, Wis., USA).

TABLE 23

Overview of all full-length and truncated human INF-α2a and IL-22 proteins and used primer sequences

| Antigen | Fragments | | Primer sequences |
|---|---|---|---|
| IL-22 | 34-76 aa | F1 | 5' TTTGGGATCCTCGCGCCCATCAGCT CCCACTGCA 3' SEQ ID NO: 62 |
| | | R1 | 5' TTTGCGGCCGCTCACCCAATGAGAC GAACGTCTGT 3' SEQ ID NO: 63 |
| | 74-111aa | F2 | 5' TTTGGGATCCTCCTCATTGGGGAGA AACTGTCC 3' SEQ ID NO: 64 |
| | | R2 | 5' TTTGCGGCCGCTCAATAAGGCTGGA ACCTATCAGA 3' SEQ ID NO: 65 |
| | 113-179aa | F3 | 5' TTTGGGATCCTCCCTTATATGCAGG AGGTGGT 3' SEQ ID NO: 66 |
| | | R3 | 5' TTTGCGGCCGCTCAAATGCAGGCAT TTCTCAGA 3' SEQ ID NO: 67 |
| | 34-114aa | F1 | 5' TTTGGGATCCTCGCGCCCATCAGCT CCCACTGCA 3' SEQ ID NO: 68 |
| | | R1 | 5' TTTGCGGCCGCTCAATAAGGCTGGA ACCTATCAGA 3' SEQ ID NO: 69 |
| | 74-179aa | F2 | 5' TTTGGGATCCTCCTCATTGGGGAGA AACTGTTCC 3' SEQ ID NO: 70 |
| | | R2 | 5' TTTGCGGCCGCTCAAATGCAGGCAT TTCTCAGA 3' SEQ ID NO: 71 |
| IFN-α2a | 24-69aa | F1 | 5' TTTGGGATCCTCTGTGATCTGCCTC AAACCCACA 3' SEQ ID NO: 72 |
| | | R1 | 5' TTTGCGGCCGCTCACTGGTTGCCAA ACTCCTCCTG 3' SEQ ID NO: 73 |
| | 67-124aa | F2 | 5' TTTGGGATCCTCGGCAACCAGTTCC AAAAGGCT 3' SEQ ID NO: 74 |
| | | R2 | 5' TTTGCGGCCGCTCACTGTATCACAC AGGCTTCCAG 3' SEQ ID NO: 75 |
| | 123-188 | F3 | 5' TTTGGGATCCTCATACAGGGGGTGG GGGTGACA 3' SEQ ID NO: 76 |
| | | R3 | 5' TTTGCGGCCGCTTACTTCTTAAACT TCTTGCA 3' SEQ ID NO: 77 |

TABLE 23-continued

Overview of all full-length and truncated
human INF-α2a and IL-22 proteins
and used primer sequences

| Antigen | Fragments | Primer sequences | |
|---|---|---|---|
| | 24-124 | F1 | 5' TTTGGGATCCTCTGTGATCTGCCTC AAACCCACA 3' SEQ ID NO: 78 |
| | | R2 | 5' TTTGCGGCCGCTCACTGTATCACAC AGGCTTCCAG 3' SEQ ID NO: 79 |
| | 67-188 | F2 | 5' TTTGGGATCCTCGGCAACCAGTTCC AAAAGGCT 3' SEQ ID NO: 80 |
| | | R2 | 5' TTTGCGGCCGCTTACTTCTTAAACT TTCTTGCA 3' SEQ ID NO: 81 |

Luciferase Immunoprecipitation System (LIPS) Assay

LIPS assays were conducted according to Burbelo et al. in 96-well MultiScreen filter HTS plates (Millipore, Bedford, Mass., USA) at room temperature using buffer A (50 mM Tris, pH 7.5, 100 mM NaCl, 5 mM $MgCl_2$, 1% Triton X-100) for all dilutions [30]. Igs from test sera (diluted 1:25, tested in two parallels) were captured onto Protein G Sepharose 4 Fast Flow beads (25 µl of 4% suspension; GE Healthcare), which were then incubated with extracts containing expressed cytokines or their fragments. For example, cytokines such as IL-22, IFN-α2a or their fragments ($10^5$ luminescence units (LU)) generated as indicated above were used. After 1 hour, washing and incubation with luciferase substrate (Promega), luminescence intensity was measured in a 1450 MicroBeta TriLux Liquid Scintillation Counter & Luminometer (PerkinElmer Life Sciences, Waltham, Mass., USA). For autoantibody subtype detection, beads (1 µl of Strepavidin Agarose Resin, Invitrogen) are incubated with biotin-conjugated human subtype-specific Abs (anti-IgG1, anti-IgG2, anti-IgG4, anti-IgE from BD Pharmingen, now BD Biosciences Heidelberg, Germany—now part of Becton, Dickinson and Company; anti-IgG3 from Invitrogen; Carlsbad USA). At the same time, APECED or control sera (1:25) were incubated with antigen preparation ($10^5$ LU of luciferase-linked IL-22 or IFN-α2a). Finally, the immune complexes were captured onto the coated beads before LU reading as above. Alternatively or in addition, anti-human IgA Agarose (Sigma) is used for capturing before LU reading.

ELISA

Binding ELISAs for detecting type I IFN-specific IgG in purified fractions from mice are done as previously described [13], similarly as described in front of Example 1 for human fractions/antibodies. IgG preparations are tested at 25 µg/ml. Preferably, microtiter wells are coated with carrier-free recombinant mouse IL-17A, IL-17F, or IL-22 (Biolegend) at 1-2 µg protein/ml (PBS, pH 7.0), overnight at 4° C. After blocking, mouse sera diluted 1:10 are incubated overnight at 4° C., before washing and development with either anti-mouse IgG [γ-chain-specific]-alkaline phosphatase conjugate (Sigma-Aldrich Corporation, Missouri, USA) or anti-mouse IgG subclass-specific (IgG1, IgG2b, IgG2b, IgG3) biotinylated antibodies (Biolegend) followed by streptavidine-conjugated horseradish peroxidase and appropriate enzyme substrate and OD reading. Any values over 2 standard deviations above the mean of the control group (wt and heterozygous mice) are considered as positive.

Statistical Analysis

GraphPad Software (California, USA) is used to calculate Spearman correlation coefficients.

Mann-Whitney or Kruskal-Wallis tests are used to compare the median values between groups. $P<0.01$ was considered statistically significant.

Identification of the Dominant Subclasses Neutralizing the Cytokines in the Patients which are Affected with an Impaired Central and/or Peripheral Tolerance or Loss of Self-Tolerance First, IgG and IgA from patient and control sera are isolated to identify the major Ig subclasses neutralizing the cytokines in the diseased, e.g., APECED patients. The Ig subclass identification is performed by ELISA, as described above. For a further characterization of autoimmunizing environments, next the prevailing IgA and/or IgG subclasses among the anti-cytokine autoantibodies are determined.

Example 11: Mapping of the Immunodominant Epitopes of Proteins of Interest

As described for autoantibodies against cytokines such as IL-22 in Kamer et al. in Clin. Exp. Immunol. (2012), doi: 10.1111/cei.12024, in order to better understand the neutralizing capacity of the autoantibodies, several cDNA fragments of the protein of interest can be cloned to map their immunodominant epitopes.

For example, a comparison of binding capacity of autoantibodies in sera from patients with an impaired central and/or peripheral tolerance or loss of self-tolerance as defined herein above or from respective mice models for these diseases towards the full-length or truncated polypeptides is used for determination, whether the epitopes recognized by these antibodies are of a conformational nature. If such a preference is observed, further tests are performed with denatured full-length constructs by Western Blots.

Binding specificity of the tested antibodies towards specific regions of the target proteins is used for prediction/confirmation of their neutralizing capacities. For example, the C-terminal regions of IFN-α2a and IL-22 contain amino acids that are more prone to make β-turns and are hydrophilic—two important qualities for evoking specific Abs that recognize intact proteins [45]. Any autoantibodies against these regions are likely to neutralize.

Example 12: Results of Induced Ear Inflammation Phenotype

Ear inflammation phenotype was induced in 8 weeks old C57BL/6J (WT) mice by intradermal injection of human cytokine IL-17A or IL-17F or PBS into each ear given on alternate days at Day 1, Day 3, Day 5 and Day 7 [20 ul/ear, 500 ng/ear, 1 µg/mouse/day]. Treatment with the exemplary anti-IL-17 24D3 antibody of the present invention was tested on these animals in respect of its neutralizing potential to reduce the induced ear inflammation phenotype. Four IP injections of 24D3 or control human IgG [200 µg/IP] were administered to the animals every other day for 8 days starting with the first IP at Day 0, prior to induction of ear inflammation. To test a potential therapeutic effect of the antibodies of the present invention body weight and ear thickness of the animals were monitored during the antibody administration. Furthermore, H&E (hematoxylin and eosin; [52, 53]) histology stainings of the ears were performed.

Combination of two independent experiments shows that the induction of ear swelling with intradermal injection of human IL-17F is reduced in the presence of 24D3 neutralizing antibody, this is significant at Day 8; see FIGS. 39A, D and F. Induction of ear swelling with intradermal injection of human IL-17A is not affected by the treatment of 24D3, validating further the specificity of this antibody for human IL-17F; see FIGS. 39A and C and FIG. 39E. The level of ear swelling following the continuous intradermal injection of PBS control is not affected by the presence of IgG or 24D3: see FIGS. 39A, B and F. Normalization of the obtained data against the values obtained in the PBS controls achieves a higher significance in respect of the values indicating the therapeutic effect of the exemplary anti-IL-17F antibody; see in particular FIGS. 39J and L. Therapeutic effect of the exemplary anti-IL-17F antibody of the present invention is further confirmed by preliminary data obtained from monitoring the weight of 24D3 treated animals showing nearly no or at least greatly reduced weight loss after inflammation induction by IL-17F injections: see FIG. 40.

Example 13: Epitope Mapping of Exemplary a-IL17 and aIL-22 Antibodies

As a first step of mapping, differential binding of a-IL17 and a-IL-22 MABs to distinct antigen binding sites was examined to determine the number of different binding sites.

For this purpose, two approaches have been used. In the first approach MABs were expressed either with human (hMAB) or mouse (hmMAB) Fc and cross-competition experiments were carried out by coating antigen on plates and by detecting binding of hmMABs in the presence of large excess of human MABs. Detection of hmMABs bound to the ligand was performed by a HRP-conjugated secondary antibody directed against the Fc portion of the primary antibody. As may be seen from FIG. 41A, exemplary a-IL-17 antibodies 17E3 and 24D3 of the present invention compete each other but not with antibody 9A2, indicating that 9A2 binds another site than 17E3 and 24D3. The results of the first approach also indicate that a-IL-22 antibodies 30G1, 35G11 and 41D11 of the present invention compete each other but not with antibody 51G4: see FIG. 41B.

In the second approach, sandwich ELISA experiments were performed, wherein the hmMABs were constructed as in the first approach but cross-competition experiments were carried out by coating human MABs on plate, capturing the antigen and detecting the antigen bound to human MAB with hmMABs; see FIG. 41 C for results. This second approach shows again antibodies 30G1, 35G11 and 41D11 competing each other but not 51G4, confirming that a-IL-22 antibodies 30G1, 35G11 and 41D11 and a-IL-22 antibody 51G4 bind two different sites.

Subsequent the binding regions of MABs to their respective antigens were attempted to map using PepStar™ analysis. Herein, overlapping 20mer peptides (15 amino acid overlap) were designed to cover IL-17A, IL-17F and IL-22 including all known variants, the peptides and full length antigen (as positive control) were spotted on microarray and the peptide microarray was incubated with the primary antibody followed by a fluorescently labelled secondary antibody directed against the Fc portion of the primary antibody. To avoid false negatives caused by sterical hindrance, an optimized hydrophilic linker moiety was inserted between the glass surface and the antigen derived peptide sequence.

Figure 43:
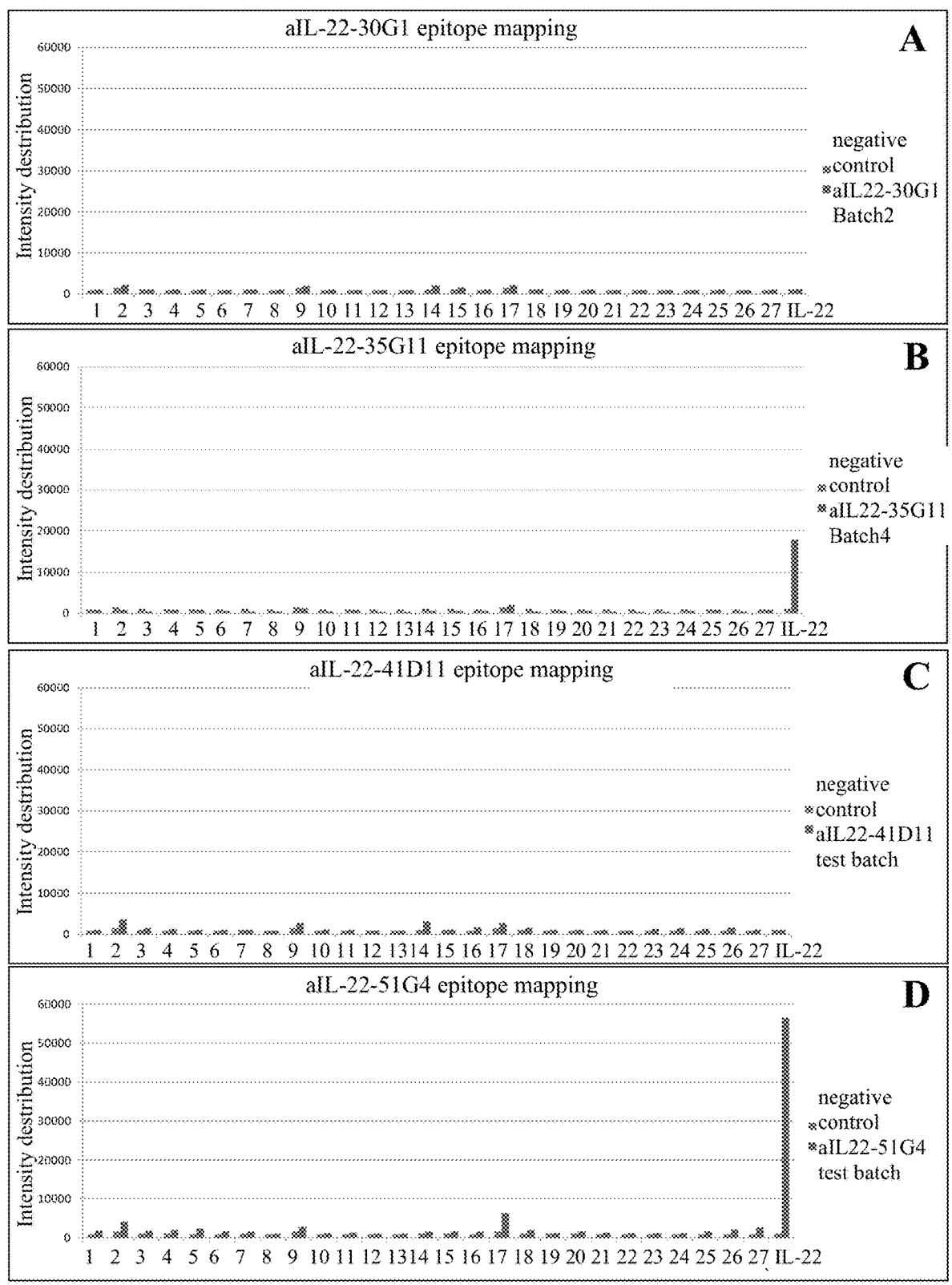

The mapping results for exemplary a-IL-17 MABs are shown in FIG. 42, the results for a-IL-22 MABs in FIG. 43. Co-spotted full length antigens were generally well-recognized on peptide microarray (IL-22 columns). Not all a-IL-17 and a-IL-22 MABs show clear binding, however, unlike peptides, due to the orientation and use of surface lysines to immobilize antigen, low signal strength or lack of signal does not necessarily correlate to a lack of binding. Expected binding intensity to be observed upon binding to a specific a peptide is in the range of 60,000. All antibodies show very weak binding patterns to microarray bound peptides indicating failure to recognise linear peptides derived from their specific antigen.

These data suggest that IL17 and IL-22 MABs bind to conformational epitopes; see Tables 25 and 26 in Example 14 for a summary of the antibodies' characteristics.

Example 14: Antibody Affinity Measurements Using Surface Plasmon Resonance (SPR) Technology For affinity determination of the antibodies of the present invention SPR measurements were performed using a ProteOn™ XPR36 instrument, according to the instructions of the manufacturer (BIO-RAD; Hercules Calif., USA). First, anti-human IgG was coupled simultaneously on 5 surfaces of the 6×6 interaction array of a GLC sensor chip by EDC/NHS chemistry, no antibody was sixth immobilized on the sixth surface, but the surface was treated with the same activation and deactivation protocol as the other five surfaces. The MABs (ligands) to be tested were injected afterwards into 6 channels of the chip (in the vertical direction) and simultaneously captured at very similar capture efficiency and percentage activity. The chip was then rotated by 90 degrees and the analyte to be tested was injected in the horizontal direction at different concentrations ranging from 100 nM to 1.23 nM with each association/dissociation curve representing a different concentration (A1-Red, 100 nM, A2-Cyan 33.33 nM, A3-Blue 11.11 nM, A4-Green 3.70 nM, A5-Pink 1.23 nM, A6-Orange running buffer alone) in FIGS. 44-46. The sensorgrams in FIG. 44 confirm binding specificity of the exemplary anti-IL-22 antibodies 30G1 and 35G11 of the present invention towards IL-22. Data was referenced using the interspot regions between the flow channels. A detailed analysis of the sensorgrams as shown in FIGS. 45 and 46 indicates a good fit of the obtained data to a 1:1 langmuir model. Binding experiments were repeated twice and data is represented as a mean of two independent experiments. The Affinities of the antibodies calculated from the SPR data were shown to be in picomolar range, i.e. KD=36.5±1.5 pM and 39±7 pM for aIL-22 antibody 30G1, and a-IL-22 antibody 35G11 respectively.

Injections of IL-17F showed concentration dependent responses on surfaces with immobilized antibodies 9A2, 17E3 and 24D3 confirming their binding specificity towards IL-17, whereas surfaces with immobilized aIL-22 antibodies 30G1 and 35G11 showed no or at most minimal non-specific ligand binding, comparable to control channel with no anti-human IgG capture antibody immobilized on the surfaces but treated with 24D3 as ligand. In the dissociation phase an 'increase' in response could be observed which appears to reflect a concurrent association and dissociation during this phase. Potential causes of this are aggregation of antigen on surface of antibody or recruitment of antigen from instrument tubing. Due to convoluted data in dissociation phase it is impossible to accurately determine kd and thus kinetics, however, affinity appears to be very high when vast majority of "dissociation" data was excluded, and ka ranging from about 3×10E+05 (17E3), over about 6×10E+05 l/Ms (24D3) to about 8×10E+05 l/Ms (9A2) can be calculated. There is no evidence of non 1:1 behaviour, i.e. no evidence of a heterogeneous ligand.

TABLE 25

Summary of characteristics of exemplary a-IL-17 antibodies 9A2, 17E3 and 24D3 of the present invention. F- IL-17F, A- IL17A, h-human

| MAB | a-IL17-9A2 | a-IL17-17E3 | a-IL17-24D3 |
|---|---|---|---|
| Patient ID | APS1-18 | APS1-16 | APS1-16 |
| ELISA binding | IL-17F (h) | IL-17A and IL-17F (h) | IL-17F (h) |
| Isotype | IgG1, K | IgG1, K | IgG1, λ |
| $EC_{50}$ (ng/ml) | 3(F) | 2 (F); 824 (A) | 2 (F) |
| Cross-competition site | I | II | II |
| Epitope Mapping | Conformational (high affinity) | Conformational (high affinity) | Conformational (high affinity) |
| Affinity (SPR) | | | |
| $IC_{50}$ Neutralization (ng/ml) | IL-17F: 45 IL-17A/F: not neutr | IL-17F: 15 IL-17A/F: 12 | IL-17F: 12-22 IL-17A/F: 6-14 |

TABLE 26

Summary of characteristics of exemplary a-IL-22 antibodies 30G1, 35G11, 41D11 and 51G4 of the present invention. Agonistic activity (EC50) against: h-human, m-murine IL-22

| MAB | a-IL-22-30G1 | a-IL-22-35G11 | a-IL-22-41D11 | a-IL-22-51G4 |
|---|---|---|---|---|
| Patient ID | APS1-16 | APS1-16 | APS1-16 | APS1-16 |
| ELISA binding | IL-22(h, m) | IL-22(h) | IL-22(h, m) | IL-22(h) |
| Isotype | IgG1, K | IgG4, λ | IgG1, λ | IgG2, λ |
| $EC_{50}$ (ng/ml) | 3 (h); 15 (m) | 7 (h) | 5 (h); 60 (m) | 67-148 (h) |
| Cross-competition site | I | I | I | II |
| Epitope Mapping | Conformational | Conformational | Conformational | Conformational |
| Affinity (SPR) | 36.5 ± 1.5 pM | 39 ± 7 pM | Not determined | Not determined |
| $IC_{50}$ Neutralization (ng/ml) | 2.1-2.5 (h); 1.5 (m) | 3.8-4 | 38 | — |

Example 15: *Gaussia*-Antigen Construct in LIPS Assay

Constructs encoding *Gaussia* luciferase (Gluc) from the marine copepod, *Gaussia princeps* fused to full-length or truncated recombinant antigens of interest such as IL-22, IL-17A or IL-17F were generated and used for luciferase assays as described in Example 10 for Firefly luciferase (from *Photinus pyralis*) containing constructs. In addition to the description below, see Table 23 for the sequences of primers used for generation of fusion constructs with the corresponding genes and the corresponding description of cloning strategies in Example 1, which were used herein in analogy for cloning of the cytokine gene fragments into the *Gaussia* vector.

The *Gaussia* full-length gene was received as a gift from Prof. Andres Merits, University of Tartu and cloned into EcoRI site of the pPK-CMV-F4 (PromoCell GmbH, Heidelberg: Germany) mammalian expression vector using T4 ligase (Invitrogen. Carlsbad, Calif. USA) replacing the firefly luciferase gene. The full-length fragments of cytokine genes (except the signaling peptide sequence) were cloned into *Gaussia* vector into the BamHI and NotI sites. The LIPS assay was performed essentially as with firefly luciferase constructs except coelenterazine was used as substrate. Briefly, LIPS assays were conducted according to Burbelo et al. in 96-well MultiScreen filter HTS plates (Millipore, Bedford, Mass., USA) at room temperature using buffer A (50 mM Tris, pH 7.5, 100 mM NaCl, 5 mM MgCl2, 1% Triton X-100) for all dilutions [30]. Igs from test sera (diluted 1:25, tested in two parallels) were captured onto Protein G Sepharose 4 Fast Flow beads (25 μl of 4% suspension; GE Healthcare), which were then incubated with extracts containing expressed cytokines ($10^1$ luminescence units (LU)). After 1 hour, washing and incubation with luciferase substrate colenterazide (TargetingSystems: El Cajon, Calif. USA; http://www.targetingsystems.net), luminescence intensity was measured in a 1450 MicroBeta TriLux Liquid Scintillation Counter & Luminometer (PerkinElmer Life Sciences, Waltham, Mass., USA). Table 27 below shows the seroreactivity observed in the LIPS assay using Firefly and/or *Gaussia* luciferase.

TABLE 27

Presence of auto-antibodies binding to indiated targets in APS1 patients shown by LIPS assays using Firefly and/or Gaussia luciferase.

| Target | Seroreactive Patients |
|---|---|
| IFNA2 | all |
| IFNA8 | all |
| IL1A | APS1-01, APS1-02, APS1-13, APS1-23 |
| IL1F10 | APS1-13 |
| IL5 | APS1-03, APS1-08, APS1-13, APS1-18, APS1-25 |
| IL6 | APS1-01, APS1-03, APS1-10, APS1-13, APS1-17, APS1-19, APS1-23, APS1-24, APS1-25, APS1-29, APS1-30 |
| IL17A | APS1-03, APS1-11, APS1-12, APS1-13, APS1-14, APS1-18, APS1-19, APS1-20, APS1-21, APS1-22, APS1-23 |
| IL17F | All except APS1-03, APS1-05, APS1-12, APS1-17, APS1-19, APS1-25, APS1-27 |
| IL20 | APS1-02, APS1-09, APS1-13, APS1-23, APS1-29 |
| IL22 | all |
| IL27 | APS1-23 |
| IL28A | APS1-07, APS1-15, APS1-16, APS1-23, APS1-24, APS1-25, APS1-26 |
| IL28B | APS1-07, APS1-15, APS1-16, APS1-24, APS1-25 |
| IL29 | APS1-04, APS1-07, APS1-13, APS1-15, APS1-18, APS1-21, APS1-24, APS1-25, APS1-26, APS1-28, APS1-29 |

Example 16: Protein Array Data Analysis

Antibody response on the protein array has been assessed for the whole sample set (FIG. 47), and separately for female and male patients (FIGS. 48 and 49). Responding proteins separate controls from carriers in all three analyses.

75% of proteins separating carriers from controls are driven by female patients in lieu with the higher amount of female samples. 11 proteins overlap in all three analyses. 14 proteins show male specific and 28 proteins can be called female specific: see Table 28, and FIG. 49B.

Two proteins could be annotated to a Gene Ontology (GO) term containing the word 'soluble' and 16 proteins to the GO term 'membrane' in the whole sample set. The two soluble proteins and one additional protein were also evident in the female only analysis. No male specific proteins were annotated as soluble; apparently there is a preference for membrane annotated responding proteins in males.

No clear relationship between antibody response and age of patients could be observed by this preliminary analysis.

TABLE 28

Proteins that differentiate between patient and control samples integrating sex parameters.

| Group | Proteins |
| --- | --- |
| Female specific (n = 28) | ABHD10, ADAM5P, AQP2, ARFGAP3, c3orf52, CBX1, CCDC40, CKAP2, *CRYGD*, *DDC*, GGA2, GAD2, HSBP1, ICAIL1, IFNA17, IFNW1, IL36A, KCTD10, MAPK9, MED4, NAP1L1, OXNAD1, *PHKG2*, PSMB5, RPL12, S100A11, SMNDC1, SPANXB1 |
| Male specific (n = 14) | ABHD1, C14orf79, CLDN20, ERO1LB, GLRX2, GPAM, LOC402176, LYPLAL1, MAX, PDK3, TPH1, TPSD1, TRIM5, USE1 |
| Shared (n = 11) | CFL2, IFNA1, IFNA13, IFNA14, IFNA2, IFNA21, IFNA4, IFNA5, IFNA6, IFNA8, IL22 |

Male and female specific, and shared responder proteins. Proteins annotated to GO term "soluble" - in italics; "membrane" - in bold; proteins not "soluble" or "membrane" - underlined. CFL2 (skeletal muscle active, cofilin-2) antibody levels down in patients, antibody levels against all other proteins were elevated.

Example 17: Isolation of Human Lymphocytes from APS1- and IPEX-Patients

As starting material for the cloning of fully human antibodies, human lymphocytes are used which were obtained, in addition to the group of 33 Finnish APECED patients as described in Example 1, from the peripheral blood of 1 Finnish patient diagnosed with immunodysregulation, polyendocrinopathy, and enteropathy X-linked syndrome (IPEX, OMIM 304790), also called X-linked autoimmunity-allergic dysregulation syndrome (XLAAD) or IDDM-secretory diarrhea syndrome (DMSD); and of 31 Finnish patients diagnosed with autoimmune polyendocrine (or polyglandular) syndrome type 2 (APS2, OMIM 269200), also called Schmidt's Syndrome or Polyglandular autoimmune syndrome, Type II (PGA II). Approval for the study was obtained from the Medicine Ethical Review Board of Helsinki and Uusimaa Joint Authority (dnro 8/13/03/01/2009, research permission IAS09 APS1 6209/T101060071) and each participant signed an informed consent.

The group of APECED patients had the following features. Of the patients, 21 were female and 12 male, the mean age being 38 yrs (females 38.3 yrs: males 37.8 yrs). The mean age at 1st symptoms of APECED had been 6.2 yrs. The mean weight of the men was 69.75 kg and of the women 59.4 kg. These 33 patients responded to a questionnaire on their clinical symptoms. As general symptoms, 30% of the patients experienced fever periods and 67% experienced asthenia.

IPEX (immunodysregulation polyendocrinopathy enteropathy X-linked syndrome) is a rare X-linked recessive disease resulting in aggressive autoimmunity and early death which is described in more detail in the "IPEX" paragraph within the "Definitions and Embodiments" section above.

APS2 is a polygenic disease with the dominant susceptibility locus on chromosome 6 within the major histocompatibility complex (MHC) described in more detail above: for review see. e.g., Baker et al., J. Clin. Endocrinol. Metab. 95 (2010), E263-E270. The prevalence of APS II has been estimated at 1.4 to 2.0 per 100,000. (Betterle et al., Endocr Rev. 23 (2002), 327-64. It occurs most commonly occurs in patients 30 to 40 years of age with women affected three times more often than men. (Schatz and Winter. Endocrinol Metab Clin North Am. 31 (2002), 339-52).

Screening of patients' sera for the presence of autoantibodies against the proteins of interest, preselection of IPEX/APS2 cases with high titer, PBMC isolation and further procedures in concern of, e.g., antibody production and purification, in-vitro cell-based neutralizing assays, validation assays are performed as described in the corresponding examples in respect of APS1/APECED isolated antibodies; see in particular Example 1 for preselection of high titer patient sera for PBMC isolation and Example 2 for further processing of the sera.

Detection of cytokine specific antibodies in the serum of APS2, respective IPEX patients by ELISA was performed as described in Example 8 above. APS2 patients were coded as APS2-1 to APS2-31 and the IPEX patient as IPEX Helsinki. Results of Antibody Screening.

The results obtained by screening the sera of the patient and control subjects to asset of about 100 selected antigens are shown below in Table 29 for APS1, in Table 30 for APS2 respective in Table 31 for IPEX patients.

TABLE 29

Additional data to Table 14 concerning presence of auto-antibodies binding to indicated targets in APS1 patients shown by ELISA-assay.

| Target | Patients with serum reactivity |
| --- | --- |
| CCL13 | APS1-23 |
| CCL21 | APS1-9 |
| CCL22 | APS1-6 |
| CXCL3 | APS1-27 |
| CXCL11 | APS1-9 |
| CXCL12a | APS1-17 |
| IFN-alpha 1beta | APS1-1 to 10, APS1-13 to -18, APS1-20 to -30 |
| IFN alpha 2beta | APS1-1 to -10, APS1-12 to -30 |
| IFNA4 | APS1-1 to -10, APS1-12 to -30 |
| IFNA5 | APS1-1 to -30 |
| IFN omega 1 | APS1-4 to -9, APS1-14 to -16, APS1-18, APS1-19, APS1-21 to -28 and APS1-30 |
| IL1F9 | APS1-7 |
| IL1F10 | APS1-23 |
| IL5 | APS1-3, -8, -13, -18, -25 |
| IL10 | APS1-12 |
| IL11 | APS1-29 |
| IL17 | APS1-13, -18, -20 |
| IL17C | APS1-1, -29 |
| IL17F | APS1-1 to -4, APS1-6 to -11, APS1-13 to -16, APS1-18, APS1-20 to -26 and APS1-28 to -30 |
| IL-22 | APS1-1 to -11, -13, -14, APS1-16 to -22, APS1-24 to -26 and APS1-28 to -30 |
| IL-32 α | APS1-2, -4, -14, -18, -19, -21, -23, -24, -26, -28, -30 |
| IL-32 γ | APS1-2, -28 |
| NY-ESO-1 | APS1-3, -4, -7, -8, APS1-17 to -19, -21, -23, -25, -30 |
| SNCAIP | APS1-5 |
| TGF-beta1 | APS1-22 |
| TMEFF2 | APS1-5 |
| TMEFF2 peptide | APS1-6 |
| TMEFF1 | APS1-5 |
| SPG20 | APS1-2 to -4, -9, -14, -18, -29, -30 |
| Sclerostin | APS1-3, -9, -12, -13 |
| CXCL16 | APS1-9 |
| IL-24 (R&D) | APS1-3, -13 |
| IFNalpha6 | APS1-5, -16 |

TABLE 29-continued

Additional data to Table 14 concerning presence
of auto-antibodies binding to indicated targets
in APS1 patients shown by ELISA-assay.

| Target | Patients with serum reactivity |
|---|---|
| IFNalpha8 | APS1-1, APS1-3 to -10, APS1-13 to -30 |
| IFNA14 | APS1-5, -9 |
| TROY | APS1-5 |

The table shows antigens recognized by the patient sera (giving an OD value over 0.5 at 1:500 dilution of the test serum). Antigenes were dissolved at 0.75 ug/ml in carbonate-bicarbonate buffer, Secondary antibody was diluted 1:10 000 in 0.5% BSA/PBS. For antigens IFNalpha6, IFNalpha8, IFNA14, PSOR1 and Troy the secondary antibody was diluted 1:4 000 in 0.5% BSA/PBS.

TABLE 30

Presence of auto-antibodies binding to indicated
targets in APS2 patients shown by ELISA-assay.

| Target | Patients with serum reactivity |
|---|---|
| CCL4 | APS2-217 |
| CCL28 | APS2-224 |
| IL-1F6 | APS2-227 |
| IL-1F9 | APS2-221, 224 |
| IL-7 | APS2-221, 224, 225 |
| IL-11 | APS2-218 |
| IL-23 | APS2-224 |
| IL-24 | APS2-216, 217, 224 |
| IL-27 | APS2-216, 224 |
| IL-28A | APS2-218, 220, 230 |
| IL-29 | APS2-218, 220, 230 |
| IL-32 α | APS2-218, 222, 223, 231 |
| IL-32 γ | APS2-218 |
| TMEFF-2 | APS2-225 |
| IFNA14 | APS2-216, 228 |
| PSOR1 | APS2-228 |

The table shows antigens recognized by the patient sera (giving an OD value over 0.5 at 1:500 dilution of the test serum). Antigenes were dissolved at 0.75 µg/ml in carbonate-bicarbonate buffer, Secondary antibody diluted 1:10 000 in 0.5% BSA/PBS. Antigens IFNA14 and PSOR were dissolved at 1 ug/ml in PBS, Secondary antibody was diluted 1:4 000 in 0.5% BSA/PBS.

TABLE 31

Presence of and OD value measured for auto-antibodies binding to
indicated targets in IPEX Helsinki patient shown by ELISA-assay.

| Target | OD value at 1:500 serum dilution |
|---|---|
| IL-32 α | 2.68 |
| IL-32 γ | 1.36 |
| IFNA4 | 2.06 |
| IFNA5 | 2.71 |
| NY-ESO-1 | 1.15 |
| SNCAIP | 1.70 |
| TMEFF-1 | 1.52 |
| TMEFF-2 | 2.95 |
| CXCL16 | 1.26 |

Antigenes were dissolved at 0.75 ug/ml in carbonate-bicarbonate buffer. Secondary antibody was diluted 1:10 000 in 0.5% BSA/PBS.

REFERENCES

1. Peterson P, Org T, Rebane A. Transcriptional regulation by AIRE: molecular mechanisms of central tolerance. Nat Rev Immunol 2008: 8:948-57.
2. Mathis D, Benoist C. Aire. Annu Rev Immunol 2009; 27:287-312.
3. Nagamine K, Peterson P. Scott H S et al. Positional cloning of the APECED gene. Nat Genet 1997: 17:393-8.
4. Finnish-German APECED Consortium. An autoimmune disease, APECED, caused by mutations in a novel gene featuring two PHD-type zinc-finger domains. Nat Genet 1997; 17:399-403.
5. Husebye E S, Perheentupa J, Rautemaa R et al. Clinical manifestations and management of patients with autoimmune polyendocrine syndrome type I. J Intern Med 2009; 265:514-29.
6. Kisand K, Lilic D, Casanova J L et al. Mucocutaneous candidiasis and autoimmunity against cytokines in APECED and thymoma patients: clinical and pathogenetic implications. Eur J Immunol 2011; 41:1517-27.
7. Ramsey C, Winqvist O, Puhakka L et al. Aire deficient mice develop multiple features of APECED phenotype and show altered immune response. Hum Mol Genet 2002: 11:397-409.
8. Kuroda N, Mitani T. Takeda N et al. Development of autoimmunity against transcriptionally unrepressed target antigen in the thymus of Aire-deficient mice. J Immunol 2005; 174:1862-70.
9. Jiang W, Anderson M S, Bronson R et al. Modifier loci condition autoimmunity provoked by Aire deficiency. J Exp Med 2005; 202:805-15.
10. Pontynen N, Miettinen A, Arstila T P et al. Aire deficient mice do not develop the same profile of tissue-specific autoantibodies as APECED patients. J Autoimmun 2006; 27:96-104.
11. Kekalainen E, Miettinen A, Arstila T P. Does the deficiency of Aire in mice really resemble human APECED? Nat Rev Immunol 2007; 7:1.
12. Hubert F X, Kinkel S A, Crewther P E et al. Aire-deficient C57BL/6 mice mimicking the common human 13-base pair deletion mutation present with only a mild autoimmune phenotype. J Immunol 2009; 182:3902-18.
13. Meager A, Visvalingam K, Peterson P et al. Anti-interferon autoantibodies in autoimmune polyendocrinopathy syndrome type 1. PLoS Med 2006: 3:e289.
14. Toth B, Wolff A S, Halasz Z et al. Novel sequence variation of AIRE and detection of interferon-omega antibodies in early infancy. Clin Endocrinol (Oxf) 2010; 72:641-7.
15. Meloni A. Furcas M, Cetani F et al. Autoantibodies against type I interferons as an additional diagnostic criterion for autoimmune polyendocrine syndrome type I. J Clin Endocrinol Metab 2008; 93:4389-97.
16. Kisand K, Link M, Wolff A S et al. Interferon autoantibodies associated with AIRE deficiency decrease the expression of IFN-stimulated genes. Blood 2008; 112:2657-66.
17. Kisand K, Peterson P. Autoimmune polyendocrinopathy candidiasis ectodermal dystrophy: known and novel aspects of the syndrome. Ann N Y Acad Sci 2011; 1246:77-91.
18. Meager A, Vincent A, Newsom-Davis J et al. Spontaneous neutralising antibodies to interferon-alpha and interleukin-12 in thymoma-associated autoimmune disease. Lancet 1997; 350:1596-7.
19. Kisand K, Boe Wolff A S, Podkrajsek K T et al. Chronic mucocutaneous candidiasis in APECED or thymoma patients correlates with autoimmunity to Th17-associated cytokines. J Exp Med 2010; 207:299-308.
20. Burbelo P D, Browne S K, Sampaio E P et al. Anti-cytokine autoantibodies are associated with opportunistic infection in patients with thymic neoplasia. Blood 2010; 116:4848-58.
21. Holbro A, Jauch A, Lardinois D et al. High prevalence of infections and autoimmunity in patients with thymoma. Hum Immunol; 73:287-90.
22. Puel A, Doffinger R, Natividad A et al. Autoantibodies against IL-17A, IL-17F, and IL-22 in patients with chronic mucocutaneous candidiasis and autoimmune polyendocrine syndrome type I. J Exp Med 2010; 207: 291-7.
23. Oftedal B E, Kampe O, Meager A et al. Measuring autoantibodies against IL-17F and IL-22 in autoimmune polyendocrine syndrome type I by radioligand binding assay using fusion proteins. Scand J Immunol 2011; 74:327-33.
24. Wolk K, Witte E, Witte K et al. Biology of interleukin-22. Semin Immunopathol 2010; 32:17-31.
25. Puel A, Picard C, Cypowyj S et al. Inborn errors of mucocutaneous immunity to *Candida albicans* in humans: a role for IL-17 cytokines? Curr Opin Immunol 2010; 22:467-74.
26. Pestka S, Krause C D, Walter M R. Interferons, interferon-like cytokines, and their receptors. Immunol Rev 2004; 202:8-32.
27. Cho J S, Pietras E M, Garcia N C et al. IL-17 is essential for host defense against cutaneous Staphylococcus aureus infection in mice. J Clin Invest 2010; 120:1762-73.
28. Conti H R, Gaffen S L. Host responses to *Candida albicans*: Th17 cells and mucosal candidiasis. Microbes Infect 2010; 12:518-27.
29. Wolff A S. Erichsen M M, Meager A et al. Autoimmune polyendocrine syndrome type 1 in Norway: phenotypic variation, autoantibodies, and novel mutations in the autoimmune regulator gene. J Clin Endocrinol Metab 2007; 92:595-603.
30. Burbelo P D, Ching K H, Klimavicz C M et al. Antibody profiling by Luciferase Immunoprecipitation Systems (LIPS). J Vis Exp (2009); 32:1549.
31. Hassler S, Ramsey C, Karlsson M C et al. Aire-deficient mice develop hematopoetic irregularities and marginal zone B-cell lymphoma. Blood 2006; 108:1941-8.
32. Teesalu K, Agardh D, Panarina M et al. A modified ELISA for improved detection of IgA, IgG, and IgM anti-tissue transglutaminase antibodies in celiac disease. Clin Chim Acta 2009: 403:37-41.
33. Dieterich W, Ehnis T. Bauer M et al. Identification of tissue transglutaminase as the autoantigen of celiac disease. Nat Med 1997: 3:797-801.
34. Kisand K E, Kisand K V, Karvonen A L et al. Antibodies to pyruvate dehydrogenase in primary biliary cirrhosis: correlation with histology. Apmis 1998; 106:884-92.
35. Brozzetti A, Marzotti S, La Torre D et al. Autoantibody responses in autoimmune ovarian insufficiency and in Addison's disease are IgG1 dominated and suggest a predominant, but not exclusive, Th1 type of response. Eur J Endocrinol 2010: 163:309-17.
36. Boe A S, Bredholt G, Knappskog P M et al. Autoantibodies against 21-hydroxylase and side-chain cleavage enzyme in autoimmune Addison's disease are mainly immunoglobulin G1. Eur J Endocrinol 2004; 150:49-56.
37. Aalberse R. The role of IgG antibodies in allergy and immunotherapy. Allergy 2011: 66 Suppl 95:28-30.
38. van der Neut Kolfschoten M, Schuurman J, Losen M et al. Anti-inflammatory activity of human IgG4 antibodies by dynamic Fab arm exchange. Science 2007; 317:1554-7.
39. Mobs C, Slotosch C, Loffler H et al. Cellular and humoral mechanisms of immune tolerance in immediate-type allergy induced by specific immunotherapy. Int Arch Allergy Immunol 2008; 147:171-8.
40. Muller U R. Bee venom allergy in beekeepers and their family members. Curr Opin Allergy Clin Immunol 2005; 5:343-7.
41. Aoki V, Sousa J X, Jr., Diaz L A. Pathogenesis of endemic pemphigus foliaceus. Dermatol Clin 2011: 29:413-8, viii.
42. Zen Y, Nakanuma Y. Pathogenesis of IgG4-related disease. Curr Opin Rheumatol 2011; 23:114-8.
43. Wang X, Laan M, Bichele R et al. Post-Aire maturation of thymic medullary epithelial cells involves selective expression of keratinocyte-specific autoantigens. Front Immun 2011: 3:doi: 10.3389/fimmu.2012.00019.
44. Vincent A C, McConville J. Newsom-Davis J. Is "seronegative" MG explained by autoantibodies to MuSK? Neurology 2005: 64:399; author reply
45. Grant G A. Synthetic peptides for production of antibodies that recognize intact proteins. Curr Protoc Protein Sci 2002: Chapter 18: Unit 18 3.
46. Quadt-Akabayov S R, Chill J H, Levy R et al. Determination of the human type I interferon receptor binding site on human interferon-alpha2 by cross saturation and an NMR-based model of the complex. Protein Sci 2006: 15:2656-68.
47. Bleicher L, de Moura P R, Watanabe L et al. Crystal structure of the IL-22/IL-22R1 complex and its implications for the IL-22 signaling mechanism. FEBS Lett 2008: 582:2985-92.
48. Ahlgren K M, Moretti S, Lundgren B A et al. Increased IL-17A secretion in response to *Candida albicans* in autoimmune polyendocrine syndrome type 1 and its animal model. Eur J Immunol 2011: 41:235-45.
49. Backes. C., Keller, A., Kuentzer, J., Kneissl, B., Comtesse, N., Elnakady, Y. A., Müller. R., Meese, E., and Lenhof, H. P. GeneTrail—advanced gene set enrichment analysis. Nucleic Acid Research, Web Server Issue 2007.
50. Keller, A., Backes, C., Al-Awadhi, M., Gerasch, A., Kuentzer, J., Kohlbacher, O., Kaufmann, M., and Lenhof, H. P. GeneTrailExpress: a web-based pipeline for the statistical evaluation of microarray experiments. BMC Bioinformatics 2008, 9:552
51. Keller, A., Backes, C., and Lenhof, H. P. Computation of significance scores of unweighted Gene Set Enrichment Analyses. BMC Bioinformatics, 2007
52. Harris H. F.: On the rapid conversion of hematoxylin into haematein in staining reactions. Journal of Applied Microscopic Laboratory Methods 1900; 3:777.
53. Mallory F. B.: Pathological technique. Philadelphia. Saunders, 1938.
54. Aranda, B. et al. 2010. The IntAct molecular interaction database in 2010. Nucleic acids research 38: D525-D531.
55. Ashbumer. M. et al. 2000. Gene Ontology: tool for the unification of biology. Nature genetics 25: 25.
56. Cerami. E. G., Gross, B. E., Demir, E., Rodchenkov, I., Babur. Ö., Anwar, N., Schultz, N., Bader, G. D., and Sander, C. 2011. Pathway Commons, a web resource for biological pathway data. Nucleic acids research 39: D685-D690.
57. Flicek, P. et al. 2009. Ensembl's 10th year. Nucleic Acids Research.
58. Kelder, T., van lersel, M. P., Hanspers. K., Kutmon, M., Conklin, B. R., Evelo. C. T., and Pico, A. R. 2012. WikiPathways: building research communities on biological pathways. Nucleic Acids Research 40: D1301-D1307.
59. Laakso, M., and Hautaniemi, S. 2010. Integrative platform to translate gene sets to networks. Bioinformatics 26: 1802-1803.

60. Zanzoni, A., Montecchi-Palazzi. L., Quondam, M., Ausiello, G., Helmer-Citterich, M., and Cesareni, G. 2002. MINT: a Molecular INTeraction database. FEBS letters 513: 135-140.

The invention claimed is:

1. A cDNA molecule encoding at least a heavy chain variable region ($V_H$) and/or light chain variable region ($V_L$) of a monoclonal anti-interleukin-17F (IL-17F) antibody or an IL-17F-binding fragment thereof, wherein the antibody comprises in its variable regions
the complementarity determining regions (CDRs) of the $V_H$ and $V_L$ variable regions comprising the amino acid sequences of
SEQ ID NO: 7 and
SEQ ID NO: 9, respectively.

2. The cDNA molecule of claim 1, wherein the antibody comprises in its variable regions a $V_H$ region comprising an amino acid sequence having at least 80% identity to SEQ ID NO:7 and a $V_L$ region comprising an amino acid sequence having at least 80% identity to SEQ ID NO:9.

3. The cDNA molecule of claim 1, wherein the antibody comprises in its variable regions a $V_H$ region comprising the amino acid of SEQ ID NO: 7 and a $V_L$ region comprising the amino acid sequence of SEQ ID NO: 9.

4. The cDNA molecule of claim 1, wherein the antibody comprises a $C_H$ comprising the amino acid sequence of SEQ ID NO: 11 and/or a $C_L$ comprising the amino acid sequence of SEQ ID NO: 13.

5. A vector comprising the cDNA molecule of claim 1.

6. The vector of claim 5, wherein the vector is an expression vector.

7. The vector of claim 5, wherein the cDNA is operatively linked to an expression control sequence allowing transcription of the cDNA into translatable mRNA in prokaryotic or eukaryotic cells.

8. An isolated host cell comprising the cDNA molecule of claim 1.

9. The isolated host cell of claim 8, wherein the host cell is a prokaryotic or eukaryotic host cell.

10. A method of producing a monoclonal antibody specific for IL-17F and encoded by the cDNA in the host cell of claim 8, comprising:
(a) culturing the host cell under conditions allowing the expression of the antibody; and
(b) isolating the antibody from the cell culture.

11. A polynucleotide linked to a heterologous nucleic acid, wherein the polynucleotide is selected from the group consisting of:
(a) a polynucleotide encoding an immunoglobulin heavy chain or a fragment thereof comprising a heavy chain variable region ($V_H$) comprising the complementarity determining regions (CDRs) of the $V_H$ of SEQ ID NO:7, wherein the immunoglobulin heavy chain $V_H$ when paired with a light chain variable region ($V_L$) comprising the amino acid sequence of SEQ ID NO: 9 binds to interleukin 17F (IL-17F);
(b) a polynucleotide encoding an immunoglobulin light chain or a fragment thereof comprising a light chain variable region (V$_L$) comprising the complementarity determining regions (CDRs) of the V$_L$ of SEQ ID NO: 9, wherein the immunoglobulin light chain V$_L$ when paired with a heavy chain variable region (V$_H$) comprising the amino acid sequence of SEQ ID NO: 7 binds to IL-17F;

(c) a polynucleotide encoding
  (i) an immunoglobulin heavy chain or a fragment thereof comprising a heavy chain variable region (V$_H$) comprising the complementarity determining regions (CDRs) of the V$_H$ of SEQ ID NO: 7; and
  (ii) an immunoglobulin light chain or a fragment thereof comprising a light chain variable region (V$_L$) comprising the complementarity determining regions (CDRs) of the V$_L$ of SEQ ID NO: 9;

(d) a polynucleotide encoding an immunoglobulin heavy chain or a fragment thereof comprising the amino acid sequence of SEQ ID NO: 7;

(e) a polynucleotide encoding an immunoglobulin light chain or a fragment thereof comprising the amino acid sequence of SEQ ID NO: 9; and (f) a polynucleotide encoding an immunoglobulin heavy chain or a fragment thereof comprising the amino acid sequence of SEQ ID NO: 7 and an immunoglobulin light chain or a fragment thereof comprising the amino acid sequence of SEQ ID NO: 9.

12. The polynucleotide of claim 11, wherein the polynucleotide comprises a nucleotide sequence encoding a C$_H$ comprising the amino acid sequence of SEQ ID NO: 11 and/or a C$_L$ comprising the amino acid sequence of SEQ ID NO: 13.

13. The polynucleotide of claim 11, wherein the heterologous nucleic acid is a regulatory element.

14. The polynucleotide of claim 13, wherein the regulatory element is a promoter, an enhancer, a transcription termination sequence or a sequence encoding a leader sequence.

15. An isolated host cell comprising one or more polynucleotides of claim 11.

16. The host cell of claim 15, which is a prokaryotic or eukaryotic host cell.

17. A vector comprising one or more polynucleotides of claim 11.

18. The vector of claim 17, wherein the vector is an expression vector.

19. The vector of claim 17, wherein the polynucleotide or polynucleotides are operatively linked to an expression control sequence allowing transcription of the polynucleotide or polynucleotides into a translatable mRNA in prokaryotic or eukaryotic cells.

20. An isolated host cell comprising one or more vectors of claim 17.

21. The host cell of claim 20, which is a prokaryotic or eukaryotic host cell.

22. A method of producing an anti-IL-17F monoclonal antibody encoded by the polynucleotide in the vector in the host cell of claim 20 which comprises:
  (a) culturing in a cell culture the host cell under conditions allowing the expression of the immunoglobulin heavy and light chains; and
  (b) isolating the monoclonal antibody comprising the immunoglobulin heavy and light chains from the cell culture.

23. The method of claim 22, wherein the isolated monoclonal antibody is a human antibody.

24. A method of producing an immunoglobulin chain selected from:
  i. an immunoglobulin chain comprising the amino acid sequence of SEQ ID NO:7,
  ii. an immunoglobulin chain comprising the amino acid sequence of SEQ ID NO:9,
  iii. an immunoglobulin chain comprising the complementarity determining regions of SEQ ID NO:7, and
  iv. an immunoglobulin chain comprising the complementarity determining regions of SEQ ID NO:9;
  the method comprising:
  (a) culturing in a cell culture a host cell comprising an expression vector comprising a nucleic acid encoding the immunoglobulin chain under conditions in which the immunoglobulin chain is expressed,
  (b) isolating the corresponding immunoglobulin chain from the cell culture.

* * * * *